US012655107B2

(12) United States Patent
An et al.

(10) Patent No.: US 12,655,107 B2
(45) Date of Patent: Jun. 16, 2026

(54) OXYNITIDINE DERIVATIVES USEFUL AS INHIBITORS OF TOPOISOMERASE IB (TOP1) AND TYROSYL-DNA PHOSPHODIESTERASE 1 (TDP1)

(71) Applicants: The United States of America, as represented by the Secretary, Department of Health and Human Services, Bethesda, MD (US); SHENZHEN XUHUA BIOTECH CO. LTD., Shenzhen (CN)

(72) Inventors: Lin-Kun An, Guangzhou (CN); Xiaoru Zhang, Guangzhou (CN); Haowen Wang, Guangzhou (CN); Yves Georges Pommier, Bethesda, MD (US); Evgeny A. Kiselev, Rockville, MD (US); Azhar Ali Ravji, Bethesda, MD (US); Keli Kisseh Agama, Bethesda, MD (US)

(73) Assignees: The United States of America, as represented by the Secretary, Department of Health and Human Services, Bethesda, MD (US); Shenzhen Xuhua Biotech Co. Ltd., Shenzhen (CN)

( * ) Notice: Subject to any disclaimer, the term of this patent is extended or adjusted under 35 U.S.C. 154(b) by 811 days.

(21) Appl. No.: 17/262,379

(22) PCT Filed: Jul. 25, 2019

(86) PCT No.: PCT/US2019/043357

§ 371 (c)(1),
(2) Date: Jan. 22, 2021

(87) PCT Pub. No.: WO2020/023700

PCT Pub. Date: Jan. 30, 2020

(65) Prior Publication Data

US 2023/0219895 A1 Jul. 13, 2023

Related U.S. Application Data

(60) Provisional application No. 62/732,885, filed on Sep. 18, 2018.

(30) Foreign Application Priority Data

Jul. 25, 2018 (CN) ......................... 201810827467.1

(51) Int. Cl.

| | |
|---|---|
| *C07D 221/18* | (2006.01) |
| *A61K 31/435* | (2006.01) |
| *A61K 31/4355* | (2006.01) |
| *A61P 25/00* | (2006.01) |
| *A61P 31/00* | (2006.01) |
| *A61P 35/00* | (2006.01) |
| *C07D 491/056* | (2006.01) |
| *C07D 491/153* | (2006.01) |
| *C07D 491/22* | (2006.01) |

(52) U.S. Cl.

CPC ............ *C07D 221/18* (2013.01); *A61P 35/00* (2018.01); *C07D 491/056* (2013.01); *C07D 491/153* (2013.01); *C07D 491/22* (2013.01)

(58) Field of Classification Search

CPC .............. C07D 221/18; C07D 491/056; C07D 491/153; A61K 31/435; A61K 31/4355; A61P 25/00; A61P 31/00; A61P 35/00

See application file for complete search history.

(56) References Cited

U.S. PATENT DOCUMENTS

| | | | | |
|---|---|---|---|---|
| 3,912,740 A * | 10/1975 | Zee-Cheng | .......... | C07D 317/70 562/466 |
| 4,014,885 A * | 3/1977 | Zee-Cheng | .......... | C07D 221/18 546/61 |
| 2010/0256164 A1* | 10/2010 | Shaw | .................. | A61K 31/497 514/280 |
| 2012/0172371 A1 | 7/2012 | Pommier | | |
| 2013/0345252 A1 | 12/2013 | Cushman et al. | | |
| 2016/0009727 A1* | 1/2016 | Kovach | ............. | C07D 491/056 435/375 |
| 2016/0340704 A1* | 11/2016 | Martin | ................ | C07D 217/02 |

FOREIGN PATENT DOCUMENTS

| | | |
|---|---|---|
| WO | 200021537 A1 | 4/2000 |
| WO | 2018118852 A1 | 6/2018 |

OTHER PUBLICATIONS

Janin et al., Synthesis and Evaluation of New 6-Amino-Substituted Benzo[c]phenanthridine Derivatives, Journal of Medicinal Chemistry, vol. 36, No. 23, pp. 3686-3692 (Year: 1993).*

Chakthong et al., "New Alkylamide from the Stems of Zanthoxylum Nitidum," Natural Product Research, Taylor & Francis, vol. 33, (No. 2), Published Online on Feb. 19, 2018, pp. 153-159.

(Continued)

*Primary Examiner* — Brenda L Coleman

(74) *Attorney, Agent, or Firm* — McDonnell Boehnen Hulbert & Berghoff LLP

(57) ABSTRACT

Compounds and pharmaceutically acceptable salts thereof of Formula I are disclosed. Certain compounds and salts of Formula I are active as Top1 and/or Tdp1 inhibitors. The disclosure provides pharmaceutical compositions containing a compound of Formula I as the only active agent, or optionally containing one or more additional active agents. Methods of using compounds of Formula I to treat cancer are provided in this disclosure. The disclosed compounds of Formula I may be used alone to treat cancer, but may also be used in combination with another active agent, such as a Top1 inhibitor, for example, camptothecin or a camptothecin analogue.

22 Claims, 22 Drawing Sheets

Specification includes a Sequence Listing.

(56) References Cited

OTHER PUBLICATIONS

Cho et al., "A Novel Synthesis of Benzoacuphenanthridine Skeleton and Biological Evaluation of Isoquinoline Derivatives," Chemical and Pharmaceutical Bulletin, vol. 47, (No. 6), (1999), pp. 900-902.
Clark et al., "Exploring DNA Topoisomerase I Inhibition by the Benzo[c]Phenanthridines Fagaronine and Ethoxidine Using Steered Molecular Dynamics," Bioorganic & Medicinal Chemistry, vol. 15, (No. 14), (2007), pp. 4741-4752.
Hanaoka et al., "Chemical Transformation of Protoberberines XVI. 1) Regioselective Introduction of an Oxy Functionality at the C12-Position of the Benzo [c]Phenanthridine Skeleton: A Convenient Synthesis of Macarpine from Oxychelirubine 2)," Chem. Phar. Bulletin, vol. 38, (No. 12), (1990), pp. 3335-3340.
Harayama et al., "Synthesis of Benzo[c] Phenanthridine Alkaloids, Using a Novel Palladium—Phosphine Combination System—Pd(OAc)2, DPPP, and Bu3P," Synthesis 2002, (No. 2), Jan. 2, 2002. Article Identifier: 1437-210X, E;2002,0,02,0237,0241,ftx,en; F07301SS; pp. 237-238.
International Search Report for International Application No. PCT/US2019/043357; International Filing Date—Jul. 25, 2019; Date of Mailing—Apr. 7, 2020.
Ishii et al., "Chelirubine," Chemical and Pharmaceutical Bulletin, vol. 26, (No. 3), (1978), pp. 864-873.
Ishii et al., "Studies on the Chemical Constituents of Rutaceous Plants. LV. 1) The Development of a Versatile Method for the Synthesis of Antitumor-Active Benzo[c]Phenanthridine Alkaloids. (5). 1) A New Method for Quaternization of the Benzo[c] Phenanthridine Nucleus," Chemical and Pharmaceutical Bulletin, vol. 32, (No. 8), (1984), pp. 2984-2994.
Kiselyov, "Reaction of Ortho-Lithiated N-Methylbenzamide With 1, 2-Diketones: A Novel Highly Efficient Route to N-Methylisoquinolin-1-Ones," Tetrahedron Letters, vol. 36 (No. 4), (1995), pp. 493-496.
Lei et al., "Chemical Constituents of Plants from Tribe Chelidonieae and their Bioactivities," Chinese Herbal Medicine, vol. 6, (No. 1), (2014), pp. 1-21.
Mathew et al., "The Benzophenanthridine Ring System" Current Science, Indian Academy of Sciences, vol. 24, (No. 6), (1955) p. 193.
Nakamura et al., "Structural Development Studies of Anti-Hepatitis C Virus Agents With a Phenanthridinone Skeleton," Bioorganic & Medicinal Chemistry, vol. 18, (No. 7), (2010), pp. 2402-2411.
Prado et al., "Synthesis and Cytotoxic Activity of Benzo[c][1,7] and [1,8] Phenanthrolines Analogues of Nitidine and Fagaronine," Bioorganic & Medicinal Chemistry, vol. 12, (No. 14), (2004), pp. 3943-3953.
Sazonova et al., "Synthesis and Antitumor Activity of Salts of O-Methylfagaronine and its Structural Analog—C-Norbenzo [C] Phenanthridine Methyl Chloride," Pharmaceutical Chemistry Journal, vol. 25, (No. 7), (1991), pp. 465-469.
Sharma et al., "Microwave-Assisted Ruthenium-Catalysed Ortho-C—H Functionalization of N-Benzoyl a-Amino Ester Derivatives," Advanced Synthesis & Catalysis, (2018) No. 360, pp. 3083-3088.
Tang et al., "Synthesis and Biological Evaluation of 5-Aminoethyl Benzophenanthridone Derivatives as DNA Topoisomerase IB Inhibitors," European Journal of Medicinal Chemistry, vol. 178, (2019), pp. 81-92.
Written Opinion for International Application No. PCT/US2019/043357; International Filing Date—Jul. 25, 2019; Date of Mailing—Apr. 7, 2020.
Yang et al., "Secondary Metabolites and Cytotoxic Activities from the Stem Bark of Zanthoxylum Nitidum," Chemistry & Biodiversity, vol. 6, (No. 6), (2009), pp. 846-857.
Yang et al., "Isoquinoline Alkaloids from Zanthoxylum Simulans and their Biological Evaluation," The Journal of Antibiotics, Nature Publishing Group, vol. 68, (No. 4), (2015), pp. 289-292.
Zhang et al., "Discovery, Synthesis, and Evaluation of Oxynitidine Derivatives as Dual Inhibitors of DNA Topoisomerase IB (TOP1) and Tyrosyl-DNA Phosphodiesterase 1 (TDP1), and Potential Anti-tumor Agents," Journal of Medicinal Chemistry, vol. 61, (No. 22), (2018), pp. 9908-9930.

* cited by examiner

SODIUM ORTHOVANADATE (7)

USNIC ACID ENAMINE (8)

AMINOADAMANTANE (9)

INDENOISOQUINOLINE (10)

HYDROXYCOUMARIN (11)

46

47

18a

OXYNITIDINE DERIVATIVES USEFUL AS INHIBITORS OF TOPOISOMERASE IB (TOP1) AND TYROSYL-DNA PHOSPHODIESTERASE 1 (TDP1)

STATEMENT OF GOVERNMENTAL INTEREST

The National Cancer Institute and the National Institutes of Health (BC 006161) funded the subject matter of this disclosure. The United States Government has certain rights in this application. This work was also supported by the National Natural Science Foundation of China (No. 81373257).

CROSS-REFERENCE TO RELATED APPLICATIONS

This application is a U.S. National Stage application of PCT/US2019/043357 filed Jul. 25, 2019, which claims priority to and the benefit of U.S. Provisional Application No. 67/732,885 filed Sep. 18, 2018 and Chinese Patent Application No 201808274671 filed on Jul. 25, 2018, and all the benefits accruing therefrom under 35 U.S.C. § 119, the contents of each of which are incorporated by reference in their entirety.

REFERENCE TO AN ELECTRONIC SEQUENCE LISTING

The instant application contains a Sequence Listing which has been submitted electronically as a text file in ASCII format and is hereby incorporated by reference in its entirety. The name of the ASCII text file is "21-0948_Sequence_Listing__20210825_ST25.txt", it was created on Aug. 25, 2021, and it is 858 bytes in size.

FIELD OF THE DISCLOSURE

Topoisomerase 1B (Top1) inhibitors are a well-known class of antineoplastic agents that includes camptothecin and its derivatives. Tdp1 is an enzyme that repairs damage caused by stalled Top1 covalent complexes, a process that occurs in the presence of Top1 inhibitors, and can limit efficacy of Top1 inhibitors. Tdp1 inhibitors can act synergistically with Top1 inhibitors for enhanced antineoplastic activity. This disclosure provides compounds of Formula I useful as Top1 inhibitors and/or Tdp1 inhibitors useful as antineoplastic agents. Certain compounds of the disclosure have both Top1 and Tdp1 inhibitory activity. This disclosure provides pharmaceutical compositions containing a compound of Formula I as a first active agent and optionally one or more additional active agents. This disclosure further provides methods of making and using compounds of Formula I, such as method of using a compound of Formula I to treat cancer.

BACKGROUND

Topoisomerase IB (Top1) is an essential nuclear enzyme controlling the topology of DNA in many cellular metabolic processes. The mechanism of Top1 action, and DNA repair of Top1 cleavages, is illustrated in FIG. 1. To perform its functions, Top1 cleaves one strand of DNA by nucleophilic attack of its active site tyrosine on the DNA phosphodiester backbone (FIG. 1, A), resulting in formation of the single-strand nick in the target DNA and a Top1-DNA covalent cleavage complex, Top1cc, (FIG. 1, B). Top1cc are transient intermediates under normal physiological circumstances and reverse via 5'-OH attack of the nicked strand on the Top1-DNA phosphotyrosyl group, thus restoring the intact DNA and releasing Top1. Top1 inhibitors, such as camptothecin (1) bind at the interface of Top1cc by intercalating between the base pairs at the site of cleavage and forming key hydrogen bonds with Top1, and stabilize Top1cc to prevent further re-ligation of the broken DNA. When replication and transcription machineries encounter the trapped Top Ice, DNA damage is generated, triggering cell death. To date, four well-known camptothecin Top1 inhibitors have been approved for clinical treatment of cancers, including irinotecan (2) and topotecan (3) approved by the U.S. F.D.A., 10-hydroxycamptothecin (4, HCPT, in China) and belotecan (5, in South Korea). Therefore, Top1 is a validated target for the discovery of antitumor agents.

Despite their effectiveness in solid tumors, camptothecin inhibitors suffer from well-established limitations, including chemically instability under physiological condition, poor solubility, bone marrow dose-limiting toxicity, severe gastrointestinal toxicity, and drug efflux-mediated resistance. Because of these shortcomings, much attention is directed toward the discovery of non-camptothecin inhibitors. Several non-camptothecin Top1 inhibitors have also been discovered, these include chemotypes having an indolocarbazoles, dibenzonaphthyridinone, or indenoisoquinoline core. LMIP744, LMP400 (Indotecan), and LMP776 (Inidotecan) are in clinical trials.

The DNA damage generated from Top1cc can be repaired through several pathways, including homologous recombination (BRCA1, BRCA2, CtIP, Mre11, Rad52), cell cycle checkpoint signaling, XPF/ERCC1, Mre11 CtIP and tyrosyl-DNA phosphodiesterase-dependent pathways, etc. Tyrosyl-DNA phosphodiesterase 1 (Tdp1) is a member of the phospholipase D superfamily. It catalytically hydrolyzes the 3'-phosphotyrosyl bond (FIG. 1, C) associated with Top1cc. Tdp1 generates DNA breaks with 5'-hydroxyl and 3-phosphate ends (FIG. 1, D) for further DNA repair by the XRCC-1-dependent pathway, including polynucleotide kinase phosphatase (PNKP), poly(ADP-ribose) polymerase 1 (PARP1), DNA ligase III (Lig3) and DNA polymerase β (Polβ), finally resulting in resealed DNA (FIG. 1, E). In this pathway, Tdp1-catalyzed hydrolysis of the 3-phosphotyrosyl bond is a key step for initiating the repair of Top1-mediated DNA damage. In addition, Tdp1 catalyzes hydrolysis of 3'-blocking lesions generated by DNA oxidation and alkylation, as well as 5'-phosphotyrosyl bond involved in topoisomerase II-mediated DNA damage, implying a broader role of Tdp1 in the maintenance of genomic stability. The physiological importance of Tdp1 is further emphasized by the discovery of a rare neurodegenerative disease called spinocerebellar ataxia with axonal neuropathy (SCAN1), in which Tdp1 bears a H493R mutation in its active site.

Because Tdp1-deficient cells are hypersensitive to Top1 inhibitors, it has been suggested that overexpression of Tdp1 will confer resistance to Top1-mediated DNA damage, and therefore Tdp1 inhibitors would have the ability to sensitize cancer cells to Top1 inhibitors. Indeed, cells overexpressing Tdp1 show resistance to camptothecin. Conversely, Tdp1 knockout mice, human cells deficient in Tdp1 and the SCAN1 mutation all show hypersensitivity to camptothecin. Some Tdp1 inhibitors show synergistic activity to camptothecin derivatives.

Among Tdp1 inhibitors, sodium orthovanadate (7, FIG. 2) was the first reported Tdp1 inhibitor mimicking the DNA substrate in the transition state, but with inhibition only at millimolar concentration. Several more potent inhibitors with $IC_{50}$ values at low micromolar or submicromolar concentrations have been reported, such as aminoglycoside neomycin, methyl-3,4-dephostatin, arylidenethioxothiazolicinone, thioxopyrimidinedione (CD00509), benzopentathiepine. A few derivatives of the clinically-developed Top1 inhibitors, the indenoisoquinoline derivatives have been reported to also inhibit Tdp1. The indenoisoquinoline 10 (FIG. 2) showed consistent Tdp1 inhibition with $IC_{50}$ value of 1.52 μM. Recently, three chemotypes (FIG. 2), 7-hydroxycoumarin derivatives (11), usnic acid enamines (8) and aminoadamantanes (9) were reported to inhibit Tdp1 and synergize with camptothecin derivatives.

Additional Top1 and Tdp1 inhibitors are desirable as new antitumor agents. Active agents, which have both Top1 and Tdp1 inhibitory activity are particularly desirable.

SUMMARY

The inventors have discovered a class of 4-thioxothiazolidine derivatives of Formula I that inhibit Topioisomerase 1 (Top1) and/or human tyrosyl-DNA phosphodiesterase (Tdp1). Certain compounds of Formula I are useful as anti-cancer agents, either alone or in combination with a chemotherapeutic agent that induces Top1-mediated DNA damage, such as camptothecin.

The disclosure includes compounds and salts of Formula I and the pharmaceutically acceptable salts thereof.

Formula I

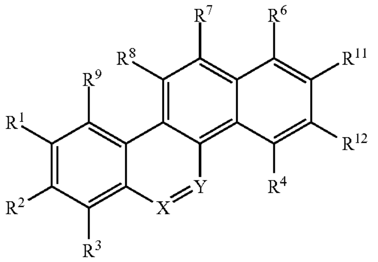

Within Formula I the variables, e.g. $R^1$-$R^{12}$ and X and Y carry the following definitions.

X is carbon and Y is nitrogen and the group

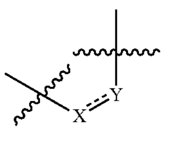

is

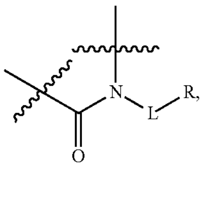

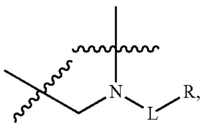

-continued

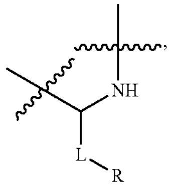

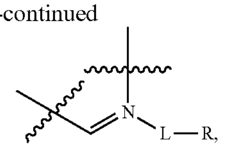

or

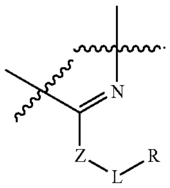

Z is O, NH, $NR^{10}$, or S.

L is $C_1$-$C_6$alkyl, which $C_1$-$C_6$alkyl can contain one or more double or triple bonds, can have one or more $CH_2$ group can be replaced by N, NH, $NR^{10}$, S, —$SO_2$—, or O, and is optionally substituted with one or more substituents independently chosen from hydroxyl, amino, cyano, halogen, oxo, and $C_3$-$C_6$cycloalkyl and $R^{10}$ is $C_1$-$C_6$alkyl or ($C_3$-$C_6$cycloalkyl)$C_0$-$C_4$alkyl.

R is hydrogen, hydroxyl, amino, cyano, P(O)(OCH3)2, or halogen; or R is $C_1$-$C_6$alkyl, R is a 3- to 7-membered saturated, partially unsaturated, aromatic, or unsaturated carbocyclic group or heterocyclic group, optionally substituted with one or more substituents independently chosen from halogen, hydroxyl, $C_1$-$C_2$alkyl, $C_1$-$C_2$alkoxy, $C_2$-$C_4$alkanoyl, $C_1$-$C_2$haloalkyl, $C_1$-$C_2$haloalkoxy, piperidine, —$C_1$-$C_2$alkyl(O)pyrrolidine, —$C_1$-$C_2$alkylpyrrolidine; $R^1$, $R^2$, and $R^3$ are independently chosen from hydrogen, hydroxyl, halogen, amino, $C_1$-$C_6$alkyl, $C_1$-$C_6$alkoxy, benzyloxy, $C_1$-$C_6$alkylthio, $C_1$-$C_2$haloalkyl, and $C_1$-$C_2$haloalkoxy.

$R^1$ and $R^2$ can alternatively be taken together to form a 5 or 6-membered heterocycloalkyl ring containing 2 oxygen atoms, which $R^1$/$R^2$ ring is unsubstituted or substituted with 1 or 2 independently chosen $R^1$ substituents, where $R^5$ is independently chosen at each occurrence from halogen, hydroxyl, $C_1$-$C_2$alkyl, and $C_1$-$C_2$alkoxy; or $R^2$ and R can be taken together to form a 5 or 6-membered heterocycloalkyl ring containing 2 oxygen atoms, which $R^2$/$R^3$ ring is unsubstituted or substituted with 1 or 2 1 or 2 independently chosen $R^5$ substituents.

$R^4$, $R^5$, $R^6$, $R^7$, and $R^8$ are independently chosen from hydrogen, halogen, hydroxyl, amino, cyano, COOH, CHO, or $C_1$-$C_6$alkyl, which $C_1$-$C_6$alkyl can contain one or more double or triple bonds, can have one or more $CH_2$ group can be replaced by NH, $NR^{10}$, S, or O, and is optionally substituted with one or more substituents independently chosen from hydroxyl, amino, cyano, halogen, oxo, and $C_3$-$C_6$cycloalkyl.

$R^7$ and $R^8$ can be taken together to form a ring.

$R^{11}$ and $R^{12}$ are independently chosen from hydrogen, hydroxyl, halogen, amino, $C_1$-$C_6$alkyl, $C_1$-$C_6$alkoxy, benzyloxy, $C_1$-$C_6$alkylthio, $C_1$-$C_2$haloalkyl, or $C_1$-$C_2$haloalkoxy.

$R^{11}$ and $R^{12}$ can alternatively be taken together to form a 5 or 6-membered heterocycloalkyl ring containing 2 oxygen atoms, which $R^{11}$/$R^{12}$ ring is unsubstituted or substituted with 1 or 2 independently chosen R substituents.

Pharmaceutical compositions comprising a compound or salt of Formula I together with a pharmaceutically acceptable carrier are also disclosed.

The disclosure includes methods of inhibiting Tdp1 and/or Top1 in vivo or in vitro comprising contacting a cell nucleus with a compound or salt of Formula I.

The disclosure includes methods of treating cancer in a patient comprising administering a therapeutically effective amount of a compound or salt of Formula I to the patient.

The disclosure includes methods of treating cancer in a patient comprising administering a therapeutically effective amount of a compound or salt of Formula I in combination with and a Top1 inhibitor that is not a compound or salt of Formula I to the patient.

The disclosure includes methods of a neurological disease or sepsis in a patient comprising administering a therapeutically effective amount of a compound or salt of Formula I to the patient.

The disclosure includes methods of treating a neurological disease or sepsis in a patient comprising administering a therapeutically effective amount of a compound or salt of Formula I in combination with and a Top1 inhibitor that is not a compound or salt of Formula I to the patient.

BRIEF DESCRIPTION OF THE DRAWINGS

FIG. 4 shows a possible transformation pathway of 46 into 18a.

FIG. 5A. A representative gel of Top1-mediated DNA cleavage assay. Lane 1, DNA alone; lane 2, DNA and Top1; lane 3, DNA and Top1 with 1 (1 μM); lane 4, DNA and Top1 with 48 (1 μM); lanes 5-8, DNA and Top1 with 19a at 0.1, 1.0, 10 and 100 μM concentration, respectively. The arrows at left indicate the cleavage site positions. FIG. 5B shows the gel of Top1-mediated unwinding assay using supercoiled pBR322 DNA. Lane 1: DNA alone; lane 2: DNA and Top1; lanes 3-5: DNA and Top1 with the known DNA intercalator, ethidium bromide (EB) at 0.3, 0.6, 1.2 μg/mL, respectively; lanes 6-8, DNA and Top1 with 19a at 1, 3, 9 M, respectively. Rx, relaxed DNA. Sc, supercoiled DNA. FIG. 5C shows a gel of relaxed pBR322 DNA as substrate. Lane 1: DNA alone; lane 2: DNA and Top1; lanes 3-5: DNA and Top1 with the known DNA intercalator, ethidium bromide (EB) at 0.3, 0.6, 1.2 μg/mL, respectively; lanes 6-8, DNA and Top1 with 19a at 1, 3, 9 μM, respectively. Rx, relaxed DNA. Sc, supercoiled DNA. FIG. 5D shows a hypothetical binding mode of 19a in the ternary Top1-DNA-drug cleavage complex (PDB ID: 1K4T). 19a was shown as a ball and stick representation. All distances were measured from heavy atom to heavy atom.

FIG. 6A shows Tdp1 inhibition curves of the active compounds determined using fluorescence assay. Tested concentrations were 0.4, 1.23, 3.70, 11.1, 33.3 and 100 μM. FIG. 6B shows a hypothetical binding mode of 41a (ball and stick representation) in the complex with Tdp1 (PDB ID: 1RFF). All distances were measured from heavy atom to heavy atom. FIG. 6C shows representative Tdp1 inhibition gels of active compounds. Lane 1, DNA alone; lane 2, DNA and recombinant Tdp1; lanes 3-26, DNA, recombinant Tdp1 and the active compounds at tested concentration. Tested concentrations were 0.05, 0.15, 0.46, 1.4, 4.1, 12.3, 37 and 111 μM. N14Y and N14P are the substrate and product of Tdp1, respectively.

FIG. 8A shows induction of Top1-DNA covalent cleavage complexes by in vivo complex of enzyme (ICE) assay in human colon cancer HCT116 cells. Upper: lane 1, untreated control; lanes 2 and 3, cells treated with 1 at 25 and 50 μM, respectively. Bottom: lanes 1-3, cells treated with 19a at 25, 50 and 100 μM, respectively. FIG. 8B shows flow cytometry histograms of apoptosis in HCT116 cells induced by 19a at 0.5, 1 and 2 M, respectively. FIG. 8C shows histone γH2AX foci induced by 19a in HCT116 cells. Cells were treated with 1 and 19a at 1 μM for 3 hours. DNA was stained with DAPT.

FIG. 9A shows percent survival of mice treated with 19a at doses of 300 mg/kg, 240 mg/kg and 192 mg/kg. FIG. 9B shows the effects of 19a on body weight at the dose of 5 mg/kg and 10 mg/kg. FIG. 9C shows the effects of 19a on tumor size at the dose of 5 mg/kg and 10 mg/kg. FIG. 9D shows the effects of 19a on tumor weight at the dose of 5 mg/kg and 10 mg/kg. Statistically significant difference in mean tumor weight compared with the control, **: P<0.01.

(FIG. 13B). All distances are measured from heavy atom to heavy atom.

FIG. 14A: detection of TOP1-DNA covalent cleavage complexes by in vivo complex of enzyme (ICE) assay in human colon cancer HCT116 cells. Left: lane 1, control; lanes 2 and 3, cells treated with CPT at 25 and 50 μM concentration, respectively. Right: lanes 1-3, cells treated with 50 at 25, 50 and 100 μM concentration, respectively. FIG. 14B shows histone γH2AX foci induced by 50 in HCT116 cells. Cells were treated with CPT or 50 at 1 μM concentration for 3 hours. DNA was stained with DAPI.

DETAILED DESCRIPTION

Chemical Description and Terminology

Figure 1:
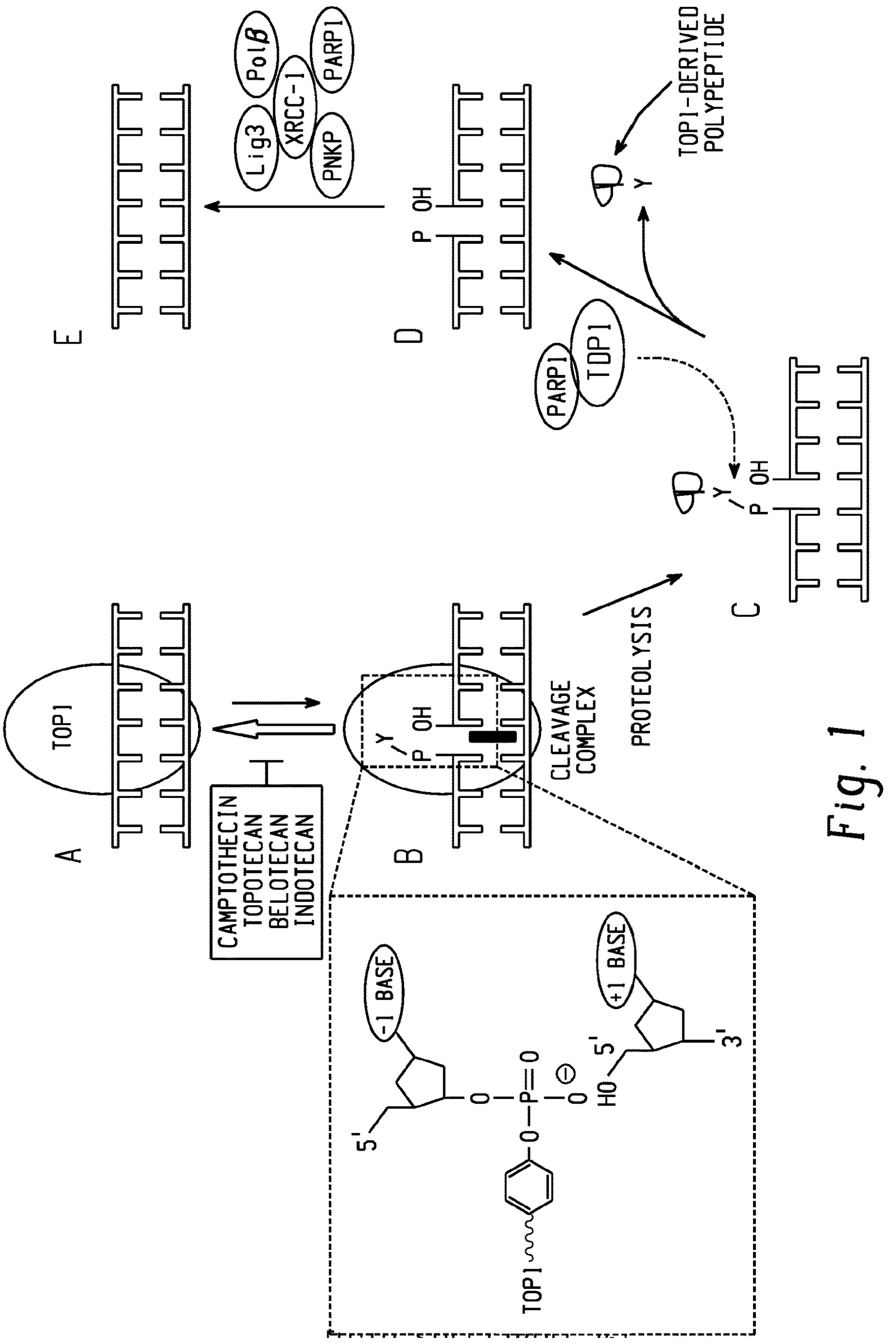
FIG. 1 shows a schematic for Top1 and Tdp1 mediated biochemical reactions. Step A shows that Top1 binds to DNA and cleaves one strand of a dsDNA by forming a reversible covalent 3-phosphotyrosyl bond. Step B shows the resulting Top1cc may be trapped and stabilized by Top1 inhibitors (stick) such as camptothecin analogues, resulting in replication/transcription-mediated DNA damage and cell death. Step C shows that Top1cc could be proteolyzed to expose the DNA-3'-phosphotyrosyl bond, which can be cleaved by Tdp1 to leave the 3'-phosphate end DNA (Step D). Step E shows that the DNA breaks may be repaired sequentially by the XRCC-1 dependent base excision repair (BER) pathway.
Figure 2:
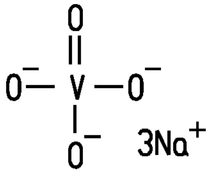
FIG. 2 shows structures of representative reported Tdp1 inhibitors.
Figure 2:
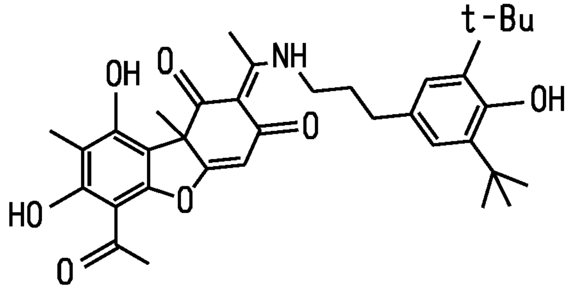
Figure 2:
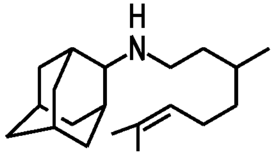
Figure 2:
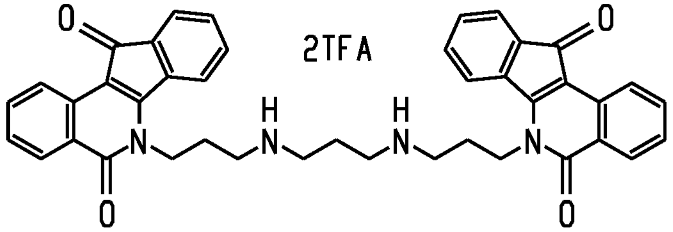
Figure 2:
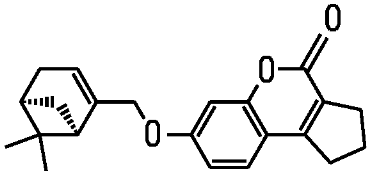
Figure 3:
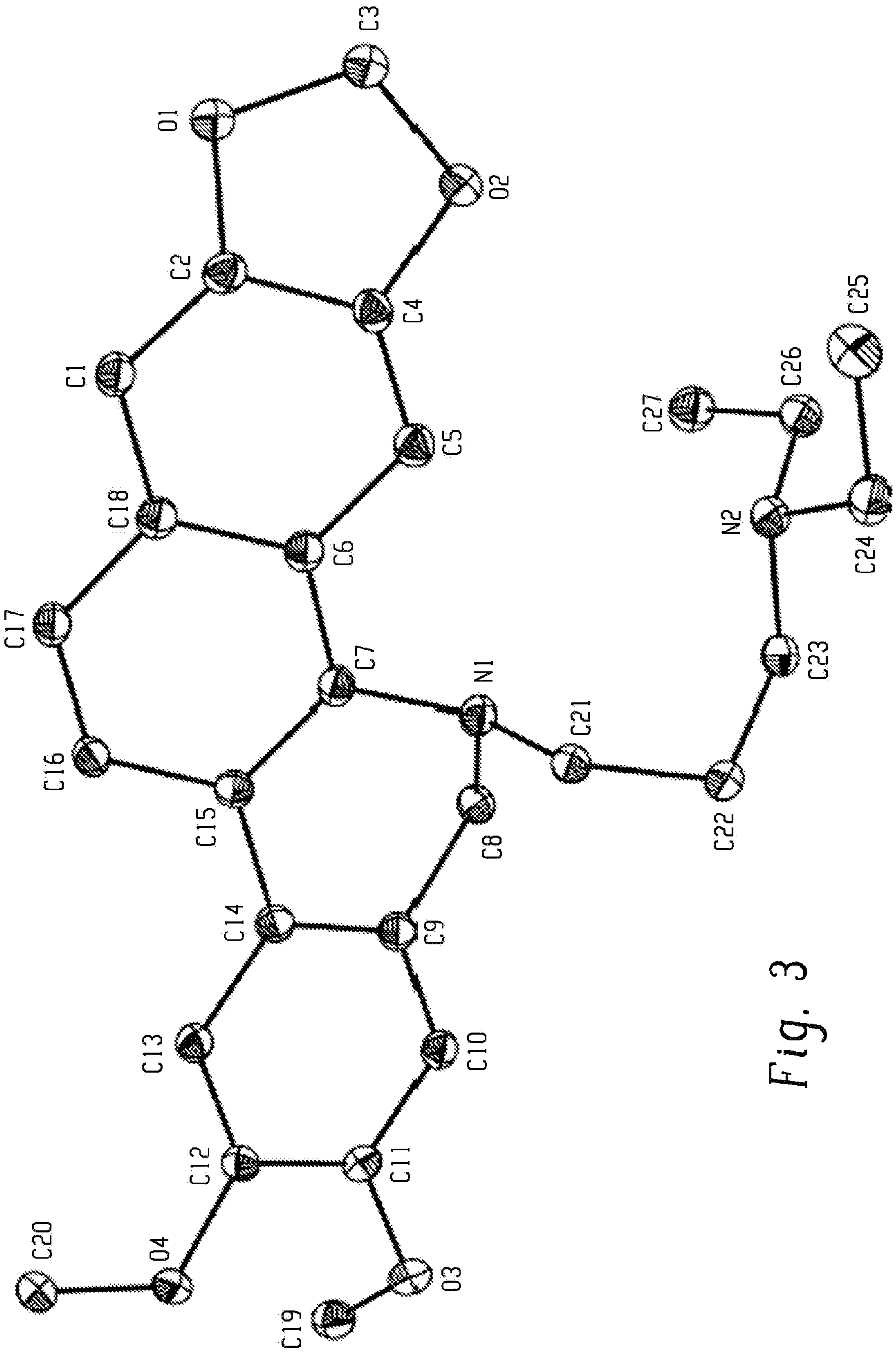
FIG. 3 shows a perspective ORTEP drawing of compound 20b.
Figure 4:
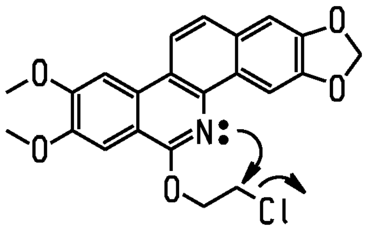
Figure 4:
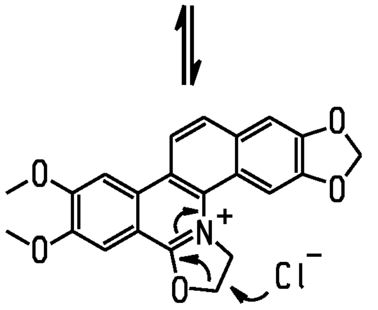
Figure 4:
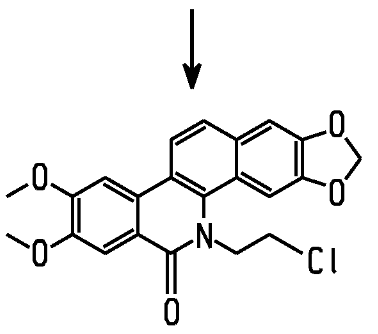

Prior to setting forth the invention in detail, it may be helpful to provide definitions of certain terms to be used in this disclosure. Compounds are described using standard nomenclature. Unless defined otherwise, all technical and scientific terms used herein have the same meaning as is commonly understood by one of skill in the art to which this invention belongs. Unless clearly contraindicated by the context each compound name includes the free acid or free base form of the compound as well as all pharmaceutically acceptable salts of the compound.

The term "compounds of Formula I" encompasses all compounds that satisfy Formula I, including any enantiomers, racemates and stereoisomers, as well as all pharmaceutically acceptable salts of such compounds. The phrase "a compound of Formula 1" includes all subgeneric groups of Formula I (e.g., Formula I-A, Formula I-B, Formula I-C, Formula I-D, Formula I-E, Formula I-F, and Formula I-G), and also includes pharmaceutically acceptable salts of a compound of Formula I, unless clearly contraindicated by the context in which this phrase is used. Formulae IA-G, which are used in connection with compound claims, are each a subgeneric group of Formula I.

A dash ("-") that is not between two letters or symbols is used to indicate a point of attachment for a substituent.

The terms "a" and "an" do not denote a limitation of quantity, but rather denote the presence of at least one of the referenced item. The term "or" means "and/or". The open-ended transitional phrase "comprising" encompasses the intermediate transitional phrase "consisting essentially of" and the close-ended phrase "consisting of." Claims reciting one of these three transitional phrases, or with an alternate transitional phrase such as "containing" or "including" can be written with any other transitional phrase unless clearly precluded by the context or art. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in any suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein. Unless defined otherwise, technical and scientific terms used herein have the same meaning as is commonly understood by one of skill in the art to which this invention belongs.

An "active agent" means a compound (including a compound disclosed herein), element, or mixture that when administered to a patient, alone or in combination with another compound, element, or mixture, confers, directly or indirectly, a physiological effect on the patient. The indirect physiological effect may occur via a metabolite or other indirect mechanism.

A dash ("-") that is not between two letters or symbols is used to indicate a point of attachment for a substituent. For example, —(C═O)OH is attached through carbon of the keto (C═O) group.

"Alkyl" is a branched or straight chain saturated aliphatic hydrocarbon group, having the specified number of carbon atoms, generally from 1 to about 8 carbon atoms. The term $C_1$-$C_6$alkyl as used herein indicates an alkyl group having from 1, 2, 3, 4, 5, or 6 carbon atoms. Other embodiments include alkyl groups having from 1 to 8 carbon atoms, 1 to 4 carbon atoms or 1 or 2 carbon atoms, e.g. $C_1$-$C_4$alkyl and $C_1$-$C_2$alkyl. When $C_0$-$C_n$ alkyl is used herein in conjunction with another group, for example, —$C_0$-$C_2$alkyl(phenyl), the indicated group, in this case phenyl, is either directly bound by a single covalent bond ($C_0$alkyl), or attached by an alkyl chain having the specified number of carbon atoms, in this case 1, 2, 3, or 4 carbon atoms. Alkyls can also be attached via other groups such as heteroatoms as in —O—$C_0$-$C_4$alkyl ($C_3$-$C_7$cycloalkyl). Examples of alkyl include, but are not limited to, methyl, ethyl, n-propyl, isopropyl, n-butyl, 3-methylbutyl, t-butyl, n-pentyl, and see-pentyl.

"Alkoxy" is an alkyl group as defined above with the indicated number of carbon atoms covalently bound to the group it substitutes by an oxygen bridge (—O—). Examples of alkoxy include, but are not limited to, methoxy, ethoxy, n-propoxy, iso-propoxy, n-butoxy, 2-butoxy, t-butoxy, n-pentoxy, 2-pentoxy, 3-pentoxy, iso-pentoxy, neopentoxy, n-hexoxy, 2-hexoxy, 3-hexoxy, and 3-methylpentoxy.

"Cycloalkyl" is a saturated hydrocarbon ring group, having the specified number of carbon atoms. Monocyclic cycloalkyl groups typically have from 3 to about 8 carbon ring atoms or from 3 to 7 (3, 4, 5, 6, or 7) carbon ring atoms. Cycloalkyl substituents may be pendant from a substituted nitrogen, sulfur, oxygen or carbon atom, or a substituted carbon atom that may have two substituents may have a cycloalkyl group, which is attached as a spiro group. Examples of cycloalkyl groups include cyclopropyl, cyclobutyl, cyclopentyl, or cyclohexyl as well as bridged or caged saturated ring groups such as norborane or adamantine.

"Haloalkyl" includes both branched and straight-chain alkyl groups having the specified number of carbon atoms, substituted with 1 or more halogen atoms, up to the maximum allowable number of halogen atoms. Examples of haloalkyl include, but are not limited to, trifluoromethyl, difluoromethyl, 2-fluoroethyl, and pentafluoroethyl.

"Haloalkoxy" is a haloalkyl group as defined herein attached through an oxygen bridge (oxygen of an alcohol radical).

"Halo" or "halogen" indicates any of fluoro, chloro, bromo, and iodo.

"Mono- and/or di-alkylamino" is a secondary or tertiary alkyl amino group, wherein the alkyl groups are independently chosen alkyl groups, as defined herein, having the indicated number of carbon atoms. The point of attachment of the alkylamino group is on the nitrogen.

Examples of mono- and di-alkylamino groups include ethylamino, dimethylamino, and methyl-propyl-amino.

The term "substituted," as used herein, means that any one or more hydrogens on the designated atom or group is replaced with a selection from the indicated group, provided that the designated atom's normal valence is not exceeded. When the substituent is oxo (i.e., =O) then 2 hydrogens on the atom are replaced. When an oxo group substitutes aromatic moieties, the corresponding partially unsaturated ring replaces the aromatic ring. For example, a pyridyl group substituted by oxo is a pyridone. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation into an effective therapeutic agent. Unless otherwise specified substituents are named into the core structure. For example, it is to be understood that when aminoalkyl is listed as a possible substituent the point of attachment of this substituent to the core structure is in the alkyl portion.

Suitable groups that may be present on a "substituted" or "optionally substituted" position include, but are not limited to, e.g., halogen; cyano; hydroxyl; oxo; amino; or 1 to about 6 carbon atoms; alkoxy groups having one or more oxygen linkages and from 1 to about 8, or from 1 to about 6 carbon atoms; haloalkyl groups having one or more halogens and from 1 to about 8, or from 1 to about 6 carbon atoms; haloalkoxy groups having one or more oxygen linkages and one or more halogens and from 1 to about 8, or from 1 to about 6 carbon atoms; and aminoalkyl groups including groups having one or more N atoms and from 1 to about 8, or from 1 to about 6 carbon atoms.

In certain embodiments an "optionally substituted group is substituted with one or more substituents independently chosen from halogen, hydroxyl, amino, cyano, oxo, —COOH, $C_1$-$C_6$alkyl, $C_1$-$C_6$alkoxy, $C_3$-$C_7$cycloalkyl, (mono- or di-$C_1$-$C_4$alkylamino)$C_0$-$C_4$alkyl, $C_1$-$C_2$haloalkyl, and $C_1$-$C_2$haloalkoxy.

A "dosage form" means a unit of administration of an active agent. Examples of dosage forms include tablets, capsules, injections, suspensions, liquids, emulsions, creams, ointments, suppositories, inhalable forms, transdermal forms, and the like.

"Pharmaceutical compositions" are compositions comprising at least one active agent, such as a compound or salt of Formula I, and at least one other substance, such as a carrier. Pharmaceutical compositions optionally contain one or more additional active agents. When specified, pharmaceutical compositions meet the U.S. FDA's GMP (good manufacturing practice) standards for human or non-human drugs.

"Pharmaceutically acceptable salts" includes derivatives of the disclosed compounds in which the parent compound is modified by making inorganic and organic, non-toxic, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like.

The term "carrier" applied to pharmaceutical compositions/combinations of the present disclosure refers to a diluent, excipient, or vehicle with which an active compound is provided. To be pharmaceutically acceptable a carrier must be safe, non-toxic and neither biologically nor otherwise undesirable.

A "patient" is a human or non-human animal in need of medical treatment. Medical treatment can include treatment of an existing condition, such as a disease or disorder, prophylactic or preventative treatment, or diagnostic treatment. In certain embodiments disclosed herein "medical treatment" means treatment of a diagnosed cancer or known tumor. In certain embodiments the patient is a human patient.

When a compound of Formula I is provided with "an additional active agent" the compound of Formula I is a first active agent and the additional active agent(s) can be provided simultaneously in a single dosage form, provided concomitantly in separate dosage forms, or provided in separate dosage forms for administration separated by some amount of time that is within the time in which both the compound of Formula I and the additional active agent are within the blood stream of a patient. In certain embodiments the compound of Formula I and the additional active agent need not be prescribed for a patient by the same medical care worker. In certain embodiments the additional active agent or agents need not require a prescription. Administration of the compound of Formula I and the additional active agent can occur via any appropriate route, for example, oral tablets, oral capsules, oral liquids, inhalation, injection, suppositories or topical contact.

"Treatment," as used herein includes providing a compound of Formula I, either as the only active agent or together with an additional active agent sufficient to: (a) prevent or decrease the likelihood a disease or a symptom of a disease from occurring in a patient who may be predisposed to the disease but has not yet been diagnosed as having it; (b) inhibiting the disease, i.e. arresting its development; and (c) relieving the disease, i.e., causing a remission of the disease. "Treating" and "treatment" also means providing a therapeutically effective amount of a compound of Formula I as the only active agent or together with at least one additional active agent to a patient having a disease or disorder that can be effectively treated with a Tdp1 or Top1 inhibitor, such a cancer, a neurological disease (e.g. Angelman syndrome, autism), or septic shock.

A "therapeutically effective amount" of a pharmaceutical composition/combination of this disclosure means an amount effective, when administered to a patient, to provide a therapeutic benefit such as an amelioration of symptoms, e.g., an amount effective to decrease the symptoms of cancer. For example, a patient having cancer may present detectable levels of certain tumor markers, including CA 125, CEA, CA19-9, AFP, PSA, and galactosyltransferase. A therapeutically effect amount is thus an amount sufficient to provide a significant reduction in elevated tumor marker levels or an amount sufficient to provide a return of tumor marker levels to the normal range. A therapeutically effective amount is also an amount sufficient to prevent a significant increase in tumor size relative that usually seen in untreated patients having the same cancer, or significantly reduce tumor size or tumor number, or causes tumors to disappear from the patient's body altogether.

A significant increase or reduction in the detectable level of tumor markers, tumor size, or tumor number, is any detectable change that is statistically significant in a standard parametric test of statistical significance such as Student's T-test, where $p<0.05$.

Chemical Description

Figure 10:
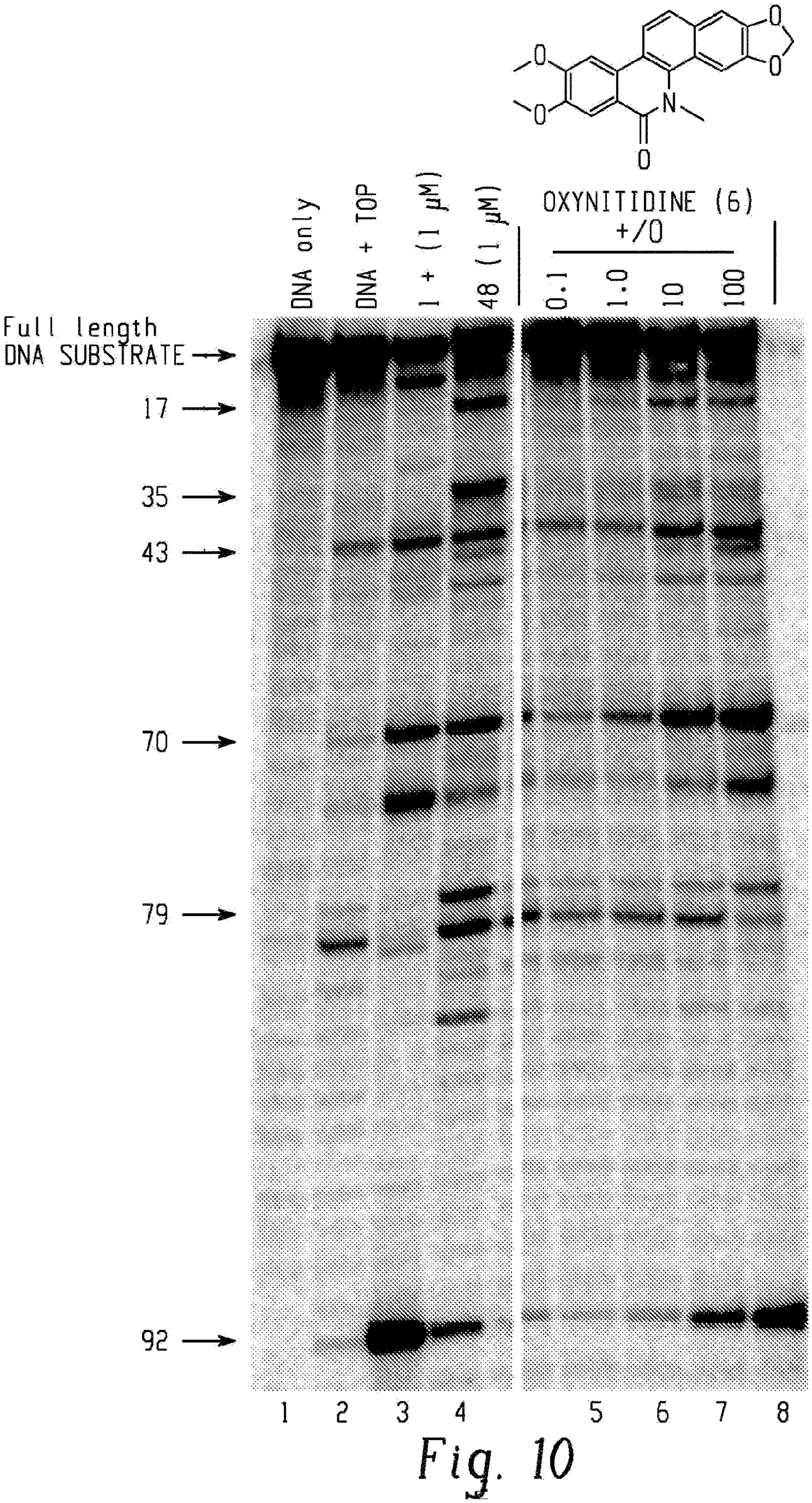
FIG. 10. A gel of Top1-mediated DNA cleavage assay. The cleavage sites induced by oxynitidine differ from those induced by camptothecin.

Natural products are an important source of novel hits for medicinal chemistry and drug development. To find novel Top1 inhibitors, an in-house natural product library containing more than 900 natural products was screened using a Top1-mediated DNA relaxation assay. Several chemotypes were found to inhibit Top1, including meroterpenoid derivatives and oxynitidine. The meroterpenoid derivatives showed high Top1 relaxing inhibition, but did not have the ability to trap and stabilize Top1cc, and therefore could be classified as Top1 catalytic inhibitors. By contrast, Top1-mediated DNA cleavage assay indicated that oxynitidine was able to induce the formation of Top1cc in dose-dependent manner. It is noteworthy that the cleavage sites induced by oxynitidine are different from that induced by camptothecin, and similar to the indenoisoquinoline 48 (FIG. 10). For example, the cleavage sites 17, 35 and 79 can be induced by oxynitidine and 48, but not by camptothecin, implying that this novel Top1 inhibitor might target the genome at different sites and translate to different cellular effects compared with camptothecin. The results indicate the oxynitidine scaffold is a novel chemotype for discovery and development of novel Top1 inhibitors.

It was reported that nitidine can intercalate into double-stranded DNA (dsDNA) and inhibit Top1. The FRET melting assay was conducted to detect the enhanced melting temperature ($\Delta T_m$) and investigate the interaction of oxynitidine with dsDNA because oxynitidine is the 6-oxo analogue of nitidine. The DNA intercalator 49 was used as positive control. The FRET melting assay using F10T (5'-FAM-dTATAGCTATAHEG-TATAGCTATA-TAMRA-3') as substrate indicated that oxynitidine showed low $\Delta T_m$ value (0.4° C.) compared to 49 with $\Delta T_m$ value of 5.8° C. (Table 1a) implying its poor binding to dsDNA.

TABLE 1a

TOP1 and TDP1 inhibitions, and the enhanced melting temperature with dsDNA

| Cpd. | n | R | TOP1 inhibition[a] | TDP1 inhibition[b] | ΔTm (°C.)[c] F10T |
|---|---|---|---|---|---|
| 1 | /[e] | / | ++++ | ND | ND |
| 6 | / | / | +/0 | ND | 0.4 |
| 17a | 2 | OH | + | 0 | 0.1 |
| 17b | 3 | | + | 0 | 0.2 |
| 19a | 2 | $NMe_2$ | +++ | 12% | 0.5 |
| 19b | 3 | | + | 0 | 0.3 |
| 20a | 2 | $NEt_2$ | + | 0 | 0.1 |
| 20b | 3 | | + | 0 | 1.3 |
| 21a | 2 | 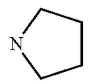 | ++ | 0 | 1.0 |
| 21b | 3 | | + | 20% | 1.2 |
| 22a | 2 | 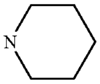 | + | 0 | 1.2 |
| 22b | 3 | | + | 27% | 1.1 |
| 23a | 2 | 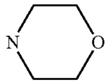 | + | 0 | 1.0 |
| 23b | 3 | | +/0 | 0 | 0.9 |
| 24a | 2 | 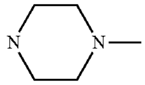 | + | 0 | 1.0 |
| 24b | 3 | | + | 0 | 1.0 |
| 25a | 2 | 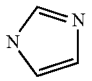 | + | 0 | 1.0 |
| 25b | 3 | | + | 0 | 0.9 |
| 26a | 2 | $NMe_2$ | + | 0 | 1.0 |
| 26b | 3 | | + | 0 | 1.3 |
| 27a | 2 | $NEt_2$ | +/0 | 0 | 0.9 |
| 27b | 3 | | + | 0 | 1.9 |
| 28a | 2 | 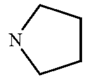 | +/0 | 0 | 0.9 |
| 28b | 3 | | + | 0 | 1.4 |
| 29a | 2 | 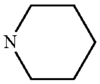 | + | 0 | 1.1 |
| 29b | 3 | | +/0 | 0 | 1.0 |
| 30a | 2 | 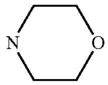 | + | 0 | 0.9 |
| 30b | 3 | | + | 0 | 1.1 |
| 31a | 2 | 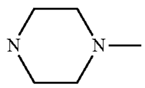 | +/0 | 0 | 1.5 |
| 31b | 3 | | +/0 | 0 | 1.0 |
| 32a | 2 | 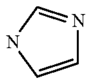 | +/0 | 0 | 0.9 |
| 32b | 3 | | ++ | 0 | 1.0 |
| 39a | 2 | $NMe_2$ | 0 | 93% | 0.2 |
| 39b | 3 | | 0 | 86% | 0.6 |
| 40a | 2 | $NEt_2$ | + | 76% | 0.3 |
| 40b | 3 | | 0 | 97% | 0.3 |
| 41a | 2 | 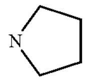 | 0 | 92% | 0.3 |
| 41b | 3 | | 0 | 98% | 0.4 |

TABLE 1a-continued

TOP1 and TDP1 inhibitions, and the enhanced melting temperature with dsDNA

| Cpd. | n | R | TOP1 inhibition[a] | TDP1 inhibition[b] | ΔTm (°C.)[c] F10T |
|---|---|---|---|---|---|
| 42a | 2 | 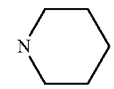 | 0 | 0 | 0.2 |
| 42b | 3 | | 0 | 90% | 0.3 |
| 43a | 2 | 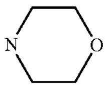 | +/0 | 0 | 0.1 |
| 43b | 3 | | 0 | 0 | 0.1 |
| 44a | 2 | 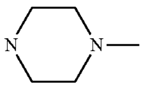 | 0 | 30% | 0.4 |
| 44b | 3 | | 0 | 34% | 0.7 |
| 45a | 2 | 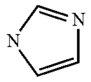 | 0 | 0 | 0.2 |
| 45b | 3 | | 0 | 0 | 0.2 |
| 49 | / | / | ND | ND | 5.8 |

Regarding Table 1a, the superscripts are defined as follows: [a]TOP1 cleavage inhibitory activity of synthesized compounds was semi-quantitatively expressed relative to CPT at 1 μM as follows: 0, no inhibition; +, between 20% and 50% activity; ++, between 50% and 75% activity; +++, between 75% and 95% activity; ++++, equal activity. [b]TDP1 inhibition was determined by using a fluorescence assay and the percentage inhibition of the compounds at 100 μM concentration was calculated. Every experiment was repeated at least three times independently. [c]$\Delta T_m = T_m$ (DNA+compound)$-T_m$(DNA). Every experiment was repeated at least twice independently. [e]"/" means inapplicable. [f]"ND" means not determined.

The disclosure provides a method of treating cancer in a patient, comprising administering a therapeutically effective amount of a compound of Formula I, which may be a Tdp1 and/or Top1 inhibitor, to a patient in need of such treatment. Formula I includes all subformulae thereof (I-A, I-B, and I-C). In certain situations, the compounds of Formula I may contain one or more asymmetric elements such as stereogenic centers, stereogenic axes and the like, e.g. asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, it should be understood that all of the optical isomers and mixtures thereof are encompassed. In addition, compounds with carbon-carbon double bonds may occur in Z- and E-forms, with all isomeric forms of the compounds being included in the present disclosure. In these situations, single enantiomers, i.e., optically active forms, can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example using a chiral HPLC column.

Where a compound exists in various tautomeric forms, the invention is not limited to any one of the specific tautomers, but rather includes all tautomeric forms.

The present disclosure includes all isotopes of atoms occurring in the present compounds. Isotopes include those atoms having the same atomic number but different mass numbers. By way of general example, and without limitation, isotopes of hydrogen include tritium and deuterium and isotopes of carbon include $^{11}C$, $^{13}C$, and $^{14}C$.

The disclosure includes compounds and salts of Formula I in which the variables, e.g. X-Y, L, R, $R^1$, $R^2$, $R^3$, $R^4$, $R^5$, $R^6$, $R^7$, $R^8$, $R^9$, $R^{10}$, $R^{11}$, $R^{12}$, carry any of the definitions set forth below. Any of the variable definitions set forth below can be combined with any other of the variable definitions so long as a stable compound results.

Formula I

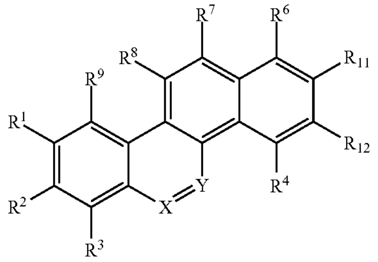

Formula I also includes subformulae I-A I-B, I-C, I-D, I-E I-F I-G, I-H, I-I, I-J, and I-K Formula I-A

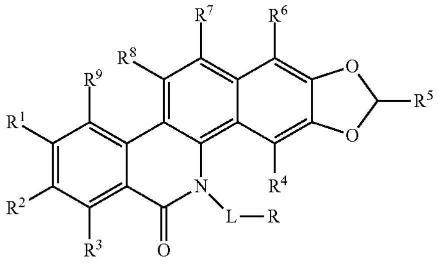

Formula I-B

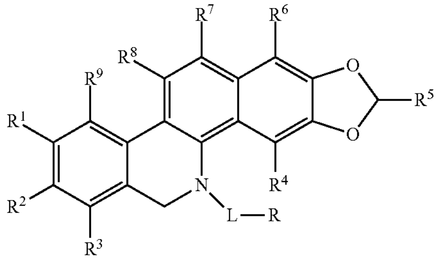

Formula I-C

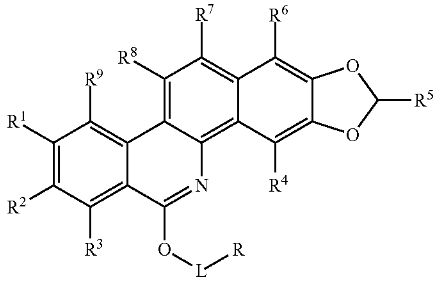

-continued

Formula I-D

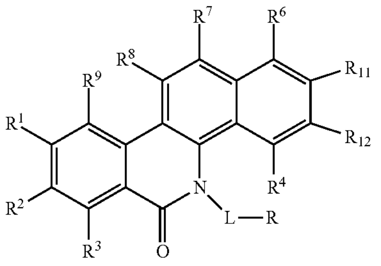

Formula I-E

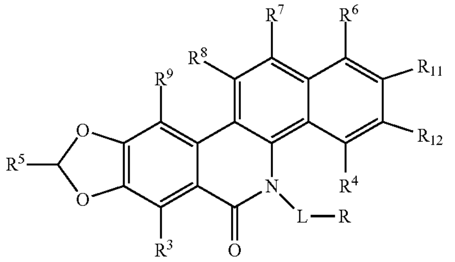

Formula I-F

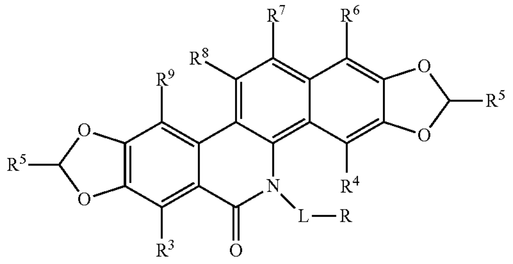

Formula I-G

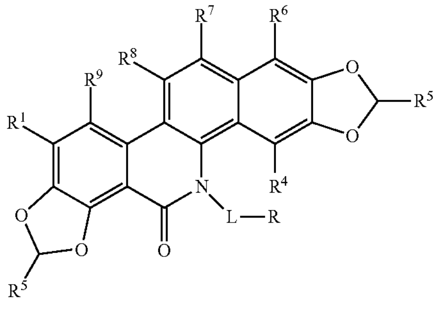

Formula I-H

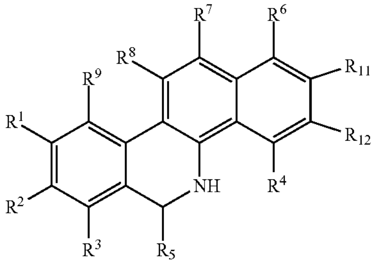

-continued

Formula I-I

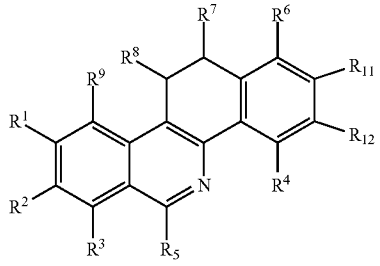

Formula I-J

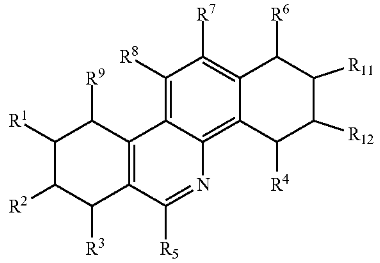

The X-Y Variable

X is carbon and Y is nitrogen and the group

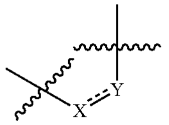

is

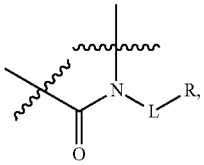

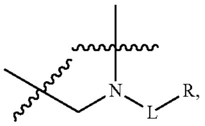

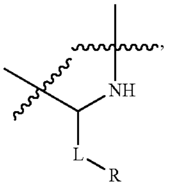

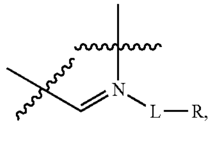

or

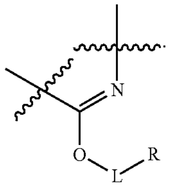

The L Variable

L is $C_2$-$C_3$ alkyl. $C_2$-$C_3$ alkyl can contain a double or triple bond, can have one or more $CH_2$ groups that can be replaced by N, NH, $NR^{10}$, S, —$SO_2$—, or O, and is optionally substituted with one or more substituents independently chosen from hydroxyl, amino, cyano, halogen, oxo, and $C_3$-$C_6$cycloalkyl and $R^{10}$ is $C_1$-$C_6$alkyl or ($C_3$-$C_6$cycloalkyl) $C_0$-$C_4$alkyl. Non-limiting examples of $C_2$-$C_3$ alkyl groups where one or more $CH_2$ groups are replaced by N, NH, $NR^{10}$, S, —$SO_2$—, or O include —$(CH_2)_2N(CH_3)$—, —$(CH_2)_2NHSO_2$—, and —$(CH_2)_2N(CH_3)SO_2N(CH_3)$—.

L is $C_2$ alkyl.

L is $C_3$ alkyl.

The R Variable (1) R is hydrogen, hydroxyl, amino, cyano, $P(O)(OCH_3)_2$, or halogen.

(2) R is a 4- to 7-membered saturated or aromatic heterocyclic group, optionally substituted with one or more substituents independently chosen from $C_1$-$C_2$alkyl, $C_1$-$C_2$alkoxy, $C_1$-$C_2$haloalkyl, and $C_1$-$C_2$haloalkoxy.

(3) R is a 4- to 7-membered saturated or aromatic heterocyclic group bound at the R position through a nitrogen atom and optionally substituted with one or more substituents independently chosen from $C_1$-$C_2$alkyl, $C_1$-$C_7$alkoxy, $C_1$-$C_2$haloalkyl, and $C_1$-$C_2$haloalkoxy.

(4) R is hydrogen, hydroxyl, amino, $C_1$-$C_6$alkylamino, $C_1$-$C_6$alkylaminoalkyl, pyrrolidinyl, piperidinyl, piperazinyl, morpholinyl, thiomorpholinyl, pyrrolyl, pyrazolyl, imidazolyl, triazolyl, oxazolyl, or thiazolyl, each or which is optionally substituted with one or more substituents independently chosen from halogen, hydroxyl, $C_1$-$C_2$alkyl, and $C_1$-$C_2$alkoxy.

The $R^1$-$R^{10}$ Variables (1) $R^3$, $R^4$, $R^6$, $R^7$, $R^8$, and $R^9$ are independently chosen from hydrogen, halogen, or $C_1$-$C_6$alkyl, which $C_1$-$C_6$alkyl can contain one or more double or triple bonds, can have one or more $CH_2$ group that can be replaced by NH, $NR^{10}$, S, or O, and is optionally substituted with one or more substituents independently chosen from hydroxyl, amino, cyano, halogen, oxo, and $C_3$-$C_6$cycloalkyl.

(2) $R^3$, $R^4$, $R^5$, $R^6$, $R^7$, $R^8$, and $R^9$ are independently chosen from hydrogen, halogen, methyl, and methoxy.

(3) $R^3$ and $R^4$ are hydrogen, and $R^1$ and $R^2$ are independently chosen from hydroxyl, halogen, amino, $C_1$-$C_6$-alkyl, $C_1$-$C_6$alkoxy, $C_1$-$C_6$alkylthio, $C_1$-$C_2$haloalkyl, or $C_1$-$C_2$haloalkoxy.

(4) $R^3$, $R^4$, $R^5$, $R^6$, $R^7$, $R^8$, and $R^9$ are hydrogen and $R^1$ and $R^2$ are independently $C_1$-$C_6$alkoxy.

(5) $R^1$ and $R^2$ are methoxy.

(6) $R^{11}$ and $R^{12}$ are methoxy.

The disclosure includes the following compounds and their pharmaceutically acceptable salts:

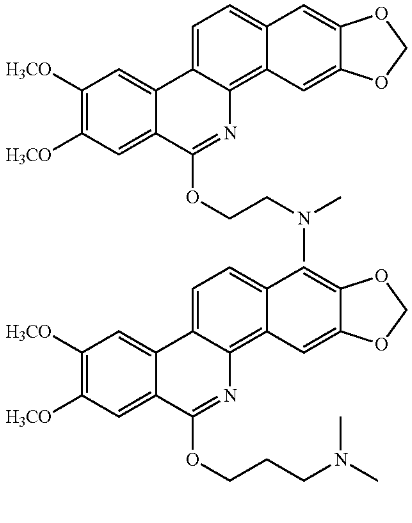

-continued

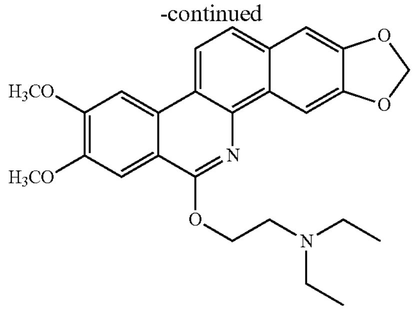

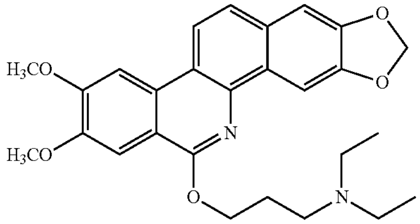

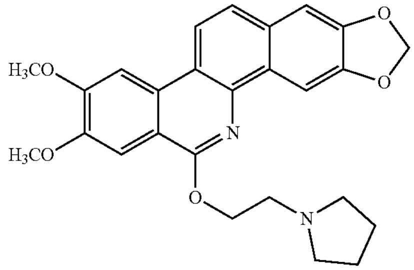

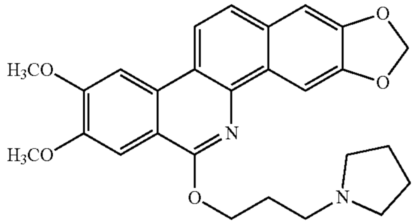

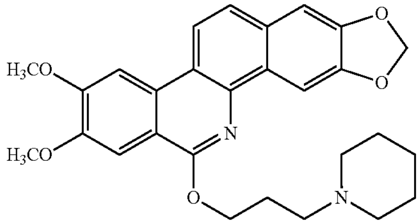

Another aspect of the above embodiment (Formula I) is a compound or salt of Table 1a.

Another aspect of the above embodiment (Formula I) is a compound or salt of Tables 6 and 7.

Another aspect of the embodiment of Formula I is a compound or salt of Formulae I-A-G wherein L is $C_2$-$C_3$ alkyl; R is hydrogen, hydroxyl, amino, mono- or di-$C_1$-$C_6$alkylamino, or R is pyrrolidinyl, piperidinyl, piperazinyl, morpholinyl, thiomorpholinyl, pyrrolyl, pyrazolyl, imidazolyl, triazolyl, oxazolyl, or thiazolyl, each or which is optionally substituted with one or more substituents independently chosen from halogen, hydroxyl, $C_1$-$C_2$alkyl, and $C_1$-$C_2$alkoxy; and $R^3$, $R^4$, $R^5$, $R^6$, $R^7$, $R^8$, and $R^9$ are independently chosen from hydrogen, halogen, methyl, and methoxy.

Top1 inhibition. All synthesized compounds were evaluated for Top1 inhibition through the Top1-mediated cleavage assay using a 3'-[$^{32}$P]-labeled double-stranded DNA fragment as substrate. The compounds were tested at 100, 10, 1 and 0.1 μM concentration using camptothecin 1 and indenoisoquinoline 48 as positive controls, and semi-quantitatively scored on the basis of visual inspection of the number and intensities of the DNA cleavage bands relative to the Top1 inhibition of 1 at 1 μM concentration: 0, no inhibitory activity; +, between 20% and 50% activity; ++, between 50% and 75% activity; +++, between 75% and 95% activity; ++++, equal activity to 1 (Table 1b).

Figure 5A:
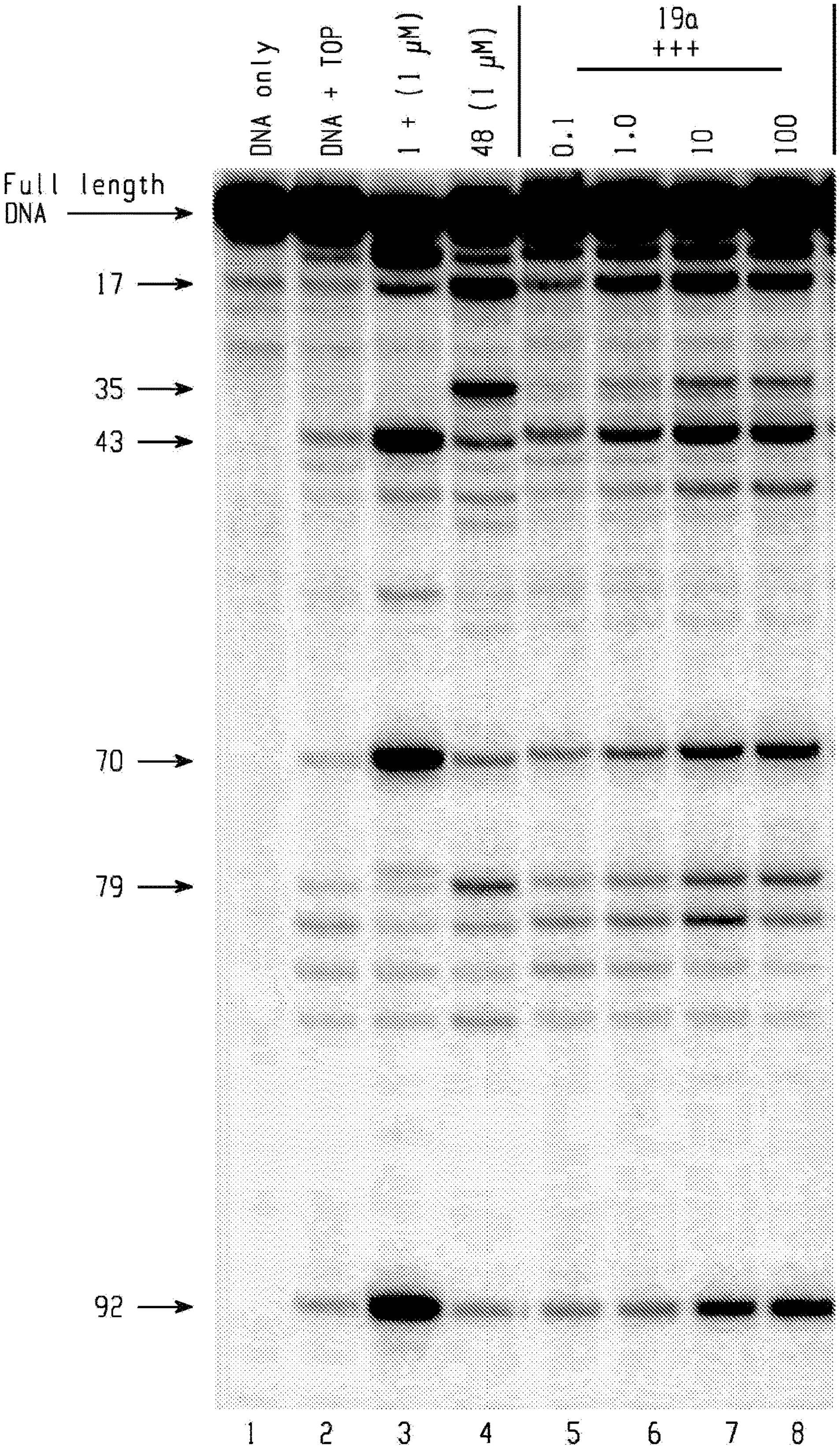
FIGS. 5A-5D.

For the benzophenanthridinone derivatives 19a/b-25a/b, both alkylaminoethyl and alkylaminopropyl substituents attached to the nitrogen atom of lactam increased the Top1 inhibition except 23b with 3-morpholinopropyl group attached at 5-position, which showed equal activity to that of parent molecule 6 (+/0, very minor activity less than 10% Top1 inhibition of 1). Bigger substituents at the 5-position decreased Top1 inhibitory activity. Most benzophenanthridinone derivatives showed Top1 inhibitory activity of +, except compounds 19a (+++) and 21a (++), with high and moderate Top1 inhibitory activity, respectively. The compounds 17a and 17b with a hydroxy terminus showed slightly increased Top1 inhibition of +. Compound 19a was the most potent with Top1 inhibition of +++ among the three synthesized chemotypes. FIG. 5A demonstrates that 19a exhibits cleavage sites similar to 48 but not to 1. It was reported that the dibenzonaphthyridinone derivative, ARC-111, a Top1 inhibitor that was developed in clinical trials,[41] exhibits different cleavage sites from 1 and 48, implying that although 19a and ARC-111 are structurally similar, they trap Top1cc at different DNA sequences.

Most of the dihydrobenzophenanthridine derivatives, such as 26a/b-31a/b and 32a showed equal or slightly increased Top1 inhibitory activity (+/0 or +) compared to the parent 6. Among this series of derivatives, the most potent compound 32b with 3-imidazolylpropyl group at 5-position showed moderate Top1 inhibitory activity (scored ++). Surprisingly, most of benzophenanthridine derivatives did not exhibit Top1 inhibitory activity except compounds 40a (+) and 43a (+/0) showing weak activity.

Figure 5B:
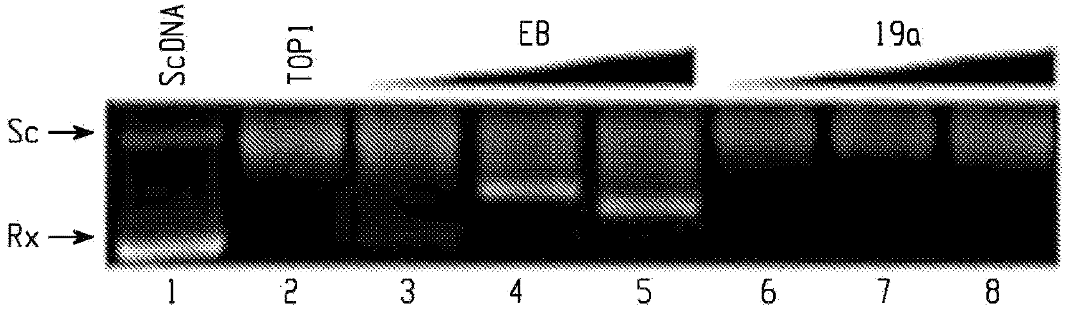
Figure 5C:
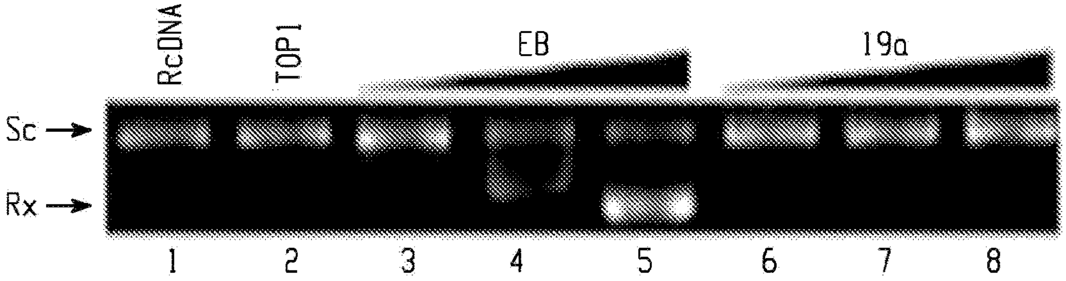
Figure 5D:
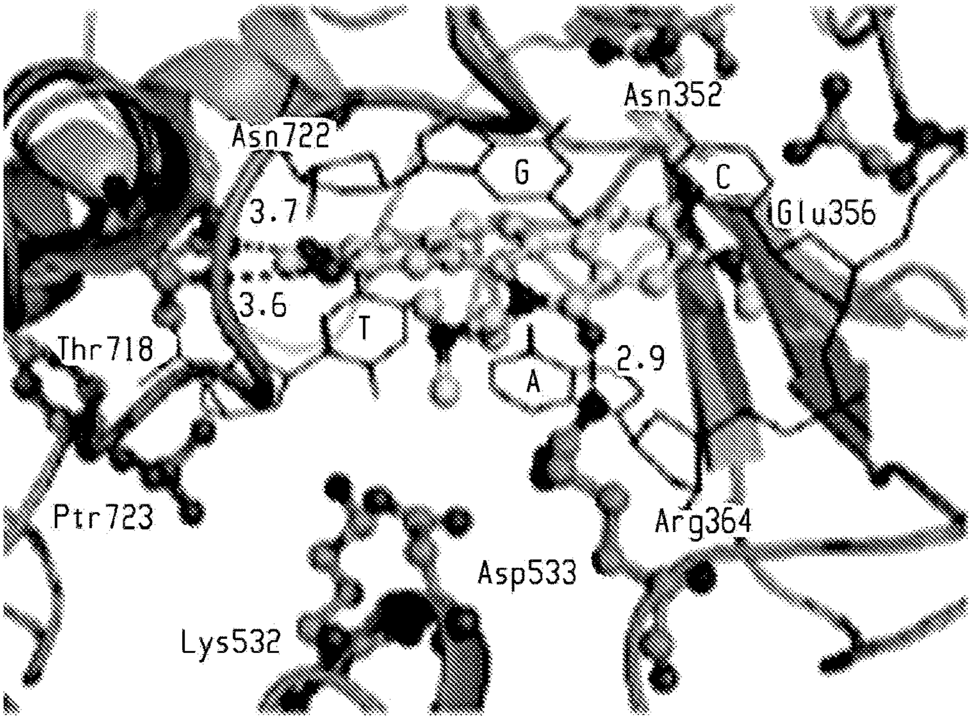

Molecular modeling was performed to determine the molecular binding mode of the benzophenanthridinone derivatives within the Top1-DNA complex. A binding model was built by using in-silico docking from the X-ray crystal of the Top1-DNA-ligand ternary complex (PDB ID: 1K4T). Compounds were energy-minimized and docked into the binding model. As shown in FIG. 5D, the benzophenanthridinone scaffold of 19a stacks with the +1 and −1 base pairs at the DNA cleavage site. The A- and B-ring of 19a stack with the bases of non-cleaved strand (C and A), while the C- and D-ring stack with the scissile strand bases (G and T). The dimethylaminoethyl substituent extends into the minor groove of the DNA. A hydrogen bond (2.9 Å) was observed between the lactam oxygen atom and Arg364, implying the importance of hydrogen bond acceptor, which is consistent with the cytotoxicity of 19a against the prostate cancer cells DU145-RC0.1, resistant cells with a R364H mutation in Top1. DU145-RC0.1 cells showed high resistance to 19a (Table 4). The interaction between the two oxygen atoms in the dioxole ring and Asn722 (3.7 Å) or Thr718 (3.6 Å), respectively, might also contribute to Top1 inhibition.

Tdp Inhibition. Because of the unique function of Tdp1 to repair Top1-mediated DNA damage, and the recently reported inhibition of Tdp1 by the indenoisoquinoline Top1 inhibitors, Tdp1 inhibition by the synthesized compounds were also screened through a fluorescence assay.[49] A quenched fluorescent single-stranded oligonucleotide (5'-FAM-AGGATCTAAAAGACTT-BHQ-3') was used as substrate. The compounds were tested at 100 μM concentration. Twelve compounds 19a, 21b, 22b, 39a/b, 40a/b, 41a/b, 42b and 44a/b exhibited Tdp1 inhibition with the percentage inhibition ranging from 12% to 98% (Table 1a). The most potent Top1 inhibitor 19a (+++) showed low Tdp1 inhibition (12% at 100 μM). None of the dihydrobenzophenanthridine derivatives exhibited Tdp1 inhibition up to 100 μM concentration.

Figure 6A:
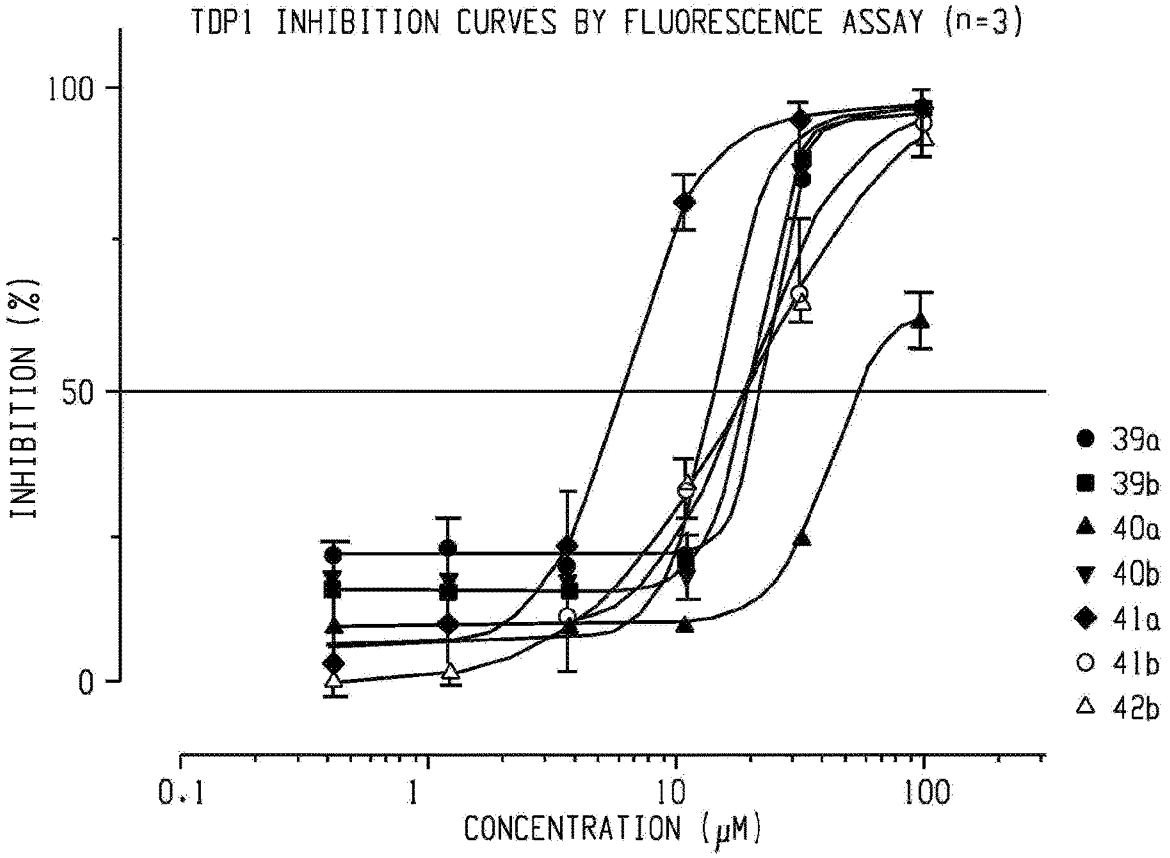
FIGS. 6A-6C.

Seven compounds 39a/b, 40a/b, 41a/b and 42b with high Tdp1 inhibition (>50%) were further tested to determine their $IC_{50}$ values (Table 2), expressed as the concentration of compound that inhibits 50% of Tdp1 activity. 41a exhibited the most potency with $IC_{50}$ value of 7.0±1.4 M in a dose-dependent manner (FIG. 6A).

Figure 6B:
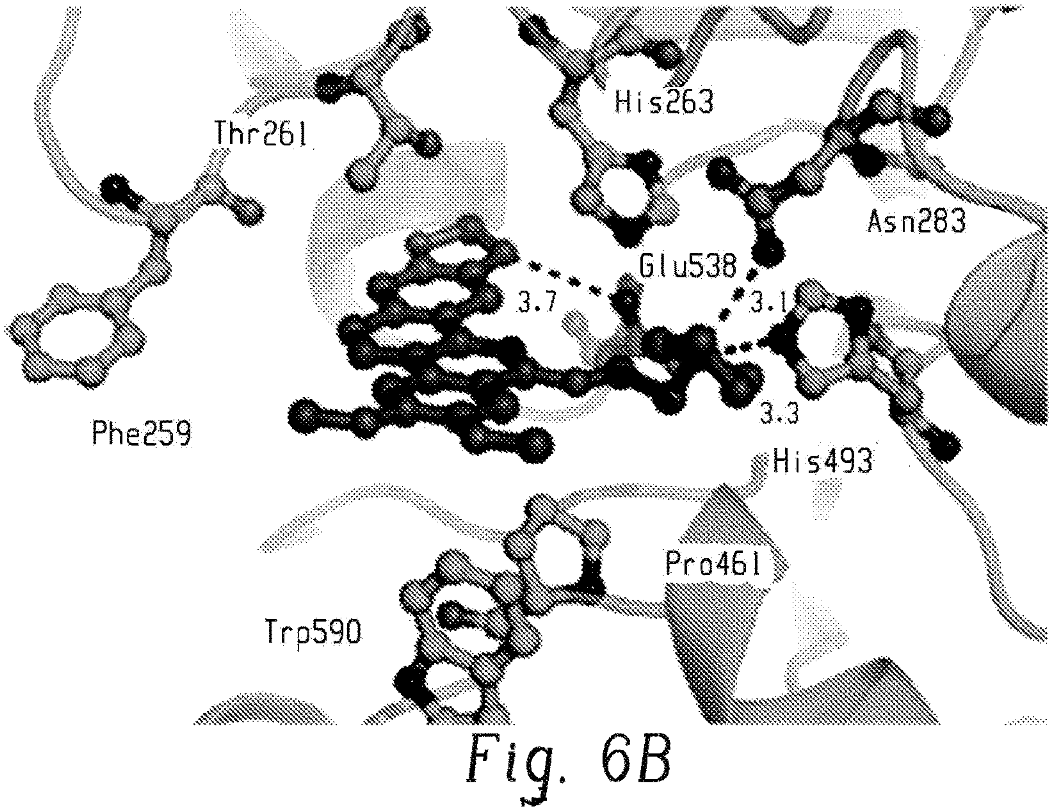
Figure 6C:
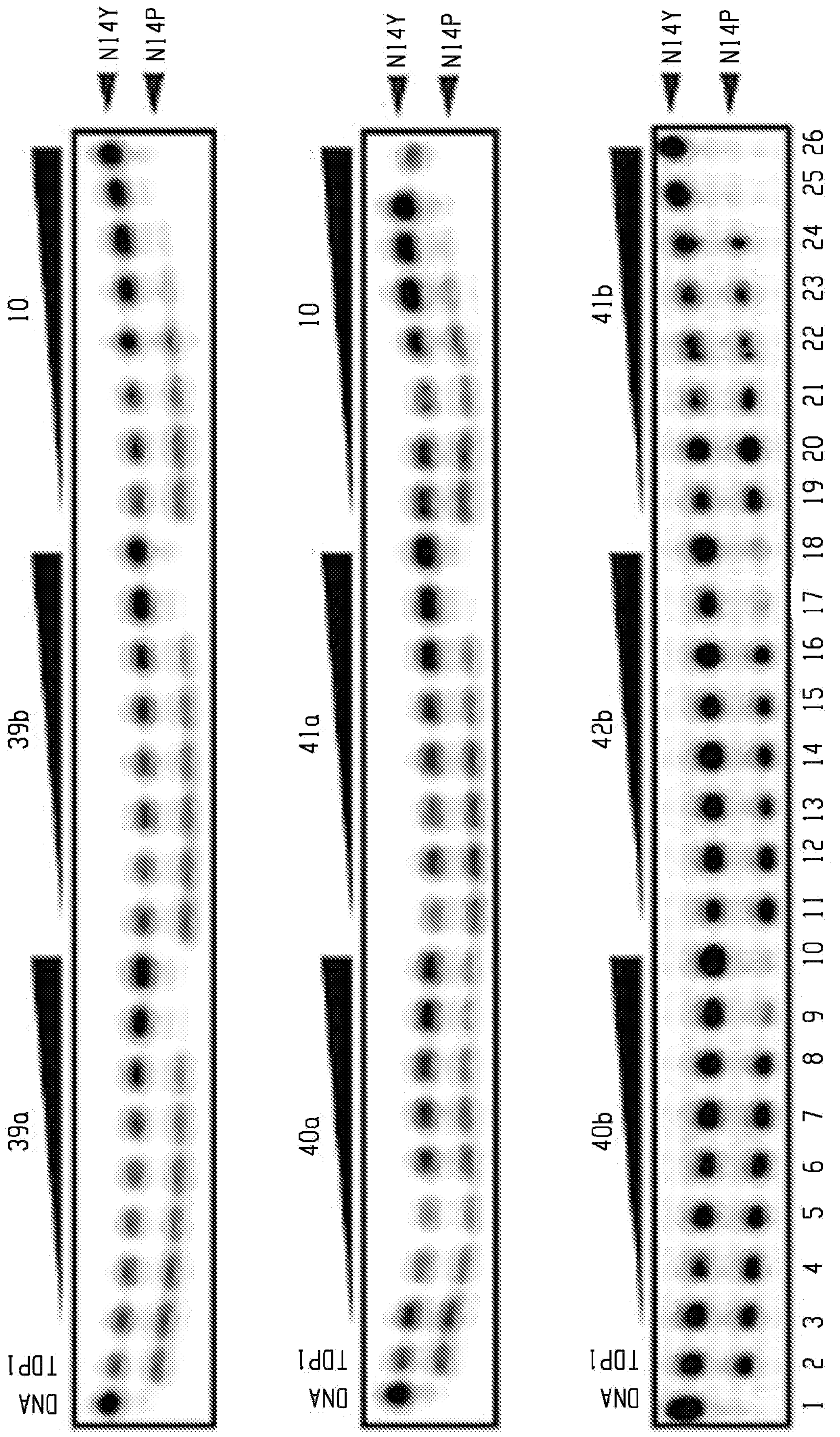

To confirm their Tdp1 inhibition, these seven active compounds 39a/b, 40a/b, 41a/b and 42b were further tested by a gel-based assay, in which a single-stranded 5'-$^{32}$P-labeled oligonucleotide N14Y containing 3-phosphotyrosyl group was used as substrate. Their $IC_{50}$ values are summarized in Table 2. Compound 41a was also found to show the most potent Tdp1 inhibition ($IC_{50}$=8.2 μM). Their Tdp1 inhibition gels are shown in FIG. 6C. The indenoisoquinoline 10 was used as the positive control. Five compounds 39a/b, 40b and 41a/b showed full inhibition at the highest concentration (111 μM) with progressive dose-independency.

TABLE 2

Tdp1 inhibition of active compounds

| Cpd. | $IC_{50}$ (μM)$^{a}$ Fluorescence assay | Gel-based assay |
|---|---|---|
| 39a | 24 ± 0.80 | 16 ± 0.40 |
| 39b | 18 ± 1.7 | 13 ± 4.0 |
| 40a | 58 ± 20 | 40 ± 14 |
| 40b | 15 ± 2.7 | 27 ± 5.2 |
| 41a | 7.0 ± 1.4 | 8.2 ± 1.3 |
| 41b | 20 ± 1.7 | 21 ± 1.2 |
| 42b | 19 ± 4.8 | 20 ± 5.4 |

To obtain a molecular view of the Tdp1 inhibitors with Tdp1, a hypothetical binding model was built by using in-silico docking. The Tdp1 catalytic region containing two lysine residues (Lys265 and Lys495) and two histidine residues (His263 and His493) was constructed as the binding site from the Tdp1 X-ray crystal structure (PDB ID: 1RFF). The inhibitors were docked into the binding site. The hypothetical structure of the top-ranked pose of 41a is shown in FIG. 6B. The polycyclic core of 41a lies along the DNA binding groove and interacts with Phe259 via π-π stacking (FIG. 6B), while the pyrrolidinyl ethyl side chain is directed to the catalytic site of Tdp1 through a narrow channel. Two hypothetical hydrogen bonds form between the nitrogen atom in the pyrrolidinyl group and His493 (3.3 Å) and Asn283 (3.1 Å), implying the importance of the side chain to Tdp1 inhibition. In addition, the 1,3-dioxole ring is close to Glu538, and hydrogen bond forms between the oxygen atom and the amide group of Glu358 with the distance of 3.7 Å, which might also contribute to Tdp1 inhibition.

Interaction with DNA. To evaluate the interaction of the synthesized compounds with DNA, FRET melting assays were performed using F10T as substrate and the AT values of the synthesized compounds are summarized in Table 1a. The FRET melting assay indicated that none of the synthesized compounds significantly increase the melting temperature of F10T at 2 μM concentration, and that 27b has the highest $\Delta T_m$ value of 1.9° C., implying that the synthesized compounds have low binding property to dsDNA. Compound 19a with the highest Top1 inhibitory activity demonstrated poor binding property to dsDNA with low $\Delta T_m$, value of 0.5° C.

The binding of classical DNA intercalators between the base pair of circular DNA produce Top1-mediated unwinding effect, thereby antagonizing Top1-mediated DNA relaxation. To further evaluate 19a, Top1-mediated unwinding assays in the presence of excess Top1 were performed. As shown in FIG. 5B, the DNA intercalator ethidium bromide (EB) showed a distributed DNA ladder along with the increased tested concentration using supercoiled pBR322 DNA as substrate. On the contrary, 19a had no Top1-mediated unwinding effect up to 9 μM concentration. The assay using relaxed pBR322 DNA as substrate was also performed (FIG. 5C) and confirm that 19a had no unwinding effect.

Thus, we conclude from the FRET and Top1-mediated unwinding assays the specificity for Top1 of 19a and its lack of detectable binding to DNA outside of Top1cc.

Cytotoxicity Assays. The cytotoxicity of the compounds was assessed through MTT assay against five human tumor cell lines, including colon cancer (HCT116), leukemia (CCRF-CEM) prostate cancer (DU-145), non-small cell lung cancer (A549) and hepatocarcinoma (Huh7) cell lines. The cells were incubated with the tested compounds for 72 hours in a five-dose assay ranging from 0.01 to 100 μM concentration. After drug treatments, MTT solution was added to test the percentage growth of tumor cells. The $GI_{50}$ values, defined as the concentrations of the compounds that resulted in 50% cell growth inhibition, were plotted and summarized in Table 1b.

TABLE 1b

Cytotoxicity of the synthesized compounds

| | $GI_{50}$ (μM)[d] | | |
|---|---|---|---|
| Cpd | HCT116 | CCRF-CEM | DU145 |
| 1 | 0.009 ± 0.001 | 0.007 ± 0.003 | 0.021 ± 0.016 |
| 6 | 74.79 ± 4.36 | 26.52 ± 5.41 | 64.23 ± 10.94 |
| 17a | 3.07 ± 0.36 | 0.53 ± 0.027 | 3.39 ± 1.76 |
| 17b | 13.38 ± 4.17 | 3.30 ± 0.31 | 7.53 ± 3.42 |
| 19a | 0.076 ± 0.007 | 0.029 ± 0.003 | 0.018 ± 0.002 |
| 19b | 1.27 ± 0.10 | 3.82 ± 0.30 | 1.48 ± 0.95 |
| 20a | 0.21 ± 0.019 | 0.18 ± 0.016 | 0.054 ± 0.025 |
| 20b | 11.79 ± 1.14 | 15.24 ± 1.28 | 8.21 ± 1.99 |
| 21a | 3.52 ± 0.99 | 0.62 ± 0.041 | 0.19 ± 0.057 |
| 21b | 11.25 ± 0.95 | 1.44 ± 0.15 | 5.74 ± 3.04 |
| 22a | 0.16 ± 0.055 | 0.32 ± 0.011 | 0.96 ± 0.29 |
| 22b | 4.51 ± 0.21 | 2.56 ± 0.53 | 5.21 ± 0.83 |
| 23a | 9.88 ± 1.94 | 6.05 ± 0.39 | 44.97 ± 15.74 |
| 23b | 26.35 ± 12.46 | 37.17 ± 0.87 | >100 |
| 24a | 19.14 ± 14.15 | 13.44 ± 3.29 | 18.16 ± 5.03 |
| 24b | 15.69 ± 3.74 | 25.96 ± 2.55 | 25.43 ± 19.49 |
| 25a | 21.60 ± 5.00 | 56.30 ± 1.95 | 87.77 ± 1.17 |
| 25b | 1.95 ± 0.070 | 1.91 ± 0.23 | 0.37 ± 0.24 |
| 26a | 7.36 ± 3.55 | 0.95 ± 0.14 | 1.93 ± 0.41 |
| 26b | 0.27 ± 0.040 | 0.12 ± 0.015 | 0.081 ± 0.017 |
| 27a | 6.43 ± 2.35 | 1.99 ± 0.11 | 3.04 ± 0.32 |
| 27b | 2.85 ± 0.21 | 1.67 ± 0.040 | 1.91 ± 0.70 |
| 28a | 4.25 ± 3.11 | 1.25 ± 0.18 | 2.04 ± 0.41 |
| 28b | 0.66 ± 0.067 | 0.47 ± 0.060 | 2.41 ± 0.62 |
| 29a | 2.80 ± 0.22 | 1.11 ± 0.13 | 1.67 ± 0.35 |
| 29b | 0.64 ± 0.061 | 0.72 ± 0.034 | 2.78 ± 2.17 |
| 30a | 6.17 ± 2.37 | 0.92 ± 0.047 | 5.26 ± 0.63 |
| 30b | 4.77 ± 0.22 | 0.82 ± 0.12 | 4.17 ± 1.70 |
| 31a | 2.43 ± 0.38 | 3.05 ± 0.22 | 4.66 ± 0.69 |
| 31b | 4.98 ± 0.59 | 2.49 ± 0.030 | 16.05 ± 8.03 |
| 32a | 8.09 ± 0.030 | 12.26 ± 0.78 | 33.90 ± 9.07 |
| 32b | 9.79 ± 3.01 | 1.82 ± 0.46 | 2.58 ± 0.24 |
| 39a | 30.92 ± 7.91 | 2.39 ± 0.34 | 2.36 ± 0.20 |
| 39b | 28.05 ± 6.24 | 2.61 ± 0.45 | 3.06 ± 0.80 |
| 40a | 61.01 ± 14.15 | 47.20 ± 3.08 | 43.68 ± 14.71 |
| 40b | 64.10 ± 2.24 | 45.18 ± 4.65 | 10.10 ± 3.21 |
| 41a | 31.04 ± 6.08 | 2.63 ± 0.16 | 4.29 ± 1.31 |
| 41b | 31.89 ± 1.51 | 3.30 ± 0.010 | 2.94 ± 0.72 |
| 42a | 35.49 ± 12.23 | 3.35 ± 0.25 | 44.70 ± 2.06 |
| 42b | >100 | 54.59 ± 3.14 | 9.58 ± 3.66 |
| 43a | 84.98 ± 26.00 | 28.20 ± 1.30 | 74.99 ± 1.22 |
| 43b | >100 | >100 | >100 |
| 44a | 53.31 ± 1.86 | 17.03 ± 2.92 | 29.13 ± 18.19 |
| 44b | 38.91 ± 21.21 | 33.48 ± 23.20 | 11.85 ± 6.51 |
| 45a | 60.72 ± 0.81 | 38.88 ± 16.22 | >100 |
| 45b | >100 | 29.07 ± 1.03 | 58.68 ± 6.44 |
| 49 | ND | ND | ND |

| | $GI_{50}$ (μM)[d] | |
|---|---|---|
| Cpd | A549 | Huh7 |
| 1 | 0.21 ± 0.069 | 0.099 ± 0.017 |
| 6 | 39.38 ± 26.20 | >100 |
| 17a | 11.75 ± 1.80 | 18.34 ± 9.70 |
| 17b | >100 | 13.04 ± 7.97 |
| 19a | 0.79 ± 0.11 | 0.12 ± 0.015 |
| 19b | 8.08 ± 1.90 | 5.38 ± 2.13 |
| 20a | 3.15 ± 2.11 | 3.16 ± 0.34 |
| 20b | 36.72 ± 8.97 | 48.82 ± 45.58 |
| 21a | 40.38 ± 11.83 | 12.06 ± 3.98 |
| 21b | 21.45 ± 9.33 | 17.39 ± 3.80 |
| 22a | 15.31 ± 1.62 | 61.00 ± 38.50 |
| 22b | 56.53 ± 21.44 | 34.62 ± 21.23 |
| 23a | >100 | >100 |
| 23b | >100 | >100 |
| 24a | 61.89 ± 14.96 | 14.49 ± 1.22 |
| 24b | >100 | >100 |
| 25a | 89.85 ± 3.15 | 78.11 ± 19.18 |
| 25b | 82.99 ± 29.45 | 74.69 ± 20.42 |
| 26a | 6.68 ± 1.93 | 7.78 ± 2.91 |
| 26b | 2.98 ± 2.21 | 3.08 ± 0.95 |
| 27a | 11.07 ± 0.83 | 45.95 ± 20.42 |
| 27b | 11.67 ± 2.18 | 20.53 ± 8.51 |
| 28a | 6.59 ± 1.29 | 8.07 ± 1.30 |
| 28b | 2.76 ± 1.91 | 6.92 ± 1.10 |
| 29a | 33.09 ± 13.29 | 65.90 ± 32.72 |
| 29b | 7.11 ± 3.14 | 8.44 ± 1.41 |
| 30a | 57.33 ± 32.60 | >100 |
| 30b | >100 | >100 |
| 31a | 2.08 ± 1.33 | 6.45 ± 2.20 |
| 31b | 9.18 ± 3.51 | 12.38 ± 4.13 |
| 32a | 27.77 ± 11.18 | 51.00 ± 11.67 |
| 32b | 12.94 ± 3.87 | 10.31 ± 1.52 |
| 39a | 3.77 ± 2.13 | 1.29 ± 0.22 |
| 39b | 3.22 ± 1.42 | 5.97 ± 1.68 |
| 40a | >100 | >100 |
| 40b | 16.96 ± 1.57 | >100 |
| 41a | 1.53 ± 0.070 | 2.78 ± 0.59 |
| 41b | 1.83 ± 0.45 | 8.95 ± 3.16 |
| 42a | 46.27 ± 32.96 | 13.21 ± 4.32 |
| 42b | >100 | >100 |
| 43a | >100 | >100 |
| 43b | >100 | >100 |
| 44a | 7.60 ± 0.61 | 95.52 ± 2.20 |
| 44b | 37.57 ± 23.74 | >100 |
| 45a | 5.39 ± 3.35 | 53.42 ± 32.83 |
| 45b | 15.67 ± 9.47 | 58.56 ± 28.37 |
| 49 | ND | ND |

Regarding Table 1b: [d]$GI_{50}$ values (means±SD) were defined as the concentrations of compounds that resulted in 50% cell growth inhibition and obtained from MTT assay. Every experiment was repeated at least three times independently. [f]"ND" means not determined.

Compared to the parent 6, most benzophenanthridinone derivatives 17a/b and 19a/b-25a/b showed increased cytotoxicity against these five human cancer cell lines, which is consistent with their Top1 inhibition. Compound 19a with the highest Top1 potency (+++) also showed the highest cytotoxicity against these five cancer cell lines with $GI_{50}$ values at nanomolar range (0.076 μM for HCT116, 0.029 μM for CCRF-CEM, 0.018 μM for DU 145, 0.79 μM for A549 and 0.12 μM for Huh7). Although compounds 20a and 22a with alkylaminoethyl substituents at 5-position showed weak Top1 inhibition of +, they showed cytotoxicity against HCT116 (0.21 μM for 20a, 0.16 μM for 22a), CCRF-CEM (0.18 μM for 20a, 0.32 μM for 22a) and DU145 (0.054 μM for 20a, 0.96 μM for 22a) cell lines. Compound 21a with Top1 inhibition of ++ showed cytotoxicity against the CCRF-CEM (0.62 μM) and DU145 (0.19 μM) cell lines with $GI_{50}$ values at submicromolar range. Compared to the compounds with hydroxyl terminus (17a/b) on the side chain at 5-position, the compounds with alkylamino termini, including dimethylanino (19a/b), diethylamino (20a/b), pyrrolidinyl (21a/b) and piperidinyl (22a/b) groups, showed increased cytotoxicity against HCT116 cells, while the morpholinyl (23a/b) and 4-methylpiperazinyl (24a/b) termini led to decreased cytotoxicity. Compounds 23a/b and 24b showed low cytotoxicity against A549 and Huh7 cell lines with $GI_{50}$ values more than 100 μM. The compounds with shorter side chain at 5-position showed more cytotoxicity than that with corresponding longer side chain against HCT116 cells, for example 17a vs. 17b and 19-23a vs. 19-23b, exceptions are the compounds with 4-methylpiperazinyl (24a/b) and imidazolyl (25a/b) termini.

Among the dihydrobenzophenanthridine derivatives (26a/b-32a/b), 26b with diethylaminopropyl substituent at 5-position exhibited the highest cytotoxicity against HCT116 ($GI_{50}$=0.27 μM), CCRF-CEM ($GI_{50}$=0.12 μM) and DU 145 ($GI_{50}$=0.081 μM) cell lines. The other five dihydrobenzophenanthridine derivatives 26a, 28b, 29b and 30a/b showed high cytotoxicity against CCRF-CEM cells with $GI_{50}$ values at submicromolar concentration, while two dihydrobenzophenanthridine derivatives 28b and 29b showed high cytotoxicity against HCT116 cells with $GI_{50}$ values of 0.66 μM and 0.64 μM, respectively. 32b showed increased cytotoxicity against these five cancer cell lines compared to parent 6, which was consistent with its Top1 inhibition of ++. Contrary to the benzophenanthridinones, the dihydrobenzophenanthridines with shorter side chain at 5-position showed lower cytotoxicity against HCT116 cells than that corresponding compounds with longer side chain (for example 26a-30a vs. 26b-30b). Exceptions are the compounds with 4-methylpiperazinyl (31a/b) and imidazolyl (32a/b) termini.

The benzophenanthridines (39a/b-45a/b) with alkoxy substituents at the 6-position generally showed decreased cytotoxicity compared to benzophenanthridinones (19a/b-25a/b) with the corresponding side chain at the 5-position. Although the benzophenanthridines 39a/b and 41a/b did not show Top1 inhibition at up to 100 M concentration, they had good Tdp1 inhibitory activity with $IC_{50}$ values at low micromolar concentration, and showed good cytotoxicity against four cancer cell lines, including CCRF-CEM, DU145, A549 and Huh7 cells, with $GI_{50}$ values between 1.29 and 8.95 μM, suggesting additional cellular targets.

Compound 19a being the most potent inhibitor of Top1 and the most cytotoxic, it was selected and submitted to the National Cancer Institute (NCI, USA) for testing against the 60 tumor cell lines representing nine tissue types (NCI-60). The tumor cells were incubated with 19a for 48 hours and stained with sulforhodamine B dye. Cell growth inhibition ($GI_{50}$ in Table 3) was calculated relative to cells without compound treatment and the time zero control. High cytotoxicity was observed for 19a with a mean graph midpoint (MGM) for growth inhibition of all cancer cell lines of 0.145 μM, and its $GI_{50}$ values against HCT116, SR, NCI-H522 and UACC-62 cell lines were at nanomolar range (<100 nM).

TABLE 3

Cytotoxicity of 19a against NCI-60 cell lines

| Panel | Cell line | $GI_{50}$ (μM)[a] |
|---|---|---|
| | MGM[b] | 0.145 |
| Leukemia | CCRF-CEM | 0.144 |
| | K-562 | 0.156 |
| | MOLT-4 | 0.118 |
| | RPMI-8226 | 0.14 |
| | SR | 0.0669 |
| Non-Small Cell Lung Cancer | A549/ATCC | 0.244 |
| | EKVX | 0.79 |
| | HOP-62 | 0.18 |
| | HOP-92 | 0.558 |
| | NCI-H226 | 0.512 |
| | NCI-H23 | 0.201 |
| | NCI-H322M | 0.428 |
| | NCI-H460 | 0.141 |
| | NCI-H522 | 0.076 |
| Colon Cancer | COLO 205 | 0.144 |
| | HCC-2998 | 0.63 |
| | HCT116 | 0.0855 |
| | HCT-15 | 0.427 |
| | HT29 | 0.149 |
| | KM12 | 0.875 |
| | SW-620 | 0.345 |
| Renal Cancer | 786-0 | 0.166 |
| | A498 | 0.347 |
| | ACHN | 0.16 |
| | CAKI-1 | 0.186 |
| | RXF 393 | 0.516 |
| | SN 12C | 0.258 |
| | TK-10 | 0.722 |
| | UO-31 | 0.157 |
| CNS Cancer | SF-268 | 0.283 |
| | SF-295 | 0.177 |
| | SF-539 | 0.186 |
| | SNB-19 | 0.233 |
| | SNB-75 | 0.239 |
| | U251 | 0.14 |
| Melanoma | LOX IMVI | 0.112 |
| | MALME-3M | 0.284 |
| | M14 | 0.149 |
| | MDA-MB-435 | 0.395 |
| | SK-MEL-2 | 0.886 |
| | SK-MEL-28 | 0.861 |
| | SK-MEL-5 | 0.181 |
| | UACC-257 | 0.528 |
| | UACC-62 | 0.0966 |
| Breast Cancer | MCF7 | 0.118 |
| | MDA-MB-231/ATCC | 0.826 |
| | HS 578T | 1.86 |
| | BT-549 | 0.291 |
| | T-47D | 0.111 |
| | MDA-MB-468 | 0.14 |
| Ovarian Cancer | IGROV1 | 0.312 |
| | OVCAR-3 | 0.582 |
| | OVCAR-4 | 0.557 |
| | OVCAR-5 | 0.595 |
| | OVCAR-8 | 0.554 |
| | NCI/ADR-RES | 0.29 |
| | SK-OV-3 | 0.24 |
| Prostate Cancer | PC-3 | 0.317 |
| | DU-145 | 0.215 |

Regarding Table 3: [a]$GI_{50}$ values were defined as the concentrations of compounds that resulted in 50% cell growth inhibition. The cells were incubated for two days with the tested compounds. [b]MGM: mean graph midpoint for growth inhibition of all human cancer cell lines.

Figure 7:
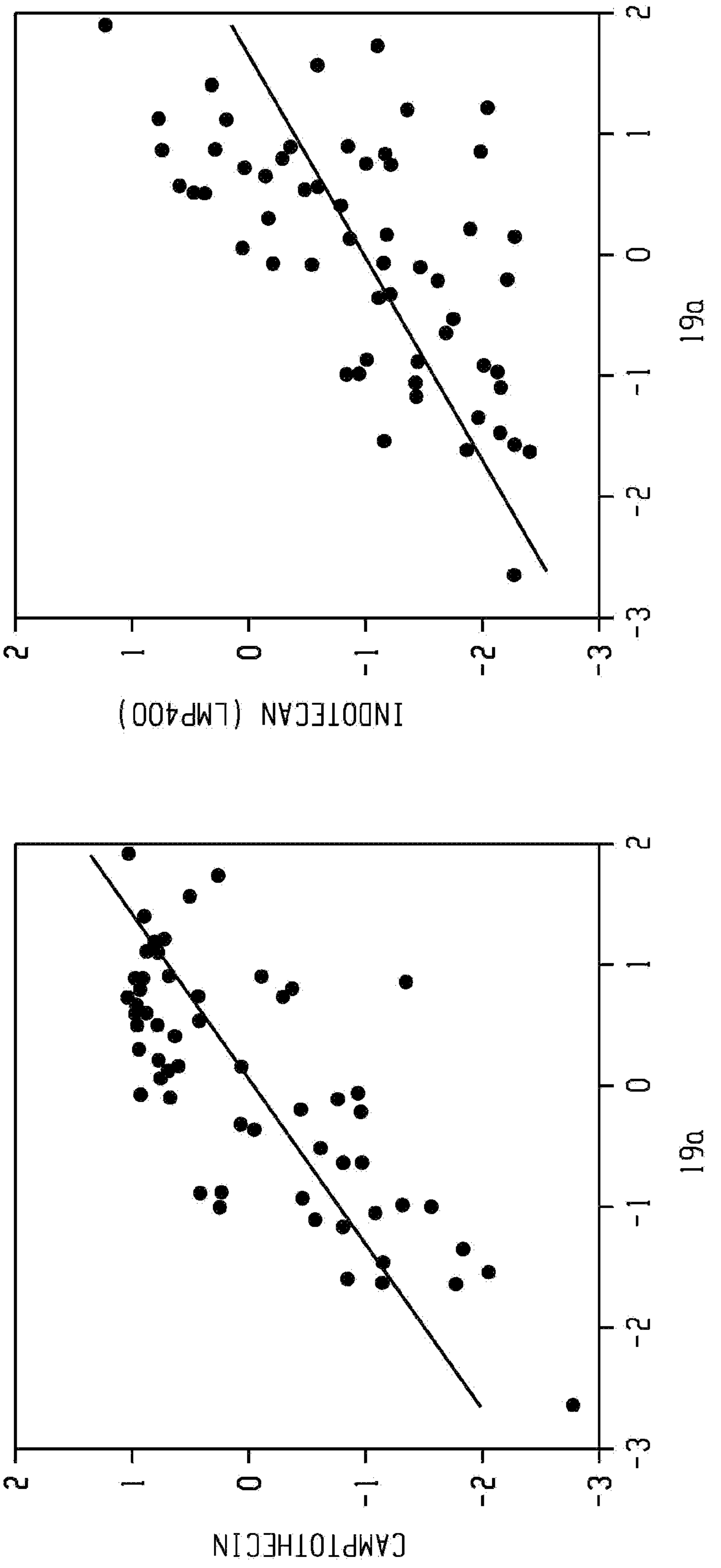
FIG. 7 shows a pattern comparison analysis of 19a using $GI_{50}$ data from NCI-60 assays. Individual dots represent a cell line of the NCI-60. The lines represent regression lines. R-square values were 0.58 and 0.40 for camptothecin and the indenoisoquinoline indotecan (LMP400), respectively. P-values were <0.0001 for both comparisons.

Because the NCI-60 database contains several thousand chemicals and anticancer drugs, which have been tested across the cancer cell line panel (http://discover.nci.nih.gov/cellminer and http://discover.nci.nih.gov/cellminerdb), we were able to perform a pattern comparison analysis with 19a. The drugs with the highest correlation with 19a were all Top1 inhibitors including camptothecin and its derivatives as well as the indenoisoquinolines. FIG. 7 shows the high correlation between the cytotoxicity of 19a and camptothecin and the clinical indenoisoquinoline LMP400.

The cytotoxicity of 19a was further evaluated against a panel of camptothecin- and doxorubicin-resistant cell lines using MTT assay (Table 4). The HCT116-siTop1 subline was developed by transfection of colon cancer parental cells HCT116 with short hairpin RNA vectors expressing siRNA for Top1. Compared to the parental cell HCT116, HCT116-siTop1 subline showed 8.3-fold resistant to 1, of which Top1 is the only known cellular target, and about 5.9-fold to 19a, implying that Top1 is a major cellular target of 19a.

TABLE 4

The cytotoxicity of the 19a in drug-resistant human cancer cell lines

| Cpd. | Parental cell line ($GI_{50}$ ± SD (μM)[a]) | Resistant subline ($GI_{50}$ ± SD (μM)[a]) | Resistance Ratio[b] |
|---|---|---|---|
| | HCT116 | HCT116-siTOP1 | |
| 19a | 0.076 ± 0.010 | 0.45 ± 0.31 | 5.9 |
| 1 | 0.009 ± 0.001 | 0.075 ± 0.014 | 8.3 |
| | DU-145 | DU145-RC0.1 | |
| 19a | 0.018 ± 0.002 | 2.38 ± 0.34 | 132 |
| 1 | 0.021 ± 0.016 | 4.73 ± 0.68 | 225 |
| | MCF-7 | MCF-7/ADR | |
| 19a | 0.34 ± 0.098 | 0.95 ± 0.35 | 2.8 |
| DOX | 0.15 ± 0.003 | 11.67 ± 1.94 | 77.8 |
| | HepG2 | HepG2/ADR | |
| 19a | 0.30 ± 0.050 | 3.20 ± 0.40 | 10.7 |
| DOX | 0.19 ± 0.048 | 9.04 ± 0.14 | 47.6 |

Regarding Table 4: [a]$GI_{50}$ values (means±SD) were defined as the concentrations of compounds that resulted in 50% cell growth inhibition and obtained from MTT assay. Every experiment was repeated at least three times. [b]Resistance ratio was calculated by dividing the $GI_{50}$ of the mutant cell line by the $GI_{50}$ of the corresponding parental cell line.

The camptothecin-resistant prostate cancer DU145-RC0.1 cells have a R364H mutation in Top1 relative to the wild-type parental DU-145. The Top1 with R364H mutation is catalytically active, but leads to RC0.1 cells to be resistant to 1 because the R364 residue is close to the catalytic tyrosine and can stabilize the open form of Top1cc. The DU145-RC0.1 cells were highly resistant to 1 (225-fold) and 19a (132-fold), which is consistent with the molecular modeling (FIG. 5D) showing hydrogen bonding between R364 and 19a.

P-glycoprotein (P-gp) mediated drug efflux is generally responsible for classical multiple drug resistance. The chemotherapeutic agent doxorubicin (DOX) is a substrate of P-gp, and both breast cancer MCF-7/ADR (77.8-fold) and hepatocellular HepG2/ADR sublines (47.6-fold), which overexpress P-gp, are highly resistant to doxorubicin (77.8- and 47.6-fold, respectively; Table 4). Compound 19a appeared to be less a P-gp substrate (Table 4) with a resistance ratio of 2.8 (MCF-7/ADR:MCF-7) and 10.7 (HepG/ADR:HepG2), respectively.

Figure 11A:
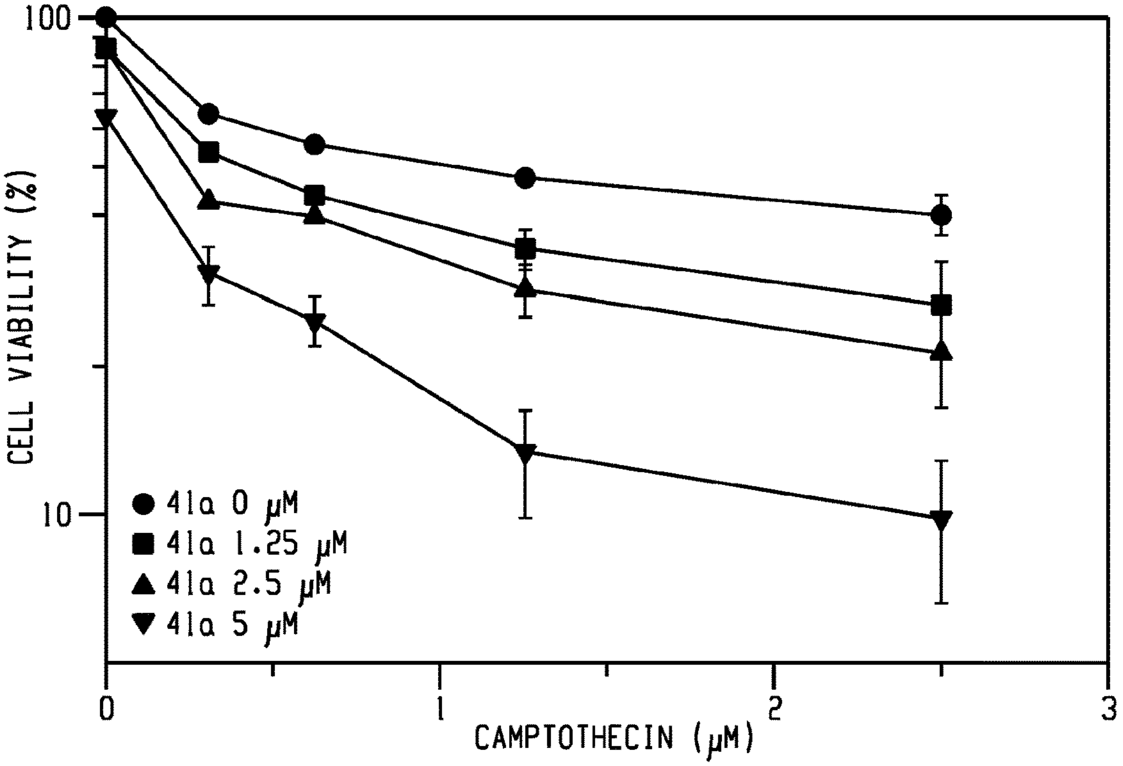
FIGS. 11A-11B show the synergistic effect of 41a (FIG. 11A) and 41b (FIG. 11B) with camptothecin. The MCF-7 cells were incubated with camptothecin and the tested compounds for 96 h. Every experiment was repeated four times.
Figure 11B:
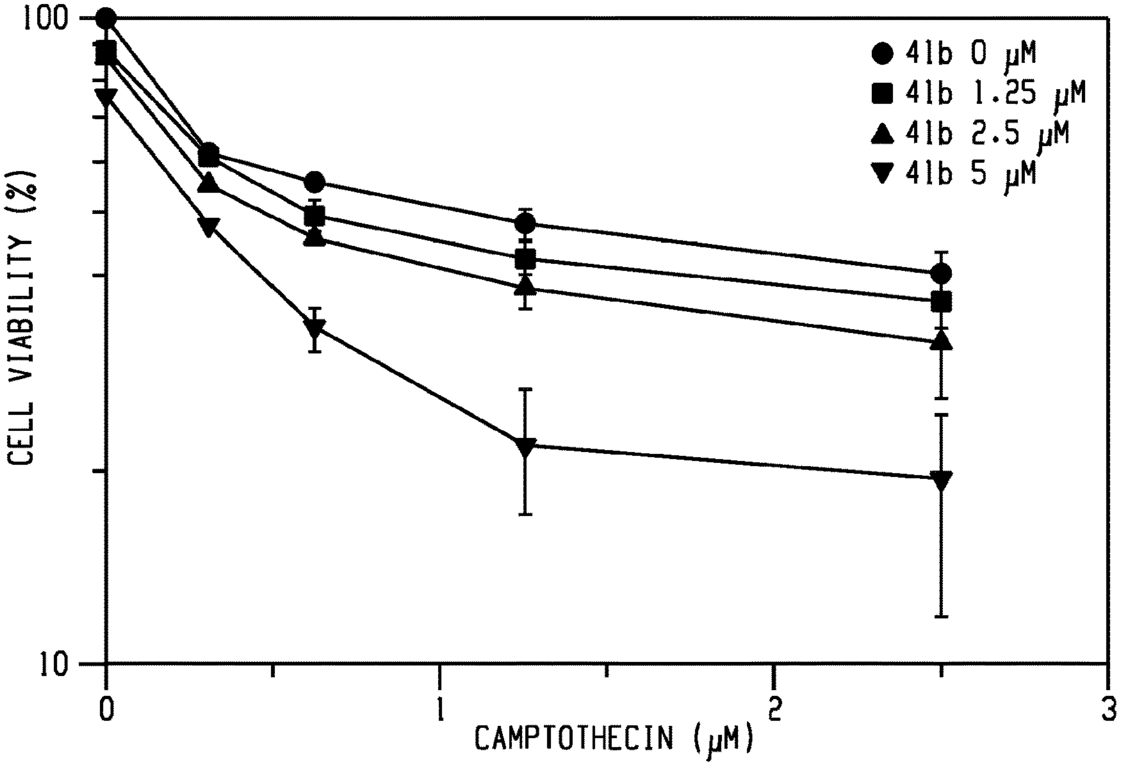

Synergistic effects of 41a and 41b with camptothecin. The combined effects of the TDP1 inhibitors 41a and 41b were tested with camptothecin in MCF-7 human breast cancer cells using MTT assay. As shown in FIG. 11A, after 96 hours incubation at 37° C., the cytotoxicity of camptothecin against MCF-7 cells increased in the presence of 41a. At 2.5 μM concentration, almost 60% cells were killed by camptothecin itself and over 90% cells were killed when being co-incubated with 41a at 5 μM concentration, which implies that a supra-additive effect of 41a with camptothecin is consistent with TDP1 inhibition in cells. Similarly, 41b showed a synergistic effect with camptothecin in MCF-7 cells (FIG. 111B).

Figure 8A:
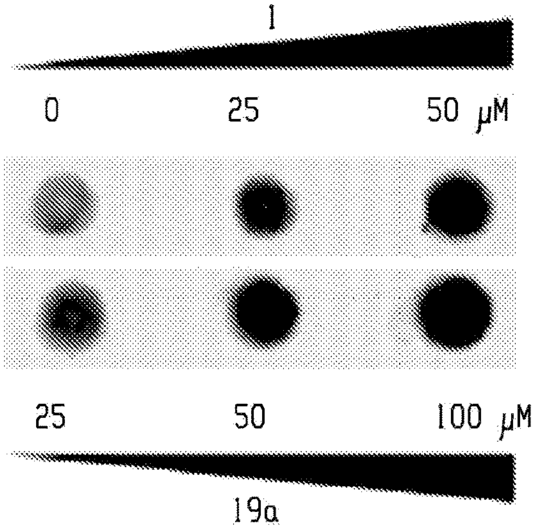
FIG. 8A-8C.

The immunocomplex of enzyme to DNA (ICE) assay was conducted to evaluate the induction of Top1cc by 19a in HCT116 cancer cells. FIG. 8A shows that 19a induces cellular Top1cc in a dose-dependent manner, similar to the positive control 1.

To assess the DNA damage in cancer cells induced by 19a, γH2AX foci were assessed by immunofluorescence microscopy in human colon cancer HCT116 cells treated with 19a. After incubation with 19a for 3 hours, HCT116 cells were stained with γH2AX antibodies. γH2AX foci were induced by 19a at 1 μM concentration (FIG. 8C), consistent with DNA damage due to the trapping of cellular Top1cc by 19a.

Figure 8B:
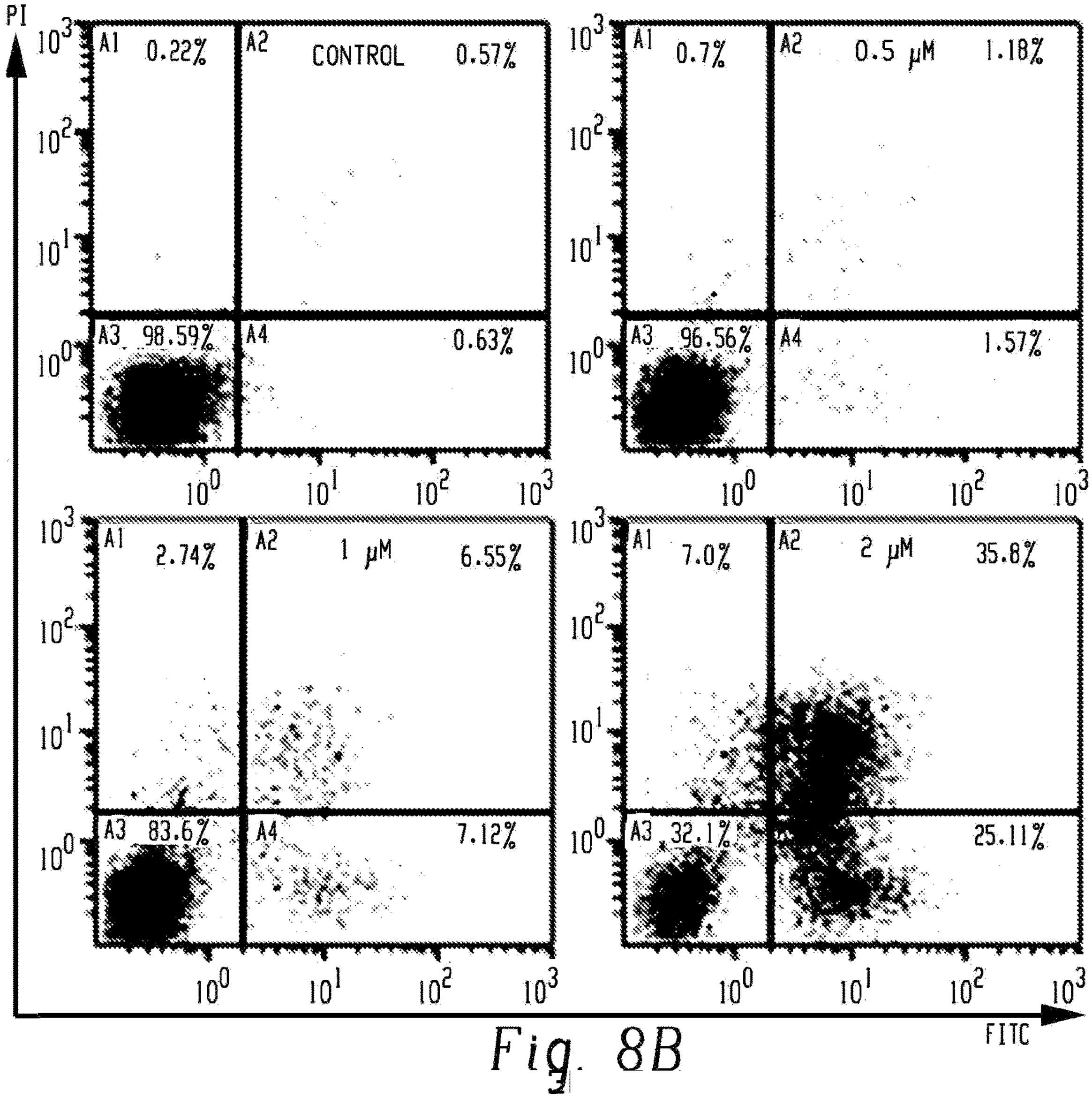
Figure 8C:
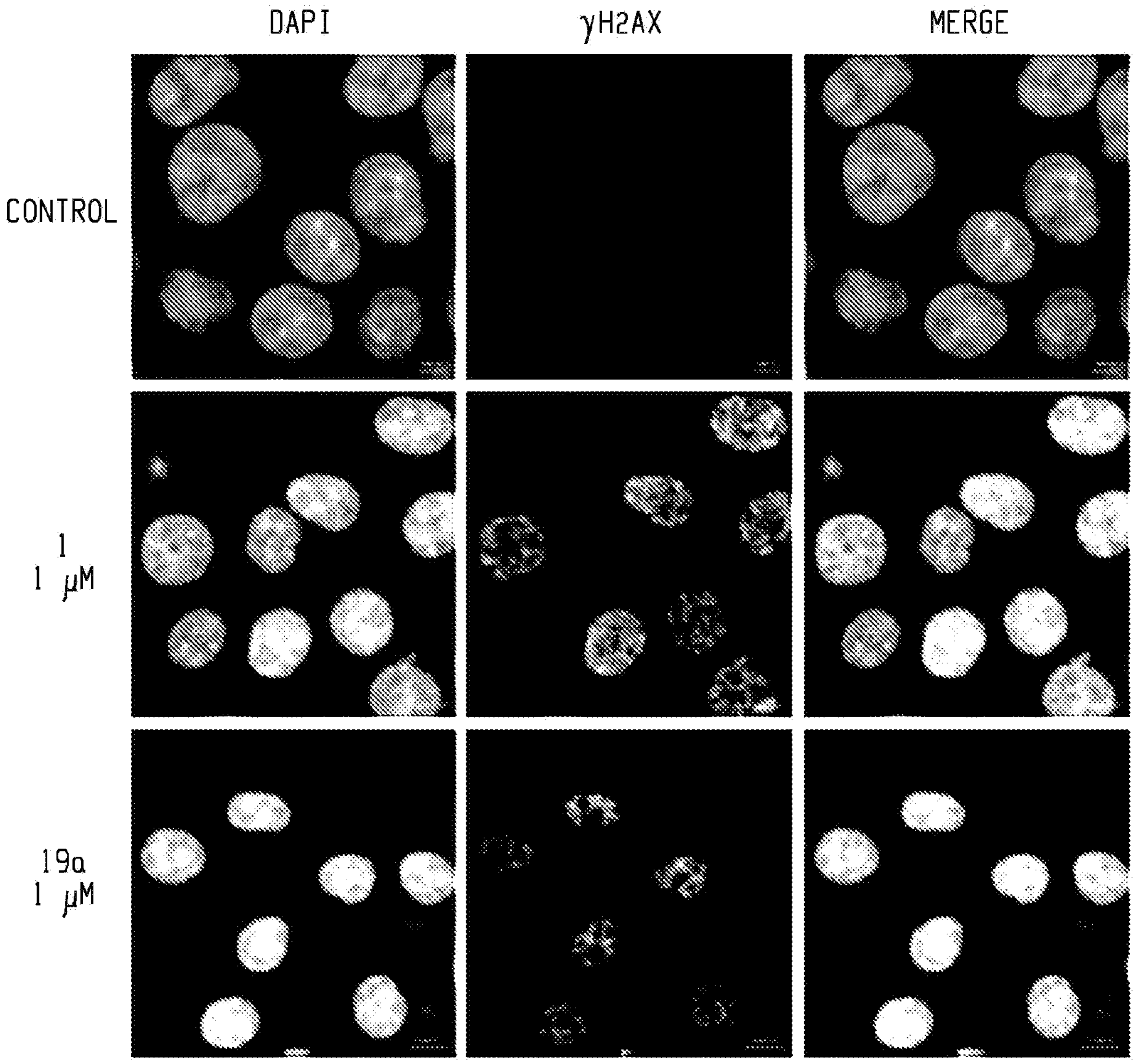

Flow cytometry assays were conducted in HCT116 cancer cells to assess the induction of apoptosis by 19a. After being incubated with 19a for 24 hours, apoptotic HCT116 cells were detected. FIG. 8B shows that 19a could significantly induce HCT116 cells apoptosis in a dose-dependent manner. Approximately 60.9% (25.11% early apoptotic cells and 35.8% late apoptotic cells) of the treated cells were scored as apoptotic following 24 hours incubation with 19a at 2 μM.

In vivo pharmacokinetic (PK) study of 19a was conducted in Sprague-Dawley (SD) rats. The SD rats were divided into two groups (n=3) and treated by intravenous injection (i.v.) at 1 mg/kg dose and intragastrical administration (i.g.) at 5 mg/kg dose, respectively. Plasma samples were collected up to 24 hours post-dosing and measured for the concentration of 19a. The PK parameters are summarized in Table 5. Following i.v. administration, the $AUC_{0\rightarrow 24\ h}$ was 119±10 h·ng/mL, and $T_{1/2}$ was 0.855±0.011 hour. After oral administration, the Imax, $C_{max}$ and $AUC_{0\rightarrow 24\ h}$ were 1.17±0.76 hour, 23.5±16 ng/mL and 89.7±36 h-ng/mL, respectively. The bioavailability (F) was 15.5%.

TABLE 5

Pharmacokinetic parameters of 19a.

| Parameters | i.v. (1 mg/kg) (Mean ± SD) | i.g. (5 mg/kg) (Mean ± SD) |
|---|---|---|
| $T_{max}$ (h) | / | 1.17 ± 0.76 |
| $C_{max}$ (ng/ml) | / | 23.5 ± 16 |
| $AUC_{0\rightarrow t}$ (h · ng/ml) | 119 ± 10 | 89.7 ± 36 |
| $AUC_{0\rightarrow \infty}$ (h · ng/ml) | 121 ± 10 | 109 ± 33 |
| $MRT_{INF}$ (h) | 1.01 ± 0.023 | 4.73 ± 3.3 |
| $T_{1/2}$ (h) | 0.855 ± 0.011 | 3.08 ± 3.4 |
| F (%) | / | 15.5 ± 5.4 |

Figure 9A:
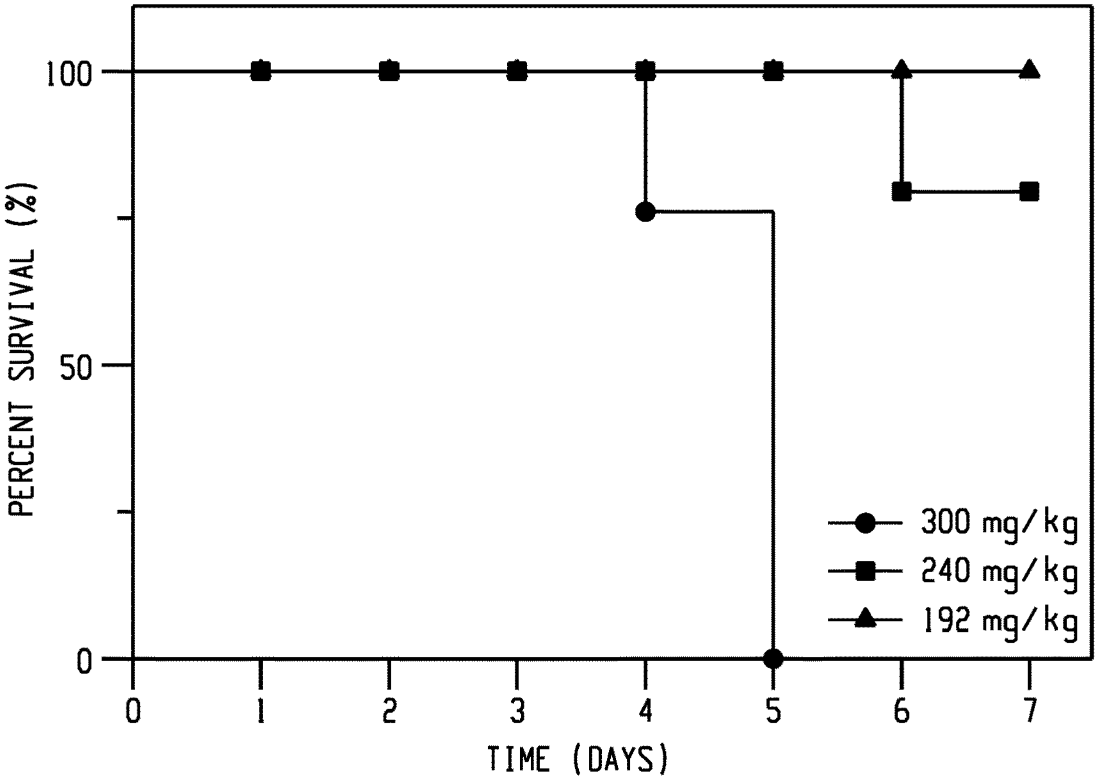
FIGS. 9A-9D. Antitumor activity of 19a in the HCT116 xenograft model.

To assess the toxicity of 19a, Kunming male mice were randomly divided into six groups (n=4) and administered with 19a by i.p. injection in a single dose of 300, 240, 192, 154 and 123 mg/kg, respectively. The control group was injected with sterile water. All mice survived after seven days of administration with 19a in the groups of 192 mg/kg dose (FIG. 9A), 154 mg/kg dose (data not shown) and 123 mg/kg dose (data not shown). Four mice died within five days in the 300 mg/kg dose group, and one mouse died within seven days in the 240 mg/kg dose group (FIG. 9A).

Figure 9B:
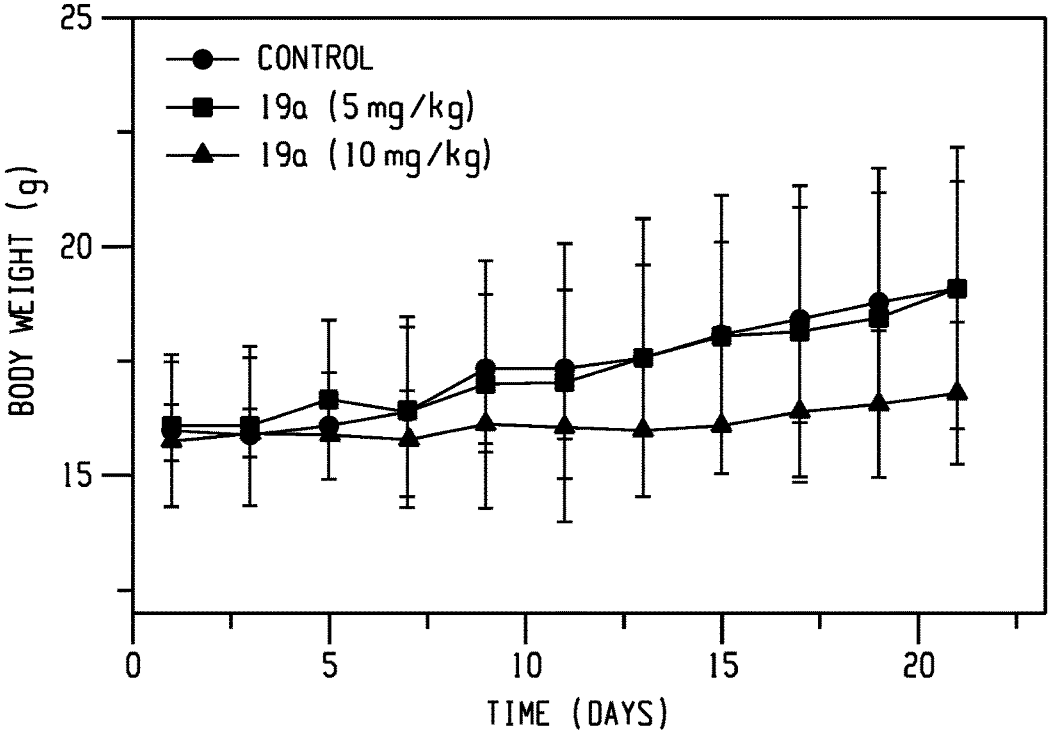
Figure 9C:
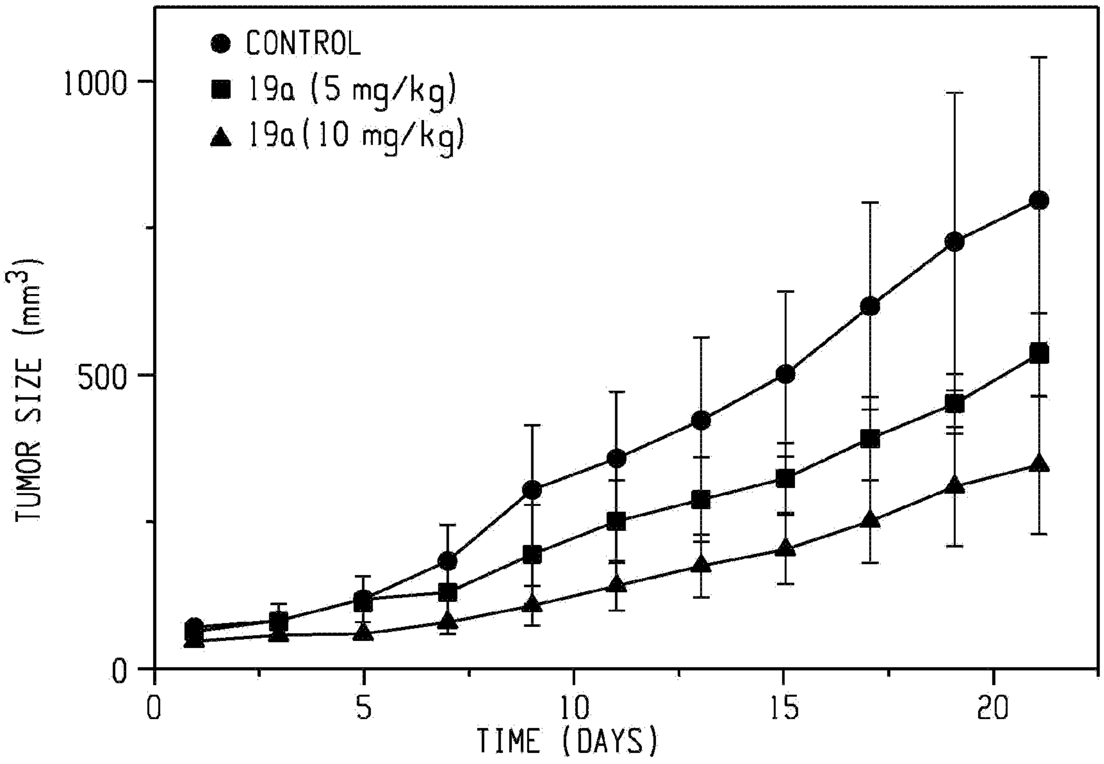
Figure 9D:
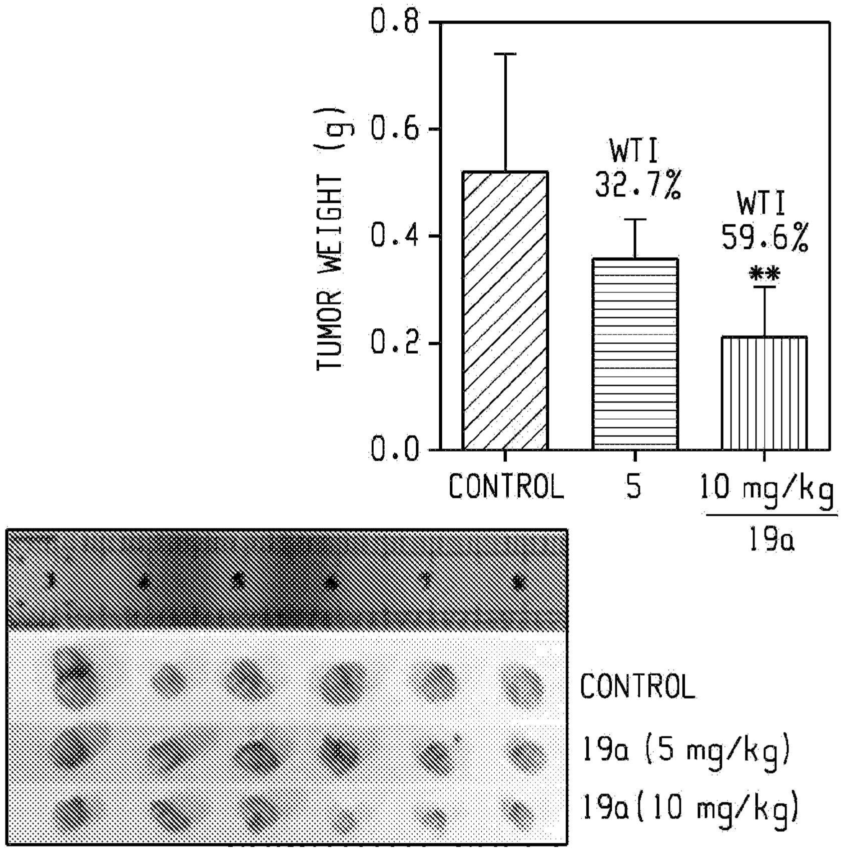

Because 19a showed high Top1 inhibition and cytotoxicity, its antitumor efficiency in vivo was assessed in a human colon cancer HCT116 xenograft nude mice model. Male nude mice were randomly divided into three groups (n=6) and administered with saline and 19a at 10 mg/kg and 5 mg/kg dose, respectively, by i.p. injection at a frequency of once every day. Administration of 19a significantly reduced tumor volume in a dose-dependent manner (FIG. 9C). Meanwhile, the weights of the mice treated with 19a at 5 mg/kg dose had no obvious body loss compared to the saline control group. Body weight loss was found in the 10 mg/kg group (FIG. 9B). Finally, the tumor weight inhibition (TWI) of 19a were 59.6% (10 mg/kg, $P<0.01$) and 32.7% (5 mg/kg), respectively (FIG. 9D). These results demonstrate the antitumor activity of 19a.

Pharmaceutical Preparations

Compounds disclosed herein can be administered as the neat chemical, but are preferably administered as a pharmaceutical composition. Accordingly, the disclosure provides pharmaceutical compositions comprising a compound or pharmaceutically acceptable salt of a Top1 and/or Tdp1 inhibitor, such as a compound of Formula 1, together with at least one pharmaceutically acceptable carrier. The pharmaceutical composition/combination may contain a compound or salt of Formula I as the only active agent, but is preferably contains at least one additional active agent. The additional active agent can be camptothecin, a camptothecin analogue, a poly(ADP-ribose) polymerase (PARP) inhibitor, a cell cycle checkpoint inhibitor targeting ATR (Ataxia Telangiectansia-related kinase), a CHEK1 (cell cycle checkpoint kinase) inhibitor, a WEE1 inhibitor, a CDK (cyclin dependent kinase) inhibitor or other chemotherapeutic compound. In certain embodiments it is preferred that the additional active agent is compound or salt thereof chosen from camptothecin, irinotecan, and topotecan. In certain embodiments the pharmaceutical composition is in a dosage form that contains from about 0.1 mg to about 2000 mg, from about 10 mg to about 1000 mg, from about 100 mg to about 800 mg, or from about 200 mg to about 600 mg of a compound of Formula I and optionally from about 0.1 mg to about 2000 mg, from about 10 mg to about 1000 mg, from about 100 mg to about 800 mg, or from about 200 mg to about 600 mg of an additional active agent in a unit dosage form. The pharmaceutical composition may also include a molar ratio of a compound of Tdp1 inhibitor, such as a compound of Formula I, and an additional active agent. For example, the pharmaceutical composition may contain a molar ratio of about 0.5:1, about 1:1, about 2:1, about 3:1 or from about 1.5:1 to about 4:1 of the compound of Formula I to the additional active agent.

Compounds disclosed herein may be administered orally, topically, parenterally, by inhalation or spray, sublingually, transdermally, via buccal administration, rectally, as an ophthalmic solution, or by other means, in dosage unit formulations containing conventional pharmaceutically acceptable carriers. The pharmaceutical composition may be formulated as any pharmaceutically useful form, e.g., as an aerosol, a cream, a gel, a pill, a capsule, a tablet, a syrup, a transdermal patch, or an ophthalmic solution. Some dosage forms, such as tablets and capsules, are subdivided into suitably sized unit doses containing appropriate quantities of the active components, e.g., an effective amount to achieve the desired purpose.

Carriers include excipients and diluents and must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound.

Classes of carriers include, but are not limited to binders, buffering agents, coloring agents, diluents, disintegrants, emulsifiers, flavorants, glidants, lubricants, preservatives, stabilizers, surfactants, tableting agents, and wetting agents. Some carriers may be listed in more than one class, for example vegetable oil may be used as a lubricant in some formulations and a diluent in others.

Exemplary pharmaceutically acceptable carriers include sugars, starches, celluloses, powdered tragacanth, malt, gelatin; talc, and vegetable oils. Optional active agents may be included in a pharmaceutical composition, which do not substantially interfere with the activity of the compound of the present disclosure.

The pharmaceutical compositions/combinations can be formulated for oral administration. These compositions contain between 0.1 and 99 weight % (wt. %) of a compound of Formula I and usually at least about 5 wt. % of a compound of Formula 1. Some embodiments contain from about 25 wt. % to about 50 wt. % or from about 5 wt. % to about 75 wt. % of the compound of Formula I.

Methods of Treatment

The p compounds/pharmaceutical compositions/combinations disclosed herein are useful for treating disease and disorders in patients in which Tdp1 or Top1 inhibition is beneficial. For example, compounds of Formula I are useful for treating cancer, neurological diseases (such as Angelman syndrome and autism), and septic shock in patients.

This disclosure provides methods of treating cancer, a neurological disease, or septic shock by providing an effective amount of a compound or pharmaceutically acceptable salt of Formula I to a patient in need of such treatment. The compound or salt of Formula I may be provided as the only active agent or may be provided together with one or more additional active agents. In certain embodiments the compound of Formula I is administered together with another active agent, such as camptothecin, a camptothecin analogue, a poly(ADP-ribose) polymerase (PARP) inhibitor, a cell cycle checkpoint inhibitor targeting ATR (Ataxia Telangiectansia-related kinase), a CHEK1 (cell cycle checkpoint kinase) inhibitor, a WEE1 inhibitor, a CDK (cyclin dependent kinase) inhibitor or other chemotherapeutic compound.

An effective amount of a pharmaceutical composition of the disclosure includes an amount sufficient to (a) inhibit the progression of cancer; (b) cause a remission; or (c) cause a cure of cancer, or (d) significantly reduce the level of cancer markers in a patient's blood, serum, or tissues.

An effective amount of a pharmaceutical composition described herein will also provide a sufficient concentration of the active agents in the concentration when administered to a patient. A sufficient concentration of an active agent is a concentration of the agent in the patient's body necessary to reduce cancer symptoms or slow cancer progression. Such an amount may be ascertained experimentally, for example by assaying blood concentration of the agent, or theoretically, by calculating bioavailability.

According to the methods of the disclosure, the compound or pharmaceutically acceptable salt of Formula I and at least one additional active agent may be: (1) co-formulated and administered or delivered simultaneously in a combined formulation; (2) delivered by alternation or in parallel as separate formulations; or (3) by any other combination therapy regimen known in the art.

When delivered in alternation therapy, the methods of the disclosure may comprise administering or delivering the compound or salt of Formula I and an additional active agent sequentially, e.g., in separate solution, emulsion, suspension, tablets, pills or capsules, or by different injections in separate syringes. In general, during alternation therapy, an effective dosage of each active ingredient is administered sequentially, i.e., serially, whereas in simultaneous therapy, effective dosages of two or more active ingredients are administered together. Various sequences of intermittent combination therapy may also be used.

Methods of treatment and pharmaceutical combinations including compounds or pharmaceutically acceptable salts of Formula I described herein together with any one or combination of the following compounds and substances as an additional active agent are provided by the disclosure:

Methods of inhibiting Tdp1 in vivo comprise providing a compound or pharmaceutically acceptable salt of Formula I to a patient having cancer, a concentration of the compound or salt of Formula I sufficient to inhibit Tdp1 in vitro are included herein. In this instance the concentration includes an in vivo concentration, such as a blood or plasma concentration. The concentration of compound sufficient to inhibit Tdp1 in vitro may be determined from an assay of Tdp1 inhibition such as the assay provided in Example 5, herein.

Methods of treatment include providing certain dosage amounts of a compound or pharmaceutically acceptable salt of Formula I to a patient. Dosage levels of each active agent of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single unit dosage form will vary depending upon the patient treated and the particular mode of administration. In certain embodiments about 0.1 mg to about 2000 mg, from about 10 mg to about 1500 mg, from about 100 mg to about 1000 ng, from about 200 mg to about 800 mg, or from about 300 to about 600 mg of a compound of Formula I and optionally from about 0.1 mg to about 2000 mg, from about 10 mg to about 1500 mg, from about 100 mg to about 1000 mg, from about 200 mg to about 800 mg, or from about 300 to about 600 mg of a compound of an additional active agent, for example a camptothecin, or camptothecin analogue are provided to a patient. It is preferred that each unit dosage form contains less than 1200 mg of active agent in total. Frequency of dosage may also vary depending on the compound used and the particular disease treated.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease in the patient undergoing therapy.

Packaged Formulations

Methods comprising providing a compound or salt of Tdp1 inhibitor, such as a compound of Formula I, in a container together with instructions for using the compound to treat a patient suffering from cancer are included herein.

Packaged pharmaceutical compositions/combinations are also included herein. Such packaged combinations include a Tdp1 inhibitor, such as a compound of Formula I, in a container together with instructions for using the combination to all cancers, including those presently treated with Top1 inhibitors: colon cancer, rectal cancer, ovarian cancer, small cell lung cancer, cervical cancer, or glioma, in a patient. Pharmaceutical combinations include at least one additional active agent. In certain embodiments the additional active agent is camptothecin or a camptothecin analog such as irinotecan or topotecan.

The packaged pharmaceutical combination may include a Tdp1 inhibitor, such as a compound of Formula I, and an additional active agent provided simultaneously in a single dosage form, concomitantly in separate dosage forms, or provided in separate dosage forms for administration separated by some amount of time that is within the time in which both the Tdp1 inhibitor, such as a compound of Formula I, and the additional active agent are within the bloodstream of the patient.

EXAMPLES

General Procedures

The major chemical reagents for synthesis were purchased from Alfa Aesar, Sigma Aldrich Co. or Aladdin Reagent Database Inc. (Shanghai), and were used without further purification unless otherwise indicated. Chemical reaction courses were monitored by silica gel $GF_{254}$ thin layer chromatography (TLC). Melting points were determined in open capillary tubes on a MPA100 Optimelt Automated Melting Point System without being corrected. Nuclear magnetic resonance spectra were recorded on a Bruker AVANCE III 400 MHz spectrometer using tetramethylsilane as an internal reference. Mass spectra were analyzed on an Agilent 6120 (Quadrupole LC-MS) mass spectrometer. The high-resolution mass spectra were analyzed on a SHIMADZU LCMS-IT-TOF mass spectrometer. All compounds tested for biological activities were analyzed by HPLC and their purities were more than 95%. The analysis condition is: detection at 220 nm, 1.0 ml/min flow rate, a linear gradient of 50% to 15% PBS buffer (pH 3) and 50% to 85% MeOH in 35 min.

All animals were obtained from Laboratory Animal Center of Sun Yat-sen University. All procedures were approved by the Animal Ethics Committee of Sun Yat-sen University, in accordance with National Institute of Health and Nutrition Guidelines for the Care and Use of Laboratory Animals.

All data are expressed as the mean±standard deviation. Statistical comparisons were conducted using a one-way analysis of variance (ANOVA) using the Prism statistical software package (GraphPad Software, USA), followed by Tukey's test.

Scheme 1 shows the synthesis of compounds benzophenanthridinone derivatives (19a/b-25a/b) and the dihydrobenzophenanthridine derivatives (26a/b-32a/b).

Scheme 1. Synthesis of compounds 19 a/b-25 a/b and 26 a/b-32 a/b

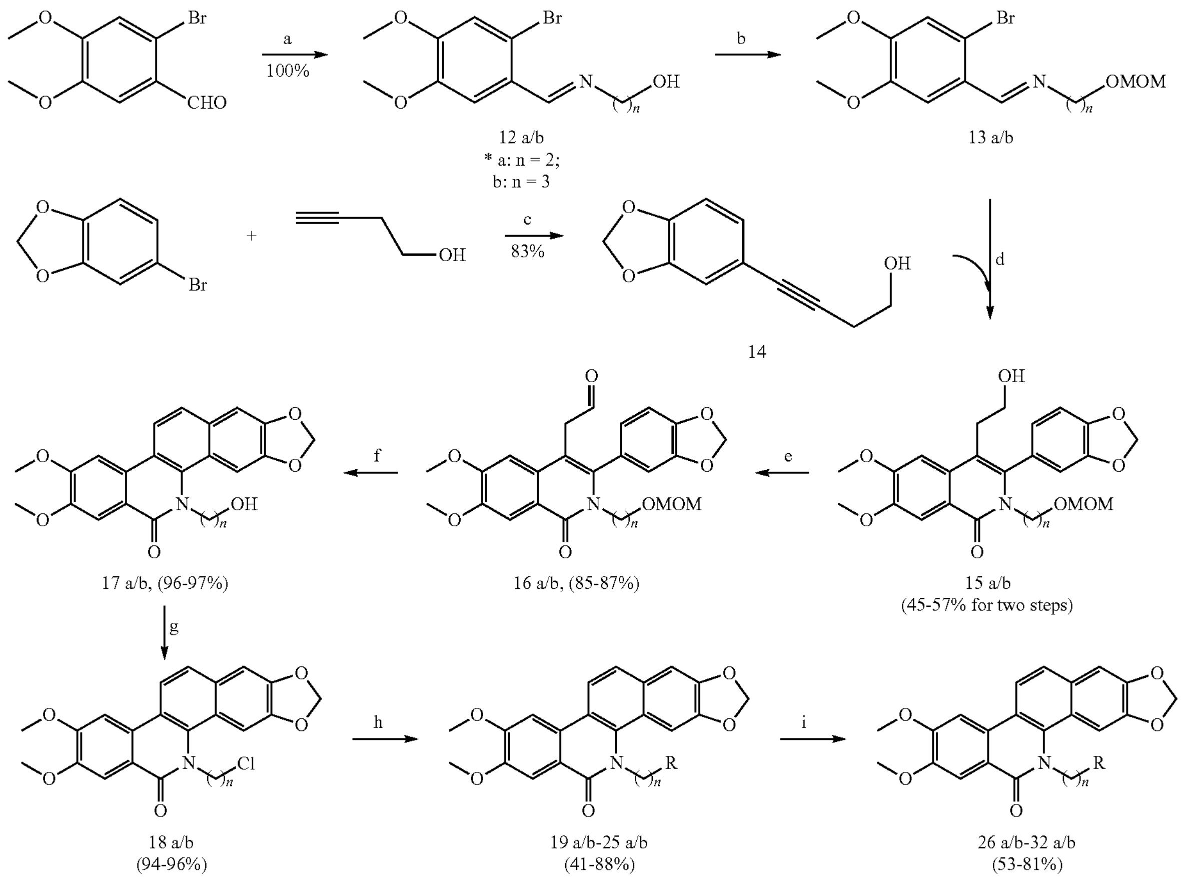

12 a/b
* a: n = 2;
b: n = 3

13 a/b

14

15 a/b
(45-57% for two steps)

16 a/b, (85-87%)

17 a/b, (96-97%)

18 a/b
(94-96%)

19 a/b-25 a/b
(41-88%)

26 a/b-32 a/b
(53-81%)

The reagents and conditions for Scheme 1 are as follows: (a) MeOH, $NH_2(CH_2)_nOH$, rt. (b) MOMCl, NaH, THF, 0° C. (c) $Pd(PPh_3)_4$, CuI, pyrrolidine, $H_2O$, 60° C. (d) i) $N_2$, $Ni(cod)_2$, $P(o\text{-}Tol)_3$, MeCN, 80° C.; ii) CsOH, $K_3[Fe(CN)_n]$, MeOH, $H_2O$, 80° C. (e) $(COC)_2$, DMSO, TEA, DCM, −60° C. (f) coned. hydrochloric acid, MeOH, rt. (g) $SOCl_2$, TCM, TEA, rt (h) amines (in Pressure Vessel for dimethylamine), PhMe, $K_2CO_3$, KI, reflux. (i) $LiAlH_4$, THE 0° C.

Abbreviations

The following abbreviations are used in the examples or elsewhere in the specification MeOH—methanol
rt—room temperature
THF—tetrahydrofuran
$Pd(PPh_3)_4$—tetrakis palladium
MOMCl—=methoxymethyl chloride
$Ni(cod)_2$—Bis(1,5-cyclooctadiene)nickel(0)
$P(o\text{-}Tol)_3$—Tri(o-tolyl)phosphine
DMSO=dimethylsulfoxide
PhMe=toluene
TEA=triethylamnine
DCM=dichloromethane
TCM=trichloromethane (chloroform)
AcOH=acetic acid
$POCl_3$=phosphoryl chloride
DMF=dimethylfornamide
$Br(CH_2)_3Br$=1,3-dibromopropane

Example 1. General Procedure for Synthesis of Compounds

General procedure for synthesis of Schiffs base 12a, 12b and 33. The reaction solution of 6-bromoveratraldehyde (9.8 g, 40 mmol) and amine (ethanolamine, 3-aminopropanol or 4-methoxybenzylamine, 42 mmol) in methanol (200 mL) was stirred at room temperature for 12 h, and then concentrated under reduced pressure. The residue was washed with petroleum ether (2×10 mL) to give a white solid. The Schiffs base intermediates were pure as shown by their $^1H$ NMR spectra and were used for next synthesis without further purification.

N-(2-hydroxylethyl)-6-bromoveratraldimine (12a). $^1H$ NMR ($CDCl_3$) δ 8.58 (s, 1H), 7.54 (s, 1H), 6.99 (s, 1H), 3.95-3.89 (m, 8H), 3.79 (t, J=4.7 Hz, 2H).

N-(3-hydroxylprapyl)-6-bromoveratraldimnine (12b). $^1H$ NMR ($CDCl_3$) δ 8.53 (s, 1H), 7.45 (s, 1H), 7.00 (s, 1H), 3.91-3.86 (m, 8H), 3.82 (t, J=6.2 Hz, 2H), 1.96 (quint, J=6.0 Hz, 2H).

N-(4-methoxybenzyl)-6-bromoveratraldimine (33). $^1H$ NMR ($CDCl_3$) δ 8.64 (t, J=1.3 Hz, 1H), 7.59 (s, 1H), 7.27-7.24 (m, 2H), 7.00 (s, 1H), 6.92-6.86 (m, 2H), 4.77 (s, 2H), 3.91 (s, 3H), 3.90 (s, 3H), 3.81 (s, 3H).

General procedure for the synthesis of 13a and 13b. Under nitrogen gas, the solution of NaH (60%, 6.69 g, 167 mmol) in THE (100 mL) was stirred and cooled to 0° C. for 15 min, and then, added dropwise to a solution of 12a (or 12b, 33 mmol) in THF (100 mL). The reaction solution was stirred at 0° C. for 1 h. And then, chloromethyl methyl ether (15 mL, 198 mmol) was added dropwise and stirred for 1 hi. The reaction was quenched by the addition of ethanol (20 mL) at 0° C. The reaction solution was concentrated under reduced pressure. The residue was dissolved in chloroform (100 mL) and was washed with saturated saline (3×50 mL). The organic layer was dried ($MgSO_4$) overnight and concentrated under reduced pressure to give crude intermediates 13a (or 13b), which was used immediately for next synthesis without further purification.

General procedure for synthesis of 15a, 15b and 34. Under nitrogen gas, the reaction solution of 13a (13b or 33, 2.7 mmol), 14 (520 mg, 2.73 mmol), $Ni(cod)_2$ (40 mg, 0.14 mmol), $P(o\text{-}Tol)_3$ (80 mg, 0.26 mmol) in freshly distilled MeCN (10 mL) was stirred at 80° C. for 3 h. Then $K_4[Fe(CN)_6]$(6.6 g, 20 mmol), CsOH solution (50% w/w in water, 3.6 mL, 40 mmol), MeOH (20 mL) and water (20 mL) were added. The reaction mixture was stirred vigorously at 80° C. for 12 h. The reaction mixture was cooled and extracted with chloroform (3×50 mL). The combined organic layers were dried ($MgSO_4$) and concentrated under reduced pressure. The residue was purified by silica gel column chromatography to give the target product.

3-(Benzo[d][1,3]dioxol-5-yl)-4-(2-hydroxethyl)-6,7-dimethoxy-2-(2-(methoxymethoxy)ethyl)isoquinolin-1(2H)-one (15a). $^1H$ NMR ($CDCl_3$) δ 7.89 (s, 1H), 7.11 (s, 1H), 6.91 (d, J==7.7 Hz, 1H), 6.79 (s, 1H), 6.77 (d, J=7.9 Hz, 1H), 6.05 (s, 2H), 4.48 (s, 2H), 4.07-3.95 (m, 8H), 3.77-3.62 (m, 4H), 3.20 (s, 3H), 2.80-2.66 (m, 2H). $^{13}C$ NMR ($CDCl_3$) δ 161.4, 153.6, 149.1, 148.0, 147.9, 140.1, 131.8, 128.3, 123.7, 119.1, 111.5, 110.5, 108.4, 108.1, 103.9, 101.5, 96.1, 64.4, 62.3, 56.1, 56.1, 55.0, 45.6, 32.1. ESI-MS m/z 458.1 $[M+1H]^+$. The structure was further confirmed with 2D NMR spectra.

3-(Benzo[d][1,3]dioxol-5-yl)-4-(2-hydroxyethyl)-6,7-dimethoxy-2-(3-(methoxymethoxy)propyl)isoquinolin-1(2H)-one (15b). $^1H$ NMR ($CDCl_3$) δ 7.90 (s, 11H), 7.11 (s, 11H), 6.92 (d, J=8.4 Hz, 1H), 6.79-6.74 (m, 2H), 6.07 (s, 2H), 4.48 (s, 2H), 4.02 (s, 3H), 4.01 (s, 3H), 3.71 (t, J=6.7 Hz, 2H), 3.44 (t, J=6.3 Hz, 2H), 3.27 (s, 3H), 2.82-2.67 (m, 2H). $^{13}C$ NMR ($CDCl_3$) δ 1613, 153.4, 149.1, 148.0, 139.9, 131.7, 128.4, 123.4, 111.3, 110.1, 108.5, 108.1, 103.7, 101.6, 96.0, 93.0, 91.5, 65.3, 62.4, 56.2, 56.1, 55.1, 44.0, 32.0, 29.2. ESI-MS m/z: 472.2 $[M+H]^+$. The structure was further confirmed with 2D NMR spectra.

3-(Benzo[d][1,3]dioxol-5-yl)-4-(2-hydroxyethyl)-6,7-dimethoxy-2-(4-methoxybenzyl)isoquinolin-1(2H)-one (34). $^1H$ NMR ($CDCl_3$) δ 7.91 (s, 1H), 7.13 (s, 1H), 6.79-6.62 (m, 5H), 6.51-6.41 (m, 2H), 5.99 (s, 1H), 5.95 (s, 1H), 5.06 (d, J=14.4 Hz, 1H), 4.94 (d, J=14.1 Hz, 11H), 3.98 (s, $^3H$), 3.94 (s, 3H), 3.69 (s, 3H), 3.64 (t, J=6.8 Hz, 2H), 2.77-2.64 (m, 2H). $^{13}C$ NMR ($CDCl_3$) δ 161.7, 158.5, 153.6, 149.1, 147.9, 147.6, 140.0, 131.9, 130.0, 128.0, 128.0, 123.8, 119.7, 113.6, 111.9, 110.4, 108.5, 108.1, 104.0, 101.4, 62.1 56.1, 56.1, 55.2, 48.6, 32.0. The structure was further confirmed with 2D NMR spectra.

General procedure for synthesis of 16a, 16b and 35. To a solution of $(COCl)_2$ (215 μL, 2.5 mmol) in freshly distilled $CH_2Cl_2$ (5 mL), DMSO (365 μL, 5 mmol) was added dropwise at −60° C. and the reaction solution was stirred for 15 min. A solution of 15a (15b or 34, 0.5 mmol) in freshly distilled $CH_2Cl_2$ (3 mL) was added dropwise and stirred at −60° C. for 30 min. And then, $Et_3N$ (1.5 mL, 10 mmol) was added dropwise. The reaction solution was brought to room temperature and stirred for 2 h. The reaction was quenched by the addition of water (1 mL) at 0° C. The reaction mixture was extracted with $CH_2Cl_2$ (3×20 mL). The organic layer was washed with saturated saline (3×30 mL) and dried ($MgSO_4$) overnight, and then concentrated under reduced pressure. The residue was purified by silica gel column chromatography to give the target product.

2-(3-(Benzo[d][1,3]dioxol-5-yl)-6,7-dimethoxy-2-(2-(methoxymethoxy)ethyl)-1-oxo-1,2-dihydroisoquinolin-4-yl)acetaldehyde (16a). $^1H$ NMR ($CDCl_3$) δ 9.57 (t J=1.8 Hz, 1H), 7.90 (s, 1H), 6.93 (d, J=7.8 Hz, 1H), 6.81-6.73 (m, 3H), 6.08 (s, 2H), 4.50 (s, 2H), 4.09 (d, J=6.8 Hz, 2H), 4.03 (s, 3H), 3.97 (s, 31H), 3.79-3.67 (m, 2H), 3.53-3.47 (m, 2H), 3.21 (s, 31H). $^{13}C$ NMR ($CDCl_3$) δ 199.7, 161.6, 153.8, 149.3, 148.4, 148.2, 141.8, 131.6, 128.0, 123.7, 119.5, 110.2, 108.7, 108.3, 106.4, 103.4, 101.7, 96.2, 64.4, 56.2, 56.1, 55.1, 45.9, 44.6. ESI-MS m/z: 455.2 $[M+H]^+$.

2-(3-(Benzo[d][1,3]dioxol-5-yl)-6,7-dimethoxy-2-(3-(methoxymethoxy)propyl)-1-oxo-1,2-dihydroisoquinolin-4-yl)acetaldehyde (16b). $^1H$ NMR ($CDCl_3$) δ 9.58 (s, 1H), 7.91 (d, J=2.4 Hz, 1H), 6.96-6.90 (m, 1H), 6.80-6.74 (m, 3H), 6.08 (s, 2H), 4.71-4.60 (m, 2H), 4.50 (s, 2H), 4.02 (s, 3H), 3.96 (s, 3H), 3.52-3.44 (m, 4H), 3.29 (s, 3H), 1.88-1.83 (m, 2H). $^{13}C$ NMR ($CDCl_3$) δ 199.6, 161.4, 153.7, 149.3, 148.4, 148.3, 141.5, 131.4, 128.0, 123.3, 119.7, 109.8, 108.8, 108.4, 106.3, 103.4, 101.7, 96.1, 65.3, 56.2, 56.1, 55.1, 44.5, 44.3, 29.2. ESI-MS m/z: 470.2 $[M+H]^+$.

2-(3-(Benzo[d][1,3]dioxol-5-yl)-6,7-dimethoxy-2-(4-methoxybenzyl)-1-oxo-1,2-dihydroisoquinolin-4-yl)acetaldehyde (35). $^1H$ NMR ($CDCl_3$) δ 9.56 (t, J=2.0 Hz, 1H), 7.98 (s, 1H), 6.87-6.72 (m, 7H), 6.52 (s, 1H), 6.05 (s, 2H), 5.19 (d, J=14.61 Hz, 1H), 5.06 (d, J=14.7 Hz, 11H), 4.05 (s, 3H), 3.99 (s, 3H), 3.76 (s, 3H), 3.50 (d, J=2.0 Hz, 2H). $^{13}C$ NMR ($CDCl_3$) δ 199.6, 161.8, 158.6, 153.8, 149.4, 148.3, 148.0, 141.7, 131.6, 129.9, 128.1, 127.7, 123.7, 119.7, 113.7, 110.0, 108.8, 108.5, 106.6, 103.5, 101.6, 56.2, 56.1, 55.1 48.8, 44.4. ESI-MS m/z: 488.2 $[M+H]^+$.

General procedure for the synthesis of 17a and 17b. The reaction solution of 16a (or 16b, 0.5 mmol) and concentrated hydrochloric acid (0.4 mL) in MeOH (10 mL) was added to a 50 mL round-bottomed flask. The flask was sealed with a rubber stopper. The reaction solution was stirred at room temperature overnight. And then, the formed precipitate was filtered and washed with saturated sodium bicarbonate and water consecutively. The crude solid was dried and purified by silica gel column chromatography to give the target product.

12-(2-Hydroxyethyl)-2,3-dimethoxy-[1,3]dioxolo[4',5':4,5]benzo[1,2-c]phenanthridin-13(12H)-one (17a). White solid, mp=228.2-229.7° C. $^1H$ NMR ($CDCl_3$) δ 8.00 (d, J=8.8 Hz, 1H), 7.91 (s, 1H), 7.59-7.57 (m, 2H), 7.25 (s, 1H), 7.19 (s, 1H), 6.11 (s, 2H), 5.08 (t, J=5.6 Hz, 1H), 4.54 (t, J=4.2 Hz, 2H), 4.37-4.33 (m, 2H), 4.12 (s, 3H), 4.06 (s, 3H). $^{13}C$ NMR ($CDCl_3$) δ 165.8, 154.0, 149.8, 147.5, 147.5, 135.4, 131.9, 129.4, 123.8, 120.8, 118.7, 118.3, 117.3, 108.5, 105.0, 102.8, 102.0, 101.7, 64.0, 56.8, 56.3, 56.2. HRMS (ESI) m/z: 394.1276 $[M+H]^+$, calcd for $C_{22}H_{20}NO_6$ 394.1285. ESI-MS m/z: 394.1 $[M+H]^+$.

12-(3-Hydroxypropyl)-2,3-dimethoxy-[1,3]dioxolo[4',5':4,5]benzo[1,2-c]phenanthridin-13(12H)-one (17b). White solid, mp=263.4-264.2° C. $^1H$ NMR ($CDCl_3$) δ 7.98 (d, J=8.8 Hz, 11H), 7.92 (s, 11H), 7.60 (s, 1H), 7.59-7.55 (m, 2H), 7.19 (s, 11H), 6.12 (s, 2H), 4.72 (t, J=6.6 Hz, 2H), 4.12 (s, 3H), 4.07 (s, 3H), 3.54 (t, J=6.6 Hz, 2H), 2.16-2.07 (m, 2H). $^{13}C$ NMR ($CDCl_3$) δ 165.0, 153.7, 149.8, 147.6, 147.4, 135.1, 131.7, 129.0, 123.5, 121.1, 119.4, 118.4, 117.5, 108.9, 104.9, 102.8, 102.3, 101.6, 60.1, 56.2, 56.2, 48.3, 32.8.

HRMS (ESI) m/z: 408.1457 $[M+H]^+$ calcd for $C_{23}H_{22}NO_6$ 408.1442. ESI-MS m/z: 408.1 $[M+H]^+$.

General procedure for the synthesis of 18a and 18b. To a solution of 17a (or 17b, 0.5 mmol) in freshly distilled chloroform (10 mL), $SOCl_2$ (0.8 mL) was added dropwise through a syringe. The reaction solution was stirred at room temperature for 1 h, and then quenched by the addition of water (5 mL) at 0° C. The precipitate was filtered and washed with saturated sodium bicarbonate and water consecutively. The residue was purified by silica gel column chromatography to give the target product.

12-(2-Chloroethyl)-2,3-dimethoxy-[1,3]dioxolo[4',5':4,5]benzo[1,2-c]phenanthridin-13(12H)-one (18a). White solid, mp=236.5-237.3° C. $^1H$ NMR (DMSO) δ 8.83 (d, J=9.0 Hz, 1H), 8.31 (s, 1H), 8.26 (s, 1H), 8.16 (d, J=9.0 Hz, 1H), 7.72 (s, 1H), 7.68 (s, 1H), 6.33 (s, 21), 5.76 (t, J=9.0 Hz, 2H), 5.35 (t, J=9.0 Hz, 2H), 4.20 (s, 3H), 4.04 (s, 3H). ESI-MS m/z: 412.1 (100%), 414.0 (33%) $[M+H]^+$.

12-(3-Chloropropyl)-2,3-dimethoxy-[1,3]dioxolo[4',5':4,5]benzo[1,2-c]phenanthridin-13(12H)-one (18b). White solid, mp=235.5-236.1° C. $^1H$ NMR ($CDCl_3$) δ 7.97 (d, i=8.8 Hz, 1H), 7.89 (s, 1H), 7.59-7.55 (m, 2H), 7.51 (s, 1H), 7.19 (s, 1H), 6.12 (s, 2H), 4.69 (t, J=6.8 Hz, 2H), 4.11 (s, 3H), 4.06 (s, 3H), 3.39 (t, J=6.4 Hz, 2H), 2.43-2.33 (m, 2H). HRMS (ESI) m/z: 426.1090 $[M+H]^+$, calcd for $C_{23}H_{21}NO_5Cl$ 426.1103. ESI-MS m/z: 426.1 (100%), 428.1 (33%) $[M+H]^+$.

General procedure for the synthesis of 19a/b-25a/b. The solution of 18a (or 18b, 0.87 mmol), $NEt_3$ (870 mg, 8.7 mmol) and amines (in Pressure Vessel for dimethylamine, 8.7 mmol) in PhMe (20 mL) was stirred and heated under reflux for 3-6 h, and then, cooled to room temperature. The solvent was evaporated under reduced pressure. The residue was purified by silica gel column chromatography to give target product.

12-(2-(Dimethylamino)ethyl)-2,3-dimethoxy-[1,3]dioxolo[4',5':4,5]benzo[1,2-c]phenanthridin-13(12H)-one (19a). White solid, mp=136.4-138.0° C. IR (KBr, $cm^{-1}$), 1632, 1611, 1590. $^1H$ NMR ($CDCl_3$) δ 7.97 (d, J=8.4 Hz, 1H). 7.91 (s, 1H), 7.66 (s, 1H), 7.57-7.54 (m, 2H), 7.18 (s, 1H), 6.10 (s, 2H), 4.66 (t, J=7.0 Hz, 2H), 4.10 (s, 3H), 4.05 (s, 3H), 2.78 (t, J=7.0 Hz, 2H), 2.21 (s, 6H). $^{13}C$ NMR ($CDCl_3$) δ 164.7, 153.6, 149.7, 147.5, 147.3, 135.5, 131.7, 128.9, 123.3, 121.3, 119.6, 118.3, 117.3, 108.8, 104.8, 102.9, 102.3, 101.5, 57.6, 56.2, 56.1, 50.1, 45.5. HRMS (ESI) m/z: 421.1761 $[M+H]^+$, calcd for $C_{21}H_{25}N_2O_5$ 421.1758.

12-(3-(Dimethylamino)propyl)-2,3-dimethoxy-[1,3]dioxolo[4',5':4,5]benzo[1,2-c]phenanthridin-13(12H)-one (19b). White solid, mp=173.2-174.3° C. IR (KBr, $cm^{-1}$). 1612 (sh.), 1582. $^1H$ NMR ($CDCl_3$) δ 7.97 (d, J=8.4 Hz, 1H), 7.91 (s, 1H), 7.58-7.53 (m, 2H), 7.48 (s, 1H), 7.19 (s, 1H), 6.13 (s, 2H), 4.55 (t, J=7.2 Hz, 2H), 4.12 (s, 3H), 4.07 (s, 3H), 2.51 (t, J=7.2 Hz, 2H), 2.34 (s, 6H), 2.18 (quint, J=7.2 Hz, 2H). $^{13}C$ NMR ($CDCl_3$) δ 164.7, 153.6, 149.6, 147.5, 147.4, 135.3, 131.7, 129.0, 123.3, 121.0, 119.5, 1183, 117.4, 108.8, 104.8, 102.9, 102.0, 101.6, 56.2, 56.1, 55.5, 49.7, 43.5, 25.1. HRMS (ESI) m/z: 435.1919 [M+H], calcd for $C_{25}H_{27}N_2O_5$ 435.1914.

12-(2-(Diethylamino)ethyl)-2,3-dimethoxy-[1,3]dioxolo[4',5':4,5]benzo[1,2-c]phenanthridin-13(12H)-one (20a). White powder, mp=129.1-129.5° C. IR (KBr, $cm^{-1}$), 1640, 1612, 1592. $^1H$ NMR ($CDCl_3$) δ 7.96 (d, J=8.4 Hz, 1H), 7.91 (s, 1H), 7.70 (s, 1H), 7.59-7.52 (m, 2H), 7.17 (s, 1H), 6.10 (s, 2H), 4.64 (t, J=6.4 Hz, 2H), 4.10 (s, 3H), 4.05 (s, 3H), 2.82 (t, J=6.4 Hz, 2H), 2.39 (q, J=7.2 Hz, 4H), 0.83 (t, J=7.2 Hz, 6H). $^{13}C$ NMR ($CDCl_3$) δ 165.0, 153.7, 149.8, 147.6, 147.5, 135.8, 131.8, 129.2, 123.3, 121.3, 119.9, 118.5, 117.6, 109.0, 104.9, 103.0, 102.8, 101.7, 56.4, 56.3, 51.6, 50.6, 47.5, 12.0. HRMS (ESI) m/z: 449.2078 $[M+H]^+$, calcd for $C_{27}H_{29}N_2O_5$ 449.2071.

12-(3-(Diethylamino)propyl)-2,3-dimethoxy-[1,3]dioxolo[4',5':4,5]benzo[1,2-c]phenanthridin-13(12H)-one (20b). White solid, mp=106.5-108.1° C. IR (KBr, $cm^{-1}$), 1637, 1613, 1581. $^1H$ NMR ($CDCl_3$) δ 7.99 (d, J=8.8 Hz, 1H), 7.92 (s, 1H), 7.59 (s, 1H), 7.57 (d, J=8.8 Hz, 1H), 7.53 (s, 1H), 7.20 (s, 1H), 6.12 (s, 2H), 4.56 (t, J=7.0 Hz, 2H), 4.13 (s, 3H), 4.07 (s, 3H), 2.63-2.43 (m, 6H), 2.22-2.10 (m, 2H), 0.98 (t, J=6.5 Hz, 6H). $^{13}C$ NMR ($CDCl_3$) δ 164.7, 153.6, 149.7, 147.6, 147.4, 135.4, 131.7, 129.0, 123.4, 121.2, 119.5, 118.4, 117.3, 108.7, 104.9, 102.8, 102.1, 101.6, 56.3, 56.2, 50.1, 49.4, 46.6, 25.3, 10.8. HRMS (ESI) m/z: 463.2233 $[M+H]^+$, calcd for $C_{27}H_3N_2O$ 463.2227. ESI-MS m/463.2 [M+H]. The structure was also confirmed with and single crystal analysis. Compound 20b was crystallized from dichloromethane as white cubic crystals. Data collections for 20b were performed at 103 K on a Xcalibur Nova diffractometer, using Cu Kα radiation (λ=1.54184 Å). The determination of crystal class and unit cell parameters was carried out by CrysAlisPro. The raw frame data was processed using CrysAlisPro (Rigaku Oxford Diffraction) to yield the reflection data file. The structure of 20b was solved by use of SHELXTL (Bruker, 2005) program. Refinement was performed on $F^2$ anisotropically for all the non-hydrogen atoms by the full-matrix least-squares method. The hydrogen atoms were placed at the calculated positions and were included in the structure calculation without further refinement of the parameters. Molecular formula =$C_{27}H_{32}N_2O_4$ molecular mass=449.57, monoclinic, a=9.41991(12) Å, b=10.11440(12) Å, c=23.7285(4) Å, β=91.6653(13)°, V=2259.82(5) Å, T=103 K. space group $P2_1/c$ (no. 14), Z=4, μ(Cu Kα)=0.710 $mm^{-1}$, 10230 reflections measured, 4283 unique ($R_{int}$=0.0458) which were used in all calculations. The final R (reflections)=0.0500, $wR^2$ (reflections)=0.1495. Crystallographic data for compound 20b has been deposited with the Cambridge Crystallographic Data Centre as supplementary publication number CCDC 1579803. Copies of the data can be obtained, free of charge, on application to CCDC, 12 Union Road, Cambridge CB2 1EZ, UK [fax: +44(0)1223-336033 or e-mail: deposit@cede.cam.ac.uk].

2,3-Dimethoxy-12-(2-(pyrrolidin-1-yl)ethyl)-[1,3]dioxolo[4',5':4,5]benzo[1,2-c]phenanthridin-13(12H)-one (21a). White solid, mp=209.2-210.3° C. IR (KBr, $cm^{-1}$), 1639, 1610, 1594. $^1H$ NMR ($CDCl_3$) δ 7.93-7.88 (m, 2H), 7.65 (s, 1H), 7.52 (s, 1H), 7.49 (d, J=8.8 Hz, 1H), 7.12 (s, 1H), 6.08 (s, 2H), 4.66 (t, J=7.2 Hz, 2H), 4.08 (s, 3H), 4.05 (s, 3H), 2.91 (t, J=7.2 Hz, 2H), 2.52-2.42 (m, 4H), 1.73-1.61 (m, 4H). $^{13}C$ NMR ($CDCl_3$) δ 164.7, 153.5, 149.6, 147.5, 147.3, 135.4, 131.6, 129.0, 123.2, 121.1, 119.6, 118.2, 117.3, 108.8, 104.7, 102.8, 102.6, 101.5, 56.2, 56.1, 54.3, 54.1, 51.0, 23.6. HRMS (ESI) m/z: 447.1916 $[M+H]^+$, calcd for $C_{26}H_{27}N_2O_5$ 447.1914. ESI-MS m/z: 447.2 $[M+H]^+$.

2,3-Dimethoxy-12-(3-(pyrrolidin-1-yl)propyl)-[1,3]dioxolo[4',5':4,5]benzo[1,2-c]phenanthridin-13(12H)-one (21b). White solid, mp=205.8-207.4° C. IR (KBr, $cm^{-1}$), 1640, 1612, 1596. $^1H$ NMR ($CDCl_3$) δ 7.95 (d, J=8.8 Hz, 1H), 7.88 (s, 1H), 7.56 (s, 1H), 7.54 (d, J=8.8 Hz, 1H), 7.48 (s, 1H), 7.16 (s, 1H), 6.10 (s, 2H), 4.57 (t, J=7.2 Hz, 2H), 4.10 (s, 3H), 4.05 (s, 3H), 2.59 (s, br. 4H), 2.52 (t, J=7.2 Hz, 2H), 2.19 (quint, J=7.2 Hz, 2H), 1.77 (s, br. 4H). $^{13}C$ NMR ($CDCl_3$) δ 164.7 153.6, 149.7, 147.6, 147.4, 135.3, 131.7, 129.0, 123.4, 121.2, 119.5, 118.3, 117.3, 108.8, 104.9, 102.9, 102.1, 101.6, 56.2, 56.2, 53.8, 53.3, 49.9, 27.4, 23.4. HRMS (ESI) m/z: 461.2067 $[M+H]^+$, calcd for $C_{27}H_{29}N_2O$, 461.2071.

2,3-Dimethoxy-12-(2-(piperidin-1-yl)ethyl)-[1,3]dioxolo [4',5':4,5]benzo[1,2-c]phenanthridin-13(12H)-one (22a). White solid, mp=178.3-180.1° C. IR (KBr, $cm^{-1}$), 1642, 1612, 1596. $^1H$ NMR ($CDCl_3$) δ 7.98 (d, J=8.8 Hz, 1H), 7.93 (s, 1H), 7.74 (s, 1H), 7.58 (s, 1H), 7.56 (d, J=8.8 Hz, 11H), 7.19 (s, 11H), 6.12 (s, 2H), 4.69 (t, J=6.6 Hz, 2H), 4.12 (s, 3H), 4.07 (s, 3H), 2.69 (t, J 6.6 Hz, 2H), 2.34-2.23 (m, 4H), 1.40-1.29 (m, 6H). $^{13}C$ NMR ($CDCl_3$) δ 165.0, 153.5, 149.5, 147.5, 147.3, 135.6, 131.6, 129.1, 123.1, 121.2, 119.7, 118.2, 117.5, 108.9, 104.7, 102.8, 102.7, 101.5, 57.2, 56.2, 56.1, 54.6, 49.8, 25.8, 24.2. HRMS (ESI) m/z: 461.2076 $[M+H]^+$, calcd for $C_{27}H_{29}N_2O_5$ 461.2071. EST-MS m/z: 461.2 $[M+H]^+$.

2,3-Dimethoxy-12-(3-(piperidin-1-yl)propyl)-[1,3]dioxolo[4',5':4,5]benzo[1,2-c]phenanthridin-13(12H)-one (22b). White solid, mp=110.6-112.3° C. IR (KBr, $cm^{-1}$), 1639, 1612, 1592. $^1H$ NMR ($CDCl_3$) δ 7.98 (d, J=8.7 Hz, 1H), 7.91 (s, 1H), 7.60-7.55 (m, 2H), 7.48 (s, 1H), 7.19 (s, 1H), 6.10 (s, 2H), 4.55 (d, J=7.2 Hz, 2H), 4.12 (s, 3H), 4.06 (s, 3H), 2.50 (d, J=7.2 Hz, 2H), 2.34-2.13 (s, 61H), 1.51-1.30 (m, 6H). $^{13}C$ NMR ($CDCl_3$) δ 164.6, 153.7, 149.7, 147.6, 147.5, 135.1, 131.7, 128.9, 123.5, 121.0, 119.4, 118.3, 117.4, 108.7, 104.9, 102.9, 102.0, 101.6, 56.2, 56.1, 55.7, 53.9, 50.1, 25.4, 25.2, 23.9. HRMS (ESI) m/z: 475.2227 $[M+H]^+$, calcd for $C_{28}H_{31}N_2O_5$ 475.2227.

2,3-Dimethoxy-12-(2-morpholinoethyl)-[1,3]dioxolo[4', 5':4,5]benzo[1,2-c]phenanthridin-13(12H)-one (23a). White solid, mp=220.5-221.1° C. IR (KBr, $cm^{-1}$), 1639, 1611, 1594. $^1H$ NMR ($CDCl_3$) δ 7.93 (d, J=8.7 Hz, 1H), 7.88 (s, 1H), 7.64 (s, 1H), 7.54 (s, 1H), 7.51 (d, J=8.7 Hz, 1H), 7.14 (s, 11H). 6.09 (s, 2H), 4.66 (t, J=6.2 Hz, 2H), 4.10 (s, 31H), 4.05 (s, 3H), 3.34 (s, br. 4H), 2.67 (t, J=6.2 Hz, 2H), 2.21 (s, br. 4H). $^1C$ NMR ($CDCl_3$) δ 165.2, 153.5, 149.6, 147.5, 147.4, 135.6, 131.5, 129.0, 123.2, 121.2, 119.7, 118.3, 117.6, 108.9, 104.8, 102.8, 102.5, 101.6, 66.9, 56.6, 56.2, 56.2, 53.4, 49.3. HRMS (ESI) m/z: 463.1875 $[M+H]^+$, calcd for $C_2H_{27}Na_2O_6$ 463.1864.

ESI-MS m/z: 463.2 $[M+H]^+$.

2,3-Dimethoxy-12-(3-morpholinopropyl)-[1,3]dioxolo [4',5':4,5]benzo[1,2-c]phenanthridin-13(12H)-one (23b). White solid, mp=203.1-205.0° C. IR (KBr, $cm^{-1}$), 1639, 1610, 1595. $^1H$ NMR ($CDCl_3$) δ 7.94 (d, J=8.5 Hz, 1H), 7.90 (s, 1H), 7.58-7.48 (m, 3H), 7.16 (s, 1H), 6.10 (s, 2H), 4.63 (t, J=6.2 Hz, 2H), 4.10 (s, 3H), 4.05 (s, 3H), 3.42 (s, br. 4H), 2.12 (s, br. 4H), 2.08-1.96 (m, 4H). $^{13}C$ NMR ($CDCl_3$) δ 164.6, 153.5, 149.7, 147.5, 147.2, 135.9, 131.6, 128.9, 123.0, 121.1, 119.7, 118.3, 117.2, 108.8, 104.8, 102.8, 102.4, 101.5, 66.9, 56.2, 56.2, 55.3, 53.3, 49.8, 25.3. HRMS (ESI) m/z: 477.2032 [M+H], calcd for $C_{27}H_{29}N_2O$ 477.2020.

2,3-Dimethoxy-12-(2-(4-methylpiperazin-1-yl)ethyl)-[1,3]dioxolo[4',5':4,5]benzo[1,2-c]phenanthridin-13(12H)-one (24a). White solid, mp=207.5-208.3° C. IR (KBr, $cm^{-1}$), 1635, 1613, 1590. $^1H$ NMR ($CDCl_3$) δ 7.93 (d, J=8.8 Hz, 1H), 7.89 (s, 1H), 7.61 (s, 1H), 7.54 (s, 1H), 7.52 (d, J=8.8 Hz, 1H), 7.15 (s, 1H), 6.10 (s, 2H), 4.67 (t, J=6.8 Hz, 2H), 4.10 (s, 3H), 4.05 (s, 3H), 2.67 (t, J=6.8 Hz, 2H), 2.64-2.56 (m, 2H), 2.38-2.32 (m, 4H), 2.23-2.16 (m, 5H). $^{13}C$ NMR ($CDCl_3$) δ 165.2, 153.5, 149.6, 147.5, 147.4, 135.5, 131.5, 129.0, 123.2, 121.2, 119.8, 118.2, 117.6, 109.0, 104.8, 102.8, 102.4, 101.5, 56.2, 56.2, 55.9, 54.7, 52.3, 49.5, 45.5. HRMS (ESI) m/z: 476.2177 $[M+H]^+$, calcd for $C_2H_{30}N_3O_5$ 476.2180. ESI-MS m/z: 476.2 $[M+H]^+$.

2,3-dimethoxy-12-(3-(4-methylpiperazin-1-yl)propyl)-[1,3]dioxolo[4',5':4,5]benzo[1,2-c]phenanthridin-13(12H)-one (24b). White solid, mp=170.9-172.8° C. IR (KBr, $cm-^1$), 1631, 1614, 1590. $^1H$ NMR ($CDCl_3$) δ 7.96 (d, J=8.7 Hz, 1H), 7.91 (s, 1H). 7.56 (s, 1H), 7.54 (d, J=8.7 Hz, 1H), 7.52 (s, 1H), 7.18 (s, 1H), 6.11 (s, 2H), 4.61 (t, J=6.8 Hz, 2H), 4.10 (s, 3H), 4.05 (s, 3H), 2.33-2.08 (m, 13H), 1.99 (t, J=6.8 Hz, 2H). $^{13}C$ NMR ($CDCl_3$) δ 164.7, 153.5, 149.7, 147.5, 147.2, 135.8, 131.6, 128.9, 123.2, 121.4, 119.7, 118.3, 117.3, 108.8, 104.8, 102.8, 102.5, 101.5, 56.3, 56.2, 54.9, 52.5, 49.9, 45.8, 29.7, 25.7. HRMS (ESI) m/z: 490.2334 $[M+H]^+$, calcd for $C_2$:$H_{32}N_3O$ 490.2336. ESI-MS m/z: 490.2 $[M+H]^+$.

12-(2-(1H-imidazol-1-yl)ethyl)-2,3-dimethoxy-[1,3]dioxolo[4',5':4,5]benzo[1,2-c]phenanthridin-13(12H)-one (25a). White powder, mp=254.2-255.6° C. IR (KBr, $cm^{-1}$), 1630, 1609, 1588. $^1H$ NMR ($CDCl_3$) δ 7.92-7.86 (m, 2H), 7.55-7.50 (m, 2H), 7.32 (s, 11H), 7.17 (s, 1H), 7.00 (s, 1H), 6.73 (s, 1H), 6.53 (s, 1H), 6.12 (s, 2H), 4.90 (t, J=6.4 Hz, 2H), 4.37 (t, J==6.4 Hz, 2H), 4.11 (s, 3H), 4.07 (s, 3H). $^{13}C$ NMR ($CDCl_3$) δ 164.7, 154.0, 149.9, 147.7, 147.7, 137.2, 134.7, 131.7, 129.6, 129.2, 123.9, 120.6, 1192, 118.5, 118.5, 117.8, 108.7, 105.3, 103.1, 101.8, 101.5, 56.4, 56.3, 51.9, 44.8. HRMS (ESI) m/z: 444.1550 $[M+H]^+$, calc'd for $C_{25}H_{22}N_3O_5$ 444.1554. ESI-MS m/z: 444.1 $[M+H]^+$.

12-(3-(1H-imidazol-1-yl)propyl)-2,3-dimethoxy-[1,3]dioxolo[4',5':4,5]benzo[1,2-c]phenanthridin-13(12H)-one (25b). White powder, mp=200.1-200.9° C. IR (KBr, cm-), 1631, 1610, 1591. $^1H$ NMR ($CDCl_3$) δ 7.99 (d, J=8.8 Hz, 1H), 7.90 (s, 1H), 7.60 (d, J=8.8 Hz, 1H), 7.58 (s, 1H), 7.31 (s, 1H), 7.19 (s, 1H), 7.06 (s, 1H), 6.89 (s, 1H), 6.61 (s, 1H), 6.11 (s, 2H), 4.51 (t, J=6.8 Hz, 2H), 4.12 (s, 3H), 4.07 (s, 3H), 3.71 (L, J=6.8 Hz, 2H), 2.35 (quint, J=6.8 Hz, 2). $^{13}C$ NMR ($CDCl_3$) δ 164.7, 153.9, 149.9, 147.8, 147.6, 136.9, 135.2, 131.8, 129.5, 129.0, 123.8, 121.1, 119.5, 118.6, 118.4, 117.5, 108.8, 105.1, 103.0, 101.8, 101.7, 56.4, 56.3, 48.8, 44.3, 30.2. HRMS (ESI) m/z: 458.1703 $[M+H]^+$, calcd for $C_{26}H_{24}N_3O_5$ 458.1710. ESI-MS m/z: 458.2 $[M+H]^+$.

General procedure for synthesis of 26a/b-32a/b. Under nitrogen gas, to a solution of oxynitidine analogue (19a/b-25a/b, 0.45 mmol) in dried THF (100 mL), the solution of $LiAlH_4$ (3.6 mL, 9.0 mmol) in THF was added at 0° C. dropwise. And then, the reaction solution was stirred and heated under reflux for 3-6 h. The reaction was quenched by the addition of aqueous NaOH solution (5%, 5 mL) at 0° C. The solvent was evaporated under reduced pressure. The residue was purified by silica gel column chromatography to give the target product.

2-(2,3-Dimethoxy-[1,3]dioxolo[4',5':4,5]benzo[1,2-c] phenanthridin-12(131)-yl)-N,N-dimethylethan-1-amine (26a). White powder, mp=109.4-109.6° C. $^1H$ NMR ($CDCl_3$) δ 7.74 (s, 1H), 7.68 (d, J=8.8 Hz, 1H), 7.50 (d, J=8.8 Hz, 1H), 7.30 (s, 1H), 7.12 (s, 1H), 6.80 (s, 1H), 6.06 (s, 2H), 4.21 (s, 2H), 4.00 (s, 3H), 3.95 (s, 3H), 2.88 (t, J=6.4 Hz, 2H), 2.60 (t, J=6.4 Hz, 2H), 2.24 (s, 6H). $^{13}C$ NMR ($CDCl_3$) δ 148.8, 148.7, 148.2, 147.6, 142.9, 131.0, 126.6, 125.5, 125.2, 124.9, 123.9, 119.9, 110.2, 106.4, 104.5, 101.2, 100.8, 58.4, 56.3, 56.2, 50.8, 50.0, 46.0. HRMS (ESI) m/z: 407.1960 $[M+H]^+$, calcd for $C_{24}H_{27}N_2O_4$ 407.1965. ESI-MS m/z: 407.2 $[M+H]^+$.

3-(2,3-Dimethoxy-[1,3]dioxolo[4',5':4,5]benzo[1,2-c] phenanthridin-12(13H)-yl)-N,N-dimethylpropan-1-amine (26b). White powder, mp=82.4-83.0° C. $^1H$ NMR ($CDCl_3$) δ 7.68 (d, J=8.8 Hz, 1H), 7.66 (s, 1H), 7.49 (d, J=8.8 Hz, 1H), 7.30 (s, 1H), 7.11 (s, 1H), 6.78 (s, 1H), 6.05 (s, 2H), 4.16 (s, 2H), 3.99 (s, 3H), 3.95 (s, 3H), 2.75 (t, J=7.6 Hz, 2H), 2.29 (t, J=7.6 Hz, 2H), 2.21 (s, 6H), 1.81 (quint, J=7.6 Hz, 2H). $^{13}C$ NMR ($CDCl_3$) δ 148.9, 148.7, 148.2, 147.5, 143.0, 131.0, 126.6, 125.6, 125.1, 125.0, 123.9, 120.0, 110

1, 106.5, 104.5, 101.1, 100.8, 57.3, 56.3, 56.2, 50.0, 45.6, 26.8. HRMS (ESI) m/z: 421.2121 [M+H], calcd for $C_{25}H_{29}N_2O_4$ 421.2122. ESI-MS m/z: 421.3 $[M+H]^+$.

2-(2,3-Dimethoxy-[1,3]dioxolo[4',5':4,5]benzo[1,2-c] phenanthridin-12(13H)-yl)-N,N-diethylethan-1-amine (27a). White powder, mp=68.1-68.2° C. $^{II}$ NMR ($CDCl_3$) δ 7.80 (s, 1H), 7.67 (d, J=8.4 Hz, 1H), 7.48 (d, J=8.4 Hz, 1H), 7.30 (s, 1H), 7.11 (s, 1H), 6.78 (s, 1H), 6.04 (s, 2H), 4.20 (s, 2H), 3.99 (s, 3H), 3.94 (s, 3H), 2.88 (t, J=6.4 Hz, 2H), 2.75 (t, J=7.2 Hz, 2H), 2.50 (q, J=7.2 Hz, 41), 1.01 (t, J=7.2 Hz, 6H). $^{13}C$ NMR ($CDCl_3$) δ 149.0, 148.8, 148.2, 147.6, 143.1, 131.1, 126.6, 125.7, 125.4, 124.9, 123.7, 119.9, 110.3, 106.8, 104.5, 101.1, 101.0, 56.4, 56.3, 52.0, 50.9, 50.0, 47.4, 11.9. HRMS (ESI) m/z: 435.2281 $[M+H]^+$, calcd for $C_{26}H_{31}N_2O_4$ 435.2278.

3-(2,3-Dimethoxy-[1,3]dioxolo[4',5':4,5]benzo[1,2-c] phenanthridin-12(13H)-yl)-N,N-diethylpropan-1-amine (27b). White solid, mp=119.5-121.5° C. $^1H$ NMR ($CDCl_3$) δ 7.68 (d, J=8.5 Hz, 1H), 7.65 (s, 1H), 7.49 (d, J=8.5 Hz, 11), 7.30 (s, 1H), 7.11 (s, 1H), 6.79 (s, 1H), 6.05 (s, 2H), 4.17 (s, 2H), 3.99 (s, 3H), 3.95 (s, 3H), 2.74 (t, J=7.6 Hz, 2H), 2.60-2.50 (m, 4H), 2.50-2.42 (m, 2H), 1.88-1.79 (m, 2H), 1.02 (t, J=7.0 Hz, 6H). $^{13}C$ NMR ($CDCl_3$) δ 148.8, 148.6, 148.1, 147.4, 143.0, 130.9, 126.5, 125.5, 125.0, 124.8, 123.7, 119.9, 110.0, 106.4, 104.4, 101.0, 100.7, 56.2, 56.1, 50.7, 50.1, 49.9, 46.8, 26.2, 11.6. HRMS (ESI) m/z: 449.2447 $[M+H]^+$, calcd for $C_{27}H_{33}N_2O_4$ 449.2435. ESI-MS m/z: 449.24 $[M+H H]^+$.

2,3-Dimethoxy-12-(2-(pyrrolidin-1-yl)ethyl)-12,13-dihydro-[1,3]dioxolo[4',5':4,5]benzo[1,2-c]phenanthrdine (28a). White solid, mp=84.3-85.8° C. $^1H$ NMR ($CDCl_3$) δ 7.70-7.64 (m, 2H), 7.48 (d, J=8.5 Hz, 1H), 7.29 (s, 1H), 7.10 (s, 1H), 6.81 (s, 1H), 6.04 (s, 2H), 4.21 (s, 2H), 3.98 (s, 3H), 3.95 (s, 3H), 3.12 (d, J=7.2 Hz, 2H), 2.86 (d, J=7.2 Hz, 2H), 2.73-2.64 (m, 41), 1.87-1.81 (m, 4H). $^{13}C$ NMR ($CDCl_3$) δ 148.9, 148.7, 148.2, 147.5, 141.7, 130.9, 126.4, 125.3, 125.2, 125.1, 124.0, 119.8, 110.1, 106.5, 104.4, 101.1, 100.5, 56.2, 56.1, 54.2, 51.2, 50.3, 23.3. HRMS (ESI) m/z: 433.2120 $[M+H]^+$, calcd for $C_{25}H_{29}N_2O_4$ 433.2122. ESI-MS m/z: 433.2 $[M+H]^+$.

2,3-Dimethoxy-12-(3-(pyrrolidin-1-yl)propyl)-12,13-dihydro-[1,3]dioxolo[4',5':4,5]benzo[1,2-c]phenanthridine (28b). White solid, mp=135.8-137.5° C. $^1H$ NMR ($CDCl_3$) δ 7.70-7.64 (m, 2H), 7.47 (d, J=8.5 Hz, 1H), 7.29 (s, 11H), 7.10 (s, 1H), 6.78 (s, 1H), 6.03 (s, 2H), 4.16 (s, 2H), 3.98 (s, 3H), 3.94 (s, 3H), 2.76 (t, J=7.2 Hz, 2H), 2.54-2.47 (m, 6H), 1.93-1.83 (m, 2H), 1.78 (s, br. 4H). $^{13}C$ NMR ($CDCl_3$) δ 148.8, 148.6, 148.0, 147.4, 143.0, 130.9, 126.5, 125.4, 124.9, 124.9, 123.7, 119.9, 110.0, 106.4, 104.4, 101.0, 100.7, 56.2, 56.1, 54.2, 53.8, 49.8, 49.7, 27.8, 23.4. HRMS (ESI) m %: 447.2273 $[M+H]^+$, calcd for $C_{27}H_{31}N_2O_4$ 447.2278.

2,3-Dimethoxy-12-(2-(piperidin-1-yl)ethyl)-12,13-dihydro-[1,3]dioxolo[4',5':4,5]benzo[1,2-c]phenanthridine (29a). White powder, mp=140.4-141.5° C. $^1H$ NMR ($CDCl_3$) δ 7.82 (s, 1H), 7.67 (d, J=8.4 Hz, 1H), 7.48 (d, J=8.4 Hz, 1H), 7.29 (s, 1H), 7.11 (s, 1H), 6.79 (s, 1H), 6.05 (s, 2H), 4.23 (s, 2H), 3.99 (s, 3H), 3.95 (s, 3H), 2.92 (t, J=5.8 Hz, 2H), 2.61 (t, J=6.4 Hz, 2H), 2.47-2.26 (m, 41H), 1.67-1.57 (n, 61-1). $^{13}C$ NMR ($CDCl_3$) δ 148.9, 148.7, 148.2, 147.6, 143.0, 131.0, 126.6, 125.6, 125.4, 124.9, 123.8, 119.9, 110.3, 106.6, 104.4, 101.1, 101.1, 58.3, 56.3, 56.2, 55.3, 50.8, 49.2, 26.0, 24.5. HRMS (ESI) m/z: 447.2275 $[M+H]^+$, calcd for $C_{27}H_{31}N_2O_4$ 447.2278. ESI-MS m/z: 447.3 $[M+H]^+$.

2,3-Dimethoxy-12-(3-(piperidin-1-yl)propyl)-12,13-dihydro-[1,3]dioxolo[4',5':4,5]benzo[1,2-c]phenanthridine (29b). White powder, mp=131.0-131.5° C. $^1H$ NMR ($CDCl_3$) δ 7.68 (d, J=8.4 Hz, 1H), 7.66 (s, 1H), 7.49 (d, J=8.4 Hz, 1H), 7.30 (s, 1H), 7.11 (s, 1H), 6.78 (s, 1H), 6.05 (s, 2H), 4.16 (s, 2H), 3.99 (s, 3H), 3.95 (s, 3H), 2.73 (t, J=7.6 Hz, 2H), 2.44-2.34 (m, 4H), 2.32 (t, J=7.6 Hz, 2H), 1.86 (quint, J=7.6 Hz, 2H), 1.62-1.55 (m, 6H). $^{13}C$ NMR ($CDCl_3$) δ 148.9, 148.6, 148.2, 147.5, 143.1, 131.0, 126.6, 125.5, 125.0, 124.9, 123.9, 120.0, 110.1, 106.5, 104.5, 101.1, 100.8, 56.8, 563, 56.2, 54.8, 50.0, 49.9, 26.0, 24.5. HRMS (ESI) m/z: 461.2432 $[M+H]^+$, calcd for $C_{28}H_{33}N_2O_4$ 461.2435. ESI-MS m/z: 461.3 $[M+H]^+$.

2,3-Dimethoxy-12-(2-morpholinoethyl)-12,13-dihydro-[1,3]dioxolo[4',5':4,5]benzo[1,2-c]phenanthridine (30a). White solid, mp=119.9-121.5° C. $^1H$ NMR ($CDCl_3$) 37.95 (s, 1H), 7.69 (d, J=8.6 Hz, 1H), 7.51 (d, J=8.6 Hz, 1H), 7.32 (s, 1H), 7.13 (s, 1H), 6.80 (s, 11H), 6.07 (s, 2H), 4.25 (s, 2H), 4.01 (s, 3H), 3.97 (s, 31H), 3.75 (t, J=4.6 Hz, 4H), 2.93 (t, J=6.2 Hz, 2H), 2.62 (t, J=6.2 Hz, 2H), 2.47 (t, J=4.2 Hz, 4H). $^{13}C$ NMR ($CDCl_3$) δ 148.8, 148.7, 148.1, 147.5, 142.7, 130.9, 126.5, 125.6, 125.2, 124.8, 123.7, 119.8, 110.1, 106.5, 104.3, 101.0, 100.9, 67.0, 57.9, 56.2, 56.1, 54.3, 50.7, 48.9. HRMS (ESI) m/z: 449.2073 $[M+H]^+$, calcd for $C_{26}H_{29}N_2O_5$ 449.2071. ESI-MS m/z: 449.2 $[M+H]^+$.

2,3-Dimethoxy-12-(3-morpholinopropyl)-12,13-dihydro-[1,3]dioxolo[4',5':4,5]benzo[1,2-c]phenanthridine (30b). White solid, mp=138.2-1139.9° C. $^1H$ NMR ($CDCl_3$) 37.70 (s, 1H), 7.68 (d, J=8.5 Hz, 1H), 7.49 (d, J=8.5 Hz, 1H), 7.30 (s, 1H), 7.11 (s, 11H), 6.77 (s, 1H), 6.05 (s, 2H), 4.16 (s, 2H), 3.99 (s, 3H), 3.95 (s, 3H), 3.72 (t, J=4.4 Hz, 4H), 2.77 (t, J=7.2 Hz, 2H), 2.44 (s, br. 4H), 2.39 (d, J=7.2 Hz, 2H), 1.83 (quint, J=7.2 Hz, 2H). $^{13}C$ NMR ($CDCl_3$) δ 148.8, 148.6, 148.1, 147.5, 142.9, 130.9, 126.5, 125.5, 124.9, 123.8, 119.9, 110.0, 106.4, 104.4, 101.0, 100.8, 67.0, 56.2, 56.1, 53.8, 49.8, 49.4, 25.3. HRMS (ESI) m/z: 463.2212 $[M+H]^+$, calcd for $C_{27}H_{31}N_2O_5$ 463.2227.

2,3-Dimethoxy-12-(2-(4-methylpiperazin-1-yl)ethyl)-12,13-dihydro-[1,3]dioxolo[4',5':4,5]benzo[1,2-c]phenanthridine (31a). White solid, mp=165.8-167.0° C. $^1H$ NMR ($CDCl_3$) 37.86 (s, 1H), 7.67 (d, J=8.6 Hz, 1H), 7.48 (d, J=8.5 Hz, 1H), 7.30 (s, 1H), 7.11 (s, 1H), 6.78 (s, 1H), 6.05 (s, 2H), 4.23 (s, 2H), 3.99 (s, 3H), 3.95 (s, 31H), 2.90 (t, J=6.4 Hz, 2H), 2.67-2.32 (m, 10H), 2.30 (s, 3H). $^{13}C$ NMR ($CDCl_3$) δ 148.7, 148.6, 148.1, 147.5, 142.8, 130.9, 126.5, 125.5, 125.1, 124.8, 123.7, 119.8, 110.0, 106.4, 104.3, 101.0, 100.9, 57.4, 56.2, 56.1, 55.1, 53.7, 50.7, 49.2, 46.0. HRMS (ESI) m/z: 462.2398 $[M+H]^+$, calcd for $C_{27}H_{32}N_3O_4$ 462.2387. EST-MS m/z: 462.2 $[M+H]^+$.

2,3-Dimethoxy-12-(3-(4-methylpiperazin-1-yl)propyl)-12,13-dihydro-[1,3]dioxolo[4',5':4,5]benzo[1,2-c] phenanthridine (31b). White solid, mp=52.9-54.8° C. $^1H$ NMR ($CDCl_3$) δ 7.71-7.65 (m, 2H), 7.49 (d, J=8.5 Hz, 1H), 7.30 (s, 1H), 7.11 (s, 1H), 6.78 (s, 1H), 6.05 (s, 2H), 4.16 (s, 2H), 3.99 (s, 3H), 3.95 (s, 3H), 2.75 (t, J=7.2 Hz, 2H), 2.60-2.35 (m, 10H), 2.29 (s, 3H), 1.84 (quint, J=7.6 Hz, 2H). $^{13}C$ NMR ($CDCl_3$) δ 148.8, 148.6, 148.0, 147.4, 142.9, 130.9, 126.5, 125.5, 124.9, 124.9, 123.8, 119.9, 110.0, 106.5, 104.4, 101.0, 100.8, 56.2, 56.1, 55.7, 55.0, 53.1, 49.8, 49.7, 45.9, 25.7. HRMS (ESI) m/z: 476.2525 $[M+H]^+$, calcd for $C_{28}H_{34}N_3O_4$ 476.2544.

12-(2-(1H-imidazol-1-yl)ethyl)-2,3-dimethoxy-12,13-dihydro-[1,3]dioxolo[4',5':4,5]benzo[1,2-c]phenanthridine (32a). White powder, mp=199.2-200.4° C. $^1H$ NMR ($CDCl_3$) δ 7.67 (d, J=8.6 Hz, 1H), 7.56-7.46 (m, 2H), 7.31 (s, 1H), 7.13 (s, 1H), 7.10 (s, 1H), 6.96 (s, 1H), 6.93 (s, 1H), 6.74 (s, 11H), 6.04 (s, 2H), 4.12 (s, 2H), 4.09 (t, J=6.4 Hz, 2H), 4.00 (s, 3H), 3.96 (s, 3H), 3.11 (t, J=6.4 Hz, 2H). $^{13}C$ NMR ($CDCl_3$) δ 149.2, 149.0, 148.5, 147.8, 141.4, 137.5, 131.1, 129.8, 126.3, 125.4, 125.4, 124.8, 124.5, 119.9, 119.3, 1101, 106.8, 104.5, 101.3, 100.0, 56.4, 56.2, 52.7, 50.8, 45.5. HRMS (ESI) m/z: 430.1759 $[M+H]^+$, calcd for $C_{25}H_{24}N_3O_4$ 430.1761.

ESI-MS m/z: 430.2 $[M+H]^+$.

12-(3-(1H-imidazol-1-yl)propyl)-2,3-dimethoxy-12,13-dihydro-[1,3]dioxolo[4',5':4,5]benzo[1,2-c]phenanthridine (32b). White powder, mp=143.2-144.3° C. $^1$H NMR ($CDCl_3$) δ 7.68 (d, J=8.4 Hz, 1H). 7.54-7.49 (m, 2H), 7.38 (s, 1H), 7.31 (s, 1H), 7.12 (s, 1H). 7.02 (s, 1H), 6.83 (s, 1H), 6.75 (s, 1H), 6.06 (s, 2H), 4.14 (s, 2H), 4.00 (s, 3H), 3.95 (s, 3H), 3.92 (t, J=7.2 Hz, 2H), 2.81 (t, J=7.2 Hz, 2H), 2.08 (quint, J=7.2 Hz, 2H). $^{13}$C NMR ($CDCl_3$) δ 149.1, 148.8, 148.3, 147.7, 142.0, 137.0, 131.0, 129.6, 126.4, 125.4, 125.2, 125.0, 124.2, 120.0, 118.8, 109.9 106.6, 104.6, 101.2, 100.3, 56.3, 56.2, 50.8, 49.6, 45.1, 30.0. FIRMS (ESI) m/z: 444.1920 $[M+H]^+$, calcd for $C_{26}H_{26}N_3O_4$ 444.1918.

Example 2. Synthesis of Compounds 39-45

The 6-alkoxy substituted benzophenanthridinone derivatives (39a/b-45a/b) were synthesized as shown in Scheme 2.

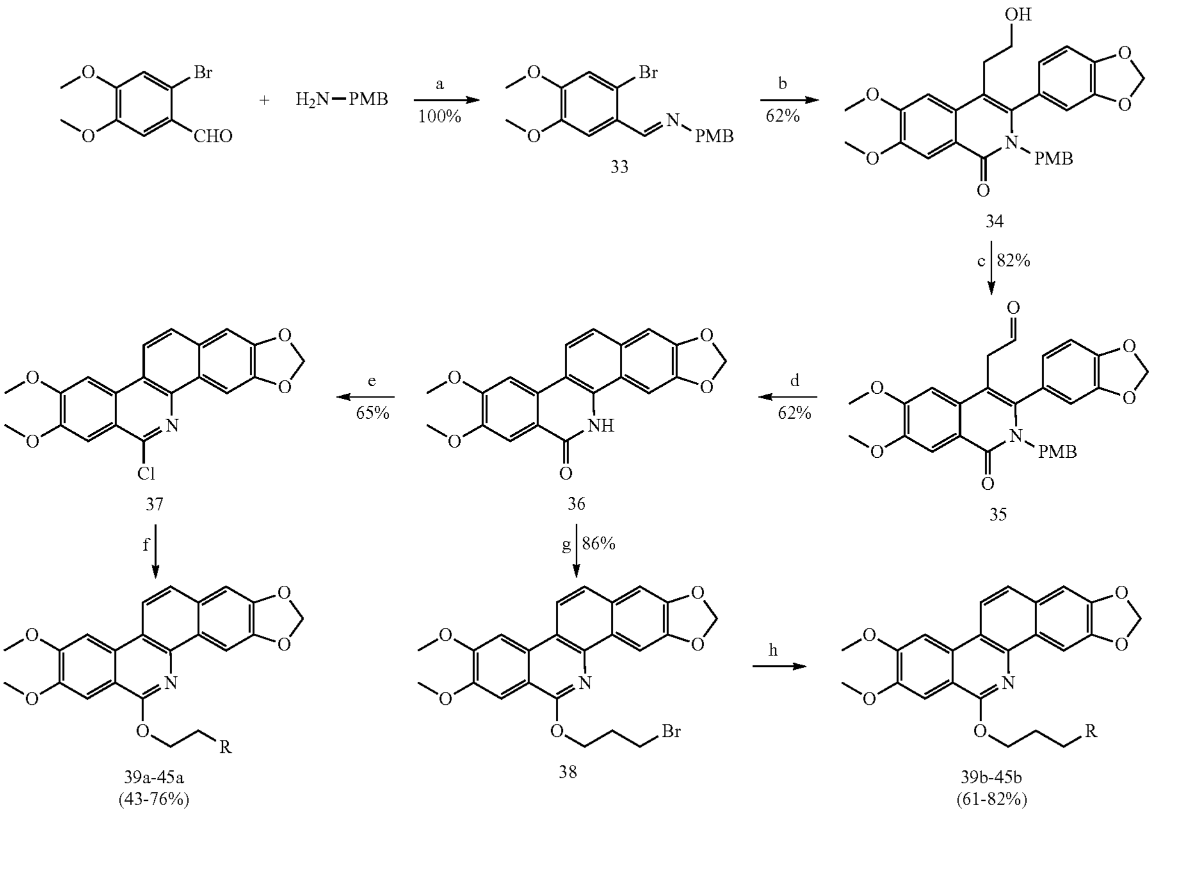

The reagents and conditions used in Scheme 2 are as follows. (a) MeOH, rt. (b) i) $N_2$, compound 1.4, $Ni(cod)_2$, $P(o\text{-}Tol)_3$, MeCN, 80° C.; ii) CsOH, $K_3Fe(CN)_6$, MeOH, $H_2O$, 80° C. (c) $(COCl)_2$, DMSO, TEA, DCM, −60° C. (d) HCl, AcOH, rt. (e) $POCl_3$, DMF, 100° C. (f) $HOCHCH_2R$, THF, NaH, 70° C. (g) $Br(CH_2)_3Br$, DMF, NaH rt. (h) amines (in Pressure Vessel for dimethylamine) DMF, $K_2CO_3$, KI, rt.

Synthesis of 2,3-dimethoxy-[1,3]dioxolo[4',5':4,5]benzo[1,2-c]phenanthridin-13(12H)-one (36). The reaction solution of 35 (270 mg, 0.5 mmol) and concentrated hydrochloric acid (0.4 mL) in acetic acid (4 mL) was added to a 50 mL round-bottomed flask. The flask was sealed with a rubber stopper. The reaction solution was stirred at room temperature overnight. And then, the formed precipitate was filtered and washed with saturated sodium bicarbonate and water consecutively. The crude solid was dried and purified by silica gel column chromatography to give white solid 36, IR (KBr, $cm^{-1}$), 1643 (sh), 1500. $^1$H NMR (DMSO) δ 11.53 (s, 1H), 8.36 (s, 1H), 8.33 (d, J=8.8 Hz, 1H), 7.92 (s, 1H), 7.75 (s, 1H), 7.62 (d, J=8.8 Hz, 1H), 7.41 (s, 1H), 6.18 (s, 2H), 4.05 (s, 3H), 3.93 (s, 3H). ESI-MS m/% 350.1 $[M+H]^+$.

Synthesis of 13-chloro-2,3-dimethoxy-[1,3]dioxolo[4',5':4,5]benzo[1,2-c]phenanthridine (37). The reaction solution of 36 (350 mg, 1 mmol), $POCl_3$ (10 mL) and two drops of DMF was stirred at 100° C. overnight. The reaction was quenched by the addition of water (20 mL) at 0° C. and diluted with ethyl acetate (20 mL). The organic layer was washed with saturated sodium bicarbonate (10 mL) and water (10 mL) consecutively, and then concentrated under reduced pressure. The residue was purified by silica gel column chromatography to give white solid 37. $^1$H NMR ($CDCl_3$) δ 8.57 (s, 1H), 8.20 (d, J=8.8 Hz, 1H), 7.84 (s, 1H), 7.80 (d, J=8.8 Hz, 1H), 7.74 (s, 1H), 7.23 (s, 1H), 6.13 (s, 2H), 4.17 (s, 3H), 4.11 (s, 3H). The $^1$H NMR spectrum is similar to that reported.[7] ESI-MS m/z: 368.1 (100%), 370.0 (35%) $[M+H]^+$.

Synthesis of 13-(3-bromopropoxy)-2,3-dimethoxy-[1,3]dioxolo[4',5':4,5]benzo[1,2-c]phenanthridine (38). The reaction solution of 36 (300 mg, 0.86 mmol) and NaH (60%, 105 mg, 2.7 mmol) in DMF (20 mL) was stirred at room temperature for 30 min. 1,3-dibromopropane (869 mg, 4.3 mmol) was added and stirred at room temperature for 3 h. And then, the reaction solution was added with water (10 mL) at 0° C., and diluted by ethyl acetate (50 mL). The organic layer was washed with saturated saline (3×20 mL) and dried over $MgSO_4$, and then concentrated under reduced pressure. The residue was purified by silica gel column chromatography to give white solid 38. IR (KBr, $cm^{-1}$), 1596. $^1$H NMR ($CDCl_3$) (8.47 (s, 1H), 8.08 (d, J=8.8 Hz, 1H), 7.73 (s, 1H), 7.62 (t, J=8.8 Hz, 1H), 7.60 (s, 1H), 7.19 (s, 1H), 6.09 (s, 2H), 4.88 (t, J=7.0 Hz, 2H), 4.11 (s, 3H), 4.05 (s, 31H), 3.69 (d, J=7.0 Hz, 2H), 2.57 (quint, J=70 Hz, 2H). $^{13}$C NMR ($CDCl_3$) δ 156.9, 152.7, 149.2, 148.0, 147.8, 138.7, 131.0, 129.9, 128.1, 123.7, 118.2, 117.4, 113.7, 104.2, 104.2, 102.2, 102.0, 101.2, 63.8, 56.1, 56.0, 32.4, 30.4. ). ESI-MS m/n: 470.0 (100%), 472.0 (100%) $[M+H]^+$.

General procedure of synthesis of 39a-45a. To a solution of ethanolamine derivatives (2 mmol) and NaH (2 mmol) in dried THF (50 mL), 37 (146 mg, 0.4 mmol) was added. The reaction solution was stirred at 70° C. overnight. The reaction was quenched by the addition of water (10 mL) at 0° C. The solvent was evaporated under reduced pressure. The residue was purified by silica gel column chromatography to give the target compound, respectively.

2,3-Dimethoxy-13-(2-(dimethylamino)ethoxyl)-[1,3]dioxolo[4',5':4,5]benzo[1,2-c]phenanthridine (39a). White powder, mp=159.8-160.5° C. IR (KBr, $cm^{-1}$), 1620, 1593. $^1$H NMR ($CDCl_3$) δ 8.54 (s, 1H), 8.17 (d, J=8.8 Hz, 1H), 7.82 (s, 1H), 7.73 (s, 1H), 7.68 (d, J=8.8 Hz, 1H), 7.23 (s, 11H), 6.11 (s, 2H), 4.91 (t, J=5.6 Hz, 21), 4.14 (s, 3H), 4.07 (s, 31H), 3.00 (t, J=5.6 Hz, 2H), 2.46 (s, 61H). $^{13}$C NMR ($CDCl_3$), 157.2, 152.6, 149.2, 148.0, 147.8, 138.8, 131.0, 130.0, 128.2, 123.6, 118.3, 117.4, 113.9, 104.5, 104.3, 102.2, 102.1, 101.2, 64.2, 58.3, 56.1, 56.1, 46.2. HRMS (ESI) m/z: 421.1763 [M+H]-,calcd for $C_{24}H_{25}N_2O_5$ 421.1758.

2,3-Dimethoxy-13-(2-(diethylamino)ethoxy)-[1,3]dioxolo[4',5':4,5]benzo[1,2-c]phenanthridine(40a). White solid, mp=161.2-162.5° C. IR (KBr, $cm^{-1}$), 1620, 1591. $^1$H NMR ($CDCl_3$) 38.53 (s, 1H), 8.13 (d, J=8.8 Hz, 1H), 7.77 (s, 1H), 7.68 (s, 11H), 7.64 (d, J=8.8 Hz, 1H), 7.20 (s, 1H), 6.10 (s, 2H), 4.84 (t, J=6.2 Hz, 2H), 4.12 (s, 3H), 4.05 (s, 3H), 3.11 (t, J=6.2 Hz, 2H), 2.77 (q, J=7.1 Hz, 4H), 1.17 (t, J=7.1 Hz, 6H). $^{13}$C NMR ($CDCl_3$) δ 157.3, 152.6, 149.2, 148.0, 147.8, 138.9, 131.0, 129.9, 128.2, 123.6, 118.3, 117.3, 113.9, 104.5, 104.2, 102.2, 102.1, 101.1, 64.6, 56.0, 51.3, 48.2, 12.3. HRMS (ESI) m/z: 449.2079 $[M+H]^+$,calcd for $C_{26}H_{27}N_2O_5$ 449.2071. ESI-MS m/z: 449.2 $[M+H]^+$.

2,3-Dimethoxy-13-(2-(pyrrolidin-1-yl)ethoxy)-[1,3]dioxolo[4',5':4,5]benzo[1,2-c]phenanthridine (41a). White powder, mp=175.2-175.8° C. IR (KBr, $cm^{-1}$), 1620, 1593. $^1$H NMR ($CDCl_3$) 38.54 (s, 1H), 8.16 (d, J=8.8 Hz, 1H), 7.81 (s, 1H), 7.72 (s, 1H), 7.67 (d, J=8.8 Hz, 1H), 7.22 (s, 11H), 6.11 (s, 2H), 4.94 (t, J=6.0 Hz, 2H), 4.14 (s, 3H), 4.07 (s, 31), 3.16 (t, J=6.0 Hz, 2H), 2.82-2.74 (m, 4H), 1.89-1.82 (m, 4H). $^{13}$C NMR ($CDCl_3$) δ 157.3, 152.7, 149.3, 148.1, 147.9, 138.9, 131.1, 130.0, 128.3, 123.7, 118.4, 117.5, 114.0, 104.6, 104.4, 102.3, 102.2, 101.3, 65.2, 56.2, 56.1, 55.1, 55.0, 23.7. HRMS (ESI) m/z: 447.1909 $[M+H]^+$, calcd for $C_{26}1H_2N_2O$ 447.1914.

2,3-Dimethoxy-13-(2-(piperidin-1-yl)ethoxy)-[1,3]dioxolo[4',5':4,5]benzo[1,2-c]phenanthridine (42a). White powder, mp=189.0-189.6° C. IR (KBr, $cm^{-1}$), 1620, 1594. $^1$H NMR ($CDCl_3$) δ 8.55 (s, 1H), 8.17 (d, J=9.2 Hz, 1H), 7.81 (s, 1H), 7.71 (s, 1H), 7.67 (d, J=8.8 Hz, 1H), 7.22 (s, 1H) 6.11 (s, 2H), 4.92 (t, J=6.4 Hz, 2H), 4.14 (s, 3H), 4.07 (s, 3H) 3.03 (t, J=6.4 Hz, 2H), 2.77-2.60 (m, 4H), 1.73-1.69 (m, 2H), 1.66-1.63 (in. 2H), 1.53-1.45 (m, 2H). $^{13}$C NMR ($CDCl_3$) δ 157.3, 152.8, 149.3, 148.1, 147.9, 139.0, 131.1, 130.1, 128.3, 123.7, 118.4, 117.5, 114.1, 104.6, 104.4, 102.31 102.2, 101.3, 64.1, 58.0, 56.2, 55.3, 26.2, 24.4. HRMS (ESI) m/z: 461.2068 $[M+H]^+$, calcd for $C_{27}H_{27}N_2O_5$ 461.2071.

2,3-Dimethoxy-13-(2-morpholinoethoxy)-[1,3]dioxolo[4',5':4,5]benzo[1,2-c]phenanthridine (43a). White powder, mp=198.4-199.6° C. IR (KBr, $cm^{-1}$), 1619, 1593. $^1$H NMR ($CDCl_3$) δ 8.53 (s, 1H), 8.17 (d, J=8.8 Hz, 1H), 7.81 (s, 1H), 7.69-7.65 (m, 2H), 7.23 (s, 1H), 6.11 (s, 2H), 4.93 (t, J=5.8 Hz, 2H), 4.14 (s, 3H), 4.07 (s, 3H), 3.82-3.75 (m, 4H), 3.05 (t, J=5.8 Hz, 2H), 2.77-2.67 (m, 4H). $^{13}$C NMR ($CDCl_3$) δ 157.2, 152.8, 149.3, 148.1, 147.9, 138.9, 131.1, 130.1, 128.3, 123.8, 118.4, 117.5, 113.9, 104.4, 104.3, 102.3, 102.1, 101.3, 67.2, 63.8, 57.7, 56.2, 54.3. HRMS (ESI) m/z: 463.1859 $[M+H]^+$, calcd for $C_{26}H_{27}N_2O_6$ 463.1864.

2,3-Dimethoxy-13-(2-(4-methylpiperazin-1-yl)ethoxy)-[1,3]dioxolo[4',5':4,5]benzo[1,2-c]phenanthridine (44a). White powder, mp=206.5-207.4° C. JR (KBr, $cm^{-1}$), 1622, 1596. $^1$H NMR ($CDCl_3$) δ 8.54 (s, 1H), 8.17 (d, J=8.8 Hz, 1H), 7.82 (s, 1H), 7.73-7.63 (m, 2H), 7.23 (s, 1H) 6.11 (s, 2H), 4.92 (t, J=6.4 Hz, 2H), 4.14 (s, 3H), 4.06 (s, 3H) 3.07 (t, J=6.4 Hz, 2H), 2.92-2.65 (m, 4H), 2.65-2.41 (m, 4H), 2.32 (s, 3H). $^{13}$C NMR ($CDCl_3$) δ 157.2, 152.7, 149.3, 148.1, 147.9, 138.9, 131.1, 130.0, 128.3, 123.7, 118.3, 117.5, 113.9, 104.5, 104.3, 102.3, 102.2 101.3, 64.1, 57.2, 56.1, 553, 53.8, 46.2. HRMS (ESI) m/z: 476.2179 $[M+H]^+$, calcd for $C_{27}H_{30}N_3O_5$ 476.2180.

13-(2-(1H-imidazol-1-yl)ethoxy)-2,3-dimethoxy-[1,3]dioxolo[4',5':4,5]benzo[1,2-c]phenanthridine (45a). White powder, mp=238.9-239.1° C. IR (KBr, $cm^{-1}$), 1621, 1597. $^1$H NMR ($CDCl_3$) δ 8.47 (s, 1H), 8.19 (d, J=8.8 Hz, 1H), 7.83 (s, 1H), 7.71 (d, J=8.8 Hz, 1H), 7.67 (s, 1H), 7.58 (s, 1H), 7.24 (s, 1H), 7.12-7.09 (m, 2H), 6.12 (s, 2H), 5.06 (t, J=5.2 Hz, 2H), 4.59 (t, J=5.2 Hz, 2H), 4.15 (s, 3H), 4.06 (s, 3H). $^{13}$C NMR ($CDCl_3$) δ 156.4, 153.1, 149.6, 148.2, 148.0, 138.5, 137.7, 131.3, 130.1, 129.8, 128.2, 124.2, 119.5, 118.4, 117.9, 113.6, 104.5, 104.1, 102.4, 101.9, 101.4, 64.9, 56.3, 56.2, 46.5. HRMS (ESI) m/z: 444.1557 $[M+H]^+$, calcd for $C_{25}H_2N_3O_5$ 444.1554.

General procedure of synthesis of 39b-45b. The solution of 38 (221 mg. 0.47 mmol), $K_2CO_3$ (163 mg, 1.18 mmol), KI (20 mg, 0.118 mmol) and amines (in Pressure Vessel for dimnethylamine. 0.7 mmol) in DMF (20 mL) was stirred at room temperature overnight. And then, the reaction solution was diluted with ethyl acetate (100 mL), and washed with saturated saline (3×50 mL). The organic layer was dried ($MgSO_4$) and concentrated under reduced pressure. The residue was purified by silica gel column chromatography to give target product, respectively.

2,3-Dimethoxy-13-(3-(dimethylamino)propoxy)-[1,3]dioxolo[4',5':4,5]benzo[1,2-c]phenanthridine (39b). White powder, mp=148.6-150.4° C. IR (KBr, $cm^{-1}$), 1618, 1593. $^1$H NMR ($CDCl_3$) δ 8.56 (s, 1H), 8.18 (d, J=8.8 Hz, 1H), 7.83 (s, 1H), 7.72 (s, 1H), 7.68 (d, J=8.8 Hz, 1H), 6.11 (s, 2H), 4.82 (t, J=7.4 Hz, 1H), 4.14 (s, 3H), 4.07 (s, 3H), 2.60 (t, J=7.4 Hz, 1H), 2.32 (s, 6H), 2.20 (quint, J=7.4 Hz, 1H). $^{13}$C NMR ($CDCl_3$) δ 157.5, 152.7, 149.3, 148.0, 147.8, 139.0, 131.1, 130.0, 128.3, 123.6, 118.4, 117.4, 114.0, 104.5, 104.4, 102.3, 102.2, 101.2, 64.5, 57.0, 56.2, 56.2, 45.7, 27.5. HRMS (ESI) n/z: 435.1921 $[M+H]^+$ calcd for $C_{25}H_{27}N_2O_5$ 435.1914. ESI-MS m/z: 435.3 [M+H]

2,3-Dimethoxy-13-(3-diethylamino)propoxy)-[1,3]dioxolo[4',5':4,5]benzo[1,2-c]phenanthridine (40b). White powder, mp=146.2-147.8° C. IR (KBr, $cm^{-1}$), 1620, 1594. $^1$H NMR (DMSO) δ 8.45 (d, J=9.0 Hz, 1H), 8.35 (s, 11H), 8.04 (s, 1H), 7.75 (d, J=9.0 Hz, 1H), 7.57 (s, 1H), 7.43 (s, 1H), 6.19 (s, 2H), 4.71 (t, J=6.4 Hz, 2H), 4.06 (s, 3H), 3.93 (s, 3H), 2.70 (t, J=6.8 Hz, 2H), 2.53 (q, J=7.2 Hz, 4H), 2.05

(quint, J=6.8 Hz, 2H), 1.01 (t, J=7.2 Hz, 6H). $^{13}C$ NMR (DMSO) δ 157.3, 153.3, 149.7, 148.2, 148.0, 138.3, 131.0, 130.1, 127.7, 123.9, 119.6, 117.5, 113.4, 104.7, 104.0, 103.6, 101.8, 101.4, 64.5, 56.4, 55.9, 49.1, 47.0, 26.4, 12.2. HRMS (ESI) m/z: 463.2233 $[M+H]^+$, calcd for $C_{27}H_{31}N_2O_5$ 463.2227. ESI-MS ml: 463.2 $[M+H]^+$.

2,3-Dimethoxy-13-(3-(pyrrolidin-1-yl)propoxy)-[1,3]dioxolo[4',5':4,5]benzo[1,2-c]phenanthridine (41b). White powder, mp=162.8-163.9° C., IR (KBr, $cm^{-1}$), 1619, 1594. $^1H$ NMR ($CDCl_3$) δ 8.48 (s, 1H), 8.07 (d, J=8.8 Hz, 1H), 7.71 (s, 1H), 7.67-7.57 (m, 2H), 7.18 (s, 1H), 6.09 (s, 2H), 4.77 (t, J=6.8 Hz, 2H), 4.10 (s, 3H), 4.05 (s, 3H), 2.78 (t, J=6.8 Hz, 2H), 2.62 (s, br, 4H), 2.24 (quint, J=6.8 Hz, 2H), 1.83 (s, br, 4H).$^{13}C$ NMR ($CDCl_3$) 157.3, 152.5, 149.1, 147.9, 147.7, 138.8, 130.9, 129.9, 128.2, 123.5, 118.2, 117.2, 113.9, 104.3, 104.2, 102.1, 101.1, 64.5, 56.1, 56.0, 54.4, 53.7, 28.8, 23.5. HRMS (ESI) m/z: 461.2082 [M+H]f, calcd for $C_{27}N_{29}N_2O_5$ 461.2071. ESI-MS m/z: 461.2 $[M+H]^+$.

2,3-Dimethoxy-13-(3-(piperidin-1-yl)propoxy)-[1,3]dioxolo[4'5':4,5]benzo[1,2-c]phenanthridine (42b). White powder, mp=153.7-155.3° C., IR (KBr, $cm^{-1}$), 1618, 1593. $^1H$ NMR (CDCl) δ 8.51 (s, 1H), 8.13 (d, J=8.8 Hz, 1H), 7.77 (s, 1H), 7.69-7.60 (m, 2H), 7.21 (s, 1H), 6.10 (s, 2H), 4.78 (t, J=6.2 Hz, 2H), 4.12 (s, 3H), 4.06 (s, 3H), 2.66 (t, J=7.6 Hz, 2H), 2.51 (s, br, 4H), 2.24 (quint, J=7.2 Hz, 2H), 1.72-1.58 (m, 4H), 1.55-1.41 (m, 2H). $^{13}C$ NMR ($CDCl_3$) δ 157.4, 152.6, 149.2, 147.9, 147.7, 138.9, 130.9, 129.9, 128.2, 123.5, 118.3, 117.3, 113.9, 104.3, 104.3, 102.2, 10211 101.1, 64.6, 56.6, 56.1, 56.0, 54.7, 26.6, 25.9, 24.4. HRMS (ESI) m/z: 475.2229 $[M+H]^+$, calcd for $C_{28}H_{31}N_2O_5$ 475.2227, EST-MS mi z: 475.2 $[M+H]^+$.

2,3-Dimethoxy-13-(3-morpholinopropoxy)-[1,3]dioxolo[4',5':4,5]benzo[1,2-c]phenanthridine (43b). White powder, mp=171.8-172.9° C., JR (KBr, $cm^{-1}$), 1618, 1593. $^1H$ NMR ($CDCl_3$) δ 8.53 (s, 1H), 8.16 (d, J=9.2 Hz, 1H), 7.82 (s, 1H), 7.69 (s, 1H), 7.67 (d, J=8.8 Hz, 1H), 7.23 (s, 1H), 6.11 (s, 2H), 4.83 (t, J=6.6 Hz, 2H), 4.13 (s, 3H), 4.07 (s, 3H), 3.76 (t, J=4.8 Hz, 4H), 2.67 (t, J=7.2 Hz, 2H), 2.56-2.53 (m, 41), 2.22 (quint, J=7.2 Hz, 2H). $^{13}C$ NMR ($CDCl_3$) δ 157.3, 152.6, 149.2, 147.9, 147.7, 138.8, 130.9, 129.9, 128.2, 123.5, 118.2, 117.3, 113.9, 104.3, 104.3, 102.2, 102.0, 101.1, 67.0, 64.3, 56.1 56.1, 56.0, 53.9, 26.3. HRMS (ESI) m/z: 477.2027 $[M+H]^+$, calcd for $C_{27}H_{29}N_2O_6$ 477.2020. EST-MS m/z: 477.2 $[M+H]^+$.

2,3-Dimethoxy-13-(3-(4-methylpiperazin-1-yl)propoxy)-[1,3]dioxolo[4',5':4,5]benzo[1,2-c]phenanthridine (44b). White powder, mp=142.5-143.8° C., IR (KBr, $cm^{-1}$), 1619, 1593. $^1H$ NMR ($CDCl_3$) δ 8.55 (s, 1H), 8.18 (d, J=9.0 Hz, 1H), 7.83 (s, 1H), 7.70 (s, 1H), 7.68 (d, J=8.8 Hz, 1H), 7.23 (s, 1H), 6.11 (s, 2H), 4.83 (t, J=6.4 Hz, 2H), 4.14 (s, 3H), 4.07 (s, 3H), 2.70 (t, J=7.2 Hz, 2H), 2.67-2.41 (m, 8H), 2.32 (s, 3H), 2.22 (quint, J=7.2 Hz, 2H). $^{13}C$ NMR ($CDCl_3$) δ157.3, 152.6, 149.2, 147.9, 147.7, 138.9, 131.0, 129.9, 128.2, 123.5, 118.3, 117.3, 114.0, 104.4, 104.2, 102.2, 102.1, 101.1, 64.5, 56.1, 56.0, 55.8, 55.2, 53.4, 46.0, 26.7. HRMS (ESI) m/z: 490.2339 $[M+H]^+$, calcd for $C_{28}H_{32}N_3O_5$ 490.2336. ESI-MS m/z: 490.23 [M+H].

13-(3-(1H-imidazol-1-yl)propoxy)-2,3-dimethoxy-[1,3]dioxolo[4',5':4,5]benzo[1,2-c]phenanthridine (45b). White powder, mp=217.4-218.5° C., IR (KBr, $cm^{-1}$), 1618, 1591. $^1H$ NMR ($CDCl_3$) δ8.47 (s, 1H), 8.19 (d, J=8.8 Hz, 1H), 7.84 (s, 1H), 7.70 (d, J=8.8 Hz, 1H), 7.64 (s, 1H), 7.60 (s, 1H), 7.25 (s, 1H), 7.12 (s, 1H), 7.03 (s, 1H), 6.13 (s, 2H), 4.83 (t, J=6.0 Hz, 2H), 4.28 (t, J=6.8 Hz, 2H), 4.16 (s, 3H), 4.11 (s, 3H), 2.53 (quint, J=6.4 Hz, 2H). $^{13}C$ NMR ($CDCl_3$) δ 156.8, 152.9, 149.4, 148.1, 147.8, 138.6, 137.1, 131.2, 130.0, 129.8, 128.1, 123.9, 118.9, 118.2, 117.5, 113.6, 104.3, 104.1, 102.4, 101.9, 101.2, 62.6, 56.1, 56.1, 44.3, 30.7. HRMS (ESI) m/z: 458.1712 $[M+H]^+$, calcd for $C_{2M}H_{24}N_3O_5$ 458.1710. ESI-MS n/: 458.2 $[M+H]^+$.

The compounds of Table 6 were synthesized by the methods described above for Schemes 1 and 2. The Top1 cleavage procedure is described in Example 3. The Tdp1 inhibition experimental procedure is described in Examples 4-5. Top1 cleavage (inhibition relative to 1 LIM CPT): 0 is inactive; + is 20-50%; ++ is 50-75%; +++ is 75-95%; and ++++: ~CPT

TABLE 6

Top1 Cleavage and Tdp Inhibition of Compounds.

| No. | Structure | Top1 cleavage | $IC_{50}$ Tdp1 (μM) | $[M + H]^+$ | $^1H$ NMR |
|---|---|---|---|---|---|
| TWL-5 | 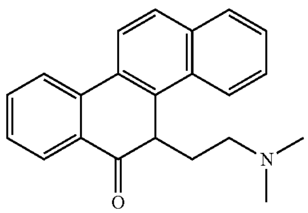 TWL-5 | + | 75.9, >111, >111, 64.6 | 317.2 | $^1H$ NMR (400 MHz, $CDCl_3$) δ 8.58-8.53 (m, 1H), 8.34 (m, 1H), 8.29 (d, J = 8.2 Hz, 1H), 8.24 (d, J = 8.7 Hz, 1H), 7.92 (m, 1H), 7.83-7.77 (m, 1H), 7.75 (d, J = 8.7 Hz, 1H), 7.62 (t, J = 7.4 Hz, 1H), 7.55 (dd, J = 6.4, 3.3 Hz, 2H), 4.79-4.73 (t, J = 6.8 Hz, 2H), 2.83-2.78 (t, J = 6.8 Hz 2H), 2.18 (s, 6H). |
| TWL-25 | 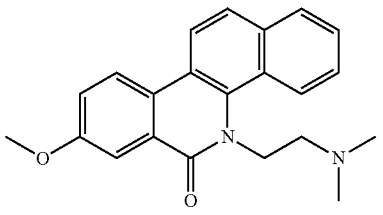 TWL-25 | + | 49.4 ± 1.4 | 347.2 | $^1H$ NMR (400 MHz, $CDCl_3$) δ 8.31 (d, J = 9.1 Hz, 1H), 8.17 (m, 2H), 7.95 (d, J = 2.7 Hz, 1H), 7.90-7.87 (m, 1H), 7.72 (d, J = 8.7 Hz, 1H), 7.51 (m, 2H), 7.37 (dd, J = 8.9, 2.7 Hz, 1H), 4.73 (t, J = 7.2, 2H), 3.98 (s, 3H), 2.87 (t, J = 7.2, 2H), 2.20 (s, 6H). |

TABLE 6-continued

Top1 Cleavage and Tdp Inhibition of Compounds.

| No. | Structure | Top1 cleavage | $IC_{50}$ Tdp1 (μM) | $[M + H]^+$ | $^1H$ NMR |
|---|---|---|---|---|---|
| TWL-25A | 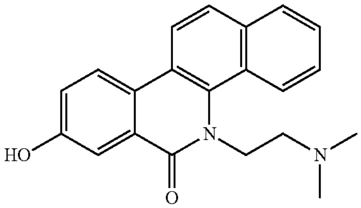 TWL-25A | + | >111, 74.1, >111, 75.9 | 333.2 | $^1H$ NMR (400 MHz, DMSO) δ 10.25 (s, 1H), 8.43-8.26 (m, 3H), 8.05-7.98 (m, 1H), 7.82 (d, J = 8.7 Hz, 1H), 7.69 (d, J = 2.4 Hz, 1H), 7.56 (m, 2H), 7.32 (dd, J = 8.7, 2.6 Hz, 1H), 4.64 (t, J = 6.6 Hz, 2H), 2.57 (t, J = 6.6 Hz, 1H), 1.94 (s, 6H). |
| TWL-53 | 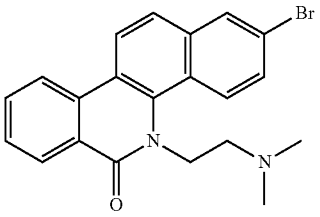 TWL-53 | + | >111 (n = 3) | 396.3 | $^1H$ NMR (400 MHz, $CDCl_3$) δ 8.53 (d, J = 7.7 Hz, 1H), 8.27-8.23 (m, 3H), 8.04 (d, J = 1.6 Hz, 1H), 7.79 (t, J = 7.2 Hz, 1H), 7.66-7.54 (m, 3H), 4.70 (t, J = 7.2 Hz, 2H), 2.76 (t, J = 7.2 Hz, 2H), 2.16 (s, 6H). |
| TWL-26 | 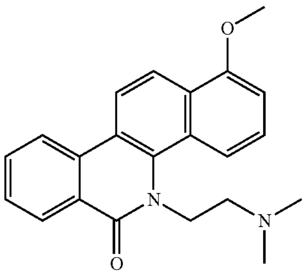 TWL-26 | + | >111 | 347.2 | $^1H$ NMR (400 MHz, $CDCl_3$) δ 8.55 (d, J = 7.4 Hz, 1H), 8.28 (d, J = 7.8 Hz, 1H), 8.11 (d, J = 8.4 Hz, 1H), 7.86-7.74 (m, 2H), 7.69 (d, J = 8.4 Hz, 1H), 7.65-7.55 (m, 2H), 7.23 (d, J = 8.2 Hz, 1H), 4.79 (t, J = 6.5 Hz, 2H), 4.02 (s, 3H), 2.76 (t, J = 6.5 Hz, 2H), 2.16 (s, 6H). |
| TWL-9 | 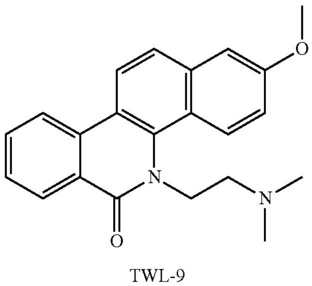 [SMILES: COc1ccc2c(ccc3c4ccccc4c(=O)n(CCN(C)C)c23)c1] TWL-9 | + | >111 | 347.2 | $^1H$ NMR (400 MHz, $CDCl_3$) δ 8.51 (d, J = 7.8 Hz, 1H), 8.24 (t, J = 8.5 Hz, 2H), 8.18 (d, J = 8.7 Hz, 1H), 7.76 (t, J = 7.4 Hz, 1H), 7.63 (d, J = 8.6 Hz, 1H), 7.59-7.53 (m, 1H), 7.19 (d, J = 9.4 Hz, 2H), 4.70 (t, J = 8.8 Hz 2H), 3.97 (s, 3H), 2.80 (t, J = 8.8 Hz 2H), 2.19 (s, 6H). |
| TWL-33 | 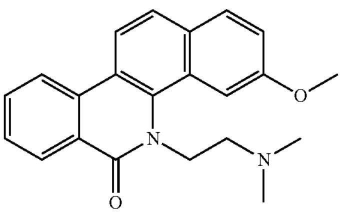 TWL-33 | + | >111 | 347.2 | $^1H$ NMR (400 MHz, $CDCl_3$) δ 8.57-8.52 (m, 1H), 8.30 (t, J = 7.6 Hz, 1H), 8.23 (s, 2H), 7.86 (d, J = 8.7 Hz, 1H), 7.83-7.77 (m, 1H), 7.62 (t, J = 7.6 Hz, 1H), 7.51-7.44 (m, 1H), 6.91 (t, J = 9.5 Hz, 1H), 4.81 (t, J = 7.6 Hz, 2H), 4.07 (s, 3H), 2.76 (t, J = 7.6 Hz, 2H), 2.18 (s, 6H). |

TABLE 6-continued

Top1 Cleavage and Tdp Inhibition of Compounds.

| No. | Structure | Top1 cleavage | $IC_{50}$ Tdp1 (μM) | $[M + H]^+$ | $^1H$ NMR |
| --- | --- | --- | --- | --- | --- |
| TWL-17 | 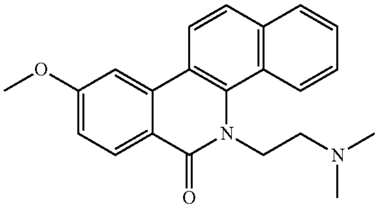 TWL-17 | + | >111 | 347.2 | $^1H$ NMR (400 MHz, $CDCl_3$) δ 8.49 (d, J = 8.8 Hz, 1H), 8.36-8.32 (m, 1H), 8.16 (d, J = 8.8 Hz, 1H), 7.95-7.88 (m, 1H), 7.74 (d, J = 8.7 Hz, 1H), 7.66 (s, 1H), 7.58-7.53 (m, 2H), 7.20-7.13 (m, 1H), 4.73 (t, J = 8.0 Hz, 2H), 4.02 (s, 3H), 2.82 (t, J = 8.0 Hz, 2H), 2.18 (s, 6H). |
| TWL-44 | 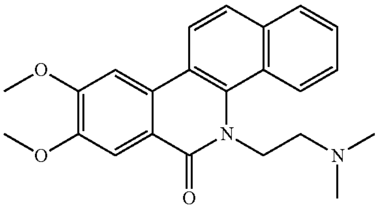 TWL-44 | + | >111 | 377.2 | $^1H$ NMR (400 MHz, $CDCl_3$) δ 8.32-8.24 (m, 1H), 8.06 (d, J = 8.8 Hz, 1H), 7.87 (s, 1H), 7.85-7.82 (m, 1H), 7.66 (d, J = 8.7 Hz, 1H), 7.55 (s, 1H), 7.47 (dd, J = 6.9, 3.0 Hz, 2H), 4.67 (t, J = 8.0 Hz, 2H), 4.05 (s, 3H), 3.99 (s, 3H), 2.77 (t, J = 8.0 Hz, 2H), 2.15 (s, 6H). |
| TWL-40 | 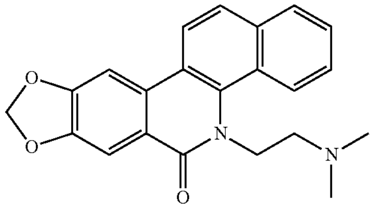 TWL-40 | + | 18.16 ± 1.15 | 361.2 | $^1H$ NMR (400 MHz, $CDCl_3$) δ 8.25 (d, J = 5.5 Hz, 1H), 7.98 (d, J = 8.7 Hz, 1H), 7.83 (s, 2H), 7.64 (d, J = 8.7 Hz, 1H), 7.56 (s, 1H), 7.46 (d, J = 8.7 Hz, 2H), 6.07 (s, 2H), 4.65 (t, J = 6.8 Hz, 2H), 2.73 (t, J = 6.8 Hz, 3H), 2.11 (s, 6H). |
| TWL-67 | 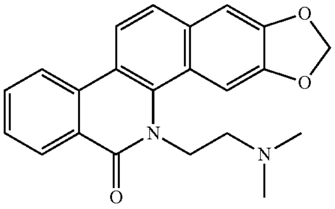 TWL-67 | + | >111 | 361.2 | $^1H$ NMR (400 MHz, $CDCl_3$) δ 8.49 (d, J = 7.8 Hz, 1H), 8.23 (d, J = 8.0 Hz, 1H), 8.07 (d, J = 8.5 Hz, 1H), 7.77 (t, J = 7.6 Hz, 1H), 7.57 (d, J = 8.3 Hz, 3H), 7.18 (s, 1H), 6.11 (s, 2H), 4.75 (t, J = 6.0 Hz, 2H), 2.87 (t, J = 6.0 Hz, 2H), 2.30 (s, 6H). |
| TWL-76H | 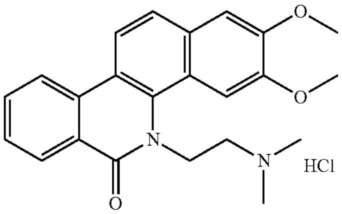 TWL-76H | + | >111 | 412.2 | $^1H$ NMR (400 MHz, $D_2O$) δ 7.86 (d, J = 7.9 Hz, 1H), 7.54 (t, J = 6.3 Hz, 2H), 7.42 (m, 1H), 7.19 (d, J = 8.7 Hz, 1H), 6.79 (d, J = 8.6 Hz, 1H), 6.51 (s, 1H), 5.76 (s, 1H), 3.84 (s, 3H), 3.67 (s, 3H), 3.66 (t, J = 4.8 Hz, 2H), 3.20 (t, J = 4.8 Hz, 2H), 2.80 (s, 6H). |
| TWL-185 | 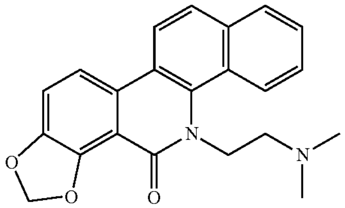 TWL-185 | + | >111 | 361.2 | $^1H$ NMR (400 MHz, $CDCl_3$) δ 8.27-8.22 (m, 1H), 8.09 (d, J = 8.8 Hz, 1H), 7.89-7.85 (m, 1H), 7.77 (d, J = 8.6 Hz, 1H), 7.69 (d, J = 8.8 Hz, 1H), 7.54-7.48 (m, 2H), 7.27-7.25 (m, 1H), 6.28 (s, 2H), 4.65 (t, J = 6.6 Hz, 2H), 2.84 (t, J = 6.6 Hz, 2H), 2.20 (s, 6H). |

TABLE 6-continued

| Top1 Cleavage and Tdp Inhibition of Compounds. | | | | | |
|---|---|---|---|---|---|
| No. | Structure | Top1 cleavage | $IC_{50}$ Tdp1 (μM) | $[M + H]^+$ | $^1H$ NMR |
| TWL-48 | 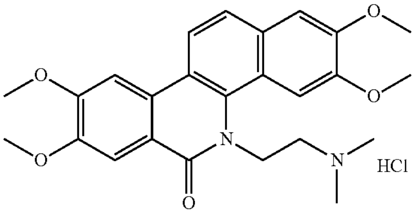 HCl<br>TWL-48 | 0/+ | >111 | 473.2 | $^1H$ NMR (400 MHz, $D_2O$) δ 6.82 (d, J = 9.0 Hz, 1H), 6.66 (d, J = 8.5 Hz, 1H), 6.33 (s, 1H), 6.25 (s, 1H), 5.66 (s, 1H), 3.77 (s, 3H), 3.61 (s, 3H), 3.58 (s, 3H), 3.57 (s, 3H), 3.53 (s, 2H), 3.22 (s, 2H), 2.79 (s, 6H). |
| TWL-37 | 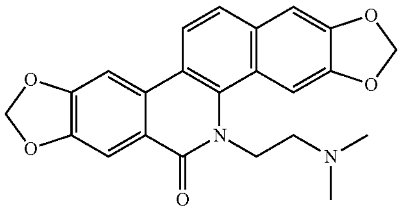<br>TWL-37 | + | 27.59 ± 19 | 405.1 | $^1H$ NMR (400 MHz, $CDCl_3$) δ 7.76 (s, 1H), 7.45 (dd, J = 32.7, 18.5 Hz, 1H), 7.05 (s, 1H), 6.02 (d, J = 7.2 Hz, 1H), 4.52 (s, 2H), 2.65 (s, 2H), 2.09 (s, 6H). |
| TWL-113 | 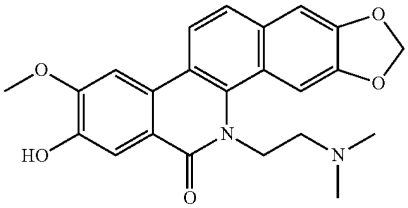<br>TWL-113 | + | >111, >111, 65 | 407.1 | $^1H$ NMR (400 MHz, DMSO) δ 9.83 (s, 1H), 8.27 (d, J = 8.2 Hz, 1H), 7.81 (s, 1H), 7.71 (s, 1H), 7.66 (s, 1H), 7.41 (s, 1H), 6.19 (s, 2H), 4.51 (s, 2H), 4.03 (s, 4H), 2.58 (s, 2H), 1.98 (s, 6H). |
| TWL-119 | 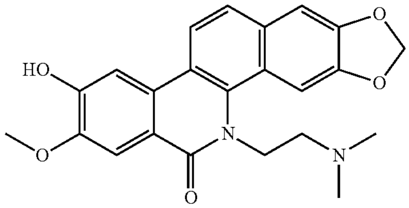<br>TWL-119 | + | >111 | 407.1 | $^1H$ NMR (400 MHz, $CDCl_3$) δ 7.86-7.78 (m, 2H), 7.58 (s, 1H), 7.51 (s, 1H), 7.46 (d, J = 8.7 Hz, 1H), 7.08 (s, 1H), 6.00 (s, 2H), 4.66 (t, J = 6.8 Hz, 2H), 4.02 (s, 3H), 2.74 (t, J = 6.8 Hz, 2H), 2.18 (s, 6H). |
| TWL-125 | 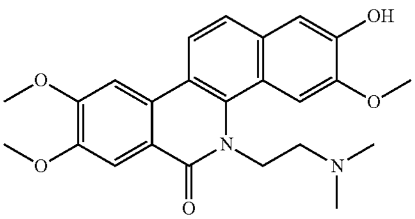<br>TWL-125 | + | 65, 50 | 423.2 | $^1H$ NMR (400 MHz, DMSO) δ 9.80 (s, 1H), 8.24 (d, J = 8.8 Hz, 1H), 7.82 (s, 1H), 7.72 (s, 1H), 7.57 (d, J = 9.4 Hz, 2H), 7.25 (s, 1H), 4.60 (t, J = 6.8 Hz, 2H), 4.02 (d, J = 3.6 Hz, 6H), 3.92 (s, 3H), 2.70 (t, J = 6.8 Hz, 2H), 2.00 (s, 6H). |

TABLE 6-continued

Top1 Cleavage and Tdp Inhibition of Compounds.

| No. | Structure | Top1 cleavage | $IC_{50}$ Tdp1 (μM) | [M + H]$^+$ | $^1$H NMR |
|---|---|---|---|---|---|
| TWL-131 | 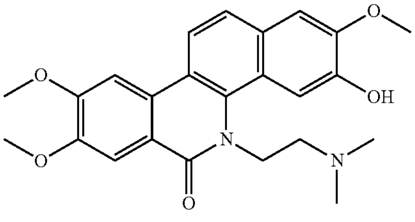 TWL-131 | 0/+ | >111 (n = 2) | 423.2 | $^1$H NMR (400 MHz, DMSO) δ 9.70 (s, 1H), 8.23 (d, J = 8.9 Hz, 1H), 7.83 (s, 1H), 7.71 (d, J = 10.2 Hz, 1H), 7.67 (d, J = 8.7 Hz, 1H), 7.60 (s, 1H), 7.41 (s, 1H), 4.63 (t, J = 6.8 Hz, 2H), 4.03 (s, 3H), 3.95 (s, 3H), 3.92 (s, 3H), 2.53-2.45 (m, 2H), 1.93 (s, 6H). |
| TWL-107 | 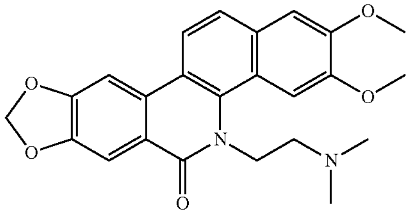 TWL-107 | 0/+ | 67.6 (n = 2) | 421.2 | $^1$H NMR (400 MHz, $CDCl_3$) δ 7.84 (d, J = 8.6 Hz, 1H), 7.79 (s, 1H), 7.55-7.46 (m, 3H), 7.10 (s, 1H), 6.05 (s, 2H), 4.63 (t, J = 6.8 Hz, 2H), 4.03 (s, 3H), 3.97 (s, 3H), 2.74 (t, J = 6.8 Hz, 2H), 2.10 (s, 6H). |
| TWL-164 | 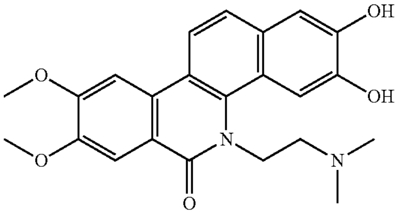 TWL-164 | ++ | >111 | 409.2 | $^1$H NMR (400 MHz, DMSO) δ 9.80 (s, 2H), 8.16 (d, J = 8.5 Hz, 1H), 7.81 (s, 1H), 7.71 (s, 1H), 7.54 (d, J = 9.0 Hz, 2H), 7.22 (s, 1H), 4.63 (t, J = 6.8 Hz, 2H), 4.03 (s, 3H), 3.91 (s, 3H), 2.59-2.51 (m, 2H), 1.99 (s, 6H). |
| TWL-189 | 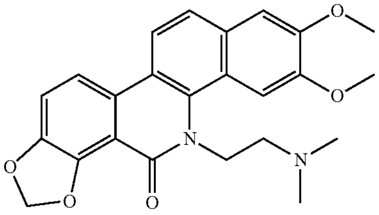 TWL-189 | + | >111 | 421.2 | $^1$H NMR (400 MHz, CDC13) δ 7.96 (d, J = 8.8 Hz, 1H), 7.73 (d, J = 8.7 Hz, 1H), 7.55 (d, J = 8.7 Hz, 1H), 7.51 (s, 1H), 7.23 (d, J = 8.5 Hz, 1H), 7.15 (s, 1H), 6.26 (s, 2H), 4.60 (t, J = 8.8 Hz, 2H), 4.09 (s, 3H), 4.03 (s, 3H), 2.80 (t, J = 8.8 Hz, 2H), 2.14 (s, 6H). |
| TWL-191 | 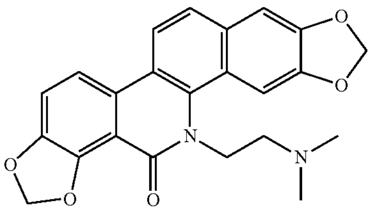 TWL-191 | + | >111 | 404.1 | $^1$H NMR (400 MHz, $CDCl_3$) δ 7.94 (d, J = 8.8 Hz, 1H), 7.72 (d, J = 8.6 Hz, 1H), 7.57 (s, 1H), 7.52 (d, J = 8.7 Hz, 1H), 7.23 (d, J = 8.5 Hz, 1H), 7.15 (s, 1H), 6.26 (s, 2H), 6.09 (s, 2H), 4.55 (t, J = 8.0 Hz, 2H), 2.75 (t, J = 8.0 Hz, 2H), 2.19 (s, 6H). |

TABLE 6-continued

| No. | Structure | Top1 cleavage | $IC_{50}$ Tdp1 (μM) | $[M + H]^+$ | $^1H$ NMR |
|---|---|---|---|---|---|
| TWL-211 | 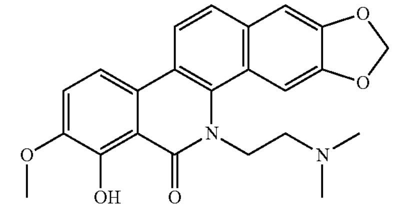 TWL-211 | + | 11, 30, 72 | 407.2 | $^1H$ NMR (400 MHz, $CDCl_3$) δ 13.43 (s, 1H), 8.00 (d, J = 8.7 Hz, 1H), 7.64 (d, J = 8.8 Hz, 1H), 7.60-7.54 (m, 2H), 7.35 (d, J = 8.8 Hz, 1H), 7.18 (s, 1H), 6.12 (s, 2H), 4.65 (t, J = 8.0 Hz, 2H), 4.02 (s, 3H), 2.66 (t, J = 8.0 Hz, 2H), 2.15 (s, 6H). |
| TWL-170 | 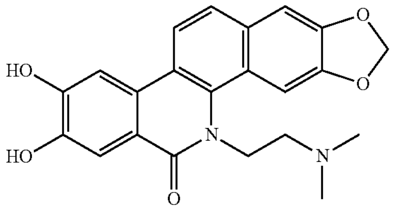 TWL-170 | + | >111 | 393.1 | $^1H$ NMR (400 MHz, DMSO) δ 7.98 (d, J = 8.8 Hz, 1H), 7.71 (s, 1H), 7.68-7.60 (m, 3H), 7.40 (s, 1H), 6.18 (s, 2H), 4.49 (t, J = 6.6 Hz, 2H), 2.56 (t, J = 6.6 Hz, 2H), 1.98 (s, 6H). |
| TWL-218A | 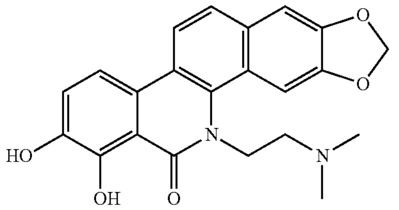 TWL-218A | +++ | | 393.1 | $^1H$ NMR (400 MHz, DMSO) δ 13.16 (d, J = 20.6 Hz, 1H), 9.56 (s, 1H), 8.15 (d, J = 8.7 Hz, 1H), 7.76 (d, J = 8.7 Hz, 1H), 7.73-7.65 (m, 2H), 7.41 (d, J = 9.8 Hz, 1H), 7.31 (d, J = 8.5 Hz, 1H), 6.20 (s, 2H), 4.59 (t, J = 6.2 Hz, 2H), 2.59 (t, J = 6.2 Hz, 2H), 1.95 (s, 6H). |
| TWL-246 | 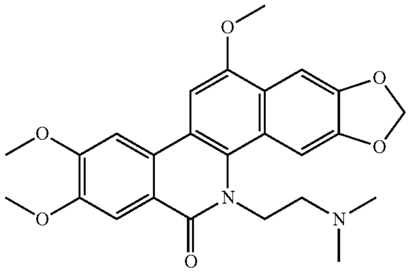 TWL-246 | ++ | | 451.2 | $^1H$ NMR (400 MHz, Chloroform-d) δ 7.92 (s, 1H), 7.64 (s, 1H), 7.59 (s, 1H), 7.46 (s, 1H), 7.23 (s, 1H), 6.10 (s, 2H), 4.682 (t, J = 8.0 Hz, 2H), 4.12 (s, 6H), 4.06 (s, 3H), 2.72 (t, J = 8.0 Hz, 2H), 2.20 (s, 6H). 13 |
| NTD-225 | 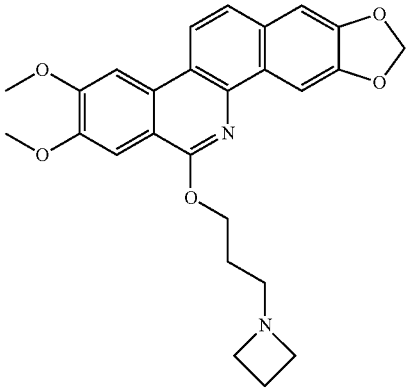 NTD-225 | 0 | 20.57 ± 4.46 (n = 3) | 447.2 | $^1H$ NMR (400 MHz, $CDCl_3$) δ 8.54 (s, 1H), 8.16 (d, J = 8.8 Hz, 1H), 7.81 (s, 1H), 7.70 (s, 1H), 7.67 (d, J = 8.8 Hz, 1H), 7.22 (s, 1H), 6.11 (s, 2H), 4.80 (t, J = 6.4 Hz, 2H), 4.14 (s, 3H), 4.08 (s, 3H), 3.38-3.29 (m, 4H), 2.76 (t, J = 7.2 Hz, 2H), 2.18-2.06 (m, 4H). |

TABLE 6-continued

| Top1 Cleavage and Tdp Inhibition of Compounds. | | | | | |
|---|---|---|---|---|---|
| No. | Structure | Top1 cleavage | $IC_{50}$ Tdp1 (μM) | $[M + H]^+$ | $^1H$ NMR |
| NTD-205 | 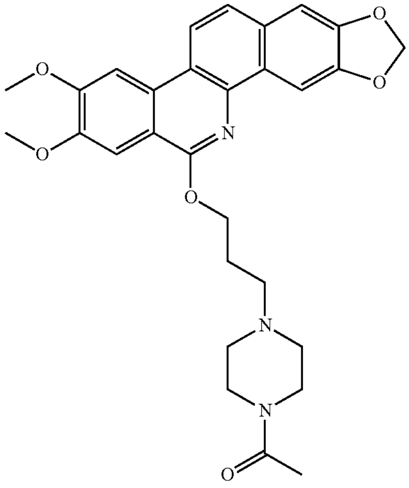 NTD-205 | ++ | >111 | 518.2 | $^1H$ NMR (400 MHz, $CDCl_3$) δ 8.51 (s, 1H), 8.14 (d, J = 8.8 Hz, 1H), 7.78 (s, 1H), 7.67-7.62 (m, 2H), 7.22 (s, 1H), 6.11 (s, 2H), 4.81 (t, J = 6.4 Hz, 2H), 4.12 (s, 3H), 4.06 (s, 3H), 3.66 (t, J = 4.4 Hz, 2H), 3.49 (t, J = 4.4 Hz, 2H), 2.67 (t, J = 7.2 Hz, 2H), 2.54-2.47 (m, 4H), 2.24-2.16 (m, 2H), 2.09 (s, 3H). |
| NTD-207 | 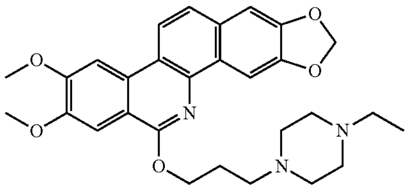 NTD-207 | + | >111 | 504.2 | $^1H$ NMR (400 MHz, $CDCl_3$) δ 8.54 (s, 1H), 8.18 (d, J = 8.8 Hz, 1H), 7.82 (s, 1H), 7.68 (s, 1H), 7.67 (d, J = 8.8 Hz, 1H), 7.23 (s, 1H), 6.11 (s, 2H), 4.83 (t, J = 6.4 Hz, 2H), 4.14 (s, 3H), 4.07 (s, 3H), 2.76-2.42 (m, 12H), 2.26-2.19 (m, 2H), 1.12 (t, J = 7.2 Hz, 3H). |
| NTD-208 | 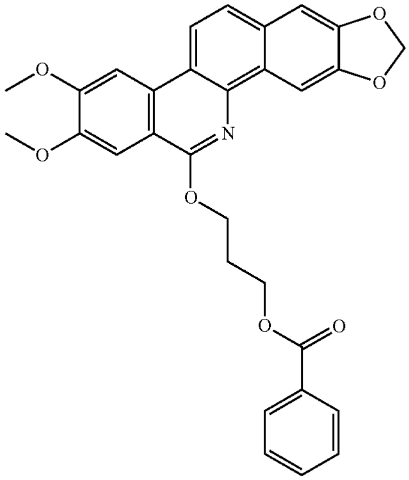 NTD-208 | + | >111 | 512.2 | $^1H$ NMR (400 MHz, $CDCl_3$) δ 8.54 (s, 1H), 8.17 (d, J = 8.8 Hz, 1H), 8.11-8.02 (m, 2H), 7.81 (s, 1H), 7.71-7.64 (m, 2H), 7.53 (t, J = 7.2 Hz, 1H), 7.44-7.36 (m, 2H), 7.23 (s, 1H), 6.11 (s, 2H), 4.97 (t, J = 6.0 Hz, 2H), 4.66 (t, J = 6.1 Hz, 2H), 4.14 (s, 3H), 4.04 (s, 3H), 2.57-2.47 (m, 2H). |

TABLE 6-continued
Top1 Cleavage and Tdp Inhibition of Compounds.
| No. | Structure | Top1 cleavage | $IC_{50}$ Tdp1 (μM) | $[M + H]^+$ | $^1H$ NMR |
|---|---|---|---|---|---|
| NTD-209 | 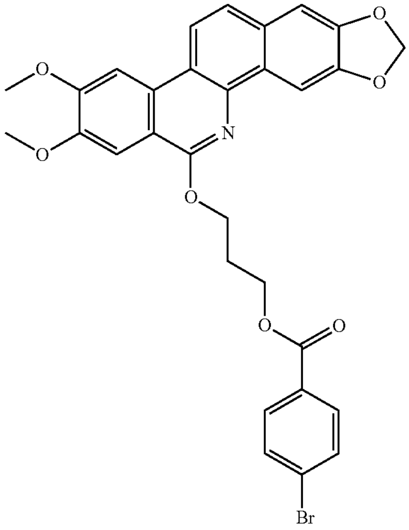 NTD-209 | + | >111 | 590.1 | $^1H$ NMR (400 MHz, $CDCl_3$) δ 8.50 (s, 1H), 8.16 (d, J = 9.2 Hz, 1H), 7.88-7.82 (m, 2H), 7.80 (s, 1H), 7.70-7.64 (m, 2H), 7.53-7.47 (m, 2H), 7.23 (s, 1H), 6.11 (s, 2H), 4.97 (t, J = 6.4 Hz, 2H), 4.64 (t, J = 6.4 Hz, 2H), 4.14 (s, 3H), 4.05 (s, 3H), 2.54-2.46 (m, 2H). |
| NTD-210 | 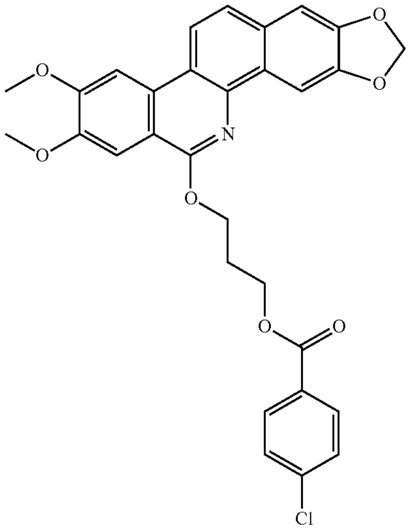 NTD-210 | + | >111 | 546.1 | $^1H$ NMR (400 MHz, $CDCl_3$) δ 8.51 (s, 1H), 8.17 (d, J = 8.2 Hz, 1H), 8.01-7.86 (m, 2H), 7.81 (s, 1H), 7.77-7.62 (m, 2H), 7.42-7.30 (m, 2H), 7.23 (s, 1H), 6.11 (s, 2H), 4.97 (t, J = 6.4 Hz, 2H), 4.64 (t, J = 6.4 Hz, 2H), 4.14 (s, 2H), 4.05 (s, 2H), 2.62-2.23 (m, 2H). |
| NTD-330 | 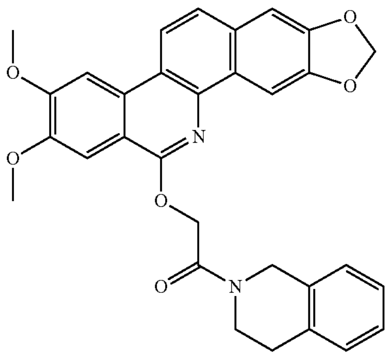 NTD-330 | | >111 | 522.2 | $^1H$ NMR (400 MHz, $CDCl_3$) δ 8.17 (s, 1H), 8.14 (d, J = 8.8 Hz, 1H), 7.78 (s, 1H), 7.65 (d, J = 8.8 Hz, 1H), 7.60 (s, 1H), 7.36 (s, 1H), 7.25-7.21 (m, 1H), 7.21-7.14 (m, 3H), 6.11 (s, 2H), 5.53 (s, 2H), 4.13 (s, 3H), 4.05 (s, 3H), 3.85 (t, J = 6.4 Hz, 2H), 2.66 (s, 2H), 1.91-1.81 (m, 2H). |

TABLE 6-continued

| Top1 Cleavage and Tdp Inhibition of Compounds. | | | | | |
|---|---|---|---|---|---|
| No. | Structure | Top1 cleavage | $IC_{50}$ Tdp1 (μM) | $[M + H]^+$ | $^1H$ NMR |
| NTD-332 | 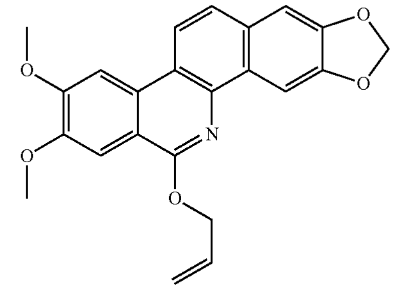 NTD-332 | | >111 | 389.1 | $^1H$ NMR (400 MHz, $CDCl_3$) δ 8.54 (s, 1H), 8.18 (d, J = 8.8 Hz, 1H), 7.83 (s, 1H), 7.75 (s, 1H), 7.68 (d, J = 8.8 Hz, 1H), 7.23 (s, 1H), 6.41-6.29 (m, 1H), 6.11 (s, 2H), 5.57 (d, J = 17.2 Hz, 1H), 5.35 (d, J = 9. Hz, 1H), 5.31 (d, J = 5.6 Hz, 2H), 4.14 (s, 3H), 4.08 (s, 3H). |
| NTD-334 | 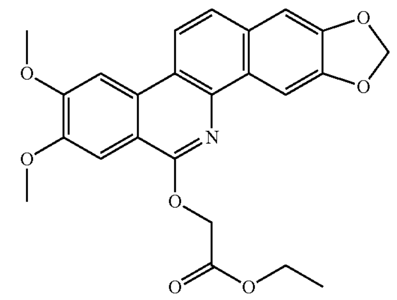 NTD-334 | | >111 | 435.1 | $^1H$ NMR (400 MHz, $CDCl_3$) δ 8.41 (s, 1H), 8.18 (d, J = 8.8 Hz, 1H), 7.83 (s, 1H), 7.80 (s, 1H), 7.69 (d, J = 8.8 Hz, 1H), 7.22 (s, 1H), 6.11 (s, 2H), 5.20 (s, 2H), 4.31 (q, J = 7.2 Hz, 2H), 4.15 (s, 3H), 4.09 (s, 3H), 1.33 (t, J = 7.2 Hz, 3H). |
| NTD-337 | 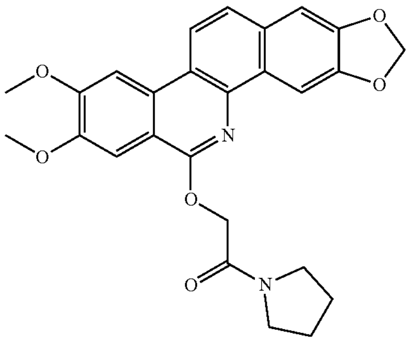 NTD-337 | 0 | | 460.2 | $^1H$ NMR (400 MHz, $CDCl_3$) δ 8.34 (s, 1H), 8.17 (d, J = 8.8 Hz, 1H), 7.84 (s, 1H), 7.82 (s, 1H), 7.68 (d, J = 8.8 Hz, 1H), 7.22 (s, 1H), 6.10 (s, 2H), 5.27 (s, 2H), 4.14 (s, 3H), 4.08 (s, 3H), 3.75 (t, J = 6.8 Hz, 2H), 3.63 (t, J = 6.8 Hz, 2H), 2.18-2.09 (m, 2H), 2.02-1.93 (m, 2H). |
| NTD-338 | 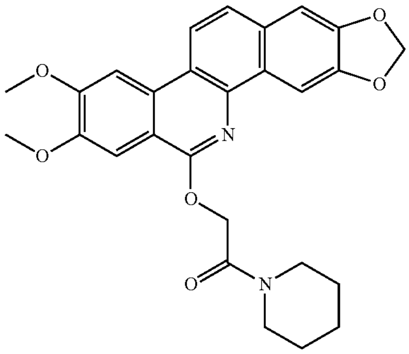 NTD-338 | 0 | | 474.2 | $^1H$ NMR (400 MHz, $CDCl_3$) δ 8.45 (s, 1H), 8.17 (d, J = 8.8 Hz, 1H), 7.83 (s, 1H), 7.82 (s, 1H), 7.68 (d, J = 8.8 Hz, 1H), 7.22 (s, 1H), 6.10 (s, 2H), 5.39 (s, 2H), 4.13 (s, 3H), 4.08 (s, 3H), 3.68-3.60 (m, 4H), 1.76-1.70 (m, 4H), 1.66-1.60 (m, 2H). |

TABLE 6-continued

Top1 Cleavage and Tdp Inhibition of Compounds.

| No. | Structure | Top1 cleavage | $IC_{50}$ Tdp1 (μM) | [M + H]+ | 1H NMR |
|---|---|---|---|---|---|
| NTD-341 | 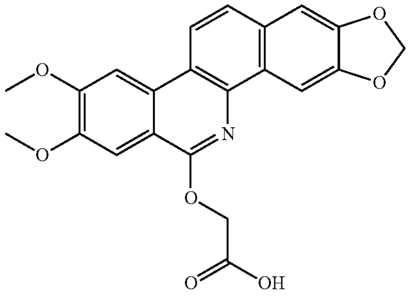 NTD-341 | + | | 407.1 | 1H NMR (500 MHz, DMSO) δ 8.46 (d, J = 9.0 Hz, 1H), 8.36 (s, 1H), 8.07 (s, 1H), 7.73 (d, J = 9.0 Hz, 1H), 7.71 (s, 1H), 7.42 (s, 1H), 6.19 (s, 2H), 4.76 (s, 2H), 4.08 (s, 3H), 3.97 (s, 3H). |
| NTD-348 | 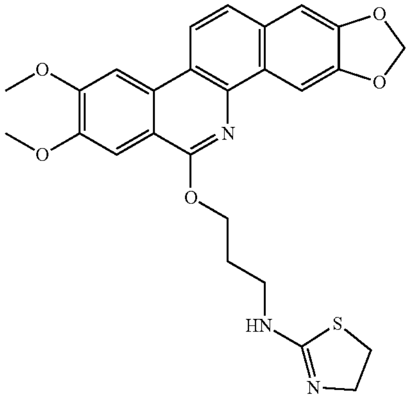 NTD-348 | + | | 491.2 | 1H NMR (400 MHz, DMSO) δ 8.79 (s, 1H), 8.51 (d, J = 8.8 Hz, 1H), 8.41 (s, 1H), 8.10 (s, 1H), 7.80 (d, J = 8.8 Hz, 1H), 7.68 (s, 1H), 7.46 (s, 1H), 6.20 (s, 2H), 4.79 (t, J = 6.0 Hz, 2H), 4.06 (s, 3H), 3.97 (s, 3H), 3.87 (t, J = 6.8 Hz, 2H), 3.73 (t, J = 6.8 Hz, 2H), 3.29 (t, J = 6.8 Hz, 2H), 2.33-2.22 (m, 2H). |
| NTD-351 | 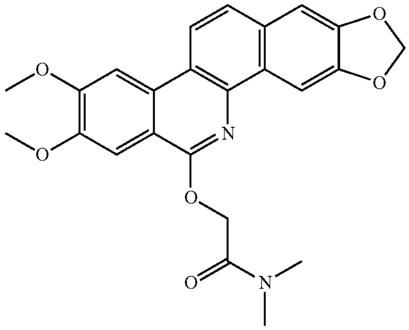 [SMILES: COc1cc2c(OCC(=O)O)nc3c4cc5c(cc4ccc3c2cc1OC)OCO5] NTD-351 | + | | 434.1 | 1H NMR (400 MHz, CDCl3) δ 8.39 (s, 1H), 8.18 (d, J = 8.8 Hz, 1H), 7.83 (s, 2H), 7.69 (d, J = 8.8 Hz, 1H), 7.23 (s, 1H), 6.11 (s, 2H), 5.40 (s, 2H), 4.15 (s, 3H), 4.08 (s, 3H), 3.27 (s, 3H), 3.08 (s, 3H). |
| NTD-352 | 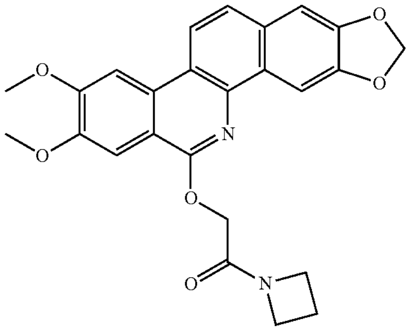 NTD-352 | ++ | | 446.1 | 1H NMR (500 MHz, DMSO) δ 8.52 (d, J = 9.0 Hz, 1H), 8.34 (s, 1H), 8.12 (s, 1H), 7.82 (d, J = 9.0 Hz, 1H), 7.66 (s, 1H), 7.47 (s, 1H), 6.20 (s, 2H), 5.11 (s, 2H), 4.40 (t, J = 7.5 Hz, 2H), 4.08 (s, 3H), 4.00-3.90 (m, 5H), 2.37-2.30 (m, 2H). |

TABLE 6-continued

Top1 Cleavage and Tdp Inhibition of Compounds.

| No. | Structure | Top1 cleavage | $IC_{50}$ Tdp1 (μM) | $[M + H]^+$ | $^1H$ NMR |
|---|---|---|---|---|---|
| NTD-353 | 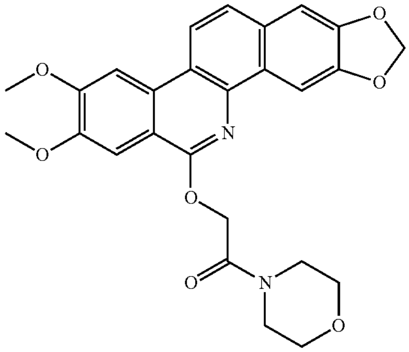 NTD-353 | 0 | | 476.2 | $^1H$ NMR (500 MHz, DMSO) δ 8.52 (d, J = 9.0 Hz, 1H), 8.34 (s, 1H), 8.12 (s, 1H), 7.80 (d, J = 9.0 Hz, 1H), 7.69 (s, 1H), 7.46 (s, 1H), 6.19 (s, 2H), 5.44 (s, 2H), 4.09 (s, 3H), 3.97 (s, 3H), 3.79-3.69 (m, 4H), 3.64-3.58 (m, 2H), 3.50-3.44 (m, 2H). |
| NTD-354 | 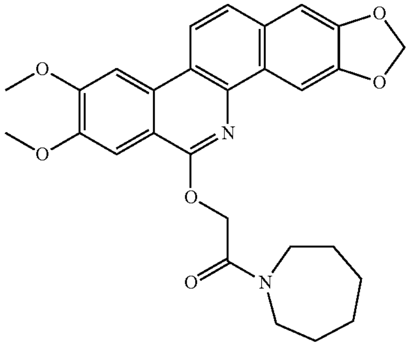 NTD-354 | 0 | | 488.2 | $^1H$ NMR (400 MHz, CDCl3) δ 8.40 (s, 1H), 8.16 (d, J = 8.8 Hz, 1H), 7.82 (s, 1H), 7.81 (s, 1H), 7.67 (d, J = 8.8 Hz, 1H), 7.21 (s, 1H), 6.10 (s, 2H), 5.41 (s, 2H), 4.14 (s, 3H), 4.08 (s, 3H), 3.70-3.61 (m, 4H), 1.96-1.88 (m, 2H), 1.81-1.75 (m, 2H), 1.74-1.68 (m, 2H), 1.68-1.62 (m, 2H). |
| NTD-355 | 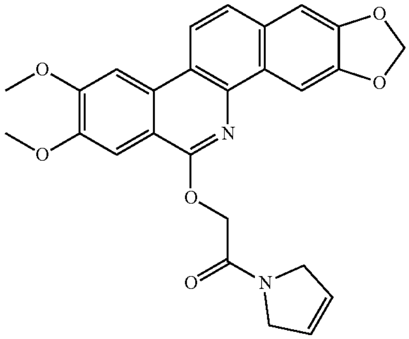 NTD-355 | + | | 458.1 | $^1H$ NMR (400 MHz, $CDCl_3$) δ 8.30 (s, 1H), 8.15 (d, J = 8.8 Hz, 1H), 7.82 (s, 1H), 7.80 (s, 1H), 7.67 (d, J = 8.8 Hz, 1H), 7.20 (s, 1H), 6.09 (s, 2H), 5.99-5.94 (m, 1H), 5.92-5.87 (m, 1H), 5.29 (s, 2H), 4.57-4.52 (m, 2H), 4.43-4.38 (m, 2H), 4.13 (s, 3H), 4.08 (s, 3H). |
| NTD-329 | 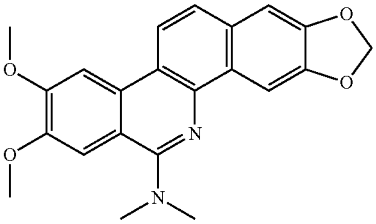 NTD-329 | | >111 | 376.1 | $^1H$ NMR (400 MHz, $CDCl_3$) δ 8.64 (s, 1H), 8.15 (d, J = 8.8 Hz, 1H), 7.84 (s, 1H), 7.64 (d, J = 8.8 Hz, 1H), 7.62 (s, 1H), 7.21 (s, 1H), 6.11 (s, 2H), 4.13 (s, 3H), 4.07 (s, 3H), 3.21 (s, 6H). |

TABLE 6-continued

Top1 Cleavage and Tdp Inhibition of Compounds.

| No. | Structure | Top1 cleavage | $IC_{50}$ Tdp1 (μM) | $[M + H]^+$ | $^1H$ NMR |
|---|---|---|---|---|---|
| NTD-325 | 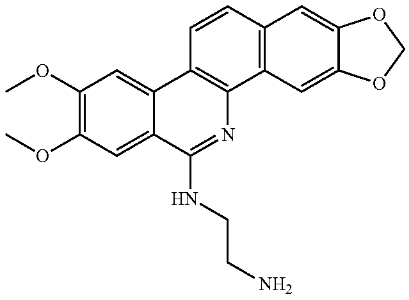 NTD-325 | 0 | 72, 107 | 392.2 | $^1H$ NMR (400 MHz, DMSO) δ 8.46 (s, 1H), 8.37 (d, J = 8.8 Hz, 1H), 8.31-8.16 (m, 2H), 8.01 (s, 1H), 7.92 (s, 2H), 7.59 (d, J = 8.8 Hz, 1H), 7.37 (s, 1H), 6.16 (s, 2H), 4.03 (d, J = 6.0 Hz, 3H), 3.99 (s, 3H), 3.31-3.26 (m, 2H), 3.06-2.99 (m, 1H), 1.24-1.15 (m, 2H). |
| NTD-301 | 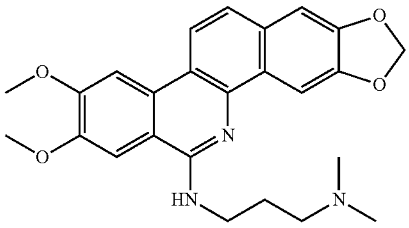 NTD-301 | 0 | 38 | 434.2 | $^1H$ NMR (400 MHz, DMSO) δ 8.43 (s, 1H), 8.33 (d, J = 8.8 Hz, 1H), 7.99 (s, 1H), 7.73 (s, 1H), 7.66 (t, J = 5.2 Hz, 1H), 7.54 (d, J = 8.8 Hz, 1H), 7.35 (s, 1H), 6.15 (s, 2H), 4.04 (s, 3H), 3.96 (s, 3H), 3.76 (dd, J = 12.8, 6.8 Hz, 2H), 2.60 (t, J = 6.8 Hz, 2H), 2.33 (s, 6H), 2.05-1.96 (m, 2H). |
| NTD-305 | 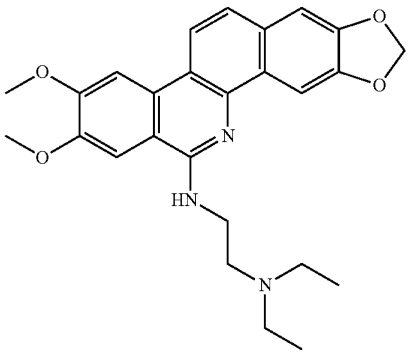 NTD-305 | + | >111 | 448.2 | $^1H$ NMR (400 MHz, $CDCl_3$) δ 8.60 (s, 1H), 8.13 (d, J = 8.8 Hz, 1H), 7.84 (s, 1H), 7.54 (d, J = 8.8 Hz, 1H), 7.36 (s, 1H), 7.20 (s, 1H), 6.09 (s, 2H), 4.13 (s, 3H), 4.08 (s, 3H), 3.93 (dd, J = 10.8, 5.2 Hz, 2H), 3.02-2.95 (m, 2H), 2.77-2.69 (m, 4H), 1.14 (t, J = 7.2 Hz, 6H). |
| NTD-307 | 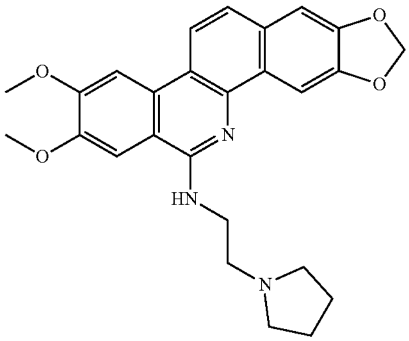 NTD-307 | + | 56.2 | 445.2 | $^1H$ NMR (400 MHz, DMSO) δ 8.41 (s, 1H), 8.34 (d, J = 8.8 Hz, 1H), 7.99 (s, 1H), 7.75 (s, 1H), 7.60 (t, J = 5.2 Hz, 1H), 7.54 (d, J = 8.8 Hz, 1H), 7.35 (s, 1H), 6.15 (s, 2H), 4.03 (s, 3H), 3.96 (s, 3H), 3.86 (dd, J = 6.4 Hz, 2H), 2.96-2.81 (m, 2H), 2.62 (t, J = 16.8 Hz 4H), 1.82-1.68 (m, 4H). |

TABLE 6-continued
Top1 Cleavage and Tdp Inhibition of Compounds.
| No. | Structure | Top1 cleavage | $IC_{50}$ Tdp1 (μM) | $[M + H]^+$ | $^1H$ NMR |
|---|---|---|---|---|---|
| NTD-309 | 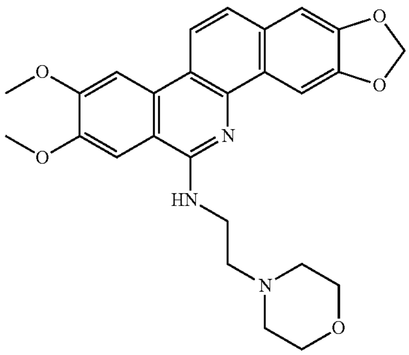 NTD-309 | + (n = 2) | >111 | 462.2 | $^1H$ NMR (400 MHz, $CDCl_3$) δ 8.59 (s, 1H), 8.12 (d, J = 8.8 Hz, 1H), 7.84 (s, 1H), 7.55 (d, J = 8.8 Hz, 1H), 7.20 (s, 1H), 6.09 (s, 3H), 4.13 (s, 3H), 4.08 (s, 3H), 3.96 (dd, J = 10.4, 5.2 Hz, 2H), 3.83-3.76 (m, 4H), 2.90 (t, J = 6.0 Hz, 2H), 2.70-2.61 (m, 4H). |
| NTD-311 | 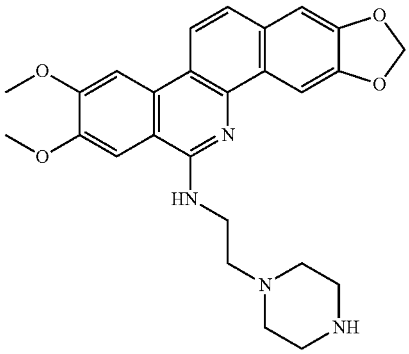 NTD-311 | + | >111 | 460.2 | $^1H$ NMR (400 MHz, DMSO) δ 8.40 (s, 1H), 8.34 (d, J = 8.8 Hz, 1H), 7.99 (s, 1H), 7.74 (s, 1H), 7.59-7.53 (m, 2H), 7.36 (s, 1H), 6.15 (s, 2H), 4.03 (s, 3H), 3.96 (s, 3H), 3.88-3.83 (m, 2H), 2.94-2.90 (m, 4H), 2.77 (t, J = 7.2 Hz, 2H), 2.65-2.59 (m, 4H), 1.94-1.86 (m, 1H). |
| NTD-312 | 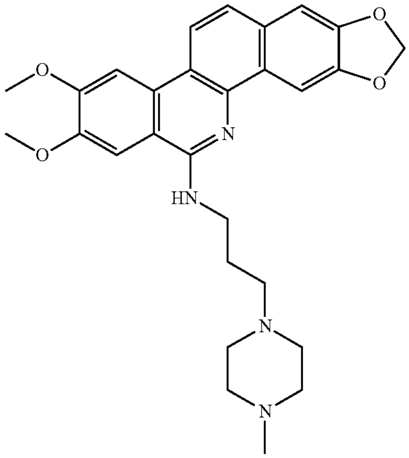 NTD-312 | + | >111 | 489.2 | $^1H$ NMR (400 MHz, $CDCl_3$) δ 8.60 (s, 1H), 8.12 (d, J = 8.8 Hz, 1H), 7.85 (s, 1H), 7.54 (d, J = 8.8 Hz, 1H), 7.28 (s, 1H), 7.19 (s, 1H), 6.31-6.18 (m, 1H), 6.09 (s, 2H), 4.13 (s, 3H), 4.09 (s, 3H), 3.95 (t, J = 6.0 Hz, 2H), 2.66 (t, J = 6.4 Hz, 2H), 2.63-2.34 (m, 8H), 2.30 (s, 3H), 2.10-2.02 (m, 2H). |

TABLE 6-continued

Top1 Cleavage and Tdp Inhibition of Compounds.

| No. | Structure | Top1 cleavage | $IC_{50}$ Tdp1 (μM) | $[M + H]^+$ | $^1H$ NMR |
|---|---|---|---|---|---|
| NTD-313 | 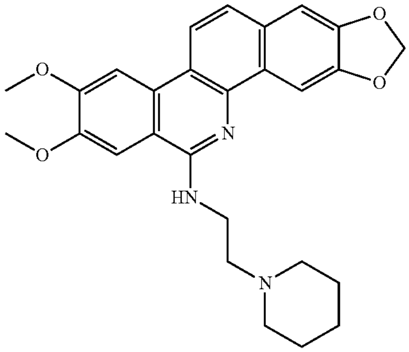 NTD-313 | + (n = 2) | >111 | 460.2 | $^1H$ NMR (400 MHz, $CDCl_3$) δ 8.62 (s, 1H), 8.12 (d, J = 8.8 Hz, 1H), 7.85 (s, 1H), 7.55 (d, J = 8.8 Hz, 1H), 7.28 (s, 1H), 7.20 (s, 1H), 6.09 (s, 2H), 4.13 (s, 3H), 4.08 (s, 3H), 3.91 (dd, J = 10.4, 5.6 Hz, 2H), 2.82 (t, J = 6.0 Hz, 2H), 2.62-2.52 (m, 4H), 1.69-1.62 (m, 5H), 1.55-1.47 (m, 2H). |
| NTD-314 | 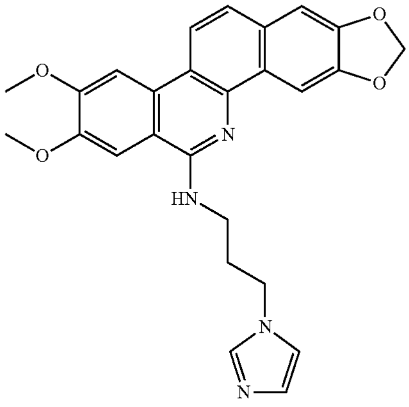 NTD-314 | + | >111 | 457.2 | $^1H$ NMR (400 MHz, DMSO) δ 8.37-8.32 (m, 2H), 7.99 (s, 1H), 7.75 (s, 1H), 7.71 (s, 1H), 7.59-7.53 (m, 2H), 7.35 (s, 1H), 7.27 (s, 1H), 6.94 (s, 1H), 6.16 (s, 2H), 4.19 (t, J = 6.8 Hz, 2H), 4.04 (s, 3H), 3.96 (s, 3H), 3.70 (dd, J = 12.4, 6.0 Hz, 2H), 2.32-2.22 (m, 2H). |
| NTD-363 | 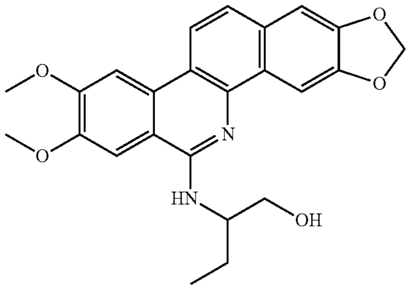 NTD-363 | + | | 421.2 | $^1H$ NMR (400 MHz, DMSO) δ 8.38 (s, 1H), 8.34 (d, J = 8.8 Hz, 1H), 7.99 (s, 1H), 7.83 (s, 1H), 7.54 (d, J = 8.8 Hz, 1H), 7.35 (s, 1H), 7.09-7.00 (m, 1H), 6.15 (s, 2H), 4.91-4.73 (m, 1H), 4.61-4.52 (m, 1H), 4.04 (s, 3H), 3.98 (s, 3H), 3.79-3.74 (m, 1H), 3.69-3.60 (m, 1H), 1.98-1.87 (m, 1H), 1.80-1.67 (m, 1H), 1.02 (t, J = 7.2 Hz, 3H). |
| NTD-342 | 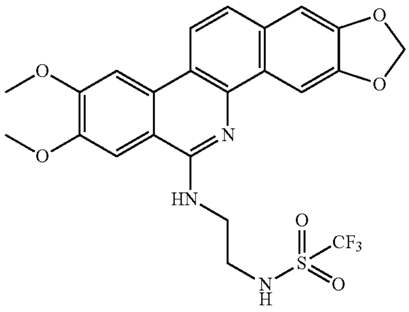 NTD-342 | 0 | | 523.1 | $^1H$ NMR (400 MHz, DMSO) δ 9.74 (t, J = 4.0 Hz, 1H), 8.45 (s, 1H), 8.36 (d, J = 8.8 Hz, 1H), 8.00 (s, 1H), 7.81-7.70 (m, 2H), 7.58 (d, J = 8.8 Hz, 1H), 7.36 (s, 1H), 6.17 (s, 2H), 4.05 (s, 3H), 3.95 (s, 3H), 3.91-3.81 (m, 2H), 3.66-3.58 (m, 2H). |

TABLE 6-continued

Top1 Cleavage and Tdp Inhibition of Compounds.

| No. | Structure | Top1 cleavage | $IC_{50}$ Tdp1 (μM) | $[M + H]^+$ | $^1H$ NMR |
|---|---|---|---|---|---|
| NTD-343 | 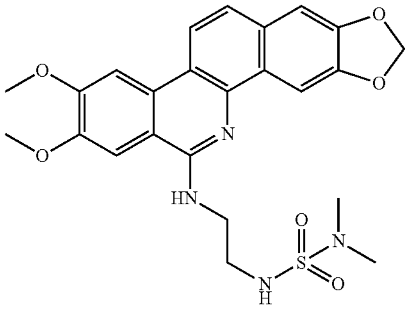 NTD-343 | 0 | | 498.2 | $^1H$ NMR (400 MHz, DMSO) δ 8.49 (s, 1H), 8.35 (d, J = 8.8 Hz, 1H), 7.99 (s, 1H), 7.74 (s, 1H), 7.71-7.62 (m, 1H), 7.56 (d, J = 8.8 Hz, 1H), 7.51 (t, J = 6.0 Hz, 1H), 7.36 (s, 1H), 6.15 (s, 2H), 4.04 (s, 3H), 3.95 (s, 3H), 3.84 (dd, J = 13.2, 6.0 Hz, 2H), 3.40-3.35 (m, 2H), 2.69 (s, 6H). |
| NTD-344 | 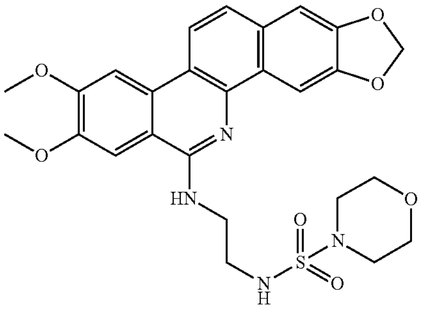 NTD-344 | 0 | | 540.2 | $^1H$ NMR (500 MHz, $CDCl_3$) δ 8.47 (s, 1H), 8.08 (d, J = 8.8 Hz, 1H), 7.78 (s, 1H), 7.53 (d, J = 8.8 Hz, 1H), 7.28 (s, 1H), 7.18 (s, 1H), 6.07 (s, 2H), 4.09 (s, 3H), 4.04 (s, 3H), 3.98 (t, J = 8.8 Hz, 2H), 3.66-3.61 (m, 4H), 3.58 (t, J = 8.8 Hz, 2H), 3.17-3.11 (m, 4H). |
| NTD-403 | 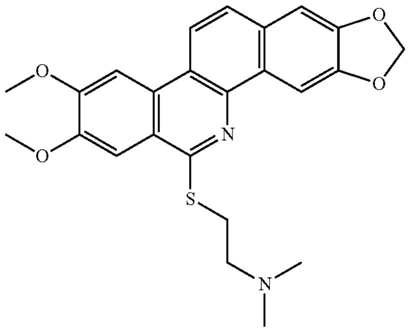 NTD-403 | ++ (n = 2) | >111 | 437.2 | $^1H$ NMR (400 MHz, $CDCl_3$) δ 8.65 (s, 1H), 8.20 (d, J = 8.8 Hz, 1H), 7.85 (s, 1H), 7.73 (d, J = 8.8 Hz, 1H), 7.60 (s, 1H), 7.24 (s, 1H), 6.13 (s, 2H), 4.14 (s, 3H), 4.08 (s, 3H), 3.80 (t, J = 6.8 Hz, 2H), 2.95 (t, J = 6.8 Hz, 2H), 2.47 (s, 6H). |
| NTD-404 | 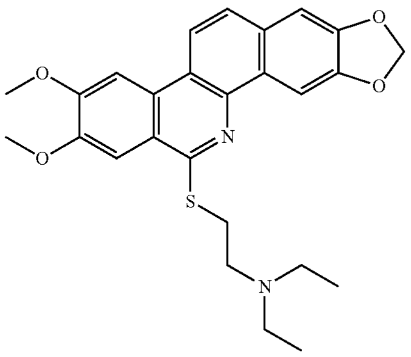 NTD-404 | ++ | >111 | 465.2 | $^1H$ NMR (400 MHz, $CDCl_3$) δ 8.70 (s, 1H), 8.22 (d, J = 8.8 Hz, 1H), 7.86 (s, 1H), 7.74 (d, J = 8.8 Hz, 1H), 7.62 (s, 1H), 7.25 (s, 1H), 6.12 (s, 2H), 4.15 (s, 3H), 4.09 (s, 3H), 3.76 (t, J = 7.2 Hz, 2H), 3.02 (t, J = 7.2 Hz, 2H), 2.80-2.70 (m, 4H), 1.13 (t, J = 6.8 Hz, 6H). |

TABLE 6-continued

| Top1 Cleavage and Tdp Inhibition of Compounds. | | | | | |
|---|---|---|---|---|---|
| No. | Structure | Top1 cleavage | $IC_{50}$ Tdp1 (μM) | $[M + H]^+$ | $^1H$ NMR |
| NTD-191 | 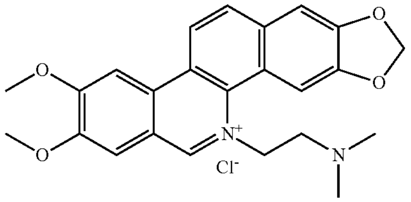 [SMILES: COc1cc2c[n+](CCN(C)C)c3c4cc5c(cc4ccc3c2cc1OC)OCO5 ; [Cl-]] | +++ | 64.2 ± 23.9 | 441.2 | $^1H$ NMR (400 MHz, $D_2O$) δ 9.39 (s, 1H), 8.03 (d, J = 8.8 Hz, 1H), 7.75 (d, J = 9.2 Hz, 1H), 7.64-7.57 (m, 3H), 7.21 (s, 1H), 6.22 (s, 2H), 5.54 (t, J = 6.4 Hz, 2H), 4.08 (s, 3H), 4.02 (s, 3H), 3.40 (t, J = 6.8 Hz, 2H), 2.59 (s, 6H). |
| NTD-192 | 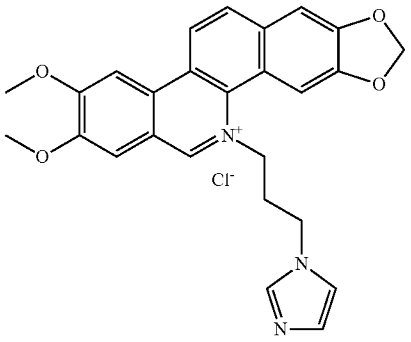 NTD-192 | +++ | 81.3 ± 14.5 | 478.2 | $^1H$ NMR (400 MHz, $D_2O$) δ 9.32 (s, 1H), 8.08 (s, 1H), 7.81 (d, J = 9.2 Hz, 1H), 7.62 (d, J = 8.4 Hz, 1H), 7.49 (s, 1H), 7.34 (s, 1H), 7.22 (s, 1H), 7.10 (s, 1H), 7.04 (s, 1H), 6.93 (s, 1H), 6.20 (s, 2H), 5.10 (t, J = 6.0 Hz, 2H), 4.03 (s, 3H), 4.01 (s, 3H), 3.97 (t, J = 6.0 Hz, 2H), 2.48-2.42 (m, 2H). |
| NTD-195 | 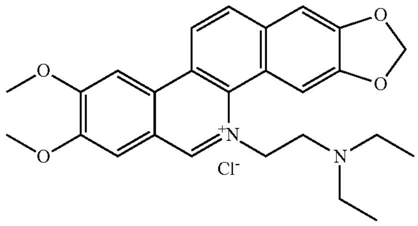 NTD-195 | ++ | >111 | 469.2 | $^1H$ NMR (400 MHz, $D_2O$) δ 9.47 (s, 1H), 8.15 (d, J = 8.8 Hz, 1H), 7.87 (d, J = 8.8 Hz, 1H), 7.74-7.67 (m, 2H), 7.64 (s, 1H), 7.32 (s, 1H), 6.27 (s, 2H), 5.63 (t, J = 7.2 Hz, 2H), 4.14 (s, 3H), 4.07 (s, 3H), 3.36 (t, J = 7.2 Hz, 2H), 2.98 (q, J = 1.2 Hz, 4H), 0.98 (t, J = 7.2 Hz, 6H). |

Example 3: Synthesis of Compounds 50-63 and 67

The synthesis of the 5-aminoethyl substituted benzophenanthridinone derivatives 50-63 and 67 is outlined in Scheme 3.

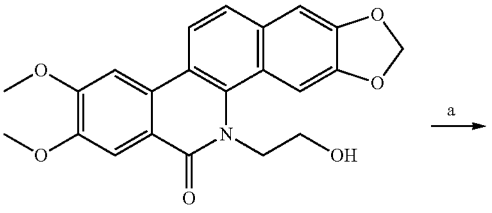

17a

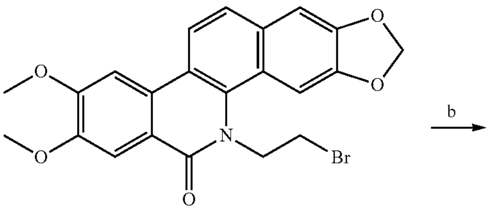

65 (91%)

-continued

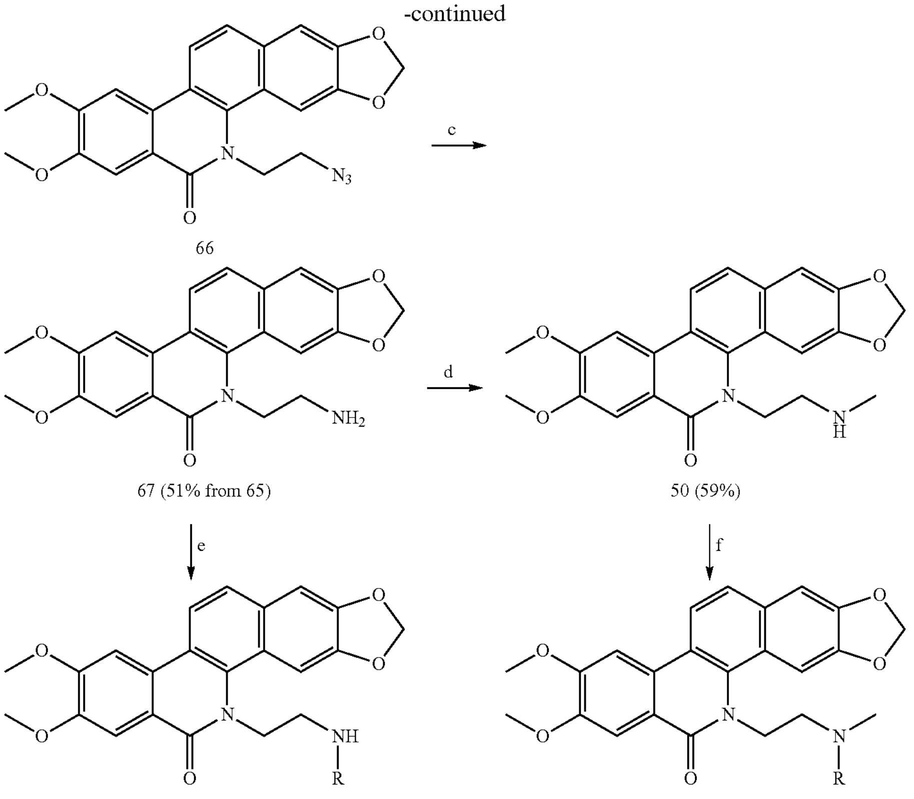

66

67 (51% from 65)

50 (59%)

58-63 (60-85%)

51-57 (30-85%)

The reagents and conditions used in Scheme 3 are as follows: (a) $PBr_3$, TCM, rt; (b) Pd/C, $H_2$(g), TIF, rt; (c) aqueous formaldehyde, Zn, $CH_3CO$—H, $H_2O$, rt; (d) RCl, DIPEA, DCM, rt.

The replacement of hydroxy group of 17a with bromine gave the bromide 65 in a 91% yield. Following displacement of the bromide with an azide group, the Pd/C catalytic reduction reaction under hydrogen atmosphere gave the target amine 67 in 51% yield from 65 (two steps). Primary amine intermediate 67 was reacted with formaldehyde to form a Schiff base, which was reduced with zinc powder to give the intermediate 50 in 59% yield. The acylation reaction of 67 and 50 with the appropriate reagent (e.g., RC(O)Cl, $RSO_2Cl$, dialkylchlorophosphate, or 2-chloro-1,3,2-dioxaphospholane-2-oxide) in dichloromethane gave the target products 58-63 and 51-57, respectively.

12-(2-bromoethyl)-2,3-dimethoxy-[1,3]dioxolo[4',5':4,5]benzo[1,2-c]phenanthridin-13(12H)-one (65). To a solution of 17a (0.5 mmol) in freshly distilled chloroform (10 mL), $PBr_3$ (1 mL) was added slowly with a syringe. The mixture was stirred at room temperature for 1 hour. The resulting gray precipitate was filtered and washed with chloroform, followed by saturated sodium bicarbonate and then water. The crude solid was dried and purified by silica gel column chromatography to give the gray solid 65, yield 91%, $^1$H NMR (DMSO) δ 8.84 (d, J=9.1 Hz, 1H), 8.31 (s, 1H), 8.26 (s, 1H), 8.16 (d, J=9.0 Hz, 1H), 7.73 (s, 1H), 7.69 (s, 1H), 6.33 (s, 2H), 5.76 (t, J 9.0 Hz, 2H), 5.35 (t, J=9.0 Hz, 2H), 4.21 (s, 3H), 4.04 (s, 3H). ESI-MS m/z: 455.1 (100%), 457.1 (100%) $[M+H]^+$.

12-(2-aminoethyl)-2,3-dimethoxy-[1,3]dioxolo[4',5':4,5]benzo[1,2-c]phenanthridin-13(12-H)-one (67). To a solution of 65 (456 mg, 1 mmol) in DMSO (50 mL), $NaN_3$ (130 mg, 2 mmol) was added. The mixture was stirred at room temperature for 16 hours. And then, the reactive solution was poured into water (100 mL). The formed gray precipitate was filtered and washed with saturated sodium bicarbonate followed by water. The crude solid (66) was dried for the next step without further purification. The crude solid 66 was dissolved in THF (100 mL) and Pd/C (42 mg) was added to the solution. The mixture was stirred at room temperature under hydrogen atmosphere for 2 hours. The reaction mixture was filtered and washed with THF. The filtrate was dried over $MgSO_4$ and concentrated under reduced pressure. The residue was purified by silica gel column chromatography to give the white solid 67, 51% yield from 65, mp=264.3-267.1° C. $^1$H NMR ($CDCl_3$) δ 7.98 (d, J=8.4 Hz, 1H), 7.91 (s, 1H), 7.59-7.54 (m, 2H), 7.52 (s, 1H), 7.18 (s, 1H), 6.10 (s, 2H), 4.60 (t, J=6.0 Hz, 21-), 4.11 (s, 3H), 4.06 (s, 3H), 3.13 (t, J=6.0 Hz, 2H). $^{13}$C NMR ($CDCl_3$) δ 164.9, 153.8, 149.9, 147.7, 147.6, 135.6, 131.9, 129.1, 123.6, 121.3, 119.6, 118.5, 117.4, 109.0, 105.0, 103.0, 102.4, 101.7, 56.4, 56.3, 55.1, 41.5. HRMS (ESI) m/z: 393.1439 $[M+H]^+$. calcd for C $_2H_{21}N_2O_5$ 393.1445.

2,3-dimethoxy-12-(2-(methylamino)ethyl)-[1,3]dioxolo[4'5':4,5]benzo[1,2-c]phenanthridin-13(12H)-one (50). To a solution of 67 (470 mg, 0.12 mmol) in acetic acid (140 mL) and water (100 mL), aqueous formaldehyde solution (40%, 90 mL) and Zn (156 mg, 2.4 mmol) was added. The mixture was stirred at room temperature overnight. Aqueous ammonia was added to quench the reaction. The solution was exacted with chloroform (3×50 ml,). The combined organic layers were dried over $MgSO_4$ and concentrated under reduced pressure. The residue was purified by silica gel column chromatography to give the white solid 50, yield 59%, mp=211.8-212.0° C. $^1$H NMR ($CDCl_3$) δ 7.97 (d, J=8.8 Hz, 1H), 7.90 (s, 1H), 7.59-7.54 (m, 2H), 7.54 (s, 1H), 7.18 (s, 1H), 6.10 (s, 2H), 4.61 (t, J=6.4 Hz, 2H), 4.10 (s, 3H), 4.05 (s, 3H), 3.11 (t, J=6.4 Hz, 2H), 2.36 (s, 3H). $^{13}$C NMR ($CDCl_3$) δ 165.0, 153.9, 149.9, 147.7, 147.6, 135.6, 131.9, 129.2, 123.6, 121.2, 119.6, 118.5, 117.4, 108.9, 105.0, 103.1, 102.4, 101.7, 56.4, 56.3, 52.0, 51.3, 36.2. HRMS (ESI) m/z: 407.1601 $[M+H]^+$, calcd for $C_{23}H_{23}N_2O_5$ 407.1601.

General procedure for the synthesis of compounds 51-63. To a solution of 67 or 50 (0.24 mmol) and DIPEA (2.4 mmol) in freshly distilled dichloromethane (30 ml) cooled in an ice bath, was added a solution of the appropriate RC(O)Cl, $RSO_2Cl$, dialkylchlorophosphate, or 2-chloro-1,3,2-dioxaphospholane-2-oxide (0.32 mmol) in dichloromethane (5 mL). The reaction solution was stirred and heated under reflux for 1 hour (for 58-63, or at room temperature for 51-57). The reaction solution was cooled to room temperature. The solvent was evaporated under reduced pressure. The residue was purified by silica gel column chromatography to provide purified 51-63.

N-(2-(2,3-dimethoxy-13-oxo-[1,3]dioxolo[4'5':4,5]benzo[1,2-c]phenanthridin-12(13H)-yl)ethyl)-1,1,1-trifluoro-N-methylmethanesulfonamide (51). White solid, yield 40%, ip=217.4-217.8° C. $^1$H NMR ($CDCl_3$), 7.99 (d, J=8.8 Hz, 1H), 7.87 (s, 1H), 7.62-7.56 (m, 2H), 7.41 (s, 1H), 7.20 (s, 1H), 6.13 (s, 2H), 4.81 (t, J=6.6 Hz, 2H), 4.11 (s, 2H), 4.06 (s, 2H), 3.82 (s, 2H), 2.87 (s, 3H). $^{13}$C NMR ($CDCl_3$) δ 164.6, 153.9, 149.8, 147.8, 147.7, 134.6, 131.8, 129.2, 123.9, 120.5, 119.2, 118.4, 117.7, 108.6, 105.2, 102.9, 101.7, 101.6, 56.2, 56.2, 49.0, 48.8, 35.9, HRMS (ESI) m/z: 539.1116 [M+H], calcd for $C_{24}H_{22}N_2O_7F_3S$ 539.1094.

N-(2-(2,3-dimethoxy-13-oxo-[1,3]dioxolo[4',5':4,5]benzo[1,2-c]phenanthridin-12(13H)-yl)ethyl)-N-methylcyclopropanesulfonanide (52). White solid, yield 80%, m/p>280° C. $^1$H NMR ($CDCl_3$) (7.96 (d, J=8.5 Hz, 1H), 7.88 (s, 1H), 7.56 (d, J=6.0 Hz, 2H), 7.52 (s, 1H), 7.17 (s, 1H), 6.11 (s, 2H), 4.74 (t, J=6.5 Hz, 2H), 4.10 (s, 2H), 4.05 (s, 2H), 3.74 (t, J=6.6 Hz, 2H), 2.78 (s, 3H), 2.08 (d, J=4.5 Hz, 1H), 1.07 (d, J=3.6 Hz, 2H), 0.83 (d, J=6.2 Hz, 2H). $^{13}$C NMR ($CDCl_3$) δ 164.6, 153.8, 149.7, 147.7, 147.7, 135.1, 131.8, 129.2, 123.7, 120.7, 119.2, 118.3, 117.4, 108.6, 104.9, 102.9, 102.1, 101.7, 56.2, 56.1, 50.2, 48.5, 35.7, 26.9, 4.5, 4.5. HRMS (ESI) m/z: 511.1536 $[M+H]^+$ calcd for $C_{26}H_{27}N_2O_7S$ 511.1533.

N-(2-(2,3-dimethoxy-13-oxo-[1,3]dioxolo[4',5':4,5]benzo[1,2-c]phenanthridin-12(13H)-yl)ethyl)-N-methyldiethylamine-1-sulfonamide (53). White solid, yield 83%, mp=234.7-235.9° C. $^1$H NMR ($CDCl_3$) δ 7.97 (d, J=8.6 Hz, 1H), 7.88 (s, 1H), 7.60-7.49 (m, 3H), 7.18 (s, 1H), 6.12 (s, 2H), 4.74 (t, J=6.5 Hz, 2H), 4.11 (s, 3H), 4.05 (s, 3H), 3.71 (t, J=6.5 Hz, 2H), 2.68 (s, 3H), 2.59 (s, 6H). $^{13}$C NMR ($CDCl_3$) δ 164.6, 153.8, 149.7, 147.7, 147.6, 135.2, 131.8, 129.2, 123.6, 120.8, 119.3, 118.3, 117.4, 108.6, 104.9, 102.8, 102.1, 101.7, 56.3, 56.2, 49.8, 48.9, 37.8, 37.8, 36.1. HRMS (ESI) m/z: 514.1669 $[M+H]^+$, calcd for $C_{25}H_{28}N_3O_7S$ 514.1642.

N-(2-(2,3-dimethoxy-13-oxo-[1,3]dioxolo[4,5':4,5]benzo[1,2-c]phenanthridin-12(13H)-yl)ethyl)-N-methylpyrrolidine-1-sulfonamide (54). White solid, yield 81%, mp=223.4-224.3° C. $^1$H NMR ($CDCl_3$) (7.97 (d, J=8.7 Hz, 1H), 7.89 (s, 1H), 7.56 (d, J=6.5 Hz, 2H), 7.54 (s, 1H), 7.18 (s, 1H), 6.12 (s, 2H), 4.75 (t J=6.6 Hz, 2H), 4.11 (s, 3H), 4.05 (s, 3H), 3.69 (t, J=6.6 Hz, 2H), 3.03 (t, J=6.7 Hz, 4H), 2.64 (s, 3H), 1.82-1.75 (m, 4H). $^{13}$C NMR ($CDCl_3$) δ 164.6, 153.8, 149.7, 147.7, 147.6, 135.3, 131.8, 129.2, 123.5, 120.9, 119.4, 118.2, 117.4, 108.7, 104.9, 102.9, 102.2, 101.7, 56.3, 56.2, 50.1, 48.8, 47.9, 47.9, 35.9, 25.5, 25.5. HRMS (ESI) nm/z: 540.1811 $[M+H]^+$, calcd for $C_{27}H_{30}N_3O_7$ 540.1799.

N-(2-(2,3-dimethoxy-13-oxo-[1,3]dioxolo[4',5':4,5]benzo[1,2-c]phenanthridin-12(13H)-yl)ethyl)-N-methylmorpholine-4-sulfonamide (55). White solid, yield 85%, mp=205.7-206.2° C. $^1$H NMR ($CDCl_3$) δ 7.96 (d, J=8.7 Hz, 1H), 7.88 (s, 1H), 7.56 (t, J==4.3 Hz, 2H), 7.27 (s, 1H), 7.17 (s, 1H), 6.11 (s, 2H), 4.75 (t, J=6.5 Hz, 2H), 4.11 (s, 3H), 4.06 (s, 3H), 3.69 (t, J=6.5 Hz, 2H), 3.55 (t, J=4.0 Hz, 4H), 2.91 (t, J=4.0 Hz, 3H). 2.64 (s, 3H). $^{13}$C NMR ($CDCl_3$) δ 164.5, 153.8, 149.8, 147.7, 147.7, 135.1, 131.7, 129.1, 123.6, 120.8, 119.3, 118.3, 117.5, 108.6, 104.9, 102.8, 102.1, 101.7, 66.2, 66.2, 56.5, 56.2, 49.9, 48.9, 45.9, 45.9, 36.3. HRMS (ESI) m/z: 556.1778 $[M+H]^+$, calcd for $C_{27}H_{30}N_3O_5S$ 556.1748.

Dimethyl(2-(2,3-dimethoxy-13-oxo-[1,3]dioxolo[4',5':4,5]benzo[1,2-c]phe-nanthridin-12(13H)-yl)ethyl)(methyl) phosphoramidate (56). White solid, yield 30%, mp=220.0-221.7° C. $^1$H NMR ($CDCl_3$) δ 7.97 (d, J=8.6 Hz, 1H), 7.90 (s, 1H), 7.57 (s, 1H), 7.54 (d, J=5.9 Hz, 2H), 7.18 (s, 1H), 6.11 (s, 2H), 4.73 (t, J=6.5 Hz, 2H), 4.10 (s, 3), 4.06 (s, 3H), 3.55-3.47 (m, 2H), 3.44 (s, 3H), 3.42 (s, 3H), 2.49 (d, J=9.8 Hz, 3H). $^{13}$C NMR ($CDCl_3$) δ 164.5, 153.6, 149.7, 147.6, 147.5, 135.3, 131.7, 129.1, 123.4, 120.9, 119.4, 118.3, 117.4, 108.8, 104.8, 102.8, 102.3, 101.6, 56.3, 56.1, 52.7, 52.7, 50.3, 47.4, 34.3. HRMS (ESI) m/z: 515.1584 [M+H]f, calcd for $C_{25}H_{25}N_2O_5P$ 515.1578.

2,3-dimethoxy-12-(2-(methyl(2-oxido-1,3,2-dioxaphospholan-2-yl)amino)ethyl)-[1,3]dioxolo[4',5':4,5]benzo[1,2-c]phenanthridin-13(12H)-one (57). White solid, yield 40%, mp=221.3-222.4° C. $^1$H NMR ($CDCl_3$) δ 7.97 (d, J=8.8 Hz, 1H), 7.86 (s, 11H), 7.56 (dd, J=11.7, 6.9 Hz, 2H), 7.51 (s, 1H), 7.18 (s, 11H), 6.12 (s, 2H), 4.74-4.66 (m, 2H), 4.32-4.25 (m, 2H), 4.24-4.19 (m, 2H), 4.11 (s, 3H), 4.05 (s, 3H), 3.53-3.41 (m, 2H), 2.65 (d, J=10.2 Hz, 2H). $^{13}$C NMR ($CDCl_3$) δ 164.6, 153.6, 149.6, 147.6, 147.5, 135.0, 131.7, 129.2, 123.5, 120.7, 119.3, 118.3, 117.5, 108.5, 104.9, 102.9, 102.0, 101.7, 65.7, 65.6, 56.3, 56.1, 49.1, 47.0, 34.5. HRMS (ESI) m/z: 513.1446 $[M+H]^+$, calcd for $C_{25}H_{36}N_2O_5P$ 513.1421.

N-(2-(2,3-dimethoxy-13-oxo-[1,3]dioxolo[4',5':4,5]benzo[1,2-c]phenanthridin-12(13H)-yl)ethyl)cyclopropanesulfonamide (58). White solid, yield 60%, mp=245.4-246.2° C. $^1$H NMR $CDCl_3$) δ 7.97 (d, J=8.7 Hz, 11H), 7.86 (s, 11H), 7.57 (d, J=9.7 Hz, 2H), 7.30 (s, 1H), 7.18 (s, 1H), 6.12 (s, 2H), 5.52 (t, J=6.1 Hz, 1H), 4.62 (t, J=5.5 Hz, 2H), 4.11 (s, 3H), 4.05 (s, 3H), 3.78 (dd, J=11.4, 5.7 Hz, 2H), 2.26 (td, J=8.0, 4.1 Hz, 1H), 1.14-1.02 (m, 2H), 0.92-0.81 (m, 2H). $^{13}$C NMR ($CDCl_3$) δ 165.0, 153.9, 149.8, 147.7, 147.6, 135.1, 131.8, 129.2 123.7, 120.7, 118.9, 118.4, 117.3, 108.6, 105.1, 102.9, 101.7, 101.7, 56.3, 56.2, 52.6, 43.5, 30.2, 5.4, 5.4. HRMS (ESI) m/z: 497.1394 $[M+H]^+$, calcd for $C_{25}H_{25}N_2O_7S$ 497.1377.

N-(2-(2,3-dimethoxy-13-oxo-[1,3]dioxolo[4',5':4,5]benzo[1,2-c]phenanthridin-12(13H)-yl)ethyl)dimethylamine-1-sulfonamide (59). White solid, yield 65%, mp>280° C. $^1$H NMR ($CDCl_3$) δ 7.98 (d, J=8.7 Hz, 11H), 7.86 (s, 11H), 7.57 (d, J=8.0 Hz, 2H), 7.29 (s, 1H), 7.19 (s, 1H), 6.11 (s, 2H), 5.58 (t, J=5.9 Hz, 1H), 4.59 (t, J=5.4 Hz, 2H), 4.11 (s, 3H), 4.06 (s, 3H), 3.70 (t, J=5.4 Hz, 2H), 2.70 (s, 6H). $^{13}$C NMR ($CDCl_3$) δ 165.1, 153.9, 149.8, 147.7, 147.6, 135.1, 131.9, 129.2, 123.8, 120.7, 118.9, 118.4, 117.3, 108.6, 105.1, 102.9, 101.7, 101.7, 56.3, 56.2, 52.4, 44.2, 37.9, 37.9. HRMS (ESI) m/z: 500.1531 [M+H]-, calcd for $C_{24}H_{26}N_3O_7S$ 500.1486.

N-(2-(2,3-dimethoxy-13-oxo-[1,3]dioxolo[4',5':4,5]benzo[1,2-c]phenanthridin-12(13H)-yl)ethyl)pyrrolidine-1-sulfonamide (60). White solid, yield 85%, mp=249.7-250.8° C. $^1$H NMR ($CDCl_3$) δ 7.98 (d, J=8.7 Hz, 1H), 7.87 (s, 1H), 7.58 (d, J=7.2 Hz, 2H), 7.31 (s, 1H), 7.19 (s, 1H), 6.12 (s, 2H), 5.41 (t, J=5.9 Hz, 1H), 4.62 (t, J=5.4 Hz, 2H), 4.11 (s, 3H), 4.06 (s, 3H), 3.70-3.67 (m, 2H), 3.19 (t, J=6.6 Hz, 4H), 1.82 (t, J=6.6 Hz, 4H). $^{13}$C NMR ($CDCl_3$) δ 165.0, 153.9, 149.8, 147.6, 147.6, 135.2, 131.9, 129.2, 123.7, 120.8, 119.1, 118.4, 117.4, 108.7, 105.1, 102.9, 101.8, 101.7, 56.3, 56.2, 52.3, 48.0, 48.0, 43.9, 25.5, 25.5. HRMS (ESI) n/z: 526.1640 [M+H]$^+$, calcd for $C_{26}H_{28}N_3O_7S$ 526.1642.

N-(2-(2,3-dimethoxy-13-oxo-[1,3]dioxolo[4',5':4,5]benzo[1,2-c]phenanthridin-12(13H)-yl)ethyl)morpholine-4-sulfonamide (61). White solid, yield 70%, mp=221.6-222.3° C. $^1$H NMR ($CDCl_3$) δ 7.98 (d, J=8.5 Hz, 1H), 7.85 (s, 1H), 7.58 (d, J=11.4 Hz, 2H), 7.27 (s, 1H), 7.19 (s, 1H), 6.12 (s, 2H), 5.66 (s, 1H), 4.61 (t, J=4.8 Hz, 2H), 4.11 (s, 3H), 4.06 (s, 3H), 3.68 (t, J=4.8 Hz, 2H), 3.64 (s, 4H), 3.06 (s, 4H). $^{13}$C NMR ($CDCl_3$) δ 165.2, 154.0, 149.9, 147.7, 147.7, 135.0, 131.9, 129.2, 123.8, 120.7, 118.9, 118.4, 117.4, 108.6, 105.1, 102.9, 101.7, 101.6, 66.1, 66.1, 56.3, 56.2, 52.3, 46.1, 44.4, 44.4. HRMS (ESI) m/z: 542.1623 [M+H]$^+$, calcd for $C_{26}H_{28}N_3O_8S$ 542.1592.

Dimethyl(2-(2,3-dimethoxy-13-oxo-[1,3]dioxolo[4',5':4,5]benzo[1,2-c]phenanthridin-12(13H)-yl)ethyl)phosphoramidate (62). White solid, yield 62%, mp=197.2-197.8° C. $^1$H NMR ($CDCl_3$) δ7.97 (d, J=8.7 Hz, 1H), 7.88 (s, 1H), 7.56 (d, J=7.5 Hz, 2H), 7.37 (s, 1H), 7.19 (s, 1H), 6.11 (s, 2H), 4.60 (t, J=5.8 Hz, 2H), 4.11 (s, 3H), 4.06 (s, 31), 3.55 (s, 3H), 3.52 (s, 31H), 3.50-3.46 (m, 2H). $^1$C NMR ($CDCl_3$) δ 164.8, 153.8, 149.8, 147.6, 147.5, 135.4, 131.7, 129.1, 123.6, 120.9, 119.3, 118.4, 117.3, 108.7, 104.9, 102.9, 101.9, 101.6, 56.3, 56.2, 53.6, 52.9, 52.9, 41.1. HRMS (ESI) m/z: 501.1423 [M+H]$^+$, calcd for $C_{24}H_{26}N_2O_8P$ 501.1421.

N-(2-(2,3-dimethoxy-13-oxo-[1,3]dioxolo[4,5':4,5]benzo[1,2-c]phenanthridin-12(13H)-yl)ethyl)cyclopropanecarboxamide (63). White solid, yield 80%, mp=237.6-238.1° C. $^1$H NMR ($CDCl_3$) δ 7.97 (d, J=8.7 Hz, 1H), 7.89 (s, 1H), 7.57 (d, J=9.7 Hz, 2H), 7.42 (s, 1H), 7.17 (s, 1H), 6.73 (s, 1H), 6.10 (s, 2H), 4.60 (t J=4.9 Hz, 2H), 4.11 (s, 3H), 4.07 (s, 3H), 3.88 (d, J=5.0 Hz, 2H), 0.87 (d, J=6.7 Hz, 1H), 0.81 (s, 2H), 0.63 (d, J=4.7 Hz, 2H). $^{13}$C NMR ($CDCl_3$) δ 173.5, 165.2, 153.8, 149.7, 147.7, 147.6, 135.4, 131.8, 129.3, 123.7, 120.9, 119.1, 118.2, 117.1, 108.5, 104.9, 102.9, 102.1, 101.7, 56.3, 56.2, 52.2, 40.3, 14.7, 7.0, 7.0. HRMS (ESI) m/z: 461.1732 [M+H]$^+$, calcd for $C_{26}H_{25}N_2O_6$ 461.1707.

Example 4. Biological Activity of Compounds 49-63

TABLE 7

TOP inhibitory activity and cytotoxicity of compounds.

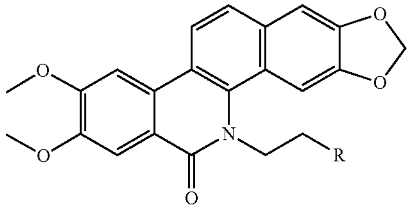

| Cmpd. | R | TOP1 inhibition | $GI_{50}$ ± SC (μM)$^b$ HCT116 | MCF-7 | DU145 | A-49 |
|---|---|---|---|---|---|---|
| CPT | /$^c$ | ++++ | 0.009 ± 0.001 | 0.012 ± 0.002 | 0.21 ± 0.069 | 0.099 ± 0.017 |
| 48 | / | 0/+ | 74 ± 4.4 | 31 ± 4.6 | 64 ± 11 | 39 ± 26 |
| 19a | $NMe_2$ | +++ | 0.076 ± 0.007 | 0.34 ± 0.098 | 0.018 ± 0.002 | 0.79 ± 0.11 |
| 67 | $NH_2$ | ++ | 0.29 ± 0.019 | 0.10 ± 0.001 | 0.014 ± 0.001 | 0.98 ± 0.014 |
| 50 | NHMe | +++ | 0.036 ± 0.003 | 0.090 ± 0.001 | 0.002 ± 0.001 | 0.97 ± 0.001 |
| 51 | 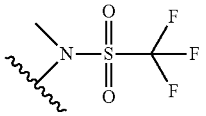 [SMILES: *N(C)S(=O)(=O)C(F)(F)F] | 0/+ | 86 ± 2.5 | 35 ± 1.7 | 65 ± 1.2 | 42 ± 0.98 |
| 52 | 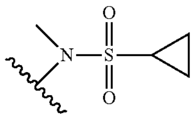 [SMILES: *N(C)S(=O)(=O)C1CC1] | + | 7.9 ± 0.15 | 5.8 ± 0.89 | 10 ± 1.2 | 15 ± 1.5 |
| 53 | 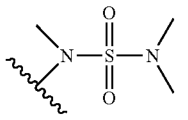 | + | 0.96 ± 0.04 | 1.5 ± 0.15 | 15 ± 0.59 | 7.9 ± 0.23 |
| 54 | 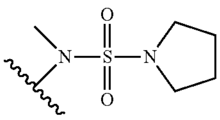 [SMILES: *N(C)S(=O)(=O)N1CCCC1] | + | 2.5 ± 0.18 | 3.8 ± 0.25 | 3.1 ± 0.30 | 5.3 ± 0.41 |

TABLE 7-continued
TOP inhibitory activity and cytotoxicity of compounds.
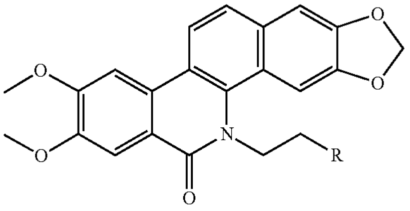
| Cmpd. | R | TOP1 inhibition | $GI_{50}$ ± SC (μM)[b] HCT116 | MCF-7 | DU145 | A-49 |
|---|---|---|---|---|---|---|
| 55 | 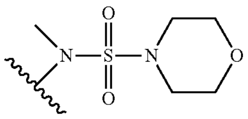 [SMILES: *N(C)S(=O)(=O)N1CCOCC1] | + | 40 ± 1.2 | 64 ± 0.57 | 48 ± 1.2 | 35 ± 2.5 |
| 56 | 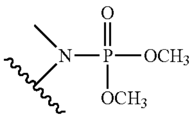 [SMILES: *N(C)P(=O)(OC)OC] | ++ | 9.2 ± 0.14 | 10 ± 0.54 | 5.3 ± 0.21 | 14 ± 1.4 |
| 57 | 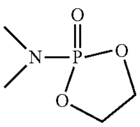 | ++ | 5.9 ± 1.2 | 1.8 ± 0.47 | 3.6 ± 0.25 | 1.9 ± 0.034 |
| 58 | 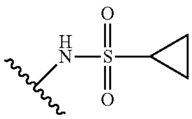 [SMILES: *NS(=O)(=O)C1CC1] | ++ | 5.2 ± 0.13 | 3.0 ± 0.63 | 1.3 ± 0.32 | 4.3 ± 0.21 |
| 59 | 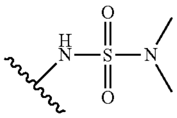 [SMILES: *NS(=O)(=O)N(C)C] | + | 30 ± 2.1 | 21 ± 1.0 | 45 ± 1.2 | 35 ± 0.14 |
| 60 | 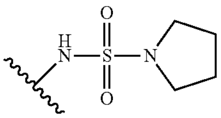 [SMILES: *NS(=O)(=O)N1CCCC1] | 0/+ | 34 ± 1.1 | 38 ± 0.78 | 79 ± 1.0 | 61 ± 0.15 |
| 61 | 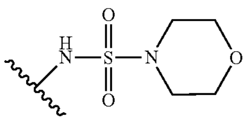 [SMILES: *NS(=O)(=O)N1CCOCC1] | ++ | 1.1 ± 0.047 | 0.89 ± 0.12 | 1.6 ± 0.021 | 2.9 ± 0.027 |
| 62 | 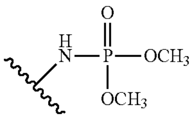 [SMILES: *NP(=O)(OC)OC] | 0/+ | 51 ± 1.5 | 48 ± 1.9 | 39 ± 2.2 | 41 ± 2.0 |
| 63 | 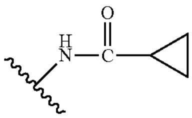 [SMILES: *NC(=O)C1CC1] | + | 5.3 ± 0.11 | 2.2 ± 0.27 | 7.8 ± 0.52 | 1.3 ± 0.006 |

Regarding Table 7, the superscripts are defined as follows: ([a]TOP1 cleavage inhibitory activity of the synthesized compounds was semi-quantitatively graded relative to CPT at 1 μM concentration: 0, no inhibition: +, between 20% and 50% activity; ++, between 50% and 75% activity: +++, between 75% and 95% activity; ++++. equal activity. [b]$GI_{50}$ values (means±SD) were calculated from MTT assay, and defined as the concentrations of compounds that resulted in 50% cell growth inhibition. The experiments were repeated at least three times independently. [c]"/" means inapplicable.

Figure 12:
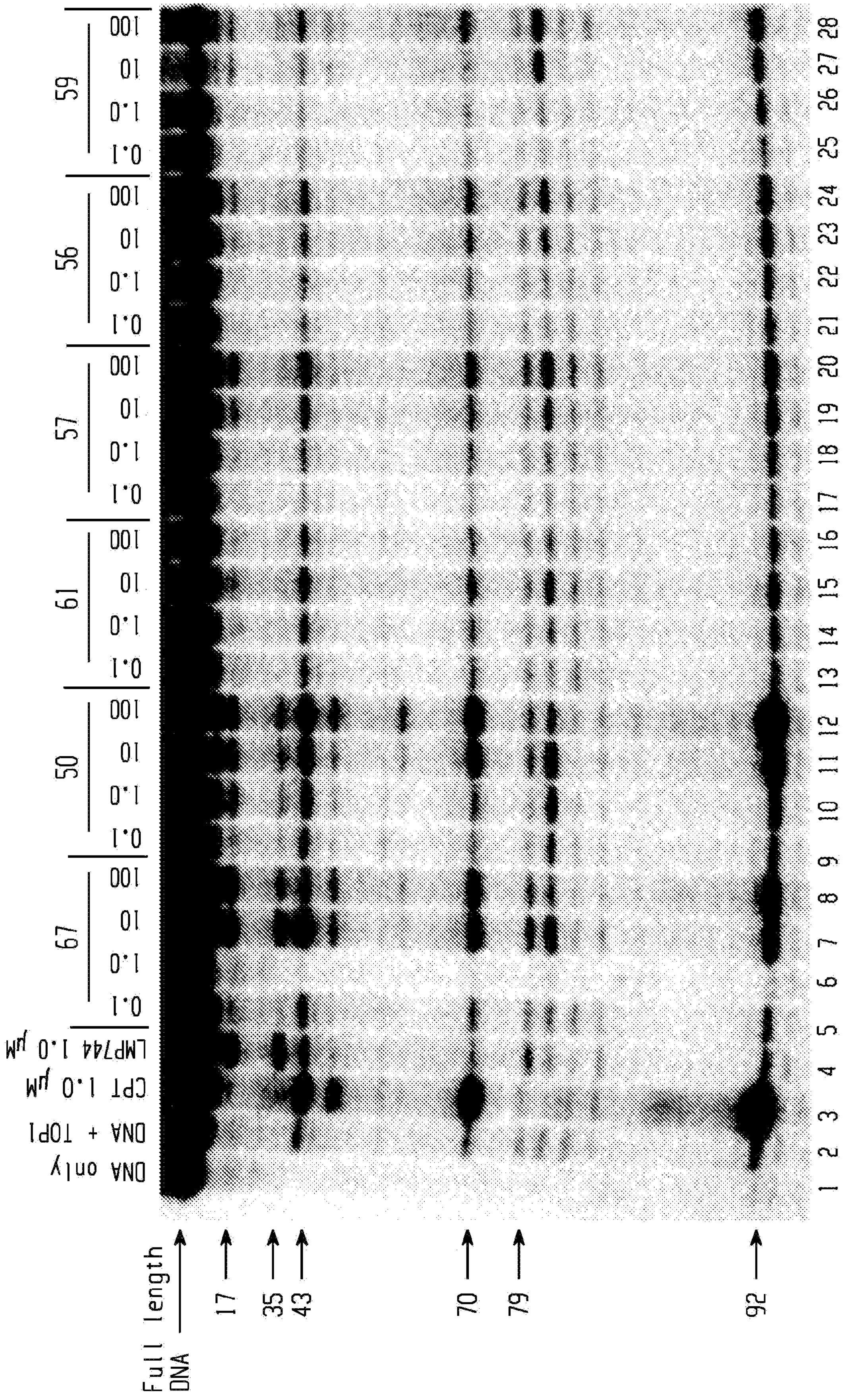
FIG. 12: A gel of TOP1-mediated DNA cleavage assay. Lane 1, DNA alone; lane 2 DNA and TOP1; lane 3, DNA and TOP1 with CPT (1.0 μM); lane 4, DNA and TOP1 with LMP744 (1.0 μM); lanes 5-28, DNA and TOP1 with the indicated compounds at 0.1, 1.0, 10 and 100 μM concentration, respectively. The arrows at left indicate the cleavage site positions.

Compounds 50-63 and 67 were tested for TOP1 inhibitory activity using a TOP1-mediated cleavage assay with a 3'-[$^{32}$P]-labeled double-stranded DNA fragment as substrate along with CPT and LMP744, an indenoisoquinoline TOP1 inhibitor, as positive controls (M. Cushman, M. Jasaraman, J. A. Vroman, A. K. Fukunaga, B. M. Fox, G. Kolilhagen, D. Stnumberg, Y. Pommier, Synthesis of New Indeno[1,2-c] isoquinolines: Cytotoxic Non-Camptothecin Topoisomerase I Inhibitors, J. Med. Chem., 43 (2000) 3688-3698; T. S, Dexheimer, Y. Pommier, DNA cleavage assay for the identification of topoisomerase I inhibitors, Nat. Protoc., 3 (2008) 1736-1750). All compounds were. tested at four concentrations, 0.1, 1.0, 10 and 100 μM. The TOP1-mediated cleavage activity of the compounds was semi-quantitatively graded based on the number and intensities of the DNA cleavage bands relative to the TOP1 inhibition of CPT at 1 μM concentration: 0, no inhibitory activity; +, between 20% and 50% inhibitory activity; ++, between 50% i and 75% inhibitory activity; +++, between 75% amid 95% inhibitory activity; ++++, equal inhibitory activity to CPT. The TOP1-mediated cleavage activity of the synthesized compounds is summarized in Table 7. Compared to 48, most of the synthesized compounds showed increased TOP1 inhibitory activity except for 51, 60 and 62, which showed similar activity to 48. Compound 50 showed the most potent TOP1 inhibition of +++, similar to compound 19a. Compounds 67, 56, 57, 58 and 61 showed moderate TOP1 inhibitory activity (++). A representative TOP1-mediated cleavage assay gel is shown in FIG. 12. Compounds 67, 50, 56-58 and 61 exhibited the ability to induce TOP1-mediated cleavage bands in a dose-dependent manner with cleavage sites similar to LMP744 but not to CPT. For example, the cleavage sites 17, 35 and 79 could be induced by 67, 50, 56-58 and 61 but not by CPT, implying that the synthesized benzophenanthridinone derivatives trap TOP1cc at a different DNA sequence than CPT.

Figure 13A:
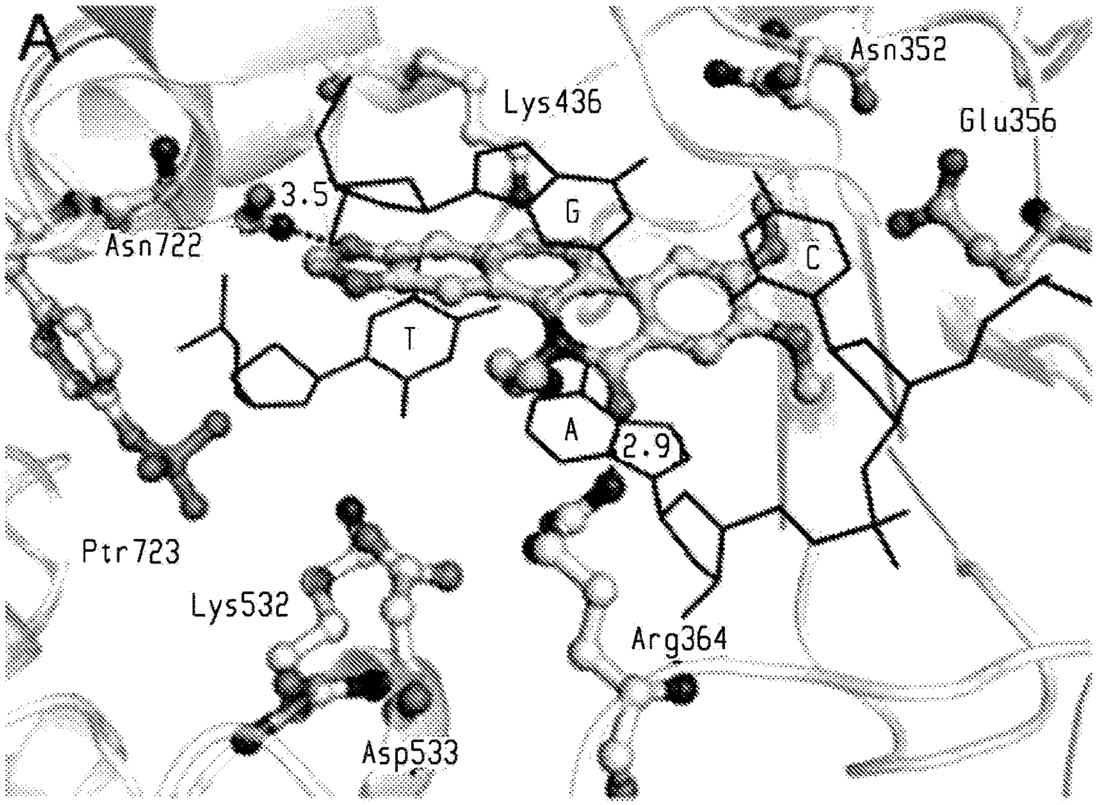
FIGS. 13A-13B show a hypothetical binding mode of 50 in the ternary TOP1-DNA-drug complex (PDB ID: 1K4T). Compound 50 is shown in a ball and stick representation and the DNA base pairs are displayed in bond-line notation (FIG. 13A). TOP1 is shown as a surface and DNA is shown as an animated structure.
Figure 13B:
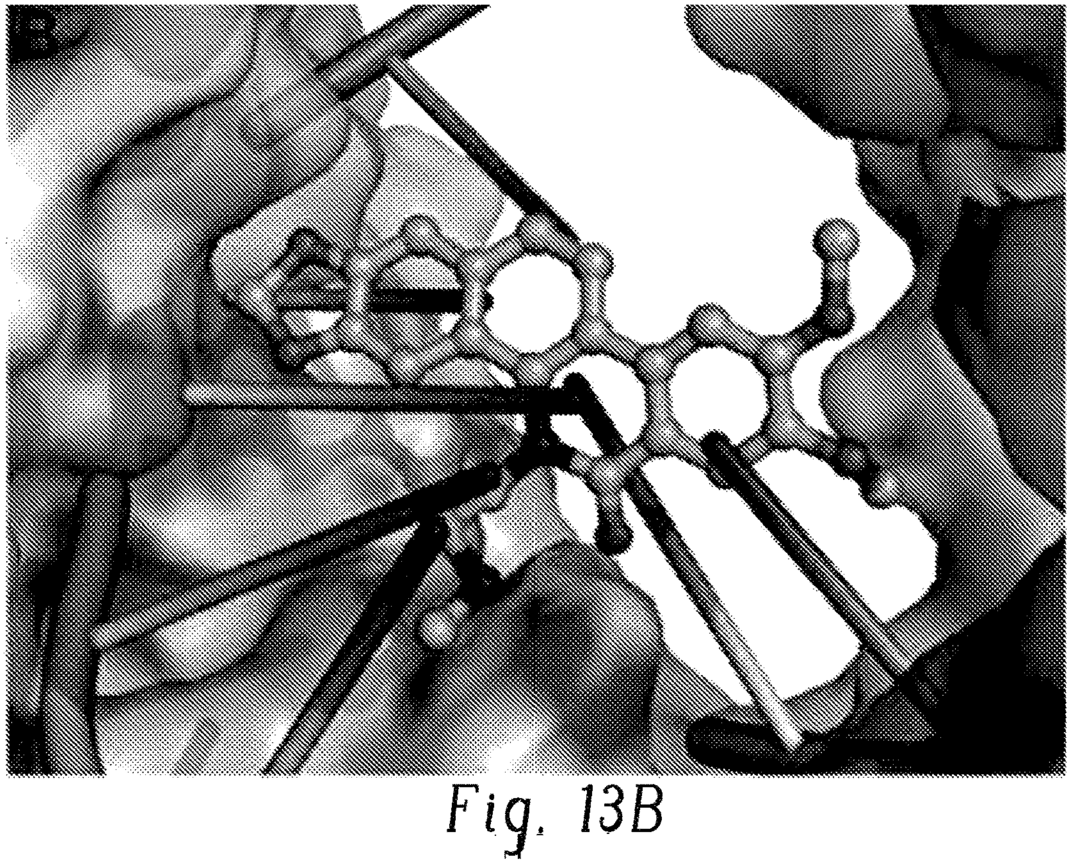

To inspect the molecular binding mode of the synthesized TOP1 inhibitors within the TOP1-DNA complex, molecular modeling was performed. A hypothetical binding model was built using in-silico docking from the X-ray crystal of the TOP1-DNA-ligand ternary complex (PDB ID: 1K4T) (B. L. Staker, K. Hjerrild, M. D. Feese, C. A. Behnke, A. B. Burgin, Jr., L. Stewart, The mechanism of topoisomerase I poisoning by a camptothecin analog, Proc. Natl. Acad. Sci. USA, 99 (2002) 15387-15392). Compounds were energy-minimized and docked into the binding model. As shown in FIG. 13A, the benzophenanthridinone scaffold of 50 intercalates in the DNA break made by TOP1 and readily stacks with the +1 and −1 base pairs flanking the DNA cleavage site, similar to that of 19a. The A- and B-ring of 50 stack with the bases of the non-cleaved strand (C and A), while the C—and D-ring stack with the scissile strand bases (G and T). In addition, the methylaminoethyl side chain of 50 extends into the minor groove of the DNA and binds to a limited space (FIG. 13B). Also, a hydrogen bond (2.9 Å) was observed between the lactam oxygen atom of 50 and the R364 residue (FIG. 13A), implying the importance of a hydrogen bond acceptor, which is consistent with the cytotoxicity of 50 against the prostate cancer cells DU145-RC0.1, which are resistant cells with a R364H mutation of TOP (Y. Urasaki, G. S. Laco, P. Pourquier, Y. Takebayashi, G. Kohlhagen, C. Gioffre, H. Zhang, D. Chatterjee, P. Pantazis, Y. Pommier, Characterization of a novel topoisomerase I mutation from a camptothecin resistant human prostate cancer cell line, Cancer Res., 61 (2001) 1964-1969). DU145-RC0.1 cells showed high resistance to 50 (Table 9). In addition, a hydrogen bond observed between the oxygen atom in the dioxole ring of 50 and Asn722 (3.5 Å) might also contribute to the TOP1cc inhibition.

The cytotoxicity of the synthesized benzophenanthridone derivatives was evaluated using an MTT assay against four human tumor cell lines: colon cancer HCT116, breast cancer MCF-7, prostate cancer DU-145 and non-small cell lung cancer A549 cell lines. The compounds were incubated with the cells for 72 hours in a five-dose assay ranging from 0.01 to 100 μM concentration. At the end of the incubation, the MTT solution was added to test the percentage growth of tumor cells. The $GI_{50}$ values, defined as the concentrations of the compounds that resulted in 50% cell growth inhibition, were calculated (Table 7).

With the increased TOP1 inhibitory activity (+, ++ and +++), the benzophenanthridone analogues 67, 50, 52-59, 61 and 63 exhibited increased cytotoxicity against these four tumor cell lines compared with the parent 48 with TOP1 inhibition of +/0, except for 55, which exhibited decreased cytotoxicity against MCF-7 cells. Compound 50 with the most potent TOP1 inhibition of +++ showed the highest cytotoxicity against HCT116 ($GI_{50}$=0.036 μM), MCF-7 ($GI_{50}$=0.090 μM), DU145 ($GI_{50}$=0.002 μM) and A549 ($GI_{50}$=0.97 μM) cell lines. Although 50 showed similar TOP1 inhibition as 48, 50 showed higher cytotoxicity against HCT116, MCF-7 and DU145 cells, which might possibly be due to improved solubility and cellular permeability. Indeed, 50 had an improved bioavailability (20.4%, Table 10) in vivo when compared to the bioavailability of 48 (15.5%) as reported by Zhang et al. Furthermore, 50 showed the highest cytotoxicity against DU145 cells at low nanomolar concentration (0.002 μM). With the bigger steric terminus of the side chain at the 5-position, the compounds 51-63 showed both decreased TOP1 inhibitory activity and cytotoxicity compared 50, which is consistent with molecular modelling analysis.

Compounds 67 and 50 were submitted to the National Cancer Institute (NCI, USA) for further study on cytotoxicity against the 60 cancer cell lines representing nine tissue types (NCI-60). The results are summarized in Table 8.

TABLE 8

| Cytotoxicity of 67 and 50 against individual NCI-60 cell lines | | | | | | | |
|---|---|---|---|---|---|---|---|
| | | $GI_{50}$ (μM)[a] | | | | $GI_{50}$ (μM) | |
| Panel | Cell line | 67 | 50 | Panel | Cell line | 67 | 50 |
| | MGM[b] | 0.525 | 0.0977 | Colon | COLO 205 | 0.29 | 0.0605 |
| Leukemia | CCRF-CEM | 0.15 | 0.0201 | Cancer | HCC-2998 | 1.02 | 0.156 |
| | K-562 | 0.161 | 0.0394 | | HCT116 | 0.285 | 0.0515 |
| | MOLT-4 | 0.0633 | 0.0234 | | HCT-15 | 0.42 | 0.116 |
| | RPMI-8226 | 0.257 | 0.0763 | | HT29 | 0.168 | 0.0508 |
| | SR | 0.0907 | 0.0173 | | KM12 | 1.1 | 0.238 |
| Non-Small | A549/ATCC | 0.584 | 0.0948 | | SW-620 | 0.243 | 0.0658 |
| Cell | EKVX | 1.36 | 0.202 | Renal | 786-0 | 0.464 | 0.0703 |
| Lung | HOP-62 | 0.399 | 0.0439 | Cancer | A498 | 1.23 | 0.127 |
| Cancer | HOP-92 | 3.56 | 0.184 | | ACHN | 0.366 | 0.0856 |
| | NCI-H226 | 1.34 | 0.172 | | CAKI-1 | 0.295 | 0.0644 |
| | NCI-H23 | 0.451 | 0.0906 | | RXF393 | 0.929 | 0.16 |
| | NCI-H322M | 0.99 | 0.147 | | SN 12C | 0.739 | 0.171 |
| | NCI-H460 | 0.23 | 0.0212 | | TK-10 | 1.35 | 0.316 |
| | NCI-H522 | 0.0875 | 0.0274 | | UO-31 | 0.35 | 0.104 |
| CNS | SF-268 | 0.442 | 0.0903 | Breast | MCF-7 | 0.164 | 0.0292 |
| Cancer | SF-295 | 0.279 | 0.0346 | Cancer | MDA-MB-231/ATCC | 1.28 | 0.362 |
| | SF-539 | 1.06 | 0.124 | | HS 578T | 1.96 | 0.904 |
| | SNB-19 | 0.398 | 0.116 | | BT-549 | 0.918 | 0.202 |
| | SNB-75 | 0.596 | 0.0885 | | T-47D | 0.368 | 0.0757 |
| | U251 | 0.26 | 0.0394 | | MDA-MB-468 | 0.157 | 0.0599 |
| Melanoma | LOX IMVI | 0.246 | 0.0389 | Ovarian | IGROV1 | 0.5 | 0.145 |
| | MALME-3M | 0.613 | 0.174 | Cancer | OVCAR-3 | 0.826 | 0.166 |
| | M14 | 0.324 | 0.0581 | | OVCAR-4 | 0.782 | 0.154 |
| | MDA-MB-435 | 0.759 | 0.118 | | OVCAR-5 | 1.2 | 0.183 |
| | SK-MEL-2 | 3.01 | 0.393 | | OVCAR-8 | 0.93 | 0.132 |
| | SK-MEL-28 | 3.05 | 0.573 | | NCI/ADR-RES | 1.01 | 0.165 |
| | SK-MEL-5 | 0.614 | 0.0909 | | SK-OV-3 | 1.24 | 0.157 |
| | UACC-257 | 1.9 | 0.122 | Prostate | PC-3 | 0.532 | 0.112 |
| | UACC-62 | 0.278 | 0.0451 | Cancer | DU145 | 0.527 | 0.13 |

Regarding Table 8, the superscripts are defines as follows:

[a]$GI_{50}$ values were defined as the compound concentrations that resulted in 50% cell growth inhibition. The cells were incubated for two days with the tested compounds.

[b]MGM: mean graph midpoint for growth inhibition of all human cancer cell lines.

Regarding Table 8, the superscripts are defined as follows: [a]$GI_{50}$ values were defined as the compound concentrations that resulted in 50% cell growth inhibition. The cells were incubated for two days with the tested compounds. [b]MGM: mean graph midpoint for growth inhibition of all human cancer cell lines.

Regarding Table 8, according to the NCI established procedures, the cells were incubated with 67 or 50 for 48 hours and stained with sulforhodamine B dye. The $GI_{50}$ values were plotted and summarized in Table 8. The results indicate that 50 has a higher mean graph midpoint (MGM) for growth inhibition of all cancer cell lines of 0.0977 μM than that of 67 (0.525 μM) and 48 (0.145 μM) (Zhang et al.). Compound 50 shows high cytotoxicity against 28 cancer cell lines at nanomolar range (<100 nM) and the most cytotoxic against leukemia SR with $GI_{50}$ of 0.0173 μM.

The cytotoxicity of 50 was further assessed against a panel of isogenic CPT- and doxorubicin-resistant cell lines using an MTT assay. The results are summarized in Table 9.

TABLE 9

| The cytotoxicity of the compound 50 in drug-resistant human cancer cell lines. | | | |
|---|---|---|---|
| | $GI_{50}$ ± SD (μM)[a] | | |
| Compd. | Parental cell line | Resistant subline | Resistance Ratio[b] |
| | HCT116 | HCT116-siTOP1 | |
| CPT | 0.009 ± 0.001 | 0.075 ± 0.014 | 8.3 |
| 50 | 0.036 ± 0.003 | 0.32 ± 0.035 | 8.9 |
| | DU145 | DU145-RC0.1 | |
| CPT | 0.021 ± 0.016 | 4.73 ± 0.68 | 225 |
| 50 | 0.002 ± 0.001 | 0.43 ± 0.006 | 215 |
| | MCF-7 | MCF-7/ADR | |
| DOX | 0.15 ± 0.003 | 11.67 ± 1.94 | 77.8 |
| 50 | 0.10 ± 0.001 | 1.37 ± 0.55 | 13.7 |

Regarding Table 9, the superscripts are defined as follows: [a]$GI_{50}$ values (means±SD) were calculated from MTT assay and defined as the concentrations of compounds that resulted in 50% cell growth inhibition after 72 h of drug exposure. The experiments were repeated at least three times independently. [b]Resistance ratio was calculated by dividing the $GI_{50}$ of the mutant cell line by the $GI_{50}$ of the corresponding parental cell line.

The HCT116-siTOP1 subline was established by transfection of colon cancer parental cells HCTII16 with short hairpin RNA vectors expressing siRNA for TOP1 (Z. H. Miao, A. Player, U. Shankavaram, Y. H. Wang, D. B. Zimonjic, P. L. Lorenzi, Z. Y. Liao, H. Liu, T. Shimura, H. L. Zhang, L. H. Meng, Y. W. Zhang, E S. Kawasaki, N. C. Popescu, M I. Aladjem, D. J. Goldstein, J. N.

Weinstein, Y. Pommier, Nonclassic functions of human topoisomerase I: genome-wide and pharmacologic analyses, Cancer Res., 67 (2007) 8752-8761). TOP1 is the only known cellular target of CPT. The HCT116-siTOP1 subline exhibited 8.3-fold resistance to CPT compared to the parental HCT116 cells (Table 9). Similarly, the HCT116-siTOP1 subline exhibited 8.9-fold resistance to 50, implying that TOP1 is a major cellular target of 50. The CPT-resistant prostate cancer DU145-RC0.1 cells had a R364H mutation in TOP1 relative to the wild-type parental DU 145 cells. The TOP1 with R364H mutation is catalytically active but leads to resistance in DU145-RC0.1 to CPT because of the proximity of the R364 residue to the catalytic tyrosine, thus stabilizing the open form of TOP1cc. Compared to the parental DU145 cells, the DU145-RC0.1 cells showed 225-fold resistance to CPT and 215-fold resistance to 50 (Table 9), which is consistent with the molecular modeling prediction (FIG. 13A) showing a hydrogen bond between 50 and R364 residue.

Classical multiple drug resistance can be attributed to P-Glycoprotein (P-gp) mediated drug efflux. The chemotherapeutic agent doxorubincin (DOX) is a substrate of P-gp. Compared to the parental MCF-7 cells, the breast cancer MCF-7/ADR cells overexpressing P-gp are highly resistant to DOX (77.8-fold) and less resistant to 50 (13.7-fold, Table 9) [34], implying 50 might not be a substrate of P-gp. These results indicate that 50 acts as TOP1 inhibitor in cancer cells, similar to 48 as disclosed in Zhang et al.

Figure 14A:
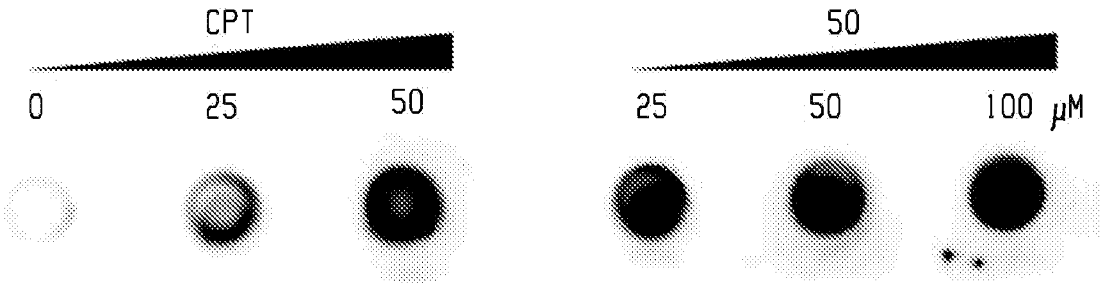
FIGS. 14A-14B show the effects of 50 on the induction of cellular TOP1cc and DNA damage.
Figure 14B:
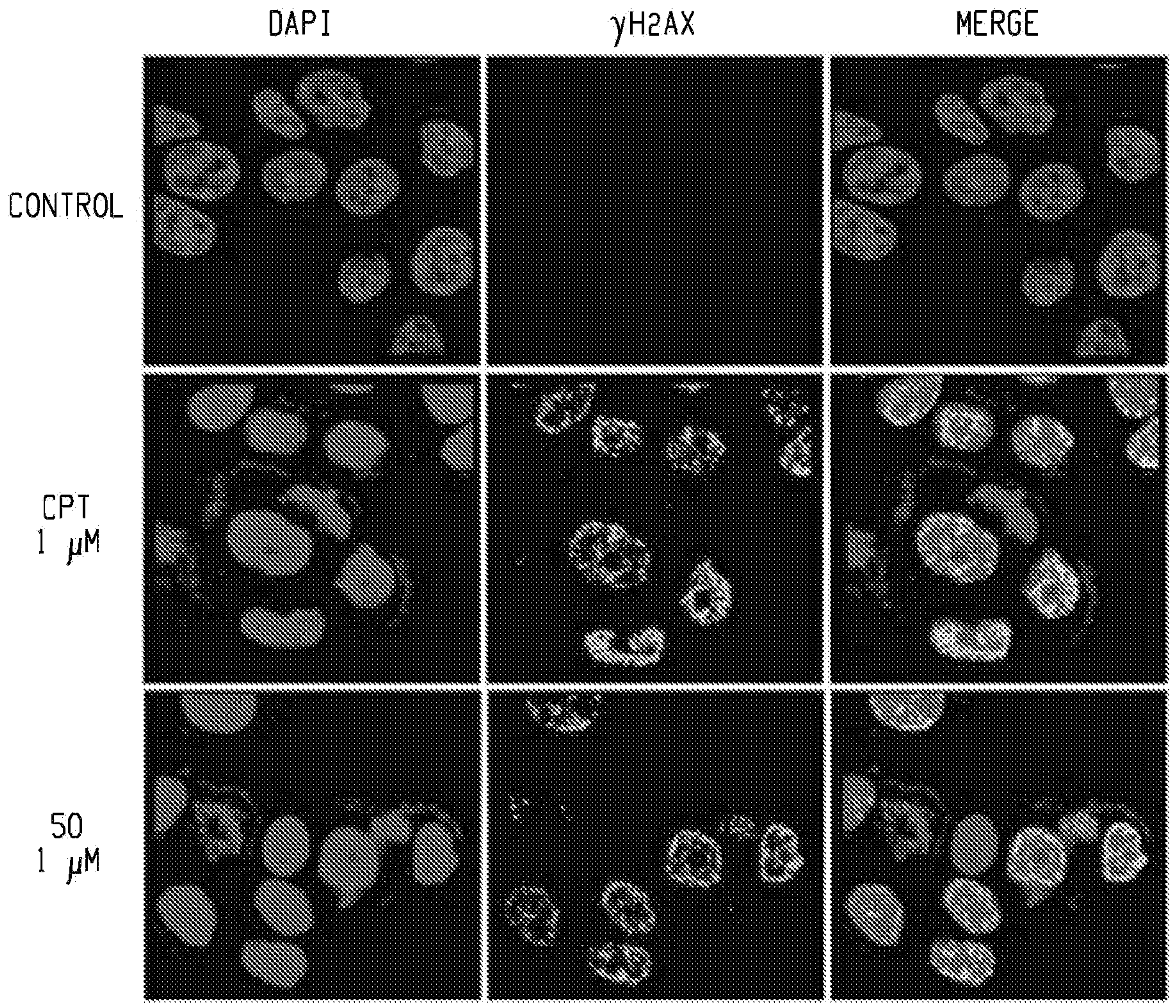

To assess the induction of TOP1cc by 50, the immunocomplex of enzyme to DNA (ICE) assay in HCT116 cells was performed. As shown FIG. 14A, both the positive control CPT and 50 induced the formation of cellular TOP1 cc in a dose-dependent manner. In addition, 50 showed improved ability to induce cellular TOP1cc at 25 M when compared with CPT. To evaluate the DNA damaging effect of 50 in cancer cells, γH2AX foci were assessed by immunofluorescence microscopy in human prostate cancer HCT116 cells. After incubation with the compounds for 3 h, the HCT116 cells were stained with γH2AX antibodies. As shown in FIG. 14B, similar to CPT, 50 effectively induced γH2AX foci at 1 concentration, implying that DNA damage was induced mainly due to the trapping of cellular TOP1cc by 50.

Figure 15:
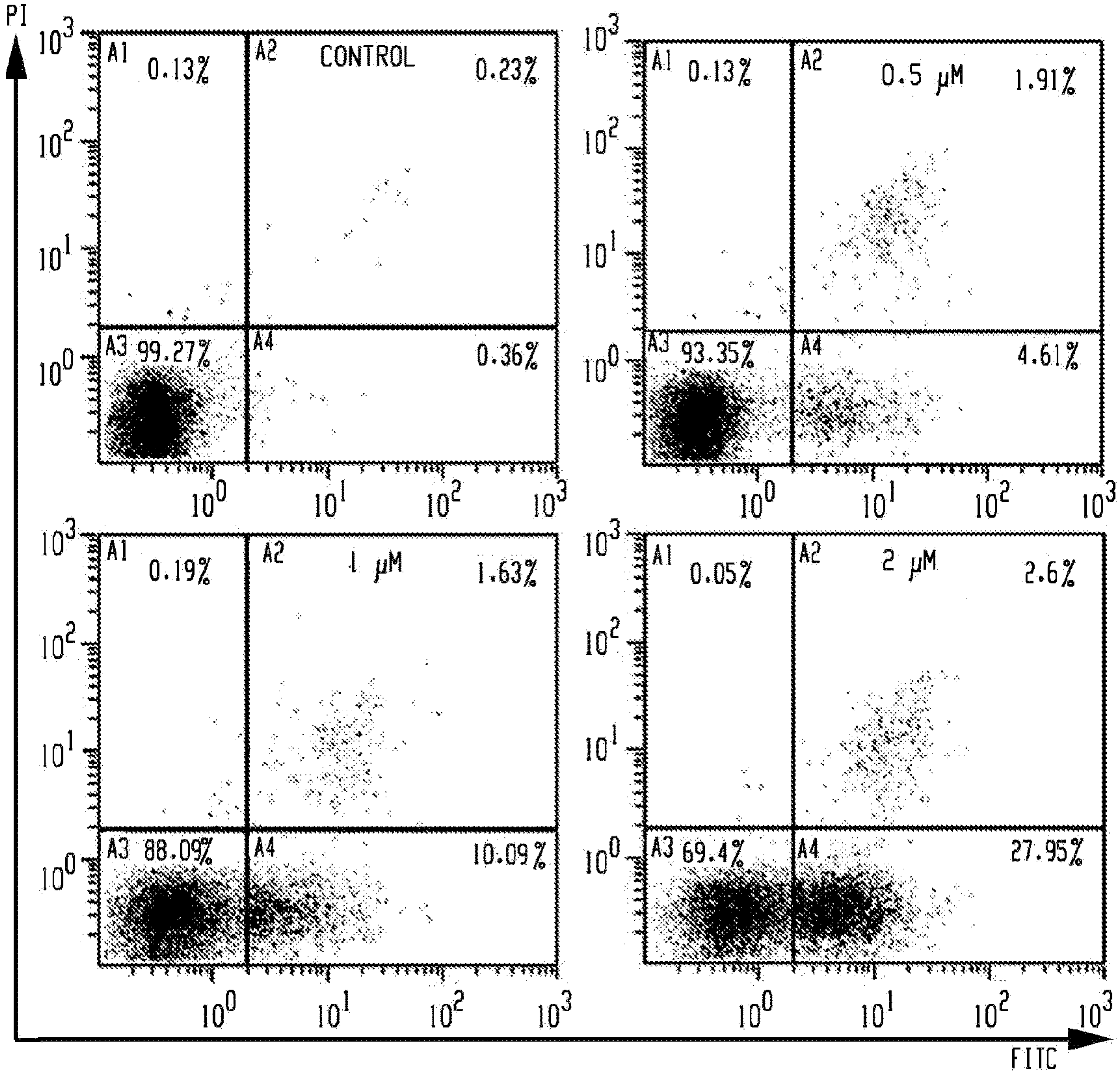
FIG. 15 shows flow cytometry histograms. HCT116 cells were incubated with 50 for 24 hours at 0.5 μM, 1 μM and 2 μM concentration, respectively.

To evaluate the induction of apoptosis by 50, flow cytometry assays were performed in HCT116 cells. HCT116 cells were incubated with 50 for 24 h and analyzed for the apoptotic cells. As shown in FIG. 15, 50 clearly induced HCT116 cells apoptosis in a dose-dependent manner. In particular, 27.95% early apoptotic cells were observed after incubation with 50 at 2 M.

A pharmacokinetic (PK) study in vivo of 50 was performed in Sprague-Dawley (SD) rats. The SD rats were randomly divided into two groups (n=2) and treated by intravenous injection (iv) at 1 mg/kg dose or an intragastrical administration (ig) at 5 mg/kg dose, respectively. Plasma samples were collected postdosing and the concentration of 50 was measured. The PK parameters were calculated and summarized in Table 10.

TABLE 10

Pharmacokinetic parameters of 50.

| Parameters | Mean ± SD (n = 2) iv (1 mg/kg)[a] | ig (5 mg/kg)[b] |
|---|---|---|
| $T_{max}$ (h) | / | 2 ± 0 |
| $C_{max}$ (ng/ml) | / | 19 ± 9 |
| $AUC_{0\rightarrow t}$ (h · ng/ml) | 47.2 ± 1.8 | 48.3 ± 28 |
| $AUC_{0\rightarrow\infty}$ (h · ng/ml) | 49.8 ± 1.5 | / |
| $MRT_{INF}$ (h) | 1.46 ± 0.027 | / |
| $T_{1/2}$ (h) | 1.21 ± 0.14 | / |
| F (%) | / | 20.4 ± 11.9 |

Regarding Table 10, the superscripts are defined as follows: [a]iv means intravenous injection. [b]ig means intragastrical administration.

Figure 17A:
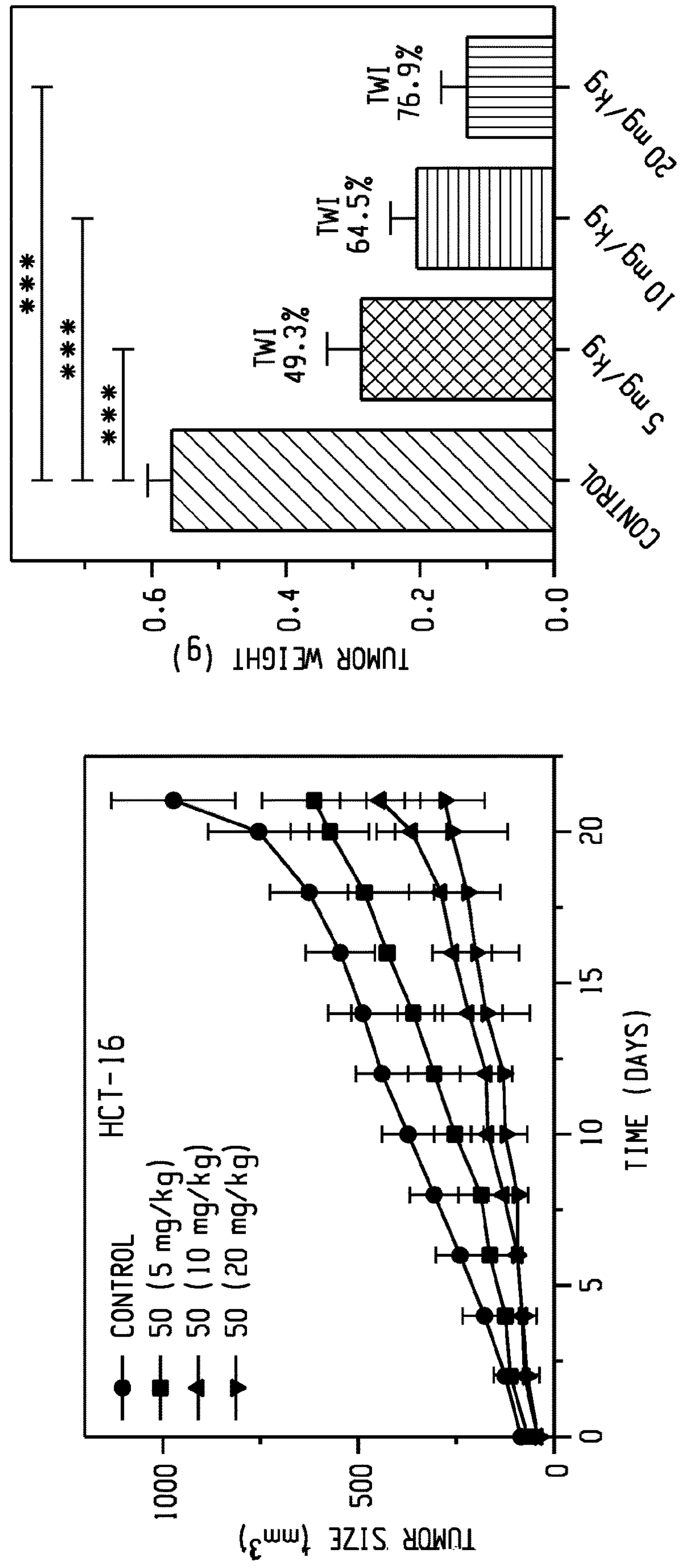
FIGS. 17A-17B shows the antitumor efficiency of 47 in in HCT116 (FIG. 17A) and MCF-7 (FIG. 17B) xenograft models. The effects of 50 on tumor size (left) and tumor weight (right) at the dose of 5 mg/kg, 10 mg/kg and 20 mg/kg, respectively. Statistically significant difference in mean tumor weight compared with the control, : P<0.01, *: P<0.001.
Figure 17B:
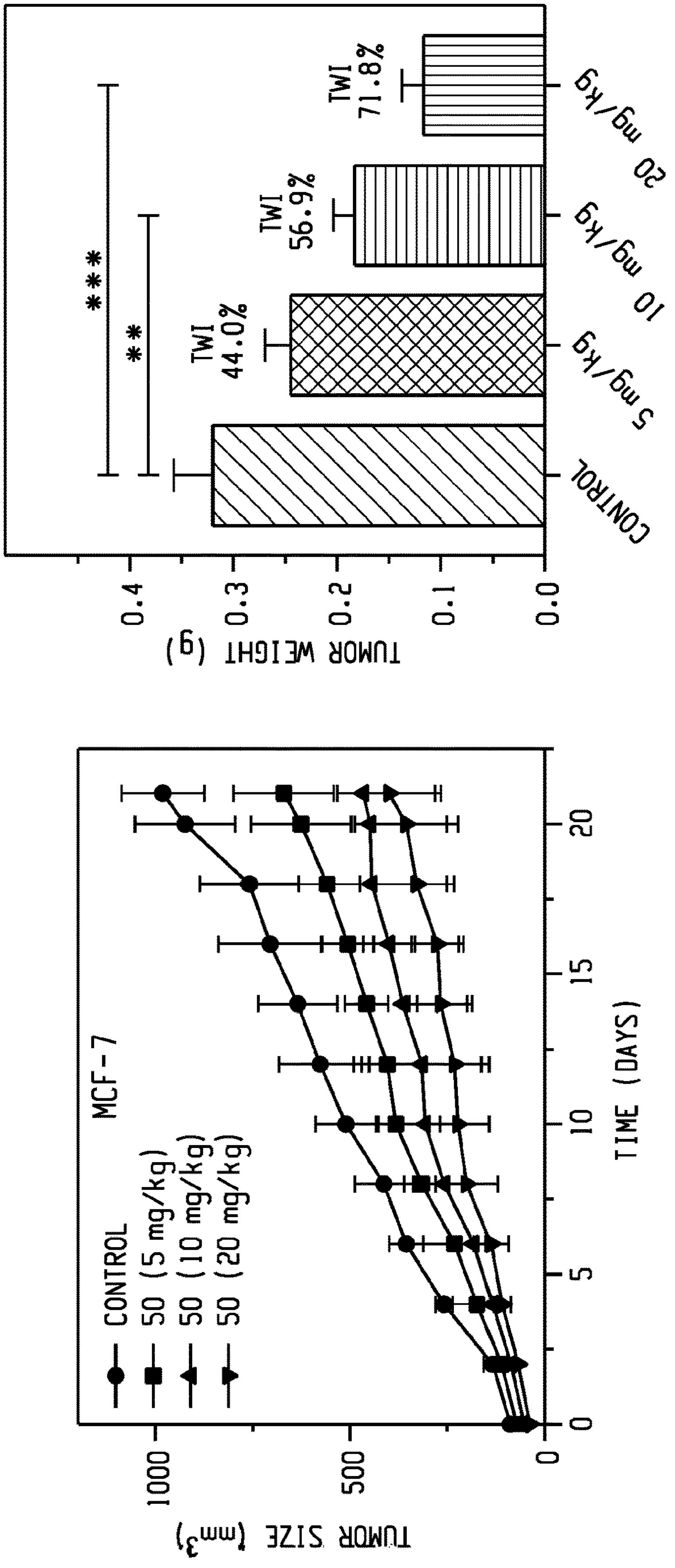

After iv treatment, the $AUC_{0\rightarrow t}$ was 47.2±1.8 h·ng/mil and $T_{1/2}$ was 1.21 i 0.14 h. After ig treatment, $T_{max}$ was 2±0 h and $C_{max}$ was 19±9 ng/mi. The bioavailability (F, 20.4%) of 50 was higher than that of 48 (15.5%), which may be a contributing factor to the improved cytotoxicity in vitro and antitumor efficiency in vivo of 50 (FIG. 17).

Figure 16:
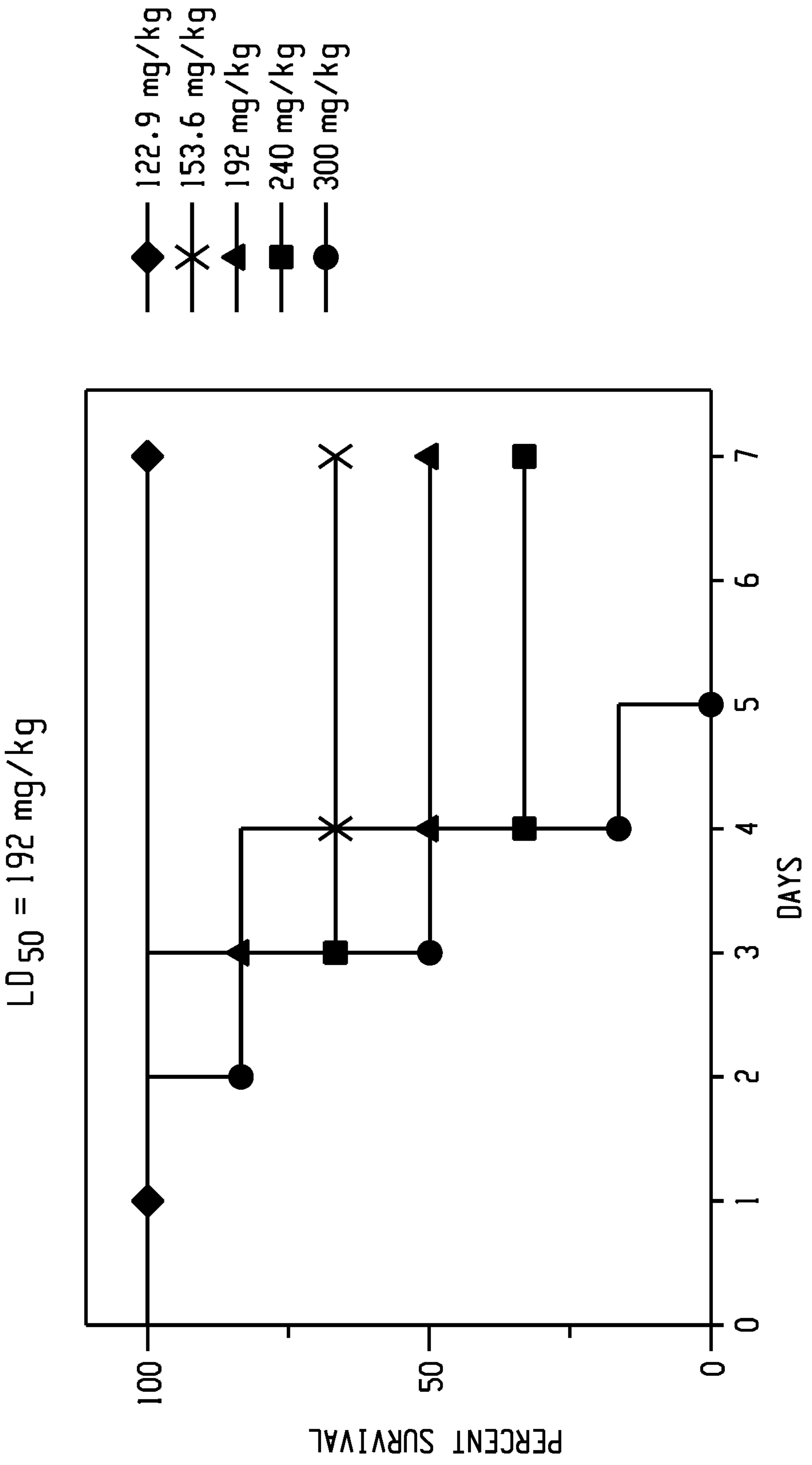
FIG. 16 shows the effect of 50 on mouse survival. Mice were treated with 50 at dose 300 mg/kg, 240 mg/kg, 192 mg/kg 153.6 mg/kg and 122.9 mg/kg, respectively.

The acute toxicity of 50 was assessed in Kunning male mice. The mice were randomly divided into six groups (n=6) and treated with 50 by intraperitoneal injection (ip) at single doses of 300, 240, 192, 153.6 and 122.9 mg/kg. The control group was treated with sterile water. As shown in FIG. 16, after 7 days of administration with 50, all mice survived in the group of 122.9 mg/kg dose, four mice survived in the 153.6 mg/kg dose group, three mice survived in the 192 mg/kg dose group, and two mice survived in the 240 mg/kg dose group. All mice died within 5 days in the 300 mg/kg dose group. The median lethal dose ($LD_{50}$), defined as the dose to kill half of mice after 7 days, was 192 mg/kg.

The in vivo antitumor efficiency of 50 was assessed in both human colon cancer HCT116 and human breast cancer MCF-7 xenograft nude mice models. For both models, the mice were randomly divided into four groups (n=6) and treated with 50 at 20 mg/kg, 10 mg/kg or 5 mg/kg dose by ip administration daily. The control group was treated with saline. As shown in FIG. 17, administration of 50 significantly reduced the tumor volume in a dose-dependent manner in both the HCT116 and MCF-7 xenograft models. 50 was more antitumor efficient in the HCT116 xenograft model than the MCF-7 xenograft model. The tumor weight inhibitions (TWI) of 50 at the 20 μM dose were 76.9% (in HCT116 model) and 71.8% (in MCF-7 model), respectively.

Example 5. TOP1-MEDIATED CLEAVAGE ASSAY

Approximately 2 nM radiolabeled DNA substrate was incubated with recombinant Top1 in 20 mL of reaction buffer (10 mM Tris-HCl pH 7.5, 50 mM KCl, 5 mM $MgCl_2$, 0.1 mM EDTA, and 15 mg/mL BSA) at 25° C. for 20 min in the presence of various concentrations of test compounds. The reactions were terminated by adding SDS (0.5% final concentration) followed by the addition of two volumes of loading dye (80% formamide, 10 mM sodium hydroxide, 1 mM sodium EDTA, 0.1% xylene cyanol, and 0.1% bronophenol blue). Aliquots of each reaction mixture were subjected to 20% denaturing PAGE. Gels were dried and visualized by using a phosphoimager and ImageQuant software (Molecular Dynamics). Cleavage sites are numbered to reflect actual sites on the 117-bp oligonucleotide.

Example 6. Top1-Mediated Unwinding Assay

The reaction mixture (20 μL) contained supercoiled or relaxed pBR322 DNA (0.5 μg), tested compounds and excess Top1 (10 units) in relaxing buffer (10 mM Tris, pH 7.5, 0.1 mM EDTA, 5 mM $MgCl_2$, 50 mM KCl, 1 mM DTT, 15 μg/mL acetylated BSA). The DNA was incubated with the tested compounds at room temperature for 10 min prior to the addition of Top1. After being incubated for 30 min at 37° C., the reaction was terminated by the addition of 4 mL loading buffer. The results were analyzed using 1% agarose gel in TAE buffer at 5 V/cm. The gel was stained with gel red and visualized with a UV transilluminator.

Example 7. Tdp1 Inhibition Assay

Fluorescence assay. A linear oligonucleotide labeled with FAM (donorfluorophore, 6-carboxyfluorescein) and BHQ (Black Hole Quencher), 5'-FAM-AGGATCTAAAA-GACTT-BHQ-3' was designed as a linear quenched fluorescent substrate. Tdp1 solution (20 μL/well, 0.02 μL purified Tdp1 (100 nM) in 10 mM Tris-HCl, pH 7.5, 50 mM KCL, I mM EDTA, 1 mM DTT) was dispensed into wells of a white 384-well plate (NEST). The tested compound solution in DMSO (5 μL) was pinned into assay plates and incubated at room temperature for 30 min. During this time, the plates were read by a Flash multimode reader (Molecular Devices) at $Ex_{485}/Em_{510}$ nm) to identify false-positive compounds that had autofluorescence. The linear oligonucleotide substrate (25 μL, 35 nM) was dispensed into the wells to start the reaction. The whole plate was immediately read five times using a kinetic read on the Flash multimode reader (Molecular Devices) ($Ex_{485}/Em_{510}$ nm). Tdp percentage inhibition of the tested compounds was calculated by comparing the rate of increase in fluorescence throughout time for the compound-treated wells to that of DMSO control wells.

Gel-based assay. Methods for identifying Tdp1 inhibitors have been described previously, for example by Marchand, et al., in *Molecular Cancer Therapeutics* (2009) 8: 240-248. The gel-based assay of Marchand, et al., is based on the cleavage by Tdp1 of the 14-mer 5'-$^{2}$P-labeled 3'-phosphotyrosyl DNA substrate $N_{14}Y$ (5'-GATCTAAAAGACTT-pY-3') SEQ ID NO: 1 to a 14-mer 5'-$^{32}$P-labeled 3'-phosphate DNA product N14P (see FIG. 1)). A 5'-[$^{32}$P]-labeled single-stranded DNA oligonucleotide containing a 3'-phosphotyrosine (N14Y) was incubated at I nM with 0.02 nM or 10 μM recombinant human Tdp1 in the absence or presence of inhibitor for 15 min at room temperature in buffer containing 50 mM Tris HCl, pH 7.5, 80 mM KCl, 2 mM EDTA, 1 mM DTT, 40 g/mL BSA, and 0.01% Tween-20. Reactions were terminated by the addition of I volume of gel loading buffer [99.5% (v/v) formamide, 5 mM EDTA, 0.01% (w/v) xylene cyanol, and 0.01% (w/v) bromophenol blue]. Samples were subjected to a 16% denaturing PAGE. Gels were dried and exposed to a PhosphorImager screen (GE Healthcare). Gel images were scanned using a Typhoon FLA 9500 scanner (GE Healthcare), and densitometry analyses were performed using the ImageQuant software (GE Healthcare).

Example 8. Molecular Modeling

The X-ray crystal structures of the ternary Top1-DNA-ligand complex (PDB ID: 1K4T) was obtained and cleaned, inspected for errors and missing residues, hydrogens were added, and the water molecules and the ligand were deleted. The ternary complex ligand centroid coordinates for docking were defined using the ligand in the complex structure as the center of the binding pocket. Compounds were constructed and optimized using ChemDraw and saved in SDFfile formats and were corrected using IOE software. Hydrogens were added, and the ligands were minimized by the conjugate gradient method using the MMFF94x force field with MMFF94 charges, a distance-dependent dielectric function, and a 0.01 kcal/mol·Å energy gradient convergence criterion. Induced fit was used for docking with the default parameters. The top 30 docking poses per ligand were inspected visually following the docking runs. The highest-ranked poses for these ligands were merged into the crystal structure. Energy minimizations were performed for the highest-ranked poses for these ligands. The AMBER forcefield was utilized within the MOE software for energy minimization.

The Tdp1 crystal structure (PDB ID: 1RFF) was prepared by removing one of the monomers along with all crystallized waters, the polydeoxyribonucleotide, the Top1-derived peptide residues and all metal ions. LigX in AMBER10 force field with MOE. Site Finder was used to get the binding pocket containing Lys265, Lys495 and His493. Docking was performed with induced fit protocol in MOE. The top ligand-binding pose (lowest score) was selected and merged with the prepared protein. The AMBER forcefield was utilized within the MOE software for energy minimization. The calculation was terminated when the gradient reached a value of 0.05 kcal/mol·Å.

Example 9. Fret Melting Assay

FRET melting assay was carried out on a real-time PCR apparatus as the following methods. The oligonucleotide labeled with FAM (donorfluorophore, 6-carboxyfluorescein) and TAMRA (acceptor fluorophore, 6-carboxytetramethyl-rhodamine), F10T (5'-FAM-d(TATAGCTATA-HEG-TATAGCTATA)-TAMARA-3') was purchased from Sangon Biotech. In the experiment, the annealed oligonucleotide (final concentration of 0.4 μM) were incubated with the tested compounds (2 μM) in a total reaction volume of Tris-HCl buffer (10 mM, pH 7.4) containing 60 mM KCl at 37° C. for 0.5 h. Fluorescence melting curves were determined with a Roche LightCycler 2 real-time PCR machine with excitation at 470 nm and detection at 530 nm. Fluorescence readings were taken at an interval of 1° C. over the range 37-99° C., with a constant temperature being maintained for 30 seconds prior to each reading to ensure a stable value.

Example 10. Cell Culture and MTT Assay

The cells were cultured on RPMI-1640 medium at 37° C. in a humidified atmosphere with 5% $CO_2$. All cells to be tested in the following assays had a passage number of 3-6. For the drug treatment experiments, the cancer cells were treated with the compounds (predissolved in DMSO) at a five-dose assay ranging from 0.01 to 100 μM concentration. After incubation for 72 h at 37° C., MTT solution (50 μL, I mg/mL) in PBS (PBS without MTT as the blank) was fed to each well of the culture plate (containing 100 mL medium).

After 4 h incubation, the formazan crystal formed in the well was dissolved with 100 mL of DMSO for optical density reading at 570 nm. The $GI_{50}$ value was calculated by nonlinear regression analysis (GraphPad Prism).

For the drug combination experiments, human breast cancer MCF-7 cells were incubated with camptothecin and the tested compounds for 96 h at 37° C., and then measured by MTT assay.

Example 11. Immunodetection of Cellular Top1-DNA Complex

The ICE assays for cellular Top1-DNA adduct was performed. Briefly, mid-log phase HCT-116 cells were incubated with drugs at the indicated concentration for 1 h. And then, the cells were lysed with DNAzol Reagent (1 mL) at 25° C. for 30 min. Ethanol (0.5 ml, 100%) was subsequently added and mixed with the lysate and the solution was incubated overnight at −20° C. The genomic DNA was collected by centrifugation (12,000 rpm) at 25° C. for 10 min and washed with 75% ethanol. The precipitated DNA was dissolved in NaOH (8 mM, 0.2 ml). The pH value was adjusted to 7.2 by adding HEPES (1 μM). After centrifugation, supernatant was used to quantify the DNA concentration. DNA (2 μg) were dissolved in 30 μL $NaH_2PO_4$ buffer (25 mM, pH 6.5) and then loaded onto nitrocellulose membranes. Membranes were incubated with rabbit monoclonal to human Top1 (Abcan, 1:1000) overnight at 4° C., and then incubated with the appropriate HRP-conjugated secondary antibodies (Cell Signaling Technology, 1:3000) at room temperature for I h. Reactive dots were detected using Immobilon Western Chemiluminescent HRP Substrate (Millipore).

Example 12. $\gamma H_2AX$ Detection

HCT116 cells ($2\times10^4$ cells/mL) were grown in culture medium and treated with compounds for 3 h at 37° C. After incubation, cells were fixed in 4% paraformaldehyde/PBS for 15 min at 25° C. and washed three times with PBS buffer. Cells were permeabilized with 0.5% Triton X-100 in PBS at 0° C. for 30 min. Dish was blocked with 5% goat serum/PBS at 37° C. for 3 h. Immunofluorescence assay was performed using standard methods, and the slides were incubated alternately with phospho-γH2AX (Serl 39; #9718, Cell Signaling Technology) at 37° C. overnight. The cover slips were washed six times with blocking buffer and then incubated with anti-rabbit alexa 488-conjugated antibody (A21206, Life Technology) and 2.0 μg/mL of 4',6-diamidino-2-phenylindole (DAPI, Invitrogen) at 37° C. for 2 h. The dishes were again washed six times with blocking buffer. Digital images were recorded using an LSM710 microscope (Zeiss, Germany) and analyzed with ZEN software.

Example 13. Flow Cytometry

HCT116 cells ($3.0\times10^4$ cells/mL) were grown in culture medium on a 6-well plate treated with compound at the indicated concentration for 24 h. Then the cells were harvested from the medium and washed with cold PBS, resuspended in 1×binding buffer, and then stained with 5.0 μL of FITC annexin V and 10.0 μL of propidium iodide (KeyGen Biotech, China) for 15 min in the dark. The stained cells were analyzed by using flow cytometry (BD, FACSCalibur, USA) within I h. The experiments were repeated three times independently.

Example 14. Pharmacokinetic Study in Rat

Male SD rats (weighing 220-250 g, n=3) were treated with compound 19a pre-dissolved in 10% DMSO and 10% Kolliphor® HS 15 (anon-ionic solubilizer) by i.v. (1 mg/kg) and by i.g. administration (5 mg/kg), respectively. Blood samples (200 L) were collected into heparinized tubes via the jugular vein at the following times: 0.083, 0.25, 0.5, L 2, 5, 7 and 24 h after dosing. Plasma samples (100 μL) were obtained after centrifugation for 10 min at 3000 rpm and stored at −20° C. until used for analysis. The plasma was detected through LC-MS-MS.

Example 15. In Vivo Acute Toxicity

Based on the preliminary experiments, the Kuning male mice were randomly divided into six groups (n=4) and administered by intraperitoneal (i.p.) injection. The control group was treated with an equivalent volume of sterile water. The testing groups were treated with compound 19a or 50 in a single dose 300, 240, 192, 154 and 123 mg/kg, respectively. The mice were kept under observation for 7 days post-treatment in order to check for any behavioral (poisoning symptoms and body weight) and death. All animals were euthanized by cervical dislocation at the end of the experiments.

Example 16. In Vivo Antitumor Activity

Athymic nude mice bearing the nu/nu gene were obtained from Laboratory Animal Center of Sun Yat-sen University and maintained in pathogen-free conditions to establish the model of xenografts of HCT116. Male nude mice 4-5 weeks old weighing 12-15 g were used. HCT116 tumor pre-induced in the mice by subcutaneously injecting of HCT116 cells (100 μL, $1\times10^7$ cells) was implanted. When the implanted tumors had reached a volume of about 80 mm % the mice were randomly divided into three groups (n=6) and administered by i.p. injection. The testing groups were treated with 19a or 50 in 10 mg/kg and 5 mg/kg dose once every day, respectively. The negative control group was treated with an equivalent volume of saline. Tumor volumes (V) were monitored by caliper measurement of the length and width, and calculated using the formula: V=(larger diameter)×(smaller diameter)⅔, and growth curves were plotted using average tumor volume within each experimental group at the set time points. All animals were at the end of. At the end of the experiment, the animals were euthanized by cervical dislocation. The tumors were removed and weighed. The tumor weight inhibition (TWI) was calculated according to the formula: TWI=(1−Mean tumor weight of the experimental group/Mean tumor weight of the control group)×100%.

The invention claimed is:

1. A compound of Formula I or a pharmaceutically acceptable salt thereof, (Formula I)

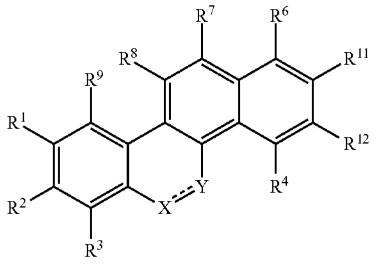

wherein the group

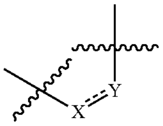

is

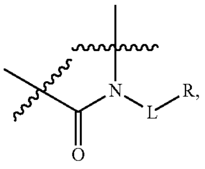

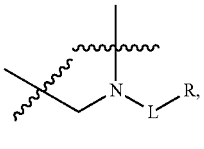

or

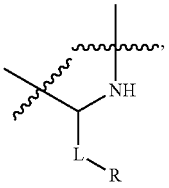

and

R is hydroxyl, amino, mono- or di-$C_1$-$C_6$alkylamino; or

R is pyrrolidinyl, piperidinyl, piperazinyl, morpholinyl, thiomorpholinyl, pyrrolyl, pyrazolyl, imidazolyl, oxazolyl, or thiazolyl, each of which is optionally substituted with one or more substituents independently chosen from halogen, hydroxyl, $C_1$-$C_2$alkyl, and $C_1$-$C_2$alkoxy;

or the group

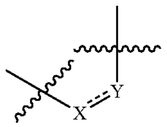

is

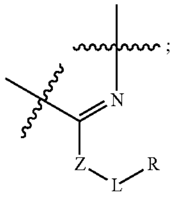

and

R is pyrrolidinyl, piperidinyl, piperazinyl, morpholinyl, thiomorpholinyl, pyrrolyl, pyrazolyl, imidazolyl, oxazolyl, or thiazolyl, each of which is optionally substituted with one or more substituents independently chosen from halogen, hydroxyl, $C_1$-$C_2$alkyl, and $C_1$-$C_2$alkoxy;

and

Z is O, NH, $NR^{10}$, or S;

L is $C_2$-$C_3$ alkyl;

$R^1$, $R^2$, and $R^3$ are independently chosen from hydrogen, hydroxyl, halogen, amino, $C_1$-$C_6$alkyl, $C_1$-$C_6$alkoxy, benzyloxy, $C_1$-$C_6$alkylthio, $C_1$-$C_2$haloalkyl, and $C_1$-$C_2$haloalkoxy; or $R^1$ and $R^2$ can be taken together to form a 5 or 6-membered heterocycloalkyl ring containing 2 oxygen atoms, which $R^1$/$R^2$ ring is unsubstituted or substituted with 1 or 2 independently chosen $R^5$ substituents, where $R^5$ is independently chosen at each occurrence from halogen, hydroxyl, $C_1$-$C_2$alkyl, and $C_1$-$C_2$alkoxy; or $R^2$ and $R^3$ can be taken together to form a 5 or 6-membered heterocycloalkyl ring containing 2 oxygen atoms, which $R^2$/$R^3$ ring is unsubstituted or substituted with 1 or 2 independently chosen $R^5$ substituents;

$R^4$, $R^6$, $R^7$, $R^8$, and $R^9$ are independently chosen from hydrogen, halogen, hydroxyl, amino, cyano, COOH, CHO, or $C_1$-$C_6$alkyl, which $C_1$-$C_6$alkyl can contain one or more double or triple bonds, can have one or more $CH_2$ group replaced by NH, $NR^{10}$, S, or O, and is optionally substituted with one or more substituents independently chosen from hydroxyl, amino, cyano, halogen, oxo, and $C_3$-$C_6$cycloalkyl;

$R^{10}$ is $C_1$-$C_6$alkyl or ($C_3$-$C_6$cycloalkyl)$C_0$-$C_4$alkyl;

$R^{11}$ and $R^{12}$ are independently chosen from hydrogen, hydroxyl, halogen, amino, $C_1$-$C_6$alkyl, $C_1$-$C_6$alkoxy, benzyloxy, $C_1$-$C_6$alkylthio, $C_1$-$C_2$haloalkyl, or $C_1$-$C_2$haloalkoxy; or $R^{11}$ and $R^{12}$ can be taken together to form a 5 or 6-membered heterocycloalkyl ring containing 2 oxygen atoms, which $R^{11}$/$R^{12}$ ring is unsubstituted or substituted with 1 or 2 independently chosen $R^5$ substituents.

2. The compound or salt of claim 1, of Formula I-A (I-A)

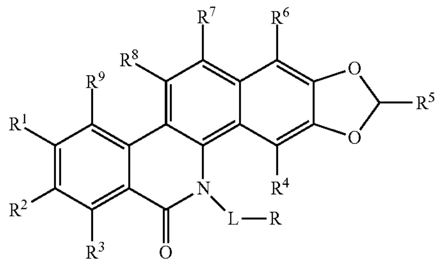

or a salt thereof, where none of $R^1$/$R^2$ and $R^2$/$R^3$ are joined to form a ring.

3. The compound or salt of claim 1, of Formula I-B, I-C, I-D, I-E, I-F, or I-G, or a salt of any of the foregoing, wherein in Formula I-B and Formula I-C none of $R^1$/$R^2$ and $R^2$/$R^3$ are joined to form a ring;

in Formula I-D none of $R^1$/$R^2$, $R^2$/$R^3$, and $R^{11}$/$R^{12}$ are joined to form a ring; and in Formula I-E $R^{11}$/$R^{12}$ are not joined to form a ring;

(I-B)

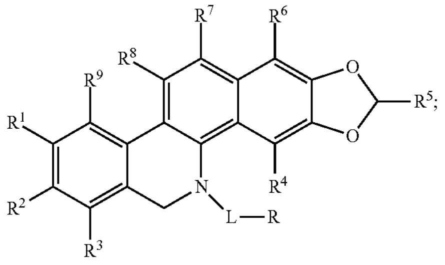

-continued (I-C)

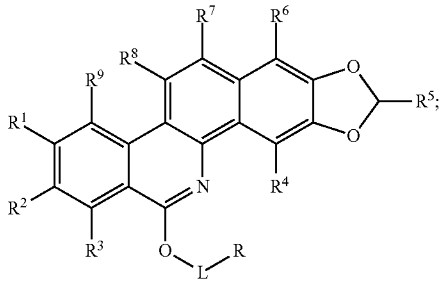

(I-D)

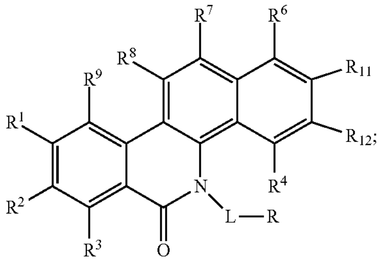

(I-E)

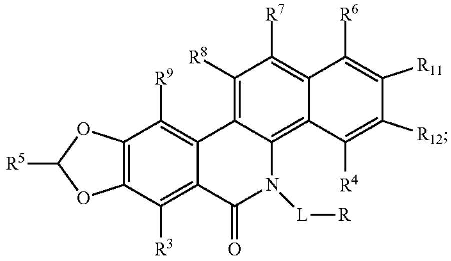

(I-F)

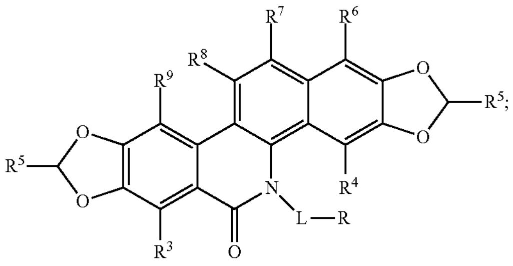

(I-G)

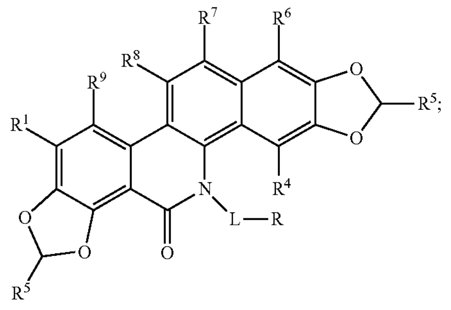

4. The compound or salt of claim 1 wherein L is $C_2$ alkyl.

5. The compound or salt according to claim 1, wherein $R^4$, $R^6$, $R^7$, $R^8$, and $R^9$ are independently chosen from hydrogen, halogen, or $C_1$-$C_6$alkyl, which $C_1$-$C_6$alkyl can contain one or more double or triple bonds, can have one or more $CH_2$ group that can be replaced by NH, $NR^{10}$, S, or O, and is optionally substituted with one or more substituents independently chosen from hydroxyl, amino, cyano, halogen, oxo, and $C_3$-$C_6$cycloalkyl.

6. The compound or salt of claim 1, wherein $R^3$, $R^4$, $R^5$, $R^6$, $R^7$, $R^8$, and $R^9$ are independently chosen from hydrogen, halogen, methyl, and methoxy.

7. The compound or salt of claim 1, wherein $R^3$, $R^4$, $R^5$, $R^6$, $R^1$, $R^8$, and $R^9$ are hydrogen and $R^1$ and $R^2$ are independently H or $C_1$-$C_6$alkoxy.

8. The compound or salt of claim 1, wherein $R^1$ and $R^2$ are methoxy.

9. The compound or salt of claim 1, wherein $R^{11}$ and $R^{12}$ are methoxy.

10. The compound or salt thereof of claim 1, wherein the compound is selected from 12-(2-(Dimethylamino)ethyl)-2,3-dimethoxy-[1,3]dioxolo[4',5':4,5]benzo[1,2-c]phenanthridin-13(12H)-one (19a);

12-(3-(Dimethylamino)propyl)-2,3-dimethoxy-[1,3]dioxolo[4',5':4,5]benzo[1,2-c]phenanthridin-13(12H)-one (19b);

12-(2-(Diethylamino)ethyl)-2,3-dimethoxy-[1,3]dioxolo[4',5':4,5]benzo[1,2-c]phenanthridin-13(12H)-one (20a);

12-(3-(Diethylamino)propyl)-2,3-dimethoxy-[1,3]dioxolo[4',5':4,5]benzo[1,2-c]phenanthridin-13(12H)-one (20b);

2,3-Dimethoxy-12-(2-(pyrrolidin-1-yl)ethyl)-[1,3]dioxolo[4',5':4,5]benzo[1,2-c]phenanthridin-13(12H)-one (21a);

2,3-Dimethoxy-12-(3-(pyrrolidin-1-yl)propyl)-[1,3]dioxolo[4',5':4,5]benzo[1,2-c]phenanthridin-13(12H)-one (21b);

2,3-Dimethoxy-12-(2-(piperidin-1-yl)ethyl)-[1,3]dioxolo[4',5':4,5]benzo[1,2-c]phenanthridin-13(12H)-one (22a);

2,3-Dimethoxy-12-(3-(piperidin-1-yl)propyl)-[1,3]dioxolo[4',5':4,5]benzo[1,2-c]phenanthridin-13(12H)-one (22b);

2,3-Dimethoxy-12-(2-morpholinoethyl)-[1,3]dioxolo[4',5':4,5]benzo[1,2-c]phenanthridin-13(12H)-one (23a);

2,3-Dimethoxy-12-(3-morpholinopropyl)-[1,3]dioxolo[4',5':4,5]benzo[1,2-c]phenanthridin-13(12H)-one (23b);

2,3-Dimethoxy-12-(2-(4-methylpiperazin-1-yl)ethyl)-[1,3]dioxolo[4',5':4,5]benzo[1,2-c]phenanthridin-13(12H)-one (24a);

2,3-dimethoxy-12-(3-(4-methylpiperazin-1-yl)propyl)-[1,3]dioxolo[4',5':4,5]benzo[1,2-c]phenanthridin-13(12H)-one (24b);

12-(2-(1H-imidazol-1-yl)ethyl)-2,3-dimethoxy-[1,3]dioxolo[4',5':4,5]benzo[1,2-c]phenanthridin-13(12H)-one (25a);

12-(3-(1H-imidazol-1-yl)propyl)-2,3-dimethoxy-[1,3]dioxolo[4',5':4,5]benzo[1,2-c]phenanthridin-13(12H)-one (25b);

2-(2,3-Dimethoxy-[1,3]dioxolo[4',5':4,5]benzo[1,2-c]phenanthridin-12(13H)-yl)-N,N-dimethylethan-1-amine (26a);

3-(2,3-Dimethoxy-[1,3]dioxolo[4',5':4,5]benzo[1,2-c]phenanthridin-12(13H)-yl)-N,N-dimethylpropan-1-amine (26b);

2-(2,3-Dimethoxy-[1,3]dioxolo[4',5':4,5]benzo[1,2-c]phenanthridin-12(13H)-yl)-N,N-diethylethan-1-amine (27a);

3-(2,3-Dimethoxy-[1,3]dioxolo[4',5':4,5]benzo[1,2-c]phenanthridin-12(13H)-yl)-N,N-diethylpropan-1-amine (27b);

2,3-Dimethoxy-12-(2-(pyrrolidin-1-yl)ethyl)-12,13-dihydro-[1,3]dioxolo[4',5':4,5]benzo[1,2-c]phenanthridine (28a);

2,3-Dimethoxy-12-(3-(pyrrolidin-1-yl)propyl)-12,13-dihydro-[1,3]dioxolo[4',5':4,5]benzo[1,2-c]phenanthridine (28b);

2,3-Dimethoxy-12-(2-(piperidin-1-yl)ethyl)-12,13-dihydro-[1,3]dioxolo[4',5':4,5]benzo[1,2-c]phenanthridine (29a);

2,3-Dimethoxy-12-(3-(piperidin-1-yl)propyl)-12,13-dihydro-[1,3]dioxolo[4',5':4,5]benzo[1,2-c]phenanthridine (29b);

2,3-Dimethoxy-12-(2-morpholinoethyl)-12,13-dihydro-[1,3]dioxolo[4',5':4,5]benzo[1,2-c]phenanthridine (30a);

2,3-Dimethoxy-12-(3-morpholinopropyl)-12,13-dihydro-[1,3]dioxolo[4',5':4,5]benzo[1,2-c]phenanthridine (30b);

2,3-Dimethoxy-12-(2-(4-methylpiperazin-1-yl)ethyl)-12,13-dihydro-[1,3]dioxolo[4',5':4,5]benzo[1,2-c]phenanthridine (31a);

2,3-Dimethoxy-12-(3-(4-methylpiperazin-1-yl)propyl)-12,13-dihydro-[1,3]dioxolo[4',5':4,5]benzo[1,2-c]phenanthridine (31b);

12-(2-(1H-imidazol-1-yl)ethyl)-2,3-dimethoxy-12,13-dihydro-[1,3]dioxolo[4',5':4,5]benzo[1,2-c]phenanthridine (32a);

12-(3-(1H-imidazol-1-yl)propyl)-2,3-dimethoxy-12,13-dihydro-[1,3]dioxolo[4',5':4,5]benzo[1,2-c]phenanthridine (32b);

2,3-Dimethoxy-13-(3-(pyrrolidin-1-yl)propoxy)-[1,3]dioxolo[4',5':4,5]benzo[1,2-c]phenanthridine (41b);

2,3-Dimethoxy-13-(3-(piperidin-1-yl)propoxy)-[1,3]dioxolo[4',5':4,5]benzo[1,2-c]phenanthridine (42b);

2,3-Dimethoxy-13-(3-morpholinopropoxy)-[1,3]dioxolo[4',5':4,5]benzo[1,2-c]phenanthridine (43b);

2,3-Dimethoxy-13-(3-(4-methylpiperazin-1-yl)propoxy)-[1,3]dioxolo[4',5':4,5]benzo[1,2-c]phenanthridine (44b);

13-(3-(1H-imidazol-1-yl)propoxy)-2,3-dimethoxy-[1,3]dioxolo[4',5':4,5]benzo[1,2-c]phenanthridine (45b);

TWL-5

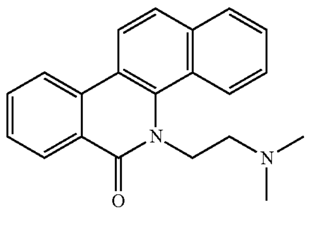
;

TWL-25

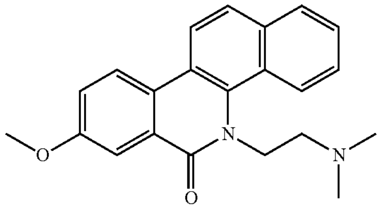
;

-continued
TWL-25A
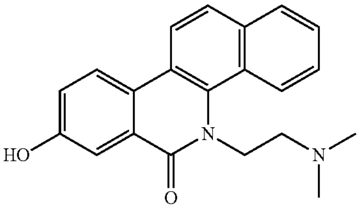
;
TWL-53
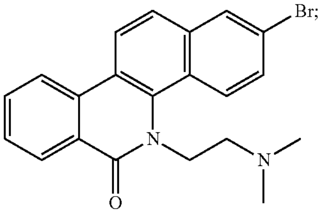
TWL-26
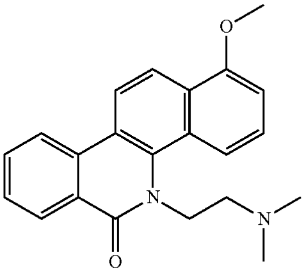
;
TWL-9
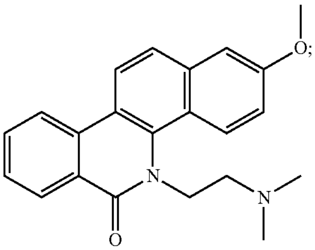
TWL-33
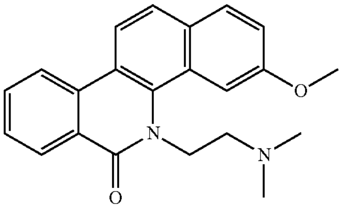
TWL-17
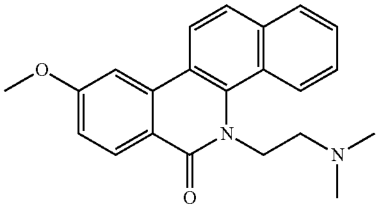
;
TWL-44
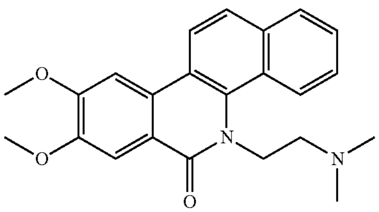
;
-continued
TWL-40
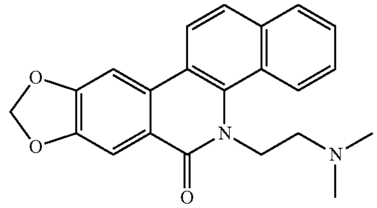
;
TWL-67
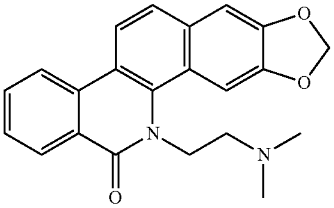
;
TWL-76H
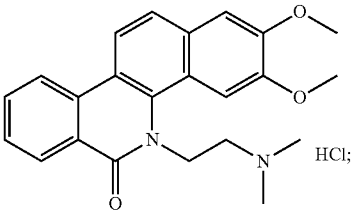
HCl;
TWL-185
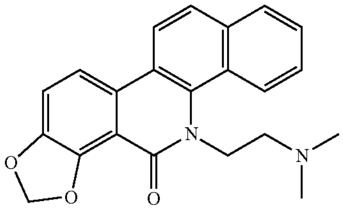
;
TWL-48
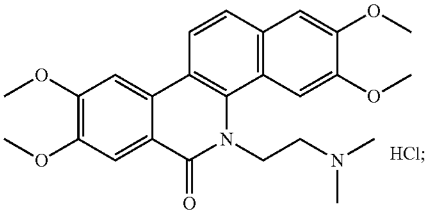
HCl;
TWL-37
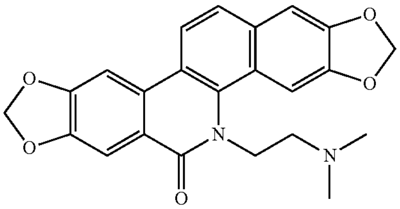
;
TWL-113
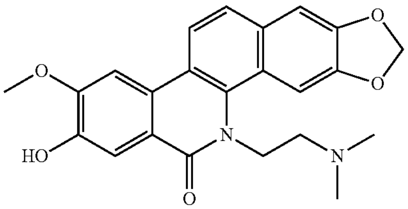
;

-continued
TWL-119
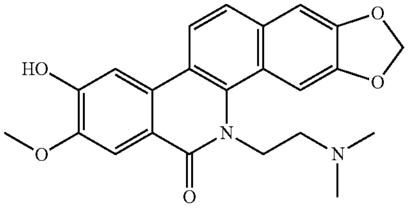
;
TWL-125
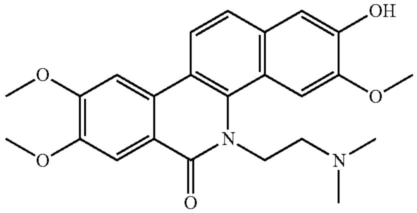
;
TWL-131
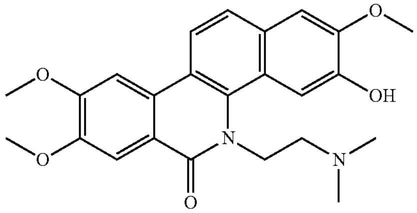
;
TWL-107
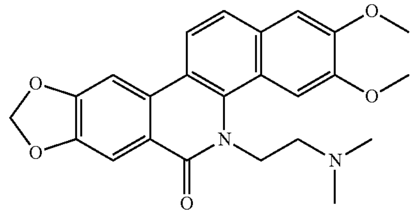
;
TWL-164
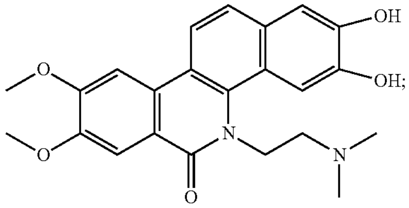
TWL-189
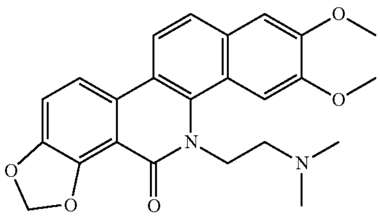
;
TWL-191
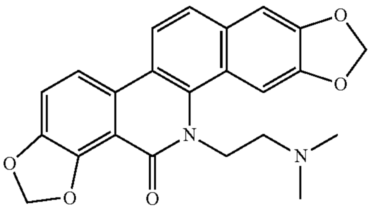
;
-continued
TWL-211
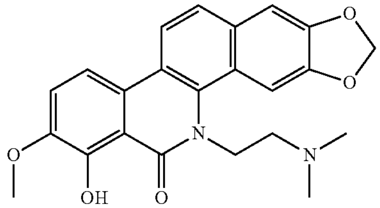
;
TWL-170
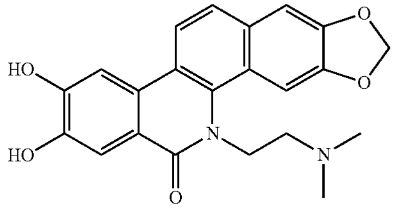
;
TWL-218A
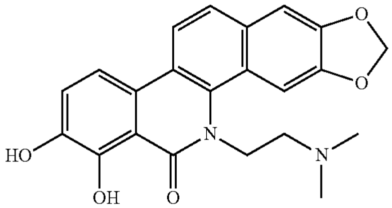
;
TWL-246
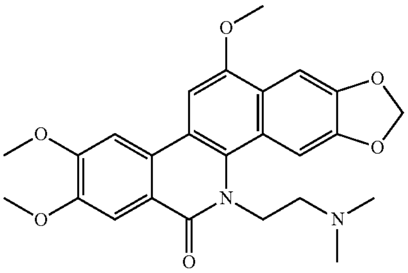
;
NTD-207
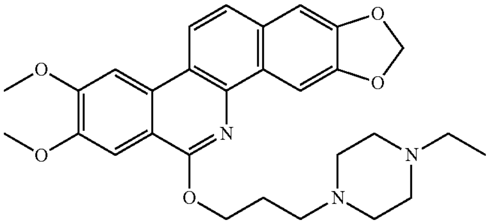
;
NTD-307
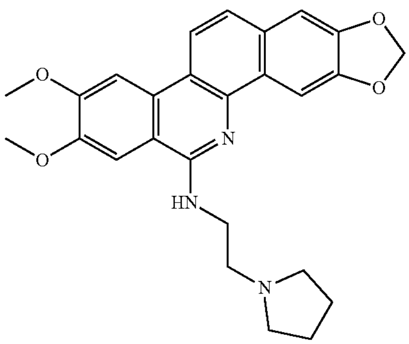
;

-continued

NTD-309

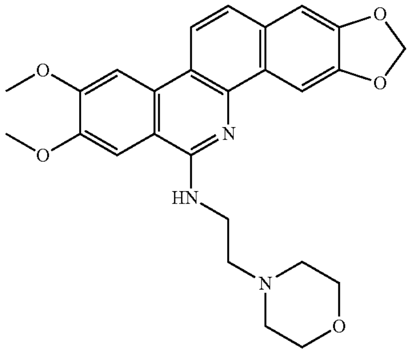

;

NTD-311

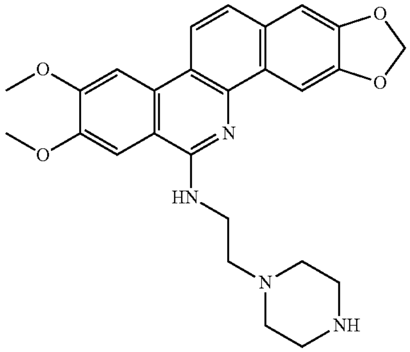

;

NTD-312

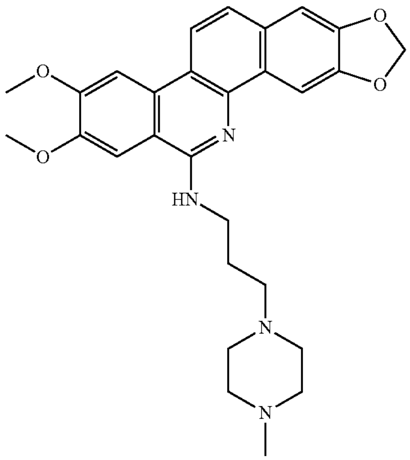

;

NTD-313

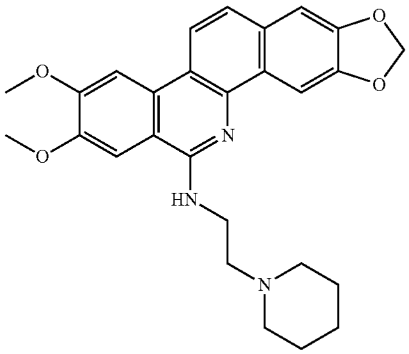

; and

-continued

NTD-314

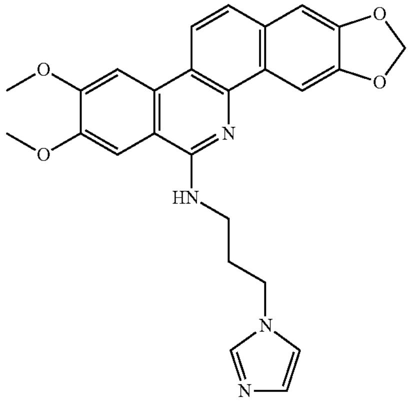

11. The compound or salt of claim 3, wherein $R^3$, $R^4$, $R^5$, $R^6$, $R^7$, $R^8$, and $R^9$ are independently chosen from hydrogen, halogen, methyl, and methoxy.

12. A pharmaceutical composition comprising a compound or salt of claim 1 together with a pharmaceutically acceptable carrier.

13. A method of treating cancer in a patient comprising administering a therapeutically effective amount of a compound or salt of claim 1 to the patient, wherein the cancer is selected from colon cancer, leukemia, prostate cancer, non-small cell lung cancer, CNS cancers, breast cancers, renal cancers, melanomas, and ovarian cancers.

14. The compound or salt of claim 2, wherein $R^3$, $R^4$, $R^5$, $R^6$, $R^7$, $R^8$, and $R^9$ are hydrogen and $R^1$ and $R^2$ are independently H or $C_1$-$C_6$alkoxy.

15. The compound or salt of claim 2, wherein $R^3$, $R^4$, $R^5$, $R^6$, $R^7$, $R^8$, and $R^9$ are hydrogen and $R^1$ and $R^2$ are independently H or $C_1$-$C_6$alkoxy, provided that at least one of $R^1$ and $R^2$ is $C_1$-$C_6$ alkoxy.

16. The compound or salt of claim 2, wherein $R^3$, $R^4$, $R^5$, $R^6$, $R^7$, $R^8$, and $R^9$ are hydrogen and $R^1$ and $R^2$ are independently H or methoxy, provided that at least one of $R^1$ and $R^2$ is methoxy.

17. A method of treating cancer in a patient comprising administering a therapeutically effective amount of a compound or salt of claim 16 to the patient, wherein the cancer is selected from colon cancer, leukemia, prostate cancer, non-small cell lung cancer, CNS cancers, breast cancers, renal cancers, melanomas, and ovarian cancers.

18. The compound of claim 1, wherein $R^1$, $R^2$, and $R^3$ are independently chosen from hydrogen, hydroxyl, halogen, and $C_1$-$C_6$alkoxy; or $R^1$ and $R^2$ can be taken together to form a 5 or 6-membered heterocycloalkyl ring containing 2 oxygen atoms, which $R^1$/$R^2$ ring is unsubstituted or substituted with 1 or 2 independently chosen $R^5$ substituents, where $R^5$ is independently chosen at each occurrence from halogen, hydroxyl, $C_1$-$C_2$alkyl, and $C_1$-$C_2$alkoxy; or $R^2$ and $R^3$ can be taken together to form a 5 or 6-membered heterocycloalkyl ring containing 2 oxygen atoms, which $R^2$/$R^3$ ring is unsubstituted or substituted with 1 or 2 independently chosen $R^5$ substituents;

$R^4$, $R^6$, $R^7$, $R^8$, and $R^9$ are independently chosen from hydrogen, halogen, hydroxyl, and $C_1$-$C_6$alkyl, which $C_1$-$C_6$alkyl can have one or more $CH_2$ group replaced by 0;

$R^{11}$ and $R^{12}$ are independently chosen from hydrogen, hydroxyl, halogen, and $C_1$-$C_6$alkoxy; or $R^{11}$ and $R^{12}$ can be taken together to form a 5 or 6-membered heterocycloalkyl ring containing 2 oxygen atoms, which $R^{11}/R^{12}$ ring is unsubstituted or substituted with 1 or 2 independently chosen $R^5$ substituents.

19. A method of treating cancer in a patient comprising administering a therapeutically effective amount of a compound or salt of claim 18 to the patient, wherein the cancer is selected from colon cancer, leukemia, prostate cancer, non-small cell lung cancer, CNS cancers, breast cancers, renal cancers, melanomas, and ovarian cancers.

20. A compound having the formula below or a pharmaceutically acceptable salt thereof,

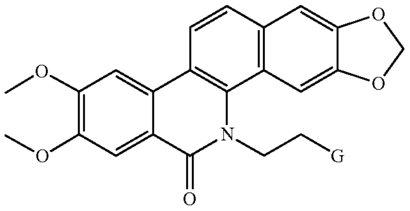

in which G is selected from —$NH_2$, NHMe;

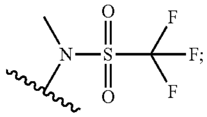 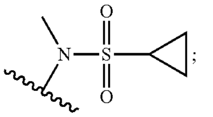

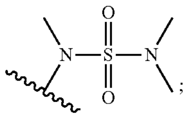 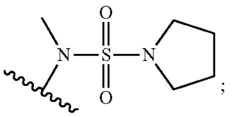

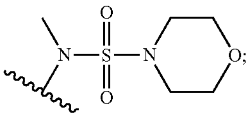 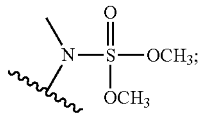

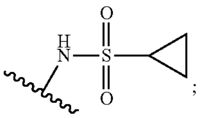 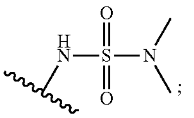

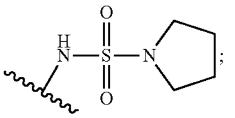 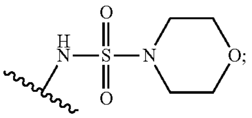

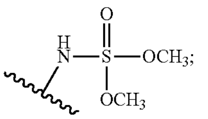 and 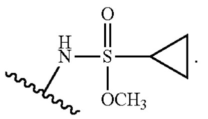

21. A method of treating cancer in a patient comprising administering a therapeutically effective amount of a compound or salt of claim 20 to the patient, wherein the cancer is selected from colon cancer, leukemia, prostate cancer, non-small cell lung cancer, CNS cancers, breast cancers, renal cancers, melanomas, and ovarian cancers.

22. A compound of Formula I or a pharmaceutically acceptable salt thereof,

Formula I

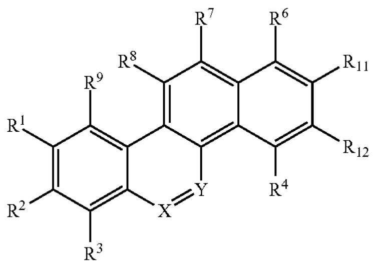

wherein the group

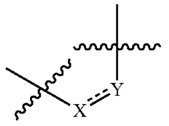

is

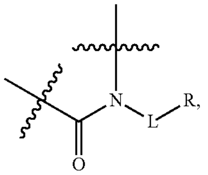 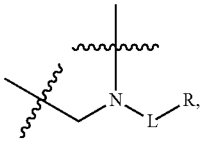

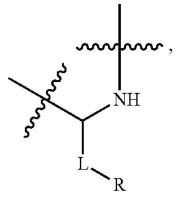, or 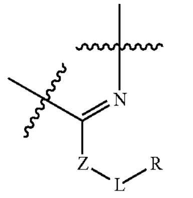

in which Z is O or S; and

R is hydroxyl, amino, mono- or di-$C_1$-$C_6$alkylamino; or

R is pyrrolidinyl, piperidinyl, piperazinyl, morpholinyl, thiomorpholinyl, pyrrolyl, pyrazolyl, imidazolyl, oxazolyl, or thiazolyl, each of which is optionally substituted with one or more substituents independently chosen from halogen, hydroxyl, $C_1$-$C_2$alkyl, and $C_1$-$C_2$alkoxy;

or the group

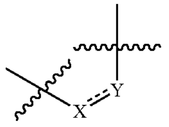

is

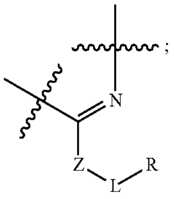

in which Z is NH or $NR^{10}$; and

R is pyrrolidinyl, piperidinyl, piperazinyl, morpholinyl, thiomorpholinyl, pyrrolyl, pyrazolyl, imidazolyl, oxazolyl, or thiazolyl, each of which is optionally substituted with one or more substituents independently chosen from halogen, hydroxyl, $C_1$-$C_2$alkyl, and $C_1$-$C_2$alkoxy;

and

L is $C_2$-$C_3$ alkyl;

$R^1$, $R^2$, and $R^3$ are independently chosen from hydrogen, hydroxyl, halogen, amino, $C_1$-$C_6$alkyl, $C_1$-$C_6$alkoxy, benzyloxy, $C_1$-$C_6$alkylthio, $C_1$-$C_2$haloalkyl, and $C_1$-$C_2$haloalkoxy; or $R^1$ and $R^2$ can be taken together to form a 5 or 6-membered heterocycloalkyl ring containing 2 oxygen atoms, which $R^1/R^2$ ring is unsubstituted or substituted with 1 or 2 independently chosen $R^5$ substituents, where $R^5$ is independently chosen at each occurrence from halogen, hydroxyl, $C_1$-$C_2$alkyl, and $C_1$-$C_2$alkoxy; or $R^2$ and $R^3$ can be taken together to form a 5 or 6-membered heterocycloalkyl ring containing 2 oxygen atoms, which $R^2/R^3$ ring is unsubstituted or substituted with 1 or 2 independently chosen $R^5$ substituents;

$R^4$, $R^6$, $R^7$, $R^8$, and $R^9$ are independently chosen from hydrogen, halogen, hydroxyl, amino, cyano, COOH, CHO, or $C_1$-$C_6$alkyl, which $C_1$-$C_6$alkyl can contain one or more double or triple bonds, can have one or more $CH_2$ group replaced by NH, $NR^{10}$, S, or O, and is optionally substituted with one or more substituents independently chosen from hydroxyl, amino, cyano, halogen, oxo, and $C_3$-$C_6$cycloalkyl;

$R^{10}$ is $C_1$-$C_6$alkyl or ($C_3$-$C_6$cycloalkyl)$C_0$-$C_4$alkyl;

$R^{11}$ and $R^{12}$ are independently chosen from hydrogen, hydroxyl, halogen, amino, C-$C_6$alkyl, $C_1$-$C_6$alkoxy, benzyloxy, $C_1$-$C_6$alkylthio, $C_1$-$C_2$haloalkyl, or $C_1$-$C_2$haloalkoxy; or $R^{11}$ and $R^{12}$ can be taken together to form a 5 or 6-membered heterocycloalkyl ring containing 2 oxygen atoms, which $R^{11}/R^{12}$ ring is unsubstituted or substituted with 1 or 2 independently chosen $R^5$ substituents.

* * * * *

SEQUENCE LISTING

<160> NUMBER OF SEQ ID NOS: 1

<210> SEQ ID NO 1
<211> LENGTH: 14
<212> TYPE: DNA
<213> ORGANISM: Artificial Sequence
<220> FEATURE:
<223> OTHER INFORMATION: 14-mer 5'-32P-labeled 3'-phosphotyrosyl DNA substrate N14Y
<220> FEATURE:
<221> NAME/KEY: misc_feature
<222> LOCATION: (14)..(14)
<223> OTHER INFORMATION: 3'-phosphotyrosine (pY)

<400> SEQUENCE: 1
gatctaaaag actt 14